(12) United States Patent
Demopulos et al.

(10) Patent No.: US 9,220,715 B2
(45) Date of Patent: *Dec. 29, 2015

(54) TREATMENT OF ADDICTION AND IMPULSE-CONTROL DISORDERS USING PDE7 INHIBITORS

(71) Applicant: Omeros Corporation, Seattle, WA (US)

(72) Inventors: Gregory A. Demopulos, Mercer Island, WA (US); George A. Gaitanaris, Seattle, WA (US); Roberto Ciccocioppo, Camerino (IT)

(73) Assignee: Omeros Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/835,607

(22) Filed: Mar. 15, 2013

(65) Prior Publication Data

US 2013/0267502 A1  Oct. 10, 2013

Related U.S. Application Data

(63) Continuation-in-part of application No. 13/290,868, filed on Nov. 7, 2011.

(60) Provisional application No. 61/643,611, filed on May 7, 2012, provisional application No. 61/482,994, filed on May 5, 2011, provisional application No. 61/411,437, filed on Nov. 8, 2010, provisional application No. 61/411,431, filed on Nov. 8, 2010.

(51) Int. Cl.

| | |
|---|---|
| *A61K 31/5513* | (2006.01) |
| *A61K 31/5377* | (2006.01) |
| *A61K 31/53* | (2006.01) |
| *A61K 31/4985* | (2006.01) |
| *A61K 31/496* | (2006.01) |
| *A61K 31/519* | (2006.01) |
| *A61K 31/527* | (2006.01) |
| *A61K 31/46* | (2006.01) |
| *A61K 31/435* | (2006.01) |
| *A61K 31/4439* | (2006.01) |
| *A61K 31/433* | (2006.01) |
| *A61K 31/4178* | (2006.01) |
| *A61K 31/4162* | (2006.01) |
| *A61K 31/4025* | (2006.01) |
| *A61K 31/35* | (2006.01) |
| *A61K 45/06* | (2006.01) |
| *A61K 31/135* | (2006.01) |
| *A61K 31/137* | (2006.01) |
| *A61K 31/197* | (2006.01) |
| *A61K 31/337* | (2006.01) |
| *A61K 31/357* | (2006.01) |
| *A61K 31/381* | (2006.01) |
| *A61K 31/385* | (2006.01) |
| *A61K 31/4015* | (2006.01) |
| *A61K 31/44* | (2006.01) |
| *A61K 31/454* | (2006.01) |
| *A61K 31/485* | (2006.01) |

(Continued)

(52) U.S. Cl.
CPC ........... *A61K 31/5513* (2013.01); *A61K 31/135* (2013.01); *A61K 31/137* (2013.01); *A61K 31/197* (2013.01); *A61K 31/337* (2013.01); *A61K 31/35* (2013.01); *A61K 31/357* (2013.01); *A61K 31/381* (2013.01); *A61K 31/385* (2013.01); *A61K 31/4015* (2013.01); *A61K 31/4025* (2013.01); *A61K 31/4162* (2013.01); *A61K 31/4178* (2013.01); *A61K 31/433* (2013.01); *A61K 31/435* (2013.01); *A61K 31/44* (2013.01); *A61K 31/4439* (2013.01); *A61K 31/454* (2013.01); *A61K 31/46* (2013.01); *A61K 31/485* (2013.01); *A61K 31/496* (2013.01); *A61K 31/4985* (2013.01); *A61K 31/505* (2013.01); *A61K 31/517* (2013.01); *A61K 31/519* (2013.01); *A61K 31/527* (2013.01); *A61K 31/53* (2013.01); *A61K 31/5377* (2013.01); *A61K 31/55* (2013.01); *A61K 45/06* (2013.01)

(58) Field of Classification Search
CPC ........... A61K 31/5513; A61K 31/5377; A61K 31/53; A61K 31/4985; A61K 31/496; A61K 31/519; A61K 31/527; A61K 31/46; A61K 31/435; A61K 31/4439; A61K 31/433; A61K 31/4178; A61K 31/4162; A61K 31/4025; A61K 31/35; A61K 45/06
See application file for complete search history.

(56) References Cited

U.S. PATENT DOCUMENTS

| | | |
|---|---|---|
| 5,610,288 A | 3/1997 | Rubenstein |
| 5,718,709 A | 2/1998 | Considine et al. |

(Continued)

FOREIGN PATENT DOCUMENTS

| | | |
|---|---|---|
| BR | 0607402-2 A2 | 9/2009 |
| DE | 199 50 647 A1 | 10/1999 |

(Continued)

OTHER PUBLICATIONS

Siuciak, J., et al., "Inhibition of the Striatum-Enriched Phosphodiesterase PDE10A: A Novel Approach to the Treatment of Psychosis," *Neuropharmacology* 51:386-396 (2006).

(Continued)

*Primary Examiner* — Renee Claytor
(74) *Attorney, Agent, or Firm* — Marcia S. Kelbon

(57) ABSTRACT

This disclosure is directed to treatment of addictions and primary impulse-control disorders using phosphodiesterase 7 (PDE7) inhibitors, alone or in combination with other therapeutic agents.

34 Claims, 47 Drawing Sheets

(51) Int. Cl.
*A61K 31/505* (2006.01)
*A61K 31/517* (2006.01)
*A61K 31/55* (2006.01)

(56) References Cited

U.S. PATENT DOCUMENTS

| | | | |
|---|---|---|---|
| 5,739,119 | A | 4/1998 | Galli et al. |
| 5,759,829 | A | 6/1998 | Shewmaker et al. |
| 5,789,573 | A | 8/1998 | Baker et al. |
| 5,801,154 | A | 9/1998 | Baracchini et al. |
| 6,146,876 | A | 11/2000 | Robision et al. |
| 6,531,498 | B1 | 3/2003 | Eggenweiler et al. |
| 6,613,778 | B1 | 9/2003 | Eggenweiler et al. |
| 6,617,357 | B2 | 9/2003 | Aubart et al. |
| 6,649,592 | B1 | 11/2003 | Larson |
| 6,737,436 | B1 | 5/2004 | Eggenweiler et al. |
| 6,753,340 | B2 | 6/2004 | Vergne et al. |
| 6,818,651 | B2 | 11/2004 | Weinbrenner et al. |
| 6,838,559 | B2 | 1/2005 | Vaccaro et al. |
| 6,849,638 | B2 | 2/2005 | Stolle et al. |
| 6,852,720 | B2 | 2/2005 | Vergne et al. |
| 6,884,800 | B1 | 4/2005 | Eggenweiler et al. |
| 6,903,109 | B2 | 6/2005 | Heintzelman et al. |
| 6,936,609 | B2 | 8/2005 | Ergüden et al. |
| 6,958,328 | B2 | 10/2005 | Heintzelman et al. |
| 7,022,849 | B2 | 4/2006 | Pitts et al. |
| 7,087,614 | B2 | 8/2006 | Guo et al. |
| 7,122,565 | B2 | 10/2006 | Vergne et al. |
| 7,214,676 | B2 | 5/2007 | Bernardelli et al. |
| 7,268,128 | B2 | 9/2007 | Inoue et al. |
| 7,491,742 | B2 | 2/2009 | Eggenweiler et al. |
| 7,498,334 | B2 | 3/2009 | Eggenweiler et al. |
| 7,579,455 | B2 | 8/2009 | Paolo et al. |
| 7,932,250 | B2 | 4/2011 | Inoue et al. |
| 2002/0156064 | A1 | 10/2002 | Aubart et al. |
| 2002/0198198 | A1 | 12/2002 | Bernardelli et al. |
| 2003/0045557 | A1 | 3/2003 | Vergne et al. |
| 2003/0092721 | A1 | 5/2003 | Pitts et al. |
| 2003/0092908 | A1 | 5/2003 | Pitts et al. |
| 2003/0100571 | A1 | 5/2003 | Vaccaro et al. |
| 2003/0104974 | A1 | 6/2003 | Pitts et al. |
| 2003/0119829 | A1 | 6/2003 | Stolle et al. |
| 2003/0162802 | A1 | 8/2003 | Guo et al. |
| 2003/0191167 | A1 | 10/2003 | Vergne et al. |
| 2003/0212089 | A1 | 11/2003 | Heintzelman et al. |
| 2004/0044212 | A1 | 3/2004 | Weinbrenner et al. |
| 2004/0082578 | A1 | 4/2004 | Heintzelman et al. |
| 2004/0106631 | A1 | 6/2004 | Bernardelli et al. |
| 2004/0127707 | A1 | 7/2004 | Sterk |
| 2004/0249148 | A1 | 12/2004 | Ergüden et al. |
| 2005/0059686 | A1 | 3/2005 | Eggenweiler et al. |
| 2005/0148604 | A1 | 7/2005 | Inoue et al. |
| 2005/0222138 | A1 | 10/2005 | Ohhata et al. |
| 2006/0116516 | A1 | 6/2006 | Pitts et al. |
| 2006/0128707 | A1 | 6/2006 | Inoue et al. |
| 2006/0128728 | A1 | 6/2006 | Inoue et al. |
| 2006/0154949 | A1 | 7/2006 | Heintzelman et al. |
| 2006/0229306 | A1 | 10/2006 | Terricabras Belart et al. |
| 2007/0049276 | A1 | 3/2007 | Bernardelli et al. |
| 2007/0072899 | A1 | 3/2007 | Johnson et al. |
| 2007/0129388 | A1 | 6/2007 | Rawson et al. |
| 2007/0208029 | A1 | 9/2007 | Barlow et al. |
| 2007/0270419 | A1 | 11/2007 | Inoue et al. |
| 2007/0292412 | A1 | 12/2007 | Salonen et al. |
| 2008/0260643 | A1 | 10/2008 | Bergmann et al. |
| 2008/0282364 | A1 | 11/2008 | Black et al. |
| 2009/0111837 | A1 | 4/2009 | Cox et al. |
| 2009/0291917 | A1 | 11/2009 | Akama et al. |
| 2010/0152213 | A1 | 6/2010 | Ayuso-Gontan et al. |

FOREIGN PATENT DOCUMENTS

| | | | |
|---|---|---|---|
| EP | 0 321 201 | A2 | 12/1988 |
| EP | 1 193 261 | A1 | 10/2000 |
| EP | 1 348 433 | A1 | 3/2002 |
| EP | 1 348 701 | A1 | 3/2002 |
| EP | 1 400 244 | A1 | 9/2002 |
| EP | 1 454 897 | A1 | 12/2002 |
| EP | 1 775 298 | A1 | 7/2005 |
| ES | 2 308 916 | | 12/1987 |
| RU | 2 351 371 | | 4/2009 |
| WO | WO 94/21244 | | 9/1994 |
| WO | WO 88/04399 | | 6/1998 |
| WO | WO 00/68203 | | 11/2000 |
| WO | WO 00/68230 | | 11/2000 |
| WO | WO 01/29049 | A2 | 4/2001 |
| WO | WO 01/32175 | A1 | 5/2001 |
| WO | WO 01/32618 | A1 | 5/2001 |
| WO | WO 01/34601 | A2 | 5/2001 |
| WO | WO 01/36425 | A2 | 5/2001 |
| WO | WO 01/62904 | A1 | 8/2001 |
| WO | WO 01/74786 | A1 | 10/2001 |
| WO | WO 01/98274 | A2 | 12/2001 |
| WO | WO 02/28847 | A1 | 4/2002 |
| WO | WO 02/40449 | A1 | 5/2002 |
| WO | WO 02/40450 | A1 | 5/2002 |
| WO | WO 02/074754 | A1 | 9/2002 |
| WO | WO 02/076953 | A1 | 10/2002 |
| WO | WO 02/085894 | A1 | 10/2002 |
| WO | WO 02/085906 | A2 | 10/2002 |
| WO | WO 02/087513 | A2 | 11/2002 |
| WO | WO 02/087519 | A2 | 11/2002 |
| WO | WO 02/088079 | A2 | 11/2002 |
| WO | WO 02/088080 | A2 | 11/2002 |
| WO | WO 02/088138 | A1 | 11/2002 |
| WO | WO 02/102313 | A2 | 12/2002 |
| WO | WO 02/102314 | A2 | 12/2002 |
| WO | WO 02/102315 | A2 | 12/2002 |
| WO | WO 02/053975 | A1 | 3/2003 |
| WO | WO 03/053975 | A1 | 7/2003 |
| WO | WO 03/055882 | A1 | 7/2003 |
| WO | WO 03/057149 | A2 | 7/2003 |
| WO | WO 03/064389 | A1 | 8/2003 |
| WO | WO 03/082277 | A1 | 10/2003 |
| WO | WO 03/082839 | A1 | 10/2003 |
| WO | WO 03/088963 | A1 | 10/2003 |
| WO | WO 2004/026818 | A1 | 4/2004 |
| WO | WO 2004/044196 | A1 | 5/2004 |
| WO | WO 2004/065391 | A1 | 8/2004 |
| WO | WO 2004/111053 | A1 | 12/2004 |
| WO | WO 2004/111054 | A1 | 12/2004 |
| WO | WO 2006/004040 | A1 | 1/2006 |
| WO | WO 2006/092691 | A1 | 9/2006 |
| WO | WO 2006/092692 | A1 | 9/2006 |
| WO | WO 2007/038551 | A2 | 4/2007 |
| WO | WO 2007/047978 | A2 | 4/2007 |
| WO | WO 2007/063391 | | 6/2007 |
| WO | WO 2008/113881 | A1 | 9/2008 |
| WO | WO 2008/130619 | A2 | 10/2008 |
| WO | WO 2008/142550 | A2 | 11/2008 |
| WO | WO 2009/140309 | A2 | 11/2009 |
| WO | WO 2010/027975 | A1 | 3/2010 |
| WO | WO 2010/030851 | A1 | 3/2010 |
| WO | WO 2010/109148 | A1 | 9/2010 |
| WO | WO 2010/116088 | A2 | 10/2010 |

OTHER PUBLICATIONS

Miro, X., et al., "Differential Distribution of cAMP-Specific Phosphodiesterase 7A mRNA in Rat Brain and Peripheral Organs," *Synapse*, 40:201-214 (2001).

Reyes-Irrisari, E., et al., "Neuronal Expression of cAMP-Specific Phosphodiesterase 7B mRNA in the Rat Brain," *Neuroscience* 132:1173-1175 (2005).

Vergne, Fabrice, et al., "Discovery of Thiadiazoles as a Novel Structural Class of Potent and Selective PDE7 Inhibitors. Part 1: Design, Synthesis and Structure-Activity Relationship Studies," *Bioorganic & Medicinal Chemistry Letters* 14:4607-4613 (2004).

Vergne, Fabrice, et al., "Discovery of Thiadiazoles as a Novel Structural Class of potent and Selective PDE7 Inhibitors. Part 2: Metabolism-Directed Optimization Studies Towards Orally Bioavailable Derivatives," *Bioorganic & Medicinal Chemistry Letters* 14:4615-4621 (2004).

(56) References Cited

OTHER PUBLICATIONS

Lorthois, Edwige, et al., "Spiroquinazolinones as Novel, Potent and Selective PDE7 Inhibitors. Part 1." *Bioorganic & Medicinal Chemistry Letters* 14:4623-4626 (2004).

Smith, Susan J., et al., "Discovery of BRL 50481 [3-(N,N-dimethylsufonamido)-4-methyl-nitrobenzene], a Selective Inhibitor of Phosphodiesterase 7: In Vitro Studies in Human Monocytes, Lung Macrophages, and CD8+T-Lymphocytes," *Molecular Pharmacology* 66(6):1679-1689 (2004).

Sasaki, Takashi, et al., "Novel Alternative Splice Variants of Rat Phosphodiesterase 7B Showing Unique Tissue-Specific Expression and Phosphorylation," *Biochemistry* 381:211-220 (2002).

Kadoshima-Yamaoka, Kumiko, et al., "ASB16165, a Novel Inhibitor for Phosphodiesterase 7A (PDE7A), Suppresses IL-12-Induced IFN-γ Production by Mouse Activated T Lymphocytes," *Immunology Letters* 122:193-197 (2009).

Kang, N.S., et al., "Docking and 3-D QSAR Studies of Dual PDE4-PDE7 Inhibitors," *Molecular Simulation* 33(14):1109-1117 (2007).

Pitts, William, et al., "Identification of Purine Inhibitors of Phosphodiesterase 7 (PDE7)," *Bioorganic & Medicinal Chemistry Letters* 14:2955-2958 (2004).

Kempson, James, et al., "Fused Pyrimidine Based Inhibitors of Phosphodiesterase 7 (PDE7): Synthesis and Initial Structure-Activity Relationships," *Bioorganic & Medicinal Chemistry Letters* 15:1829-1833 (2005).

Yamamoto, Satoshi, et al., "Pharmacological Profile of a Novel Phosphodiesterase 7A and -4 Dual Inhibitor, YM-393059, on Acute and Chronic Inflammation Models," *European Journal of Pharmacology* 550:166-172 (2006).

Castro, Ana, et al., "CODES, a Novel Procedure for Ligand-Based Virtual Screening: PDE7 Inhibitors as an Application Example," *European Journal of Medicinal Chemistry* 43:1349-1359 (2008).

Bloom, Timothy, et al., "Identification and Tissue-Specific Expression of PDE7 Phosphodiesterase Splice Variants," *Pharmacology* 93:14188-14192 (1996).

Banks, William, et al., "Delivery Across the Blood-Brain Barrier of Antisense Directed Against Amyloid β: Reversal of Learning and Memory Deficits in Mice Overexpressing Amyloid Precursor Protein," *The Journal of Pharmacology and Experimental Therapeutics* 297(3):1113-1121 (2001).

Barnes, Matthew J., et al., "Synthesis and Structure—Activity Relationships of Guanine Analogues as Phosphodiesterase 7 (PDE7) Inhibitors," *Bioorganic & Medicinal Chemistry Letters* 11:1081-1083 (2001).

Bernardelli, Patrick, et al., "Spiroquinazolinones as Novel, Potent and Selective PDE7 Inhibitors. Part 2: Optimization of 5,8-disubstituted Derivatives," *Bioorganic & Medicinal Chemistry Letters* 14:4627-4631 (2004).

Hetman, J.M., et al., "Cloning and Characterization of PDE7B, a cAMP-Specific Phosphodiesterase," *PNAS* 97(1):472-476 (2000).

Yang, Guchen, et al., "Phosphodiesterase 7A-Deficient Mice Have Functional T Cells," *The Journal of Immunology* 171:6414-6420 (2003).

Siuciak, J.A., et al., "Behavioral and Neurochemical Characterization of Mice Deficient in the Phosphodiesterase-1B (PDE1B) Enzyme," *Neuropharmacology* 53:113-124 (2007).

Cifani, Carlo, et al., "A Preclinical Model of Binge Eating Elicited by Yo-yo Dieting and Stressful Exposure to Food: Effect of Sibutramine, Fluoxetine, Topiramate, and Midazolam." *Psychopharmacology* 204:113-125 (2009).

Gearhardt, Ashley, et al., "Binge Eating Disorder and Food Addiction," *Current Drug Abuse Reviews* 4:201-207 (2011).

Williams, Jennifer, "Omeros announces expansion of potential indications for PDE7 inhibitors," PR Newswire, May 2011. (Business announcement online). <URL http://www.drugs.com/clinical_trials/omeros-announces-expansion-potential-indications-pde7-inhibitors-11674.html>.

Compton, William, et al., "Major Increases in Opioid Analgesic Abuse in the United States: Concerns and Strategies," *Drug and Alcohol Dependence* 81:103-107 (2006).

Delva, Jorge, et al., "The Epidemiology of Alcohol, Marijuana, and Cocaine Use Among Mexican American, Puerto Rican, Cuban American and Other Latin American Eighth-Grade Students in the United States: 1991-2002," *American Journal of Public Health* 95(4):696-702 (2005).

Liu, Xiu, et al., "Additive Effect of Stress and Drug Cues on Reinstatement of Ethanol Seeking Exacerbation by History of Dependence and Role of Concurrent Activation of Corticotropin-Releasing Factor and Opioid Mechanisms," *The Journal of Neuroscience* 22(18):7856-7861 (2002).

Ramsey, Nick, et al., "Emotional but not Physical Stress Enhances Intravenous Cocaine Self-Administration in Drug-Naïve Rats," *Brain Research* 608:216-222 (1993).

Shaham, Yavin, et al., "Stress Reinstates Heroin-Seeking in Drug-Free Animals: an Effect Mimicking Heroin, not Withdrawal," *Psychopharmacology* 119:334-341 (1995).

Merlo Pich, Emilio, et al., "Increase of Extracellular Corticotropin-Releasing Factor-Like Immunoreactivity Levels in the Amygdala of Awake Rats During Restraint Stress and Ethanol Withdrawal as Measured by Microdialysis." *The Journal of Neuroscience* 15(8):5439-5447 (1995).

Childress, A., et al., "Conditioned Craving and Arousal in Cocaine Addiction: a Preliminary Report," *NIDA Research Monograph* 81:74-80 (1988).

Weiss, Friedbert, "Control of Cocaine-Seeking Behavior by Drug-Associated Stimuli in Rats: Effects on Recovery of Extinguished Operant-Responding and Extracellular Dopamine Levels in Amygdala and Nucleus Accumbens," *PNAS* 97(8):4321-4326 (2000).

Katner, Simon, et al., "Reinstatement of Alcohol-Seeking Behavior by Drug-Associated Discriminative Stimuli after Prolonged Extinction in the Rat," *Neuropsychopharmacology* 20:471-479 (1999).

Lee, Buyean, et al., "Pharmacological Blockade of α2-Adrenoceptors Induces Reinstatement of Cocaine-Seeking Behavior in Squirrel Monkeys," *Neuropsychopharmacology* 29:686-693 (2004).

Lêe A.D., et al., "The Role of Corticotropin-Releasing Factor in Stress-Induced Relapse to Alcohol-Seeking Behavior in Rats," *Psychopharmacology* 150:317-324 (2000).

Shea, Kenneth J., "Molecular Imprinting of Synthetic Network Polymers: The De Novo Synthesis of Macromolecular Binding and Catalytic Sites," *TRIP* 2(5):166 (1994).

Pachori, Alok, et al., "Blood Pressure-Dependent Attenuation of Cardiac Hypertrophy by AT1R-AS Gene Therapy," *Hypertension* 39:969-975 (2002).

Scherr, Michael, et al., "Rapid Determination and Quantitation of the Accessibility to Native RNAs by Antisense Oligodeoxynucleotides in Murine Cell Extracts," *Nucleic Acids Research* 26(22):5079-5085 (1998).

Lloyd, B.H., et al., "Determination of Optimal Sites of Antisense Oligonucleotide Cleavage within TNFα mRNA," *Nucleic Acids Research* 29(17):3664-3673 (2001).

Altschul, Stephen, et al., "Gapped BLAST and PSI-BLAST: a New Generation of Protein Database Search Programs," *Nucleic Acids Research* 25(17):3389-3402 (1997).

Fedor, Martha, et al., "Substrate Sequence Effects on "Hammerhead" RNA Catalytic Efficiency," *PNAS USA* 87:1668-1672 (1990).

Yamamoto, Satoshi, et al., "The Effects of a Novel Phosphodiesterase 7A and -4 Dual Inhibitor, YM-393059, on T-Cell-Related Cytokine Production In Vitro and In Vivo," *European Journal of Pharmacology* 541:106-114 (2006).

Martinez, Ana, et al., "Benzyl Derivatives of 2,1,3-Benzo- and Benzothieno[3,2-a]thiadiazine 2,2-Dioxides: First Phosphodiesterase 7 Inhibitors," *Journal of Medicinal Chemistry* 43:683-689 (2000).

Ohman, E.M., et al., "Early Clinical Experience with Integrelin, an Inhibitor of the Platelet Glycoprotein IIb/IIIa Integrin Receptor," *European Heart Journal* 16(Supplement L):50-55 (1995).

Murayama, Ohoshi, et al., "Novel Peptide Ligands for Integrina α6β1 Selected from a Phage Display Library," *Journal of Biochemistry* 120:446-451 (1996).

Zhang, Li, et al., "A Discrete Site Modulates Activation of I Domains," *The Journal of Biological Chemistry* 271(47):29953-29957 (1996).

(56) References Cited

OTHER PUBLICATIONS

Jackson, David, et al., "Potent α4β1 Peptide Antagonists as Potential Anti-Inflammatory Agents," *Journal of Medicinal Chemistry* 40:3359-3368 (1997).
Merrifield, R.B., "Solid Phase Peptide Synthesis I. The Synthesis of a Peptide," *Journal of the American Chemical Society* 85(14):2149-2154 (1963).
Mautino, Mario, et al., "Enhanced Inhibition of Human Immunodeficiency Virus Type 1 Replication by Novel Lentiviral Vectors Expressing Human Immunodeficiency Virus Type 1 Envelope Antisense RNA," *Human Gene Therapy* 13:1027-1037 (2002).
Jensen, Silke, et al., "Taming of Transposable Elements by Homology-Dependent Gene Silencing," *Nature Genetics* 21(2):209-12 (1999).
Haseloff, Jim, et al., "Simple RNA Enzymes with New and Highly Specific Endoribonuclease Activities," *Nature* 334:585-591 (1998).
Cech, Thomas, et al., "Biological Catalysis by RNA," *Annual Review of Biochemistry* 55:599-629 (1986).
Compton, Wilson, et al., "Abuse of Prescription Drugs and the Risk of Addiction," *Drug and Alcohol Dependence* 838:S4-S7 (2006).
Siegal, H.A., et al., "Probable Relationship Between Opioid Abuse and Heroin Use," *American Family Physician* 68(11):2134-2141 (2003).
Ciccocioppo, Robert, et al., "Reversal of Stress- and CRF-Induced Anorexia in Rats by the Synthetic Nociceptin/Orphanin FQ Receptor Agonist, Ro 64-6198," *Psychopharmacology* 161:113-119 (2002).
McKay, James, et al., "An Examination of the Cocaine Relapse Process," *Drug and Alcohol Dependence* 38:35-43 (1995).
Goeders, Nick, et al., "Non-Contingent Electric Footshock Facilitates the Acquisition of Intravenous Cocaine Self-Administration in Rats," *Psychopharmacology* 114:63-70 (1994).
Brown, Sandra, et al., "Stress, Vulnerability and Adult Alcohol Relapse," *Journal of Studies on Alcohol* 56(5):538-545 (1995).
Haney, Margaret, et al., "Social Stress Increases the Acquisition of Cocaine Self-Administration in Male and Female Rats," *Brain Research* 698:46-52 (1995).
Wallace, Barbara, "Psychological and Environmental Determinants of Relapse in Crack Cocaine Smokers," *Journal of Substance Abuse Treatment* 6:95-106 (1989).
Ahmed, Serge, et al., "Cocaine-but not Food-Seeking Behavior is Reinstated by Stress after Extinction." *Psychopharmacology* 132:289-295 (1997).
Nash, Frank, et al., "The Role of the Hypothalamic-Pituitary-Adrenocortical Axis in Post-Stress induced Ethanol Consumption by Rats," *Progress in Neuro-Psychopharmacology & Biological Psychiatry* 12:653-671 (1988).
Mollenauer, Sandra, et al., "EtOH Self-Administration in Anticipation of Noise Stress in C57BL/6J Mice," *Pharmacology Biochemistry and Behavior* 46:35-38 (1991).
Blanchard, Robert, et al., "Social Structure and Ethanol Consumption in the Laboratory Rat," *Pharmacology Biochemistry & Behavior* 28:437-442 (1987).
Higley, J.D., et al., "Nonhuman Primate Model of Alcohol Abuse: Effects of Early Experience, Personality, and Stress on Alcohol Consumption," *PNAS USA* 88:7261-7265 (1991).
Shaham, Yavin, "Immobilization Stress-Induced Oral Opioid Self-Administration and Withdrawal in Rats: Role of Conditioning Factors and the Effect of Stress on "Relapse" to Opioid Drugs," *Psychopharmacology* 111:477-485 (1993).
Dunn, Adrian, et al., "Physiological and Behavioral Responses to Corticotropin-Releasing Factor Administration: is CRF a Mediator of Anxiety or Stress Responses?" *Brain Research Review* 15:71-100 (1990).
Merali, Zui, et al., "Aversive and Appetitive Events Evoke the Release of Corticotropin-Releasing Hormone and Bombesin-Like Peptides at the Central Nucleus of the Amygdala," *The Journal of Neuroscience* 18(12):4758-4766 (1998).
Heinrichs, Stephen, et al., "Corticotropin-Releasing Factor Antagonist Reduces Emotionality in Socially Defeated Rats Via Direct Neurotropic Action," *Brain Research* 581:190-197 (1992).
Swiergiel, Arthur, et al., "Attenuation of Stress-Induced Behavior by Antagonism of Corticotropin-Releasing Factor Receptors in the Central Amygdala in the Rat," *Brain Research* 623:229-234 (1993).
Ehrman, Ronald, et al., "Conditioned Responses to Cocaine-Related Stimuli in Cocaine Abuse Patients," *Psychopharmacology* 107:523-529 (1992).
Monti, Peter, et al., "Alcohol Cue Reactivity: Effects of Detoxification and Extended Exposure," *Journal of Studies on Alcohol and Drugs* 54:235-245 (1993).
Pomerleau, Ovide, et al., "Reactivity to Alcohol Cues in Alcoholics and Non-Alcoholics: Implications for a Stimulus Control Analysis of Drinking," *Addictive Behaviors* 8:1-10 (1983).
Morten Stormark, Kjell, et al., "Autonomic Cued Reactivity in Alcoholics: the Effect of Olfactory Stimuli," *Addictive Behaviors* 20(5):571-584 (1995).
Miller, Norman, et al., "Dissociation of "Conscious Desire" (Craving) from and Relapse in Alcohol and Cocaine Dependence," *Annals of Clinical Psychiatry* 6(2):99-106 (1994).
Tiffany, Stephen, et al., "Is Craving the Source of Compulsive Drug Use?" *Journal of Psychopharmacology* 12(1):23-30 (1998).
Katner, Simon, et al., "Ethanol-Associated Olfactory Stimuli Reinstate Ethanol-Seeking Behavior After Extinction and Modify Extracellular Dopamine Levels in the Nucleus Accumbens," *Alcoholism: Clinical and Experimental Research* 23(11):1751-1760 (1999).
Gracy, K. Noelle, et al., "Heroin-Specific Stimuli Reinstate Operant Heroin-Seeking Behavior in Rats After Prolonged Extinction," *Pharmacology Biochemistry and Behavior* 65(3):489-494 (2000).
Lê, A.D., et al., "Reinstatement of Alcohol-Seeking by Priming Injections of Alcohol and Exposure to Stress in Rats," *Psychopharmacology* 133:169-174 (1998).
Volpicelli, Joseph, et al., "Naltrexone in the Treatment of Alcohol Dependence," *Archives of General Psychiatry* 49:876-880 (1992).
O'Brien, Charles, "A Range of Research-Based Pharmacotherapies for Addiction," *Science* 278(5335):66-70 (1997).
Michaeli, Tamar, et al., "Isolation and Characterization of a Previously Undetected Human cAMP Phosphodiesterase by Complementation of cAMP Phosphodiesterase-Deficient Saccharomyces cerevisiae" *The Journal of Biological Chemistry* 268(17):12925-12932 (1993).
Han, Ping, et al., "Alternative Splicing of the High Affinity cAMP-Specific Phosphodiesterase (PDE7A) mRNA in Human Skeletal Muscle and Heart," *The Journal of Biological Chemistry* 272(26):16152-16157 (1997).
Gardner, Clare, et al., "Cloning and Characterization of the Human and Mouse PDE7B, a Novel cAMP-Specific Cyclic Nucleotide Phosphodiesterase," *Biochemical and Biophysical Research Communications* 272:186-192 (2000).
Sasaki, Takashi, et al., "Identification of Human PDE7B, a cAMP-Specific Phosphodiesterase," *Biochemical and Biophysical Research Communications* 271:575-583 (2000).
Packer, Milton, et al., "Effect of Oral Milrinone on Mortality in Severe Chronic Heart Failure," *The New England Journal of Medicine* 325:1468-1475 (1991).
Lehnart, Stephan, et al., "Phosphodiesterase 4D Deficiency in the Ryanodine-Receptor Complex Promotes Heart Failure and Arrhythmias," *Cell* 123(1):25-35 (2005).
Ma, Zhenkun, et al., "Asymmetric Dipolar Cycloaddition Reactions: A Practical, Convergent Synthesis of Chiral Pyrrolidines," *Tetrahedron: Asymmetry* 8(6):883-887 (1997).
Weiss, Frank, et al., "Environmental Stimuli Potently Reinstate Alcohol-Seeking Behavior: Effect of Repeated Alcohol Intoxication," *Society for Neuroscience Abstract* 25:1081 (1999).
Bardelle, Catherine, et al., "Phosphodiesterase 4 Conformers: Preparation of Recombinant Enzymes and Assay for Inhibitors," *Analytical Biochemistry* 275:148-155 (1999). (Abstract only).
Koob, George, et al., "Corticotropin Releasing Factor, Stress and Behavior," *Seminars in the Neurosciences* 6:221-229 (1994).
Castro, Ana, et al., "CoMFA of Benzyl Derivatives of 2,1,3-Benzo and Benzothieno[3,2-α]Thiadiazine 2,2-Dioxides: Clues for the Design of Phosphodiesterase 7 Inhibitors," *European Journal of Medicinal Chemistry* 36:333-338 (2001).

(56) References Cited

OTHER PUBLICATIONS

Barnes, Matthew, et al., "Synthesis and Structure-Activity Relationships of Guanine Analogues as Phosphodiesterase 7 (PDE7) Inhibitors," *Bioorganic & Medicinal Chemistry Letters* 11:1081-1083 (2001).

Yoshida, Masaru, et al., "Study of Biodegradable Copoly(L-Lactic Acid/Glycolic Acid) Formulations with Controlled Release of Z-100 for Application in Radiation Therapy," *International Journal of Pharmaceutics* 115:61-67 (1995).

Banwell, Martin, et al., "4,5-Diaryl-1H-Pyrrole-2-Carboxylates as Combretastatin A-4/Lamellarin T Hybrids: Synthesis and Evaluation as Anti-Mitotic and Cytotoxic Agents," *Bioorganic & Medicinal Chemistry* 14:4627-4638 (2006).

Lê, A.D., et al., "Role of Alpha-2 Adrenoceptors in Stress-Induced Reinstatement of Alcohol Seeking and Alcohol Self-Administration in Rats," *Psychopharmacology* 179:366-373 (2005).

Gibson, L.C.D., et al., "The inhibitory profile of Ibudilast against the human phosphodiesterase enzyme family," *European Journal of Pharmacology* 538:39-42 (2006).

Liu, X, et al., "Reinstatement of Ethanol-Seeking Behavior by Stress- and Drug-Related Cues in Rats with a History of Ethanol-Dependence," Program No. 290.11. 2000 Neuroscience Meeting Planner, New Orleans, LA: Society for Neuroscience, 2000. Online. (Meeting Abstract).

Ciccocioppo, Roberto, et al., "Cocaine-Predictive Stimulus Induces Drug-Seeking Behavior and Neural Activation in Limbic Brain Regions after Multiple Months of Abstinence: Reversal by D1 Antagonists," *PNAS* 98(4):1976-1981 (2001).

Erb, Suzanne, et al., "The Role of Corticotropin-Releasing Factor and Corticosterone in Stress- and Cocaine-Induced Relapse to Cocaine Seeking in Rats," *The Journal of Neuroscience* 18(14):5529-5536 (1998).

Kenny, Paul J., "Common Cellular and Molecular Mechanisms in Obesity and Drug Addiction," *Nature Reviews Neuroscience* 12:638-651 (2011).

Avena, Nicole, et al., "Evidence for Sugar Addiction: Behavioral and Neurochemical Effects of Intermittent, Excessive Sugar Intake," *Neurosci Biobehav Rev* 32(1):20-39 (2008).

Avena, Nicole, et al., "Dysregulation of Brain Reward Systems in Eating Disorders: Neurochemical Information from Animal Models of Binge Eating, Bulimia Nervosa, and Anorexia Nervosa," *Neuropharmacology* 63(1):87-96 (2012).

Corwin, Rebecca L, et al., "Feeding and Reward: Perspectives from Three Rat Models of Binge Eating," *Physiology and Behavior* 104:87-97 (2011).

Ghitza, Udi E., et al., "The Axiogenic Drug Yohimbine Reinstates Palatable Food Seeking in a Rat Relapse Model: a Role of $CRF_1$ Receptors," *Neuropsychopharmacology* 31(10):2188-2196 (2006).

Pickens, Charles L., et al., "Effect of Fenfluramine on Reinstatement of Food Seeking in Male and Female Rats: Implications for the Predictive Validity of the Reinstatement Model," *Psychopharmacology* 221(2):341-353 (2012).

Johnson, Paul M., et al., "Addiction-Like Reward Dysfunction and Compulsive Eating in Obese: Role for Dopamine D2 Receptors," *Nat Neurosci* 13(5):635-641 (2010).

Hoebel, Bartley G., "Brain Neurotransmitters in Food and Drug Reward[1-3]," *The American Journal of Clinical Nutrition* 42:1133-1150 (1985).

Gearhardt, Ashley N., et al., "Neural Correlates of Food Addiction," *Arch Gen Psychiatry* 68(8):808-816 (2011).

Wang, Gene-Jack, et al., "Enhanced Striatal Dopamine Release During Food Stimulation in Binge Eating Disorder," *Obesity* 19(8):1601-1608 (2011).

Hudson, James I., "The Prevalence and Correlates of Eating Disorders in the National Comorbidity Survey Replication," *Biol Psychiatry* 61(3):348-358 (2007).

Grucza, Richard A., et al., "Prevalence and Correlates of Binge Eating Disorder in a Community Sample," *Compr Psychiatry* 48(2):124-131 (2007).

Polivy, Janet, et al., "Food Restriction and Binge Eating: A Study of Former Prisoners of War," *Journal of Abnormal Psychology* 103(2):409-411 (1994).

Gold, Mark S., et al., "Overeating, Binge Eating and Eating Disorders as Addictions," *Psychiatric Annals* 33(2):112-116 (2003).

Pelchat, Marcia L., et al., "Images of Desire: Food-Craving Activation During fMRI," *Neuroimage* 23:1486-1493 (2004).

Ifland, J.R., et al., "Refined Food Addiction: A Classic Substance Abuse Disorder," *Medical Hypotheses* 72:518-526 (2009).

Gearhardt, Ashley N., et al., "Food Addiction: An Examination of the Diagnostic Criteria for Dependence," *Journal of Addiction Medicine* 3(1):1-7 (2009).

Mizes, J. Scott, "Bulimia: A Review of its Symptomatology and Treatment," *Adv Behav Res Ther* 7:91-142 (1985).

Crowther, Janis H., et al., "The Role of Daily Hassles in Binge Eating," *International Journal of Eating Disorders* 29:449-454 (2001).

Herman, C, Peter, et al., "Anxiety, Restraint, and Eating Behavior," *Journal of Abnormal Psychology* 84(6):666-672 (1975).

Cifani, Carlo, et al., "Pre-exposure to Environmental Cues Predictive of Food Availability Elicits Hypothalamic-Pituitary-Adrenal Axis Activation and Increases Operant Responding for Food in Female Rats," *Addiction Biology* 14: 397-407 (2009).

Volkow, Nora D., et al., "How Can Drug Addiction Help Us Understand Obesity?" *Nature Neuroscience* 8(5):555-560 (2007).

Stunkard, Albert J., "Eating Patterns and Obesity," *Psychiatr. Q.* 33:284-295 (1959).

Javaras, Kristin N., et al., "Co-Occurrence of Binge Eating Disorder with Psychiatric and Medical Disorders," *J Clin Psychiatry* 69(2): 266- 273 (2008).

Foulds Mathes, Wendy, et al., "The Biology of Binge Eating," *Appetite* 52(3):545-553 (2009).

Yanovski, Susan Z., "Binge Eating Disorder and Obesity in 2003: Could Treating an Eating Disorder Have a Positive Effect on the Obesity Epidemic," *International Journal of Eating Disorders* 34:S117-S120 (2003).

Koob, George F., et al., "Neurobiological Mechanisms for Opponent Motivational Processes in Addiction," *Phil Trans R Soc B* 363:3113-3123 (2008).

Nestler, Eric J., "Is There a Common Molecular Pathway for Addiction?" *Nature Neuroscience* 8(11):1445-1449 (2005).

Drevets, Wayne C., et al., "Amphetamine-Induced Dopamine Release in Human Ventral Striatum Correlates with Euphoria," *Society of Biological Psychiatry* 49:81-96 (2001).

Brody, Arthur L., et al., "Smoking-Induced Ventral Striatum Dopamine Release," *American Journal of Psychiatry* 161:1211-1218 (2004).

Volkow, Nora D., et al., "Dopamine in Drug Abuse and Addiction," *Arch Neurol* 64(11): 1575-1579 (2007).

Fehr, Christoph, et al., "Association of Low Striatal Dopamine D2 Receptor Availability with Nicotine Dependence Similar to That Seen with Other Drugs of Abuse," *Am J Psychiatry* 165:507-514 (2008).

Lüscher, Christian, et al., "The Mechanistic Classification of Addictive Drugs," *PLoS Medicine* 3(11):e437 (2006).

Johnson, S.W., et al., "Opioids Excite Dopamine Neurons by Hyperpolarization of Local Interneurons," *The Journal of Neuroscience* 12(2):483-488 (1992).

Volkow, N.D, et al., "Dopamine in Drug Abuse and Addiction: Results from Imaging Studies and Treatment Implications," *Molecular Psychiatry* 9:557-569 (2004).

Wardle, Jane, "Stress, Dietary Restraint and Food Intake," *Journal of Psychosomatic Research* 48:195-202 (2000).

Yacono Freeman, Lisa M., et al., "Daily Stress, Coping, and Dietary Restraint in Binge Eating," *International Journal of Eating Disorders* 36:204-212 (2004).

Waters, Anne, et al., "Internal and External Antecedents of Binge Eating Episodes in a Group of Women with Bulimia Nervosa," *International Journal of Eating Disorders* 29:17-22 (2001).

Stice, Eric, et al., "Subtyping Binge Eating-Disordered Women Along Dieting and Negative Affect Dimensions," *International Journal of Eating Disorders* 30:11-27 (2001).

(56) References Cited

OTHER PUBLICATIONS

Pierce, R. Christopher., et al., "The Mesolimbic Dopamine System: The Final Common Pathway for the Reinforcing Effect of Drugs of Abuse?" *Neuroscience and Biobehavioral Reviews* 30:215-238 (2006).

Berridge, Kent C., et al., "What is the Role of Dopamine in Reward: Hedonic Impact, Reward Learning, or Incentive Salience?" *Brain Research Reviews* 28:309-369 (1998).

Bonci, Antonello, et al., "Increased Probability of GABA Release during Withdrawal from Morphine," *The Journal of Neuroscience* 17(2):796-803 (1997).

Brodie, Mark S., et al., "Cocaine Effects in the Ventral Tegmental Area: Evidence for an Indirect Dopaminergic Mechanism of Action," *Naunyn-Schmiedeberg's Arch Pharmacol* 342:660-665 (1990).

Olajide, Olumayokun A., et al., "Anti-neuroinflammatory Properties of Synthetic Cryptolepine in Human Neuroblastoma Cells: Possible Involvement in NF-κB and p38 MAPK inhibition," *European Journal of Medicinal Chemistry* 63:333-339 (2013).

Liu, Liwang, et al., "Nicotine Persistently Activates Ventral Tegmental Area Dopaminergic Neurons via Nicotinic Acetylcholine Receptors Containing $\alpha 4$ and $\alpha 6$ Subunits," *Molecular Pharmacology* 81:541-548 (2012).

Thiele, Jonathan W., et al., "GABAergic Transmission Modulates Ethanol Excitation of Ventral Tegmental Area Dopamine Neurons," *Neuroscience* 172:94-103 (2011).

Jalabert, Marion, et al., "Neuronal Circuits Underlying Acute Morphine Action on Dopamine Neurons," *PNAS* 108(39):16446-16450 (2011).

Laviolette, Steven R., et al., "The Neurobiology of Nicotine Addiction: Bridging the Gap from Molecules to Behaviour," *Nature Reviews Neuroscience* 5(1):55-65 (2004).

Pidoplichko, Volodymyr I., et al., "Nicotine Activates and Desensitizes Midbrain Dopamine Neurons," *Nature* 390(6658):401-404 (1997).

McWilliams, N., "Understanding Personality Structure in the Clinical Process," *Psychoanalytic Diagnosis*, Guilford Press, 2011, Chapter 13. Accessed from http://www.group-analysis.ru/publications/Nancy_McWilliams_PSYCHOANALYTIC_DIAGNOSIS_Understanding_Personaly_Structure_in_the_Clinical_Process.php#TOC_id2925495. Russian Language.

McWilliams, N., "Understanding Personality Structure in the Clinical Process," Psychoanalytic Diagnosis, Guilford Press, 2011, Chapter 13, English Language Translation.

Effect of OMS182056 on Cocaine Self-Administration

Effect of OMS181869 on Cocaine Self-Administration

Effect of OMS182401 on Cocaine Self-Administration

**P: <0.01

Effect of SKF82958 on Cocaine Self-Administration

Effect of OMS182056 on Non-Reinforced Lever Press Response

Effect of SKF82958 on Non-Reinforced Lever Press Response

Effect of OMS182056 on First Day of Extinction

Effect of OMS182056 on Yohimbine-Induced Relapse to Cocaine Seeking

Effect of OMS182401 on Yohimbine-Induced
Relapse to Cocaine Seeking

*P: < 0.05 (vs Vehicle)
**P: < 0.001 (vs Extinction)

Effect of OMS182056 on Cue-Induced Relapse to Cocaine Seeking

Effect of OMS182401 on Cue-Induced Relapse to Cocaine Seeking

*P: < 0.05 (vs Vehicle)
***P: < 0.001 (vs Vehicle)

Effect of OMS182056 on Cocaine Priming-Induced Relapse

Effect of SKF82959 on Cocaine Priming-Induced Relapse

**p<0.01

*p<0.05

Effect of OMS182399 on Nicotine Self-Administration (ShA 120 min)

**P<0.01

Effects of OMS182399 on food self-administration

Effects of OMS182401 on food self-administration 19A  19B  19C

***p: <0.001 (vs vehicle);
p: <0.001 (vs extinction)

***p: <0.001 (vs vehicle);
p: <0.001 (vs extinction)

Effect of OMS 182399 (9 mg/kg ip) on NAc shell/core extracellular DA levels

Effect of nicotine (0.4 mg/kg sc) on NAc shell extracellular DA levels in rats pre-treated with OMS182399 (9 mg/kg ip; 10 min before nicotine)

Effect of OMS182401 and SKF82958 on dopanimergic VTA neurons

Effect of OMS182401 on dopanimergic VTA neurons

Effect of PDE7 Inhibition on VTA GABA Release

Miniature $GABA_A$ Inhibitory Postsynaptic Potentials (mIPSPs)

*P<0.05

*p<0.05; ***p<0.01

Effects of Direct Administration of PDE7 Inhibitor into Rat VTA

Nicotine Self-Administration

Effect of OMS182401 on dopamine D1-mediated stimulation of open field activity

TREATMENT OF ADDICTION AND IMPULSE-CONTROL DISORDERS USING PDE7 INHIBITORS

CROSS-REFERENCE TO RELATED APPLICATIONS

This application is a continuation in part of and claims priority from the filing date of Application Ser. No. 13/290,868 filed Nov. 7, 2011 and also claims the benefit of Application Nos. 61/643,611 filed May 7, 2012, 61/411,431, filed Nov. 8, 2010, 61/411,437, filed Nov. 8, 2010 and 61/482,994, filed May 5, 2011, the disclosures of which are incorporated herein by reference in their entirety.

STATEMENT REGARDING SEQUENCE LISTING

The sequence listing associated with this application is provided in text format in lieu of a paper copy and is hereby incorporated by reference into the specification. The name of the text file containing the sequence listing is NE_1_0172_SequenceListingFinal_ST25; and is being submitted via EFS-Web with the filing of the specification.

FIELD OF THE INVENTION

This disclosure is directed to prevention and treatment of substance and behavioral addictions using phosphodiesterase 7 (PDE7) inhibitors, alone or in combination with other therapeutic agents or addictive agents.

BACKGROUND OF THE INVENTION

The World Health Organization (WHO) defines substance addiction as using a substance repeatedly, despite knowing and experiencing harmful effects. Substance addiction is a chronic, relapsing disease characterized by a loss of control over drug use, compulsive drug seeking and craving for a substance, use that persists despite negative consequences, and physical and/or psychological dependence on the substance. Substance addiction typically follows a course of tolerance, withdrawal, compulsive drug taking behavior, drug seeking behavior, practice of addictive behavior, and relapse. Substance abuse and addiction are public health issues with significant social and economic impact on both the addict and society by playing a major role in violent crime and the spread of infectious diseases. Addictive substances include alcohol, caffeine, nicotine, cannabis (marijuana) and cannabis derivatives, opiates and other morphine-like opioid agonists such as heroin, phencyclidine and phencyclidine-like compounds, sedative hypnotics such as benzodiazepines and barbiturates and psychostimulants such as cocaine, amphetamines and amphetamine-related drugs such as dextroamphetamine and methylamphetamine.

Alcohol is one of the most commonly abused substances at a global level. Additionally, alcoholism leads to serious liver and cardiovascular disease and generates dependence resulting in severe mental disorders, social problems and adverse consequences including the division of families, tragic accidents and the reduction of work performance. According to the WHO, alcohol consumption is responsible for 20-30% of oesophageal and liver cancer, liver cirrhosis, homicides, epilepsy, and motor vehicle accidents worldwide. Globally, alcohol abuse leads to about 1.8 million deaths per year. Compulsive behavior towards the consumption of alcohol is a core symptom of the disorder. In recent years several approaches have been investigated to help alcoholic patients to not only control alcohol drinking but also alcohol cravings and relapse (Monti et al., *J Stud Alcohol* 54:235-45 (1993); Volpicelli et al., *Arch Gen Psychiatry* 49:876-880 (1992); and O'Brien *Science* 278: 66-70 (1997)).

Medications such as naltrexone, acamprosate, ondansetron, disulfuram, gamma hydroxybutyrate (GHB), and topiramate tested for their potential therapeutic effect on alcohol abuse belong to several classes (Volpicelli et al. 1992; O'Brien et al. 1997). Few of these pharmacotherapeutics, such as naltrexone, acamprosate, and disulfuram, have been proven to be of a certain utility and approved for the treatment of alcoholism. Among these medications, the non-selective opioid antagonist naltrexone is currently considered the pharmacological best option. However, despite some promising results none of these medications, including naltrexone, is of sufficient efficacy in alcoholism and prognosis remains poor.

Nicotine is one of the most widely used addictive drugs, and nicotine abuse is the most common form of substance abuse. The WHO estimates that there are 1.25 billion smokers worldwide, representing one third of the global population over the age of 15. The WHO further estimates that 5 million deaths occur each year as a direct result of tobacco use, making nicotine abuse the largest single preventable cause of death worldwide. In industrialized countries, 70-90% of lung cancer, 56-80% of chronic respiratory disease, and 22% of cardiovascular disease instances are attributed to nicotine addiction. Cigarette smoking is associated with 430,000 deaths per year in the US alone and is estimated to cost the nation 80 billion dollars yearly in health care costs. Tobacco use accounts for one third of all cancers, including cancer of the lung, mouth, pharynx, larynx, esophagus, cervix, kidney, ureter, and bladder. The overall rates of death from cancer are twice as high among smokers as among nonsmokers. Smoking also causes lung diseases such as chronic bronchitis and emphysema; exacerbates asthma symptoms; and increases the risk of heart disease, including stroke, heart attack, vascular disease, and aneurysm. An estimated 20% of the deaths from heart disease are attributable to smoking. Expectant women who smoke are at greater risk than nonsmokers for premature delivery, spontaneous abortion, and infants with decreased birth weight.

Nicotine use results in increased levels of the neurotransmitter dopamine, which activates the reward pathways to regulate feelings of pleasure and to mediate the desire to consume nicotine. Symptoms associated with nicotine withdrawal include craving, irritability, anger, hostility, aggression, fatigue, depression, and cognitive impairment, which lead the abuser to seek more nicotine. Environmental conditioning factors and exposure to psychological stress represent additional factors motivating nicotine use in smokers. Repeated nicotine use results in the development of tolerance, requiring higher doses of nicotine to produce the same initial stimulation.

Most therapies developed for nicotine addiction have shown only moderate success in preventing relapse, leading to a high failure rate in attempts to quit smoking. Treatments include the use of nicotine replacement products, anti-depressants, anti-hypersensitives, and behavioral therapy.

The National Institute on Drug Abuse estimates that 72 million Americans, about one third of the population, have tried marijuana. Acute effects of marijuana use include memory and learning problems, distorted perception, difficulty problem solving, loss of coordination, and increased heart rate. Long term abuse can cause the same respiratory problems observed in tobacco smokers, such as daily cough, phlegm production, increased risk of lung infections, and an increased chance of developing cancer of the head, neck and lungs. Depression, anxiety, and job-related problems have been associated with marijuana use. Long term marijuana use can result in addiction with compulsive use that interferes with daily activities. Cravings and withdrawal symptoms, such as irritability, increased aggression, sleeplessness, and anxiety make it difficult for addicts to stop using marijuana. There are no pharmaceutical treatments available for treating marijuana addiction and relapse.

According to the WHO, an estimated 13 million people abuse opioids worldwide, including 9 million heroin addicts. More than 25% of opioid abusers die from suicide, homicide, or an infectious disease, such as HIV and hepatitis, within 10-20 years of becoming addicted. Tolerance and physical dependence can develop within two to three days. While abuse and addiction to opioid agents is a known phenomenon, what is new is the worsening of this problem in the recent years (Compton and Volkow, *Drug Alcohol Depend* 83 Suppl 1: S4-7 (2006A) and Compton and Volkow, *Drug Alcohol Depend* 81(2): 103-7 (2006B)). Epidemiological surveys of youth in the United States in 2003 indicated that opioid analgesics were among the most frequently abused illicit drugs among secondary students (12th graders), second only to marijuana (Delva et al., *Am J Public Health* 95(4): 696-702 (2005)). Furthermore, the past few years have seen a marked increase in the use of opioid medications in the United States and an even greater increase in problems associated with such use. This upsurge in use and problems is particularly concerning because it seems to represent an expanded pathway to opioid addiction (Siegal et al., *Am Fam Physician* 67: 942-945 (2003)).

According to recent epidemiological data, 4.7% (i.e., 11.0 million) United States household residents over the age of twelve abused an opioid medication in 2002 and 13.7% of these persons (i.e., 1.5 million) met the criteria of a DSM-IV opioid use disorder (American Psychiatric Association, *Diagnostic and Statistical Manual of Mental Disorders, Fourth Edition*. (1994); Substance Abuse and Mental Health Services Administration, Mortality Data from the Drug Abuse Warning Network, 2002, (2004)). As recently reviewed by Compton and Volkow, the annual incidence of opioid analgesic abuse increased from 628,000 initiates in 1990 to 2.4 million initiates in 2001 (Substance Abuse and Mental Health Services Administration, Overview of Findings from the 2002 National Survey on Drug Use and Health, (2003); Substance Abuse and Mental Health Services Administration, Emergency Department Trends From the Drug Abuse Warning Network, Final Estimates 1995-2002, (2003)). One of the reasons fostering the expansion of opioid addiction is the increased use of analgesic secondary to medical prescription. Short-term use of opioid medication is rarely associated with addiction. Conversely, protracted treatments with these agents have been associated with development of addiction in up to 18% of patients.

The goals for treatment of opiate addiction, as with other types of substance addictions, are to discontinue the use of the opioid while minimizing painful withdrawal symptoms and preventing relapse. Current treatments involve replacing the addictive drug with a substitution of an opioid receptor agonist or mixed agonist/antagonist. An alternative approach consists of the use of an opioid receptor antagonist to block the effect of the agonist. Antagonists provide no relief from pain or other withdrawal symptoms; rather, they can precipitate withdrawal, and their therapeutic use was associated with increased accidental opioid agonists overdosing and increased lethality. Use of agonists with a lower affinity for the receptors results in the least severe withdrawal symptoms, but it can lead to a dependence on the substitute opiate. Also, many substitution therapies take 3-6 months, allowing time for addicts to stop treatment midway.

Psychostimulants, such as cocaine and amphetamines, temporarily cause euphoria, increased alertness, and increased physical capacity in humans. These substances first increase dopamine transmission, but long term drug usage results in a reduction of dopamine activity, leading to dysregulation of the brain reward system and dysphoria. The WHO estimates 33 million people around the world abuse amphetamines.

Chronic cocaine abuse can result in hyperstimulation, tachycardia, hypertension, mydriasis, muscle twitching, sleeplessness, extreme nervousness, hallucinations, paranoia, aggressive behavior, and depression. Cocaine overdose may lead to tremors, convulsions, delirium, and death resulting from heart arrhythmias and cardiovascular failure. Desipramine, amantadine and bromocriptine have been shown to decrease cocaine withdrawal symptoms.

Amphetamine withdrawal symptoms include EEG changes, fatigue, and mental depression. Tolerance develops over time and may be associated with tachycardia, auditory and visual hallucinations, delusions, anxiety reactions, paranoid psychosis, exhaustion, confusion, memory loss, and prolonged depression with suicidal tendencies. Current treatments for amphetamine addiction include phenothiazines, haloperidol, and chlorpromazine for hallucinations, but potential side effects of these drugs include postural hypotension and severe extrapyramidal motor disorders. Subjects who are addicted to pyschostimulants will sometimes go through psychological withdrawal as well as physiological withdrawal, making relapse potentially more likely.

In the past, treatment for substance addictions focused on behavioral therapy, but dependence on many of these highly addictive substances is hard to break. In particular, addictions to alcohol, cocaine, and heroin are considered chronic, relapsing disorders. Also, concurrent abuse of multiple substances, such as nicotine, heroin, cocaine and alcohol, is common.

The long-lasting, chronic nature of many addictions and high rates of recidivism present a considerable challenge for the treatment of drug and alcohol addiction, such that understanding of the neurobiological basis of relapse has emerged as a central issue in addiction research. Emotional and environmental factors (conditioning stimuli) were listed among the main causes of relapse. For example, it is known that specific stress conditions such as loss of work and economic difficulties, or stimuli predictive of the presence of alcohol previously associated with its use such as a bottle of the preferred wine and a bar-like environment, may strongly facilitate relapse in detoxified former alcoholics.

The growing incidence of obesity in the United States, Europe and other westernized societies also is indicative of the prevalence of food addiction-like behavior. As distinguished from normal eating behaviors, food addiction is a maladaptive behavior, making people who eat in response to addiction rather than hunger feel worse rather than better. The overeating of a food addict is also persistent and habitual, eating an excessive amount of food on a regular basis, and often eating excessive quantities of unhealthy foods. Food addiction not only leads to obesity, but paradoxically may also lead to malnutrition. There are several similarities between food addiction and drug substance addiction, including effects on mood, external cues causing the addictive behavior, expectancies, restraint, ambivalence and attribution.

Two major theoretical positions exist to explain the persistence of addictive behavior and vulnerability to relapse associated with drug and alcohol addiction, homoeostatic hypotheses and conditioning hypotheses.

Homeostatic hypotheses relate relapse risk to neuroadaptive changes and disruption of neuroendocrine homeostasis that are thought to underlie anxiety, mood dysregulation and somatic symptoms that accompany acute withdrawal, and that can persist for considerable periods of time during what has been referred to as the "protracted withdrawal" phase. This view, therefore, implicates alleviation of discomfort and negative affect as a motivational basis for relapse.

Conditioning hypotheses are based on observations that relapse is often associated with exposure to drug-related environmental stimuli. This view holds that specific environmental stimuli that have become associated with the rewarding actions of a drug by means of classical conditioning can elicit subjective states that trigger resumption of drug use. The homeostatic and conditioning hypotheses are not mutually exclusive. In fact, homeostatic and conditioning factors are likely to exert additive effects in that exposure to drug-related environmental stimuli may augment vulnerability to relapse conveyed by homeostatic disturbances.

Clearly, there is a need in the art for new methods for treating and preventing addiction and the relapse use of addictive agents. The present invention meets these needs by providing methods and pharmaceutical combinations useful in treating and preventing addiction and recidivism.

SUMMARY OF THE INVENTION

The present invention provides a method of treating or preventing an addiction by determining that a subject has an addiction or is at risk of developing an addiction and then administering an inhibitor of a phosphodiesterase 7 (PDE7) effective to the subject for the treatment or prevention of the addiction.

In one aspect of the invention, the subject is addicted to an addictive agent. Examples of addictive agents include alcohol, nicotine, marijuana, a marijuana derivatives, opioid agonists, benzodiazepines, barbiturates, and psychostimulants. In one embodiment, the addictive agent is alcohol. In another embodiment, the addictive agent is nicotine. In a further embodiment, the addictive agent is an opioid, e.g., morphine, methadone, fentanyl, sufentanil, codeine, oxycodeine, and heroin. In a further embodiment, the addictive agent is a psychostimulant, e.g., cocaine, amphetamine or an amphetamine derivative. In another embodiment, the addictive agent is cocaine.

In one aspect of the invention, the subject is addicted to an addictive or compulsive behavior or suffers from an impulse-control disorder. In another aspect of the invention, the subject suffers from a primary impulse-control disorder, i.e., an impulse-control disorder in which the disorder is a primary disorder rather than a disorder that is either iatrogenic (secondary to medical treatment) or that is secondary to another primary disease or disorder. Addictive or compulsive behaviors that are primary impulse-control disorders include the following: binge eating, pathological gambling, pathological use of electronic devices, pathological use of electronic video games, pathological use of electronic communication devices, pathological use of cellular telephones, addiction to pornography, sex addiction, compulsive spending, anorexia, bulimia, intermittent explosive disorder, kleptomania, pyromania, trichotillomania, compulsive over-exercising, and compulsive overworking. In another embodiment, the addictive or compulsive behavior is a food addiction. In another embodiment, the addictive or compulsive behavior is binge eating. In another aspect of the invention, the addictive or compulsive disorder is an obsessive-compulsive disorder.

In one aspect of the invention, the PDE7 inhibitory agents for treatment of addiction are selected from the following disclosed herein: formula 1A, formula 1B, formula 29, formula 30, formula 31, formula 32, formula 33, formula 34, formula 35, formula 36, formula 37, formula 38, formula 39, formula 40, formula 41, formula 42, formula 43A, formula 43B, formula 44, formula 45, formula 46, formula 47, formula 48, formula 49, formula 50, formula 51, formula 52, formula 53, formula 54, formula 6A, formula 6B, formula 6C, formula 6D, formula 6E, formula 6F, formula 6G, formula 6H, formula 16A, compound 1, compound 2, compound 3, and compound 4.

In one aspect of the invention, the PDE7 inhibitory agent has an $IC_{50}$ for inhibiting PDE7A and/or PDE7B activity of less than about 1 µM. In one embodiment, the PDE7 inhibitory agent has an $IC_{50}$ for inhibiting PDE7A and/or PDE7B activity of less than about 100 nM. In another embodiment, the PDE7 inhibitory agent has an $IC_{50}$ for inhibiting PDE1B activity of greater than 5 times the lesser of the $IC_{50}$ for inhibiting PDE7A activity and the $IC_{50}$ for inhibiting PDE7B activity. In another embodiment, the PDE7 inhibitory agent has an $IC_{50}$ for inhibiting PDE10 activity of greater than 5 times the lesser of the $IC_{50}$ for inhibiting PDE7A activity and the $IC_{50}$ for inhibiting PDE7B activity. In a further embodiment, the PDE7 inhibitory agent has an $IC_{50}$ for inhibiting PDE3 activity of greater than 10 times the lesser of the $IC_{50}$ for inhibiting PDE7A activity and/or the $IC_{50}$ for inhibiting PDE7B activity. In another embodiment, the PDE7 inhibitory agent has an $IC_{50}$ for inhibiting PDE3 and PDE4 activity of greater than 10 times the lesser of the $IC_{50}$ for inhibiting PDE7A activity and the $IC_{50}$ for inhibiting PDE7B activity. In a further embodiment, the PDE7 inhibitory agent has an 1050 for inhibiting PDE 4 and PDE 8 activity of greater than 10 times the lesser of the $IC_{50}$ for inhibiting PDE7A activity and the $IC_{50}$ for inhibiting PDE7B activity. In another embodiment, the PDE7 agent has an $IC_{50}$ for inhibiting PDE1, PDE2, PDE3, PDE 4, PDE 8, PDE10, and PDE11 activity of greater than 10 times the lesser of the $IC_{50}$ for inhibiting PDE7A activity and the $IC_{50}$ for inhibiting PDE7B activity. In a further embodiment, the PDE7 inhibitory agent is a selective PDE7 inhibitor for which the lesser of the $IC_{50}$ for inhibiting PDE7A activity and the $IC_{50}$ for inhibiting PDE7B activity is less than one tenth the $IC_{50}$ that the agent has for inhibiting the activity of any other PDE enzyme from the PDE1-6 and PDE8-11 enzyme families. In another embodiment, the PDE7 inhibitory agent is a highly selective PDE7 inhibitor for which the lesser of the $IC_{50}$ for inhibiting PDE7A activity and the $IC_{50}$ for inhibiting PDE7B activity is less than one fiftieth the $IC_{50}$ that the agent has for inhibiting the activity of any other PDE enzyme from the PDE1-6 and PDE8-11 enzyme families. In a further embodiment, the PDE7 inhibitory agent has a molecular weight of less than about 450 g/mole. In another embodiment, the PDE7 inhibitory agent is able to cross the blood/brain barrier.

The present invention provides a method of treating or preventing an addiction by determining that a subject has an addiction or is at risk of developing an addiction and then administering a chemical compound that inhibits PDE7 activity. The chemical compound has the following characteristics: (i) an $IC_{50}$ for inhibiting PDE7A and/or PDE7B activity of less than about 1 µM; and (ii) an $IC_{50}$ for inhibiting PDE 3 greater than 10 times the lesser of the $IC_{50}$ for inhibiting PDE7A activity and/or the $IC_{50}$ for inhibiting PDE7B activity.

In one embodiment, the chemical compound has an $IC_{50}$ for inhibiting PDE7A and/or PDE7B activity of less than about 100 nM. In another embodiment, the PDE7 inhibitory agent has an $IC_{50}$ for inhibiting PDE1B activity of greater than 5 times the lesser of the $IC_{50}$ for inhibiting PDE7A activity and the $IC_{50}$ for inhibiting PDE7B activity. In another embodiment, the PDE7 inhibitory agent has an $IC_{50}$ for inhibiting PDE10 activity of greater than 5 times the lesser of the $IC_{50}$ for inhibiting PDE7A activity and the $IC_{50}$ for inhibiting PDE7B activity. In another embodiment, the PDE7 inhibitory agent has an $IC_{50}$ for inhibiting PDE4 activity of greater than 10 times the lesser of the $IC_{50}$ for inhibiting PDE7A activity and the $IC_{50}$ for inhibiting PDE7B activity. In a further embodiment, the PDE7 inhibitory agent has an $IC_{50}$ for inhibiting PDE8 activity of greater than 10 times the lesser of the $IC_{50}$ for inhibiting PDE7A activity and the $IC_{50}$ for inhibiting PDE7B activity. In another embodiment, the PDE7 agent has an $IC_{50}$ for inhibiting PDE1, PDE2, PDE3, PDE 4, PDE 8, PDE10, and PDE11 activity of greater than 10 times the lesser of the $IC_{50}$ for inhibiting PDE7A activity and the IC50 for inhibiting PDE7B activity. In a further embodiment, the PDE7 inhibitory agent is a selective PDE7 inhibitor for which the lesser of the IC50 for inhibiting PDE7A activity and the $IC_{50}$ for inhibiting PDE7B activity is less than one tenth the $IC_{50}$ that the agent has for inhibiting the activity of any other PDE enzyme from the PDE1-6 and PDE8-11 enzyme families. In another embodiment, the PDE7 inhibitory agent is a highly selective PDE7 inhibitor for which the lesser of the $IC_{50}$ for inhibiting PDE7A activity and the $IC_{50}$ for inhibiting PDE7B activity is less than one fiftieth the $IC_{50}$ that the agent has for inhibiting the activity of any other PDE enzyme from the PDE1-6 and PDE8-11 enzyme families. In a further embodiment, the PDE7 inhibitory agent has a molecular weight of less than about 450 g/mole. In another embodiment, the PDE7 inhibitory agent is able to cross the blood/brain barrier.

In one aspect of the invention, the subject is addicted to an addictive agent. Examples of addictive agents include alcohol, nicotine, marijuana, a marijuana derivatives, opioid agonists, benzodiazepines, barbiturates, and psychostimulants. In one embodiment, the addictive agent is alcohol. In another embodiment, the addictive agent is nicotine. In a further embodiment, the addictive agent is an opioid, e.g., morphine, methadone, fentanyl, sufentanil and heroin. In a further embodiment, the addictive agent is a psychostimulant, e.g., cocaine, amphetamine or an amphetamine derivative. In another embodiment, the addictive agent is cocaine.

In one aspect of the invention, the subject treated with a PDE7 inhibitor is addicted to an addictive or compulsive behavior or suffers from an impulse-control disorder. In another aspect of the invention, the subject suffers from a primary impulse-control disorder, i.e., an impulse-control disorder in which the disorder is a primary disorder rather than a disorder that is either iatrogenic (secondary to medical treatment) or that is secondary to another primary disease or disorder. Addictive or compulsive behaviors that are primary impulse-control disorders include the following: binge eating, pathological gambling, pathological use of electronic devices, pathological use of electronic video games, pathological use of electronic communication devices, pathological use of cellular telephones, addiction to pornography, sex addiction, compulsive spending, anorexia, bulimia, intermittent explosive disorder, kleptomania, pyromania, trichotillomania, compulsive over-exercising, and compulsive overworking. In another embodiment, the subject suffers from food addiction. In another embodiment, the addictive or compulsive behavior is binge eating. In another aspect of the invention, the subject to be treated in accordance with the present invention has an obsessive-compulsive disorder.

The present invention also provides a method of treating or preventing an addiction, comprising providing to a subject having an addiction, an inhibitor of a phosphodiesterase 7 (PDE7) and an additional therapeutic agent, wherein each of the PDE7 inhibitor and the additional therapeutic agent contribute to the effective treatment or prevention of the addiction. Additional therapeutic agents include, e.g., opioid antagonists, mixed opioid partial agonist/antagonists, antidepressants, antiepileptics, antiemetics, corticotrophin-releasing factor-1 (CRF-1) receptor antagonists, selective serotonin-3 (5-HT3) antagonists, 5-HT2A/2C antagonists, cannabinoid-1 (CB1) receptor antagonists and dopamine receptor agonists or other dopaminergic agents.

Exemplary opioid antagonists include naltrexone and nalmefene. Exemplary antidepressants include fluoxetine, mirtazapine, and bupropion. Exemplary antiepileptics include topiramate, levetiracetam, and gabapentin. Antalarmin is an exemplary CRF-1 receptor antagonist. Ondensetrom is an exemplary selective serotonin-3 (5-HT3) antagonist. Exemplary cannabinoid-1 (CB1) receptor antagonists are rimonabant and tanarabant. Buprenorphine is an exemplary mixed opioid agonist/antagonist. Exemplary opioid agonists include morphine, methadone, fentanyl, sufentanil and heroin.

Exemplary dopaminergic agents include, for example, levodopa (also referred to as "L-dopa"), carbidopa, and dopamine receptor agonists and precursors such as bromocriptine, pergolide, pramipexole, ropinirole, cabergoline, apomorphine, lisuride, rotigotine and quinagolide, as well as fenoldopam, which is selective for dopamine receptor D1.

In one aspect, the subject is addicted to an addictive agent, e.g., alcohol, nicotine, marijuana, a marijuana derivative, an opioid agonist, a benzodiazepine, a barbiturate, and a psychostimulant. In one embodiment, the addictive agent is alcohol and the additional therapeutic agent is an opioid antagonist, such as naltrexone, or a mixed opioid antagonist/partial agonist, such as buprenorphine. In another embodiment, the subject is addicted to a psychostimulant such as cocaine, amphetamine, an amphetamine derivative, or methamphetamine and the additional therapeutic agent is an antidepressant, such as bupropion. In a further embodiment, the subject is addicted nicotine and the additional therapeutic agent is an antidepressant, such as bupropion.

In another aspect, the subject is addicted to an addictive or compulsive behavior, such as a primary impulse-control disorder, including, for example, pathological gambling, binge eating, pathological use of electronic devices, pathological use of electronic video games, pathological use of electronic communication devices, pathological use of cellular telephones, addiction to pornography, sex addiction, compulsive spending, anorexia, bulimia, intermittent explosive disorder, kleptomania, pyromania, trichotillomania, compulsive over-exercising, and compulsive overworking. In one embodiment, the addictive or compulsive behavior is binge eating and the additional therapeutic agent is topiramate. In another aspect of the invention, the subject to be treated in accordance with the present invention has an obsessive-compulsive disorder.

The present invention provides a method of preventing relapse use of an addictive agent or practice of an addictive or compulsive behavior, by treating a subject who has undergone a period of abstinence from, or limited or reduced use of, the addictive agent or the addictive or compulsive behavior by administering a PDE7 inhibitor to the subject. The present invention also provides a method of preventing relapse of an addictive or compulsive behavior associated with a primary impulse-control disorder, by treating a subject who has undergone a period of remission from, or limited or reduced practice of, the addictive or compulsive behavior associated with the primary impulse-control disorder by administering a PDE7 inhibitor to the subject. The present invention also provides a method of preventing relapse of addictive or compulsive behavior associated with an obsessive-compulsive disorder, by treating a subject who has undergone a period of remission from, or limited or reduced practice of, the addictive or compulsive behavior associated with the obsessive-compulsive disorder by administering a PDE7 inhibitor to the subject. Additional therapeutic agents that contribute to the effect prevention of relapse can be administered with the PDE7 inhibitor. This treatment can be administered to subjects that have previously been treated with a different anti-addiction treatment that is no longer being used.

In one aspect, the relapse use of addictive agents such as alcohol, nicotine, marijuana, marijuana derivatives, opioid agonists, benzodiazepines, barbiturates, and psychostimulants is prevented through the administration of PDE7 inhibitors. In a preferred embodiment, the relapse use of cocaine, amphetamine, or methamphetamine is prevented.

In another aspect, the relapse of an addictive or compulsive behavior, in particular addictive or compulsive behavior associated with a primary impulse-control disorders, is prevented through the administration of PDE7 inhibitors. In a preferred embodiment, the relapse of the following behaviors is prevented: binge eating, pathological gambling, pathological use of electronic devices, pathological use of electronic video games, pathological use of electronic communication devices, pathological use of cellular telephones, addiction to pornography, sex addiction, compulsive spending, anorexia, bulimia, intermittent explosive disorder, kleptomania, pyromania, trichotillomania, compulsive over-exercising, and compulsive overworking. In one embodiment, the addictive or compulsive behavior is binge eating that has been induced by stress. In another embodiment, the subject is treated to prevent relapse of addictive or compulsive behavior associated with an obsessive-compulsive disorder.

The present invention provides a pharmaceutical composition that includes a PDE7 inhibitor and an additional therapeutic agent, where both the PDE7 inhibitor and the additional therapeutic agent contribute to the effective treatment or prevention of an addiction. Unit dosages of the pharmaceutical composition are also provided.

In one aspect of the invention, the subject is addicted to an addictive agent. Examples of addictive agents include alcohol, nicotine, marijuana, marijuana derivatives, opioid agonists, benzodiazepines, barbiturates, cocaine and other psychostimulants. In one embodiment, the addictive agent is alcohol. In another embodiment, the addictive agent is nicotine. In a further embodiment, the addictive agent is an opioid, e.g., morphine, methadone, fentanyl, sufentanil and heroin. In a further embodiment, the addictive agent is a psychostimulant, e.g., cocaine, amphetamine or an amphetamine derivative. In a preferred embodiment, the addictive agent is cocaine.

In one aspect of the invention, the subject is addicted to an addictive or compulsive behavior or suffers from an impulse-control disorder. In another aspect of the invention, the subject suffers from a primary impulse-control disorder, i.e., an impulse-control disorder in which the disorder is a primary disorder rather than a disorder that is either iatrogenic (secondary to medical treatment) or that is secondary to another primary disease or disorder. Addictive or compulsive behaviors that are primary impulse-control disorders include the following: binge eating, pathological gambling, pathological use of electronic devices, pathological use of electronic video games, pathological use of electronic communication devices, pathological use of cellular telephones, addiction to pornography, sex addiction, compulsive spending, anorexia, bulimia, intermittent explosive disorder, kleptomania, pyromania, trichotillomania, compulsive over-exercising, and compulsive over-working. In a preferred embodiment, the addictive or compulsive behavior is binge eating. In another aspect of the invention, the subject to be treated in accordance with the present invention has an obsessive-compulsive disorder.

In one embodiment, the additional therapeutic agent of the pharmaceutical composition is an opioid antagonist, a mixed opioid partial agonist/antagonist, an antidepressant, an antiepileptic, an antiemetic, a corticotrophin-releasing factor-1 (CRF-1) receptor antagonist, a selective serotonin-3 (5-HT3) antagonist, a 5-HT2A/2C antagonist, or a cannabinoid-1 (CB1) receptor antagonist.

Exemplary opioid antagonists include naltrexone or nalmefene. Exemplary antidepressants include fluoxetine, mirtazapine, or bupropion. Exemplary antiepileptics include topiramate, levetiracetam, and gabapentin. Antalarmin is an exemplary CRF-1 receptor antagonist. Ondensetrom is an exemplary selective serotonin-3 (5-HT3) antagonist. Exemplary cannabinoid-1 (CB1) receptor antagonists are rimonabant and tanarabant. Buprenorphine is an exemplary mixed opioid agonist/antagonist.

In one aspect, the subject is addicted to an addictive agent, e.g., alcohol, nicotine, marijuana, a marijuana derivative, an opioid agonist, a benzodiazepine, a barbiturate, and a psychostimulant. In one embodiment, the addictive agent is alcohol and the additional therapeutic agent is an opioid antagonist, such as naltrexone, or a mixed opioid antagonist/partial agonist, such as buprenorphine. In another embodiment, the addictive agent is nicotine and the additional therapeutic agent is varenicline. In another embodiment, the subject is addicted to a psychostimulant such as cocaine, amphetamine, an amphetamine derivative, or methamphetamine and the additional therapeutic agent is an antidepressant, such as bupropion. In a further embodiment, the subject is addicted nicotine and the additional therapeutic agent is an antidepressant, such as bupropion. In another embodiment, the subject is addicted to more than one addictive agents and the additional therapeutic agent is an opioid antagonist, such as naltrexone, or a mixed opioid antagonist/partial agonist, such as buprenorphine.

The present invention provides a kit for the treatment or prevention of an addiction. The kit includes a first container containing a PDE7 inhibitor and a second container containing an additional therapeutic agent. Both the PDE7 inhibitor and the additional therapeutic agent contribute to the effective treatment or prevention of an addiction.

In one embodiment, the additional therapeutic agent of the pharmaceutical composition is an opioid antagonist, a mixed opioid partial agonist/antagonist, an antidepressant, an antiepileptic, an antiemetic, a corticotrophin-releasing factor-1 (CRF-1) receptor antagonist, a selective serotonin-3 (5-HT3) antagonist, a 5-HT2A/2C antagonist, or a cannabinoid-1 (CB1) receptor antagonist.

Exemplary opioid antagonists include naltrexone and nalmefene. Exemplary antidepressants include fluoxetine, mirtazapine, and bupropion. Exemplary antiepileptics include topiramate, levetiracetam, and gabapentin. Antalarmin is an exemplary CRF-1 receptor antagonist. Ondensetrom is an exemplary selective serotonin-3 (5-HT3) antagonist. Exemplary cannabinoid-1 (CB1) receptor antagonists are rimonabant and tanarabant. Buprenorphine is an exemplary mixed opioid agonist/antagonist.

In one aspect, the subject is addicted to an addictive agent, e.g., alcohol, nicotine, marijuana, a marijuana derivative, an opioid agonist, a benzodiazepine, a barbiturate, and a psychostimulant. In one embodiment, the addictive agent is alcohol and the additional therapeutic agent is an opioid antagonist, such as naltrexone, or a mixed opioid antagonist/partial agonist, such as buprenorphine. In another embodiment, the subject is addicted to a psychostimulant such as cocaine, amphetamine, an amphetamine derivative, or methamphetamine and the additional therapeutic agent is an antidepressant, such as bupropion. In a further embodiment, the subject is addicted nicotine and the additional therapeutic agent is an antidepressant, such as bupropion. In another embodiment, the subject is addicted to more than one addictive agents and the additional therapeutic agent is an opioid antagonist, such as naltrexone, or a mixed opioid antagonist/partial agonist, such as buprenorphine.

In another aspect of the invention, a subject at risk of addiction to an addictive substance is administered the addictive substance in combination with a PDE7 inhibitor. For example, a subject that will be administered an opioid agonist for the relief of acute or chronic pain is administered an opioid agonist in combination with a PDE7 inhibitor such that non-addictive or less addictive analgesia is provided. Examples of addictive agents that may be administered in combination with a PDE7 inhibitor, as either a fixed-dose combination or as a kit, include benzodiazepines, barbiturates, and pain medications including alfentanil, allylprodine, alphaprodine, anileridine benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, OXYCONTIN®, oxymorphone, papaveretum, pentazocine, phenadoxone, phenomorphan, phenazocine, phenoperidine, piminodine, piritramide, propheptazine, promedol, properidine, propiram, propoxyphene sufentanil, tramadol, tilidine, salts thereof, mixtures of any of the foregoing, and mixed µ-agonists/antagonists.

In some embodiments, for any of the methods and compositions described herein, the following PDE7 inhibitors are used formula 1A, formula 1B, formula 29, formula 30, formula 31, formula 32, formula 33, formula 34, formula 35, formula 36, formula 37, formula 38, formula 39, formula 40, formula 41, formula 42, formula 43A, formula 43B, formula 44, formula 45, formula 46, formula 47, formula 48, formula 49, formula 50, formula 51, formula 52, formula 53, formula 54, formula 6A, formula 6B, formula 6C, formula 6D, formula 6E, formula 6F, formula 6G, formula 6H, formula 16A, compound 1, compound 2, compound 3, and compound 4.

In another embodiment of the invention, a PDE7 inhibitor is provided to a subject that is addicted or at risk of becoming addicted to an addictive substance to reduce the motivation of the subject to seek or acquire the addictive substance.

BRIEF DESCRIPTION OF THE DRAWINGS

The present invention will now be described in greater detail, by way of example, with reference to the accompanying drawings in which:

FIG. 23A shows the results for control animals, which were not stressed or subjected to dietary restriction. FIG. 23B shows the results for experimental animals that were not stressed and were subjected to dietary restriction. FIG. 23C shows the results for experimental animals that were stressed and were not subjected to dietary restriction. FIG. 23D shows the results for experimental animals that were stressed and were subjected to dietary restriction.

FIG. 24A shows the results for control animals, which were not stressed or subjected to dietary restriction. FIG. 24B shows the results for experimental animals that were not stressed and were subjected to dietary restriction. FIG. 24C shows the results for experimental animals that were stressed and were not subjected to dietary restriction. FIG. 24D shows the results for experimental animals that were stressed and were subjected to dietary restriction.

FIGS. 25A-30D demonstrates the effect of topiramate, as a comparator, on stress induce binge eating by rats. FIG. 25A shows the results for control animals, which were not stressed or subjected to dietary restriction. FIG. 26D shows the results for experimental animals that were stressed and were subjected to dietary restriction.

FIG. 26 demonstrates the effect of the PDE7 inhibitor OMS182399 on yohimbine-induced relapse to food seeking in a food addiction model.

FIGS. 27 and 28 demonstrates the effect of OMS182399, a PDE7 inhibitor, on basal and nicotine-induced, respectively, dopamine release in the nucleus and accumbens of Wistar rats by an in vivo microdialysis study.

FIG. 30 demonstrates the effect of the PDE7 inhibitor OMS182401 on VTA GABA release.

DETAILED DESCRIPTION OF THE PREFERRED EMBODIMENT

Figure 1:
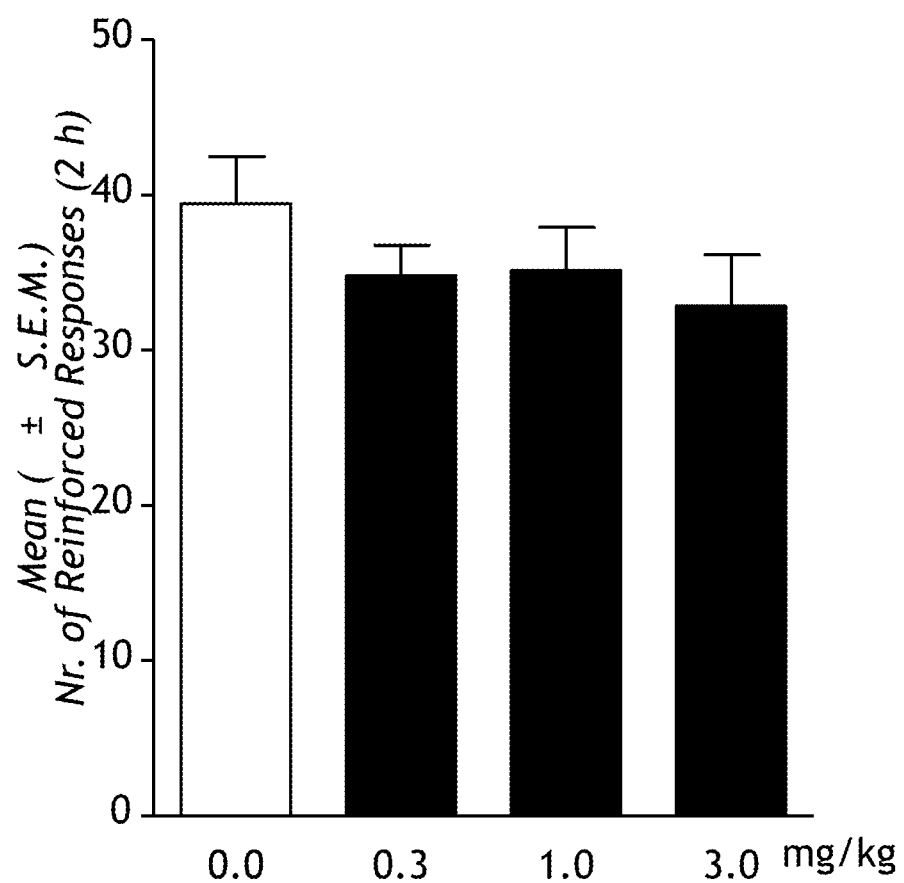
FIG. 1 demonstrates the effect of OMS182056, a PDE7 inhibitor, on cocaine self-administration by rats.

The present invention is based upon the surprising discovery by the present inventors that selective inhibitors of the type 7 cyclic nucleotide phosphodiesterase (PDE7) cause a striking decrease in relapse of addiction. Using rat models, the decreases were demonstrated in subjects addicted to addictive agents and in subjects that exhibited compulsive behaviors.

A. Methods of Treating and Preventing Addictions Using PDE7 Inhibitor(s)

Thus, the present invention includes methods of treating or preventing an addiction, comprising administering one or more PDE7 inhibitors to a subject having an addiction or at risk for developing an addiction. In various embodiments, the subject is addicted to an addictive agent or behavior, including, but not limited to, any of the addictive agents and behaviors described herein. The subject may be physically or physiologically dependent on the substance or behavior; the subject may be psychologically dependent; or the subject may be both physically and psychologically dependent. The subject may be addicted to one or more than one addictive agent or behavior.

As used herein, unless the context makes clear otherwise, "treat," and similar word such as "treatment," "treating" etc., is an approach for obtaining beneficial or desired results, including and preferably clinical results. Treatment can involve optionally either the reducing or amelioration of a disease or condition, (e.g., addiction or relapse use or behavior), or the delaying of the progression of the disease or condition (e.g., addiction, or relapse use or behavior).

As used herein, unless the context makes clear otherwise, "prevent," and similar word such as "prevention," "preventing" etc., is an approach for preventing the onset or recurrence of a disease or condition, (e.g., addiction, or relapse use or behavior) or preventing the occurrence or recurrence of the symptoms of a disease or condition, or optionally an approach for delaying the onset or recurrence of a disease or condition or delaying the occurrence or recurrence of the symptoms of a disease or condition.

As used herein the term "PDE7" is used generically to refer to all translation products coded by transcripts of either or both of these two genes: PDE7A and/or PDE7B.

As used herein, the term "PDE7 inhibitory agent" or "inhibitor of PDE7" refers to an agent, such as a chemical compound, a peptide, or a nucleic acid molecule, that directly or indirectly inhibits or blocks the phosphodiesterase activity of PDE7A, PDE7B, or PDE7A and PDE7B. In some cases, the agent may bind or interact directly with PDE7 protein. An agent that binds to PDE7 may act to inhibit or block the PDE7 activation by any suitable means, such as by inhibiting the binding of cAMP or substrate ligand with PDE7. In other cases, the PDE7 inhibitory agent may inhibit PDE7 activity indirectly, such as by decreasing expression of the PDE7 protein. In some cases, the PDE7 inhibitory agent may inhibit PDE7 activity by altering the cellular distribution of PDE7, for example, by interfering with the association between PDE7 and an intracellular anchoring protein.

As used herein, the term "dopaminergic agent" refers to an agent that functions to enhance or replicate the effects mediated by dopamine in the central nervous system, including dopamine (if a clinically effective method of delivery should be developed), dopamine precursors, such as levodopa (L-dopa), dopamine cofactors, inhibitors of enzymes that metabolize dopamine, other dopamine receptor agonists and precursor compounds that are metabolically converted to a dopamine receptor agonist, as well as dopamine reuptake inhibitors and facilitators of dopamine release.

As used herein, the term "dopamine receptor agonist" refers to any molecule that causes the activation of one or more of the subtypes of the dopamine receptor protein family.

As used herein, the term "mammalian subject" includes all mammals, including without limitation humans, non-human primates, dogs, cats, horses, sheep, goats, cows, rabbits, pigs, and rodents.

Generally, a subject is provided with an effective amount of a PDE7 inhibitor. As used herein, an "effective amount" or a "therapeutically effective amount" of a substance, e.g., a PDE7 inhibitor, is that amount sufficient to affect a desired biological or psychological effect, such as beneficial results, including clinical results. For example, in the context of treating addiction using the methods of the present invention, an effective amount of a PDE7 inhibitor is that amount sufficient to cause the subject to reduce or discontinue use of an addictive agent. In the case of an addictive behavior, an effective amount of a PDE7 inhibitor is that amount sufficient to cause the subject to reduce or discontinue the addictive behavior.

In one embodiment, a therapeutically effective dose is an amount of PDE7 inhibitory agent sufficient to inhibit PDE7 enzyme activity in a neuronal cell. In another embodiment of the methods of the invention, a therapeutically effective dose is an amount of PDE7 inhibitory agent sufficient to inhibit PDE7 enzyme activity in striatal neurons or nucleus acumbens. The determination of an effective dose of a PDE7 inhibitory agent sufficient to cross a cellular membrane and inhibit PDE7 enzyme activity within a cell may be determined using a cellular assay for PDE7 inhibition, such as described by Smith S. J. et al., *Molecular Pharmacology* 66(6): 1679-1689 (2004), hereby incorporated by reference. The determination of an effective dose of a PDE7 inhibitory agent sufficient to inhibit PDE7 enzyme activity in the striatum may be determined using an assay for measuring the effect of a PDE inhibitory agent on cAMP levels in the striatum, as described in Siuciak J. A. et al., *Neuropharmacology* 51: 386-396 (2006), hereby incorporated by reference.

According to certain embodiments of the present invention, a subject is provided with a PDE7 inhibitor alone, while in other embodiments, a subject is provided with a PDE7 inhibitor in combination with an additional therapeutic agent. It is understood that the effective amount of either or both of a PDE7 inhibitor and an additional therapeutic agent may be different when either is provided alone than when provided in combination. For example, when the PDE7 inhibitor and the additional therapeutic agent act synergistically, then a lower amount of the PDE7 inhibitor, a lower amount of the additional therapeutic agent, or lower amounts of both the PDE7 inhibitor or the additional therapeutic agent may be required to achieve the same therapeutic effect that would be provided by either the PDE7 inhibitor or the additional therapeutic agent alone. In other embodiments, the same amount of the PDE7 inhibitor and the additional therapeutic agent are used to provide an enhanced therapeutic effect relative to the therapeutic effect provided by either the PDE7 inhibitor or the additional therapeutic agent alone.

According to certain embodiments of the present invention, a subject is provided with a PDE7 inhibitor in combination with an addictive therapeutic agent, with the dosage of the addictive therapeutic agent being determined to achieve the desired therapeutic effect and the dosage of the PDE7 inhibitor being determined to eliminate or reduce the potential for addiction to the addictive therapeutic agent.

The subject may be any animal, including a mammal, and, particularly, a human.

In one aspect of the invention, the subject is first determined or diagnosed to have an addiction, or to be at risk of developing an addiction, by diagnostic testing, observation or analysis by a medical care provider. An effective amount of a PDE7 inhibitor, or an effective amount of a PDE7 inhibitor and one additional therapeutic agent, are then provided to the subject for treatment or prevention of the addiction. In another aspect of the invention, the subject is first determined or diagnosed to have an addiction, or to be at risk of developing an addiction, by diagnostic testing, observation or analysis by a medical care provider, but the subject has not been diagnosed or determined to have diabetes or other insulin disorder. An effective amount of a PDE7 inhibitor, or an effective amount of a PDE7 inhibitor and one additional therapeutic agent, are then provided to the subject for treatment or prevention of the addiction. The dosage of the PDE7 inhibitor, or the PDE7 inhibitor and the one additional therapeutic agent, may be specifically determined by the medical practitioner for treatment or prevention of the addiction rather than for any other disorder or disease.

In particular embodiments, the subject is suffering from or at risk for addiction to any physically addictive agent or addictive or compulsive behavior, including, e.g., any of those described below. In particular embodiments, the subject is addicted to alcohol, cocaine, nicotine, marijuana, an opiate or other opioid agonist or methamphetamine or other psychostimulant, or phencyclidine and phencyclidine derivatives. In another embodiment, the subject suffers from a primary impulse-control disorder. In still another embodiment, the subject suffers from obsessive-compulsive disorder. In still another embodiment, the subject has a history of repeated dieting and is at risk of binge eating.

In particular embodiments, a subject is considered at risk of addiction or relapse to use of an addictive agent or practice of an addictive behavior when the subject has previously been addicted to the same or a different addictive agent or addictive or compulsive behavior. In certain embodiment, the subject is considered at risk of addiction or relapse to use of an addictive agent or practice of an addictive behavior when the subject is psychologically addicted to an addictive agent or addictive or compulsive behavior, even if the subject is no longer physically addicted. In one embodiment, the subject suffers from food addiction. In other embodiments, the addictive behavior is binge eating. Subjects at risk of binge eating typically have at least one of the following in their history: recurring food restrictions or yo-yo dieting, eating in response to environmental stress, preference for highly palatable and high caloric food, eating after reaching fullness, and eating to the point of discomfort. In another embodiment, the subject suffers from a primary impulse-control disorder.

In certain embodiments, the subject is addicted to or at risk of becoming addicted to a therapeutic agent provided to the patient to treat a disease or disorder, e.g., a pain medication. In a related embodiment, the subject may be at risk of abusing an addictive therapeutic agent, such as a pain medication. Abusing an addictive therapeutic agent, in certain embodiments, is understood to indicate using the agent for a reason different than or in addition to its prescribed use. In such a situation, a subject may be provided with both an addictive therapeutic agent and a PDE7 inhibitor, alone or in combination with an additional therapeutic agent. For example, a subject suffering from pain, or at risk of pain, may be provided with an opioid agonist and a PDE7 inhibitor, to both provide analgesia and prevent or treat addiction to the opioid agonist.

In various embodiments, the subject is provided with the PDE7 inhibitor at the same time that the subject is using an addictive agent, after the subject has discontinued use of an addictive agent, or before the subject begins using an addictive agent.

Addictive Agents and Impulse Control Disorders

The term "addiction" is used to describe a recurring compulsion by an individual to engage in some specific activity, despite harmful consequences to the individual's health, mental state or social life. The term is often reserved for drug addictions, but it is applied to other compulsions, such as problem gambling, and binge eating. Factors that have been suggested as causes of addiction include genetic, biological/pharmacological and social factors.

The medical community now makes a careful theoretical distinction between physical or physiological dependence (characterized by symptoms of withdrawal) and psychological dependence (sometimes referred to simply as addiction).

Addiction is now narrowly defined as "uncontrolled, compulsive use." If there is no harm being suffered by, or damage done to, the patient or another party, then clinically it may be considered compulsive, but to the definition of some it is not categorized as "addiction". In practice, the two kinds of addiction (physiological dependence and psychological dependence) are not always easy to distinguish. Addictions often have both physical and psychological components.

"Physical dependence" (or "drug dependence") refers to a state resulting from habitual use of a drug, where negative physical withdrawal symptoms result from abrupt discontinuation. Examples of addictive agents for which a user may develop a physical dependence include nicotine, opioids, barbiturates, benzodiazepines, alcohol, i.e., ethyl alcohol, GHB, and methaqualone.

Commonly abused stimulants such as cocaine or amphetamine class drugs are not believed to cause significant physical dependence. However, their potential for extreme psychological addiction can compel the user to consume amounts which become physically damaging, but life-threatening withdrawal effects have not been observed.

As used herein, "addictive agent(s)" includes any and all agents to which a subject can become addicted, either physically or psychologically, or both. As noted above, addiction includes addiction to chemical entities, such as drugs, as well as addiction to behaviors, as in impulse control disorders.

Addictive agents include addictive recreational drugs, as well as addictive medications. Examples of addictive agents include, but are not limited to, alcohol, e.g., ethyl alcohol, gamma hydroxybutyrate (GHB), caffeine, nicotine, cannabis (marijuana) and cannabis derivatives, opiates and other morphine-like opioid agonists such as heroin, phencyclidine and phencyclidine-like compounds, sedative hypnotics such as benzodiazepines, methaqualone, mecloqualone, etaqualone and barbiturates and psychostimulants such as cocaine, amphetamines and amphetamine-related drugs such as dextroamphetamine and methylamphetamine. Other examples include LSD, psilocybin, ecstasy and other hallucinogens. Examples of addictive medications include, e.g., benzodiazepines, barbiturates, and pain medications including alfentanil, allylprodine, alphaprodine, anileridine benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofenitanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, OXYCONTIN®, oxymorphone, papaveretum, pentazocine, phenadoxone, phenomorphan, phenazocine, phenoperidine, piminodine, piritramide, propheptazine, promedol, properidine, propiram, propoxyphene sufentanil, tramadol, tilidine, salts thereof, mixtures of any of the foregoing, mixed µ-agonists/antagonists, and the like.

In certain embodiments, a subject may be addicted to an opioid agonist. The terms "opioid agonist," "opioid" and "opiate" are used interchangably herein and are used to designate a group of drugs that are, to varying degrees, opium- or morphine-like in their properties. Their main use is for pain relief. These agents work by binding to opioid receptors which are found principally in the central nervous system and the gastrointestinal tract. Opiates are also addictive agents.

Opiates include alfentanil, allylprodine, alphaprodine, anileridine, apomorphine, benzylmorphine, beta-hydroxy 3-methylfentanyl, bezitramide, carfentanil, clonitazene, codeine, desomorphine, dextromoramide, diacetylmorphine (heroin), diampromide, dihydro codeine, dihydroetorphine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene, etorphine, fentanyl, hydrocodone, hydromorphone, hydroxypethidine, isomethadone, ketobemidone, LMM, levorphanol, levophenacylmorphan, lofentanil, meperidine, metapon, metazocine, methadone, methadyl acetate, metopon, morphine, myrophine, narceine, nicomorphine, norlevorphanol, normethadone, normorphine, norpipanone, opium, oxycodone, oxymorphone, papaverine, phenadoxone, phenomorphan, phenoperidine, piminodine, piritramide, propheptazine, promedol, properidine, propoxyphene, remifentanil, sufentanil, thebaine, tildine, and tramadol.

Naturally occurring opiates include codeine, morphine, noscapine, papaverine, and thebaine. Semi-synthetic opioids include diacetylmorphine, hydrocodone, hydromorphone, levorphanol, metapon, nalorphine, naloxone, naltrexone, oxycodone, oxymorphone, and tramadol. Synthetic opioids include ethoheptazine, fentanyl, levorphanol, meperidine, methadone, phenazocine, propoxyphene and sufentanil.

Three broad classifications of opiates are phenanthrenes, phenylheptylamines, and phenylpiperidines. Examples of phenanthrenes include codeine, etorpine, hydrocodone, hydromorphone, morphine, oxycodone, and oxymorphone. Examples of phenylheptylamines include dimeheptanol, dimenoxadol, dipipanone, isomethadone, methadone, methadyl acetate, and propoxyphene. Examples of phenylpiperidines include alfentanyl, alphaprodine, beta-promedol, carfentanyl, fentanyl, lofentanil, meperidine, properidine, and sufentanil.

Specific psychostimulants include, by way of example, amphetamine, cocaine, dextroamphetamine, methamphetamine, pemoline, Ritalin, Adderall and methylenedioxymethamphetamine.

As noted above, addiction includes addiction to behaviors, e.g., food addiction, binge eating disorder, pathological gambling, pathological use of electronic devices, e.g., BlackBerry®, pathological use of electronic video games, pathological use of electronic communication devices, pathological use of cellular telephones, addiction to pornography, sex addiction, obsessive-compulsive disorder, compulsive spending, intermittent explosive disorder, kleptomania, pyromania, trichotillomania, compulsive overexercising, and compulsive overworking.

In one aspect of the invention, a subject treated with a PDE7 inhibitor suffers from food addiction or binge eating disorder, often with secondary health problems such as obesity due to excessive consumption of food and/or malnutrition due to excessive consumption of foods that are high in fat and/or sugar and low in vitamins and minerals.

As used herein "binge eating disorder" or "binge eating" includes at least one of the following episodic symptoms: eating large amounts of food, eating even when full, rapid eating, feeling that eating behavior is out of control, eating substantial amounts of food when not hungry, frequent dieting possibly without weight loss, eating alone, feeling depressed or disgusted about eating habits, eating in response to stress. Binge eating disorder is distinguished from other types of eating disorders, including food addiction, bulimia and binge-purge syndromes. Unlike bulimia and binge-purge syndromes, a subject suffering from binge eating disorder and food addiction-like behavior is that subjects suffering from binge eating disorder and food addiction-like behavior do not undertake compensatory behavior to attenuate excessive calorie consumption.

A body of scientific literature is building to support the characterization of certain types of problematic eating behaviors as addictions, given that binge eating and chronic excess eating share many characteristics with addictive behaviors (e.g., diminished control, continued use despite negative consequences). Despite similarities, binge eating disorder and food addiction may represent unique yet overlapping conditions. Gearhardt, A. N., et al., *Binge Eating Disorder and Food Addiction*, Curr. Drug Abuse Rev, 4:201-207 (2011).

As used herein, the term "food addiction" refers to a regular, persistent and habitual pattern of overeating characterized by craving and seeking high caloric foods, overeating in response to stimuli other than hunger, diminished control over food consumption, continued consumption despite negative consequences and diminished ability to cut down and abstain from consumption of an excess of food. Food addiction is a chronic relapsing disorder that typically follows a course of over-eating, tolerance, withdrawal, high caloric food seeking behavior and relapse (initiation of overeating after a period of abstinence).

A natural preference for highly palatable foods rich in fat and carbohydrate has developed for evolutionary reasons due to the high caloric support associated with such foods. Although it is indisputable that feeding behavior is regulated by homeostatic mechanisms, eating and overeating are also regulated by emotional, affective and learning processes. Polivy, et al., "Food restriction and binge eating: a study of a former prisoner of war," *J Abnorm Psychol* 103:409-411 (1994). In this respect several commonalities exist between excessive eating and drug abuse (reward, reinforcement, effects on mood, external cue-control of appetite, stress-induced motivation). Evidence is accumulating that excessive intake of certain foods under specific conditions produces behaviors and changes in the brain that resemble an addiction-like state. Gold, et al., "Overeating, binge eating, and eating disorders as addictions," *Psychiatr Ann* 33:112-116 (2003); Kenny, et al., "Common cellular and molecular mechanisms in obesity and drug addiction," *Nat Rev Neurosci* 12:638-651 (2011); Pelchat, et al., "Images of desire: food-craving activation during fMRI," Neuroimage 23:1486-1493 (2004); Avena, et al., "Evidence for sugar addiction: behavioral and neurochemical effects of intermittent, excessive sugar intake," *Neurosci Biobehav Rev* 32:20-39 (2008); Ifland, et al., "Refined food addiction: a classic substance use disorder," *Med Hypotheses* 72:518-526 (2009); Gearhardt, et al., "Food addiction: an examination of the diagnostic criteria for dependence," *J Addict Med* 3:1-7 (2011).

Drug addiction can be characterized by progressive escalation in drug use, tolerance development, abstinence following abrupt cessation of their use and recurrent relapse, and similar phenomena have been described for high sucrose high fat food. For example, rats fed with highly palatable sucrose solution experience opiate-like withdrawal symptoms following sucrose removal. Cross sensitization between sucrose and drugs of abuse has also been described. Avena, et al., "Evidence for sugar addiction: behavioral and neurochemical effects of intermittent, excessive sugar intake," *Neurosci Biobehav Rev* 32:20-39 (2008); Avena, et al., "Dysregulation of brain reward systems in eating disorders: Neurochemical information from animal models of binge eating, bulimia nervosa, and anorexia nervosa," *Neuropharmacology* (Epub ahead of print) (Nov. 27, 2011). Moreover, it has been well documented that psychological stress and dysphoric mood states play a major role in facilitating overeating as well as excessive drug use, and contribute to the high rate of recidivism typical of both disorders. Corwin, et al., "Feeling and reward: perspective from three rat models of binge eating," *Physiol Behav* 104:87-97 (2011); Ghitza, et al., "The anxiogenic drug yohimbine reinstates palatable food seeking in a rat relapse model: a role of CRF1 receptors," *Neuropsychopharmacology* 31(10):2188-2196 (2006); Mizes, et al., "Bulimia: A review of its symptomatology and treatment," *Adv. Behav. Res. Ther.* 7:91-142 (1985); Crowther, et al., "The role of daily hassles in binge eating," *Int J Eat Disord* 29:449-454 (2001); Herman, et al., "Anxiety, restraint, and eating behaviour," *J Abnorm Psychol* 84:66-72 (1975).

Exposure to environmental conditioning stimuli has also been shown to play a critical role in eliciting drug craving in addicted individuals as well as food craving in obese patients meeting the criteria for food addiction. Gearhardt, et al., "Food addiction: an examination of the diagnostic criteria for dependence," *J Addict Med* 3:1-7 (2011). Consistent with studies in humans, in laboratory animals it has been shown that exposure to environmental conditioning factors and exposure to stress (i.e., yohimbine) are similarly effective in eliciting reinstatement behaviors for drugs of abuse and for highly palatable food. Cifani, et al., "Preclinical model of binge-eating elicited by yo-yo dieting and stressful exposure to food: effect of sibutramine, fluoxetine, topiramate and midazolam," *Psychopharmacology* 204:113-25 (2009); Cifani, et al., "Pre-exposure to environmental cues predictive of food availability elicits hypothalamic-pituitary-adrenal axis activation and increases operant responding for food in female rats," *Addict Biol.* 14(4):397-407 (September 2009); Pickens, et al., "Effect of fenfluramine on reinstatement of food seeking in female and male rats: implications for the predictive validity of the reinstatement model," *Psychopharmacology (Berl)* 221(2):341-353 (May 2012). Neural systems that motivate and reinforce drug abuse have also been proposed to underlie behaviors associated with compulsive food seeking and excessive food intake. Johnson, et al., "Dopamine D2 receptors in addiction-like reward dysfunction and compulsive eating in obese rats," *Nat Neurosci* 13:635-641 (2010); Hoebel, et al., "Brain neurotransmitters in food and drug reward," *Am J Clin Nutr* 42(5 Suppl):1133-1150 (1985); Volkow, et al., "How can drug addiction help us understand obesity?" *Nat Neurosci* 8:555-560 (2005); Corwin, et al., "Feeling and reward: perspective from three rat models of binge eating," *Physiol Behav* 104:87-97 (2011); Gearhardt, et al., "Neural correlates of food addiction," *Arch Gen Psychiatry* 68:808-816 (2011); Wang, et al., "Enhanced striatal dopamine release during food stimulation during binge eating disorder," *Obesity* 19(8):1601-1608 (August 2011). For example, studies suggest that like in drug addicts, an altered regulation of striatal dopamine (DA) may exist in patients with bulimia nervosa.

Interest in the concept of food addiction has recently received greater attention, in large part due to the similarities between the behavioral indicators of addiction and binge eating disorder (BED). Episodes of binge eating in humans are characterized by compulsive, non-homeostatic consumption of an unusually large quantity of highly palatable food in a short period of time. Even though they are not hungry, subjects eat more rapidly than normal until feeling uncomfortably full. As described by the DMS-IV-TR (American Psychiatric Association, "Diagnostic and statistic manual of mental disorders," Washington, D.C. (2000)), these episodes are accompanied by a subjective sense of loss of control over eating, and are associated with feeling of distress, disgust, depression, being guilty about overeating, and eating alone because of embarrassment.

BED, described for the first time by Stunkard, "Eating patterns and obesity," *Psychiatry Q* 33:284-295 (1959), is probably the most prevalent eating disorder. Hudson, et al., "The prevalence and correlates of eating disorders in the National Comorbidity Survey Replication," *Biol Psychiatry* 61:348-58 (2007). It is characterized by repeated episodes of binge eating in the absence of compensatory behaviors to avoid weight gain. The diagnostic criteria for BED in the DSM-IV-TR include that binge eating episodes should occur at least 2 days per week for six months. BED is associated with significant medical and psychiatric co-morbidity. Javaras, et al., "Co-occurrence of binge eating disorder with psychiatric and medical disorders," *J Clin Psychiatry* 269:266-273 (2008); Grucza, et al., "Prevalence and correlates of binge eating disorder in a community sample," *Compr Psychiatry* 48:124-131 (2007). It is estimated that binge eating afflicts approximately 5% of the US adult population at some time during their lives (Foulds, et al., "The biology of binge eating," *Appetite* 52:545-553 (2009)) and that it contributes to aggravate obesity and associated pathologies. Hudson, et al., "The prevalence and correlates of eating disorders in the National Comorbidity Survey Replication," *Biol Psychiatry* 61:348-58 (2007); Yanovski, "Binge eating disorder and obesity in 2003: could treating an eating disorder have a positive effect on the obesity epidemic?" *Int J Eat Disord* 34 Suppl: S117-S1120 (2003).

A large body of evidence suggests that dieting, stress and negative affective states represent important triggers of binge eating in patients suffering from BED or bulimia nervosa. Wardle, et al., "Stress, dietary restraint and food intake," *J Psychosom Res* 48:195-202 (2000); Freeman, et al., "Daily stress, coping, and dietary restraint in binge eating," *Int J Eat Disord* 36: 204-212 (2004). Indeed, dieting periods are common in the histories of binge eaters, although hunger itself does not appear to be enough to induce bing eating in the absence of stress and negative affective state. Polivy, et al., "Food restriction and binge eating: a study of former prisoner of war," *J Abnorm Psychol* 103:409-411 (1994); Waters, et al., "Internal and external antecedents of binge eating episodes in a group of women with bulimia nervosa," *Int J Eat Disord* 29:17-22 (2001). Considerable evidence suggests that binge eating may be caused by a unique interaction between dieting and stress; thus, environmental stress and a history of cyclic food restrictions may be responsible for its precipitation and maintenance. Stice, et al. "Subtyping binge eating-disordered women along dieting and negative affect dimensions," *Int J Eat Disord* 30:11-27 (2001); Crowther, et al., "The role of daily hassles in binge eating," *Int J Eat Disord* 29:449-454 (2001). Accordingly, recurring food restrictions are consistently the strongest predictor of overeating in response to stress. Wardle, et al., "Stress, dietary restraint and food intake," *J Psychosom Res* 48:195-202 (2000).

While a subject may be addicted to a single addictive agent or behavior, frequently subject is addicted to two or more addictive agents or behaviors. Addiction to two or more addictive agents or addictive behaviors is referred to as poly-addiction.

B. Methods of Treating and Preventing Addiction and Impulse Control Disorders Using PDE7 Inhibitor(s) in Combination with Other Therapeutic Agents PDE7 inhibitors may be effectively used in combination with one or more additional therapeutic agents to treat or prevent addiction, including addiction to one or more of the addictive agents described herein and compulsive or addictive behavior. Accordingly, the present invention includes methods of treating or preventing an addiction, comprising administering to a subject addicted to an addictive agent one or more PDE7 inhibitor(s) and one or more additional therapeutic agent(s), in which each of the PDE7 inhibitor(s) and the additional therapeutic agent(s) contribute to the effective treatment or prevention of the addiction. In one embodiment, a subject is provided with or administered one PDE7 inhibitor and one additional therapeutic agent. In another embodiment, a subject is addicted to two or more addictive agents.

The PDE7 inhibitor and the additional therapeutic agent may be administered at the same time (i.e., concurrently), or either may be administered before the other (i.e., sequentially). In general, both the PDE7 inhibitor and the additional therapeutic agent are present in the subject at the same time for a duration of time and at levels sufficient to provide a therapeutic benefit to the subject, i.e., in the treatment or preventing of an addiction or the prevention of a relapse use (or reinstatement) of an addictive agent or compulsive or addictive behavior. The PDE7 inhibitor and the additional therapeutic agent may be administered by the same or different routes of administration. Typically, the PDE7 inhibitor and the additional therapeutic agent are each provided to a subject according to a standard route of administration of a commercially available or other pharmaceutical composition. In one embodiment, the PDE7 inhibitor and the additional therapeutic agent are co-administered using a composition comprising both agents.

The additional therapeutic agent provided in combination with a PDE7 inhibitor may be any therapeutic agent that contributes to an aspect of the effective treatment or prevention of the addiction. For example, the additional therapeutic agent may be a drug used to treat an addiction or a drug used to alleviate side-effects associated with physiological withdrawal from an addictive agent. In addition, the additional therapeutic agent may be any drug that affects brain serotonin neurotransmission, such as selective serotonin reuptake inhibitors (SSRIs), and tricyclic and tetracyclic serotonin and norepinephrine reuptake inhibitors (SNRIs) as described below, and serotonin agonists such as sumatriptan, ergonovine, dihydroergotamine and buspirone. In certain embodiments, the additional therapeutic agent is an opioid antagonist, including mixed opioid partial agonist/antagonists, an antidepressant, an antiepileptic, an antiemetic, a dopaminergic agent such as a dopamine D1 receptor agonist, a corticotrophin-releasing factor-1 (CRF-1) receptor antagonist, a selective serotonin-3 (5-HT3) antagonist, a 5-HT2A/2C antagonist such as mianserin, mirtazapine and ketanserin, or a cannabinoid-1 (CB1) receptor antagonist, including but not limited to those therapeutic agents specifically described herein.

In one embodiment, the addictive agent is alcohol and the additional therapeutic agent is an opioid antagonist or a mixed opioid antagonist/partial agonist. In a particular embodiment, the opioid antagonist is naltrexone. In another embodiment, the mixed opioid partial agonist/antagonist is buprenorphine.

In one embodiment, the addictive agent is alcohol, and the additional therapeutic agent is topiramate or levetiracetam.

In one embodiment, the addictive agent is nicotine and the additional therapeutic agent is an antidepressant. In a particular embodiment, the antidepressant is bupropion.

In one embodiment, the addictive agent is cocaine, and the additional therapeutic agent is buprenorphine.

In one embodiment, the addictive agent is a psychostimulant and the additional therapeutic agent is an antidepressant. In a particular embodiment, the antidepressant is bupropion.

In one embodiment, the addictive behavior is binge eating and the additional therapeutic agent is an antidepressant or an antiepileptic. In one particular embodiment, the antidepressant is sibutramine. In another particular embodiment, the antidepressant is fluoxetine. In one particular embodiment, the antiepileptic is topiramate.

In one embodiment, the addictive agent is nicotine, and the additional therapeutic agent is an anti-epileptic. In a particular embodiment, the anti-epileptic is levetiracetam. In another particular embodiment, the anti-epileptic agent is naltrexone.

In one embodiment, the subject is addicted to two or more addictive agents and the additional therapeutic agent is an opioid antagonist or a mixed opioid partial agonist/antagonist. In a particular embodiment, the mixed opioid partial agonist/antagonist is buprenorphine.

In one embodiment, the subject is addicted to both alcohol and nicotine, and the additional therapeutic agent is an anti-epileptic. In a particular embodiment, the anti-epileptic is naltrexone.

For treatment of alcohol addiction, combinations to be administered in accordance with the present invention include a PDE7 inhibitor and an opioid agonist or a mixed opioid antagonist/partial antagonist, a PDE7 inhibitor and an antidepressant, a PDE7 inhibitor and a CB1 receptor antagonist/inverse agonist, a PDE7 inhibitor and varenicline, a PDE7 inhibitor and acamprosate, and a PDE7 inhibitor and disulfuram.

For treatment of a psychostimulant addiction, combinations to be administered in accordance with the present invention include, e.g., a PDE7 inhibitor and an antidepressant or a PDE7 inhibitor and a partial opioid agonist/antagonist, e.g., buprenorphine.

For treatment of nicotine addiction, combinations to be administered in accordance with the present invention include, e.g., a PDE7 inhibitor and an antidepressant, a PDE7 inhibitor and nicotine (as a replacement, in an oral, transcutaneous or other conventional formulation), a PDE7 inhibitor and an opioid antagonist, a PDE7 inhibitor and a CB1 receptor antagonist/inverse agonist, and a PDE7 inhibitor and varenicline. In one embodiment, an addictive agent, such as nicotine, and a PDE7 inhibitor are administered together using a transdermal patch delivery system. In another aspect of the invention, a kit including multiple transdermal patches, including dosages of nicotine in diminishing levels and dosages of a PDE7 inhibitor in either constant or diminishing levels, are provided for sequential use by a subject addicted to nicotine to wean the subject from nicotine addiction.

For treatment of polysubstance addiction, combinations to be administered in accordance with the present invention include, e.g., a PDE7 inhibitor and an opioid agonist or a mixed opioid antagonist/partial antagonist.

For treatment of gambling addiction, combinations to be administered in accordance with the present invention include, e.g., a PDE7 inhibitor and an antidepressant or a PDE7 inhibitor and an agent affecting dopamine neurotransmission, e.g., a direct or indirect dopamine antagonist.

The effective amount of either or both of a PDE7 inhibitor and an additional therapeutic agent may be reduced when administered in combination than when either is provided alone. For example, when the PDE7 inhibitor and the additional therapeutic agent act additively or synergistically, then a lower amount of the PDE7 inhibitor, a lower amount of the additional therapeutic agent, or lower amounts of both the PDE7 inhibitor or the additional therapeutic agent may be required to achieve the same therapeutic effect that would be provided by either the PDE7 inhibitor or the additional therapeutic agent alone.

1. Opioid Antagonists

An opioid antagonist acts on one or more opioid receptors. At least three types of opioid receptors, mu, kappa, and delta opioid receptors, have been reported, and opioid antagonists are generally classified by their effects on the opioid receptors. Opioid antagonists may antagonize central receptors, peripheral receptors or both. Naloxone and naltrexone are commonly used opioid antagonist drugs that are competitive in that they bind to the opioid receptors with higher affinity than agonists, but do not activate the receptors. This effectively blocks the receptor, preventing the body from responding to opiates and endorphins.

Many opioid antagonists are not pure antagonists but also produce some weak opioid partial agonist effects, and can produce analgesic effects when administered in high doses to opioid-naive individuals. Examples of such compounds include nalorphine, and levallorphan. However, the analgesic effects from these drugs are limited and tend to be accompanied by dysphoria, most likely due to action at the kappa opioid receptor. Since they induce opioid withdrawal effects in people who are taking, or have previously used, opioid full agonists, these drugs are considered to be antagonists.

Naloxone is one example of an opioid antagonist that has no partial agonist effects. Instead, it is a weak inverse agonist at mu opioid receptors, and is used for treating opioid overdose.

Specific examples of opioid antagonists that may be used according to the invention include alvimopan, binaltorphimine, buprenorphine, cyclazocine, cyclorphan, cypridime, dinicotinate, beta-funaltrexamine, levallorphan, methylnaltrexone, nalbuphine, nalide, nalmefene, nalmexone, nalorphine, nalorphine dinicotinate, naloxone, naloxonazine, naltrendol, naltrexone, naltrindole, oxilorphan, and pentazocine.

2. Antidepressents

Antidepressants are drugs used to treat depression. The three neurotransmitters believed to be involved in depression are serotonin, dopamine, and norepinephrine. Certain types of antidepressants increase the levels of one or more of these neurotransmitters in the brain by blocking their reabsorption.

Several different classes of antidepressants have been identified, including selective serotonin reuptake inhibitors (SSRIs), tricyclic and tetracyclic serotonin and norepinephrine reuptake inhibitors (SNRIs), norepinephrine reuptake inhibitors (NRIs), norepinephrine and dopamine reuptake inhibitors (NDRIs), azaspirones, monoamine oxidase inhibitors (MAOIs), and atypical antidepressants.

SSRIs include, e.g., cericlamine, citalopram, clomipramine, cyanodothiepin, dapoxetine, duloxetine, escitalopram, femoxetine, fluoxetine, fluvoxamine, ifoxetine, imipramine, indalpine, indeloxazine, litoxetine, lofepramine, mianserine, milnacipran, mirtazapine, nefazadone, nortriptyline, paroxetine, sertraline, sibutramine, tomoxetine, trazodone, venlafaxine, and zimeldine.

Amitriptyline, amoxapine, butriptyline, clomipramine, demexiptiline, desipramine, dibenzepin, dimetacrine, dothiepin, doxepin, imipramine, iprindole, lofepramine, maprotiline, melitracen, metapramine, mianserin, mirtazpine, nortriptyline, propizepine, protriptyline, quinupramine, setiptiline, tianeptine, and trimipramine are all tricyclic and tetracyclic antidepressants.

SNRIs include, e.g., amoxapine, atomoxetine, bicifadine, desipramine, desvenlafaxine, duloxetine, maprotiline, milnacipran, nefazodone, reboxetine, sibutramine, and venlafaxine.

Nisoxetine, nortriptyline, reboxetine, talsupram, and tomoxetine are all examples of NRIs.

NDRIs include, e.g., bupropion, hydroxybupropion, and tesofensine.

Azaspirones include, e.g., buspirone, gepirone, ipsapirone, tandospirone, and tiaspirone. Buspirone is an anxiolytic (partial agonist at 5-HT1 autoreceptors) that may be provided with an anti-depressant such as an SSRI.

Specific MAOIs include, e.g., amiflamine, brofaromine, clorgyline, alpha-ethyltryptamine, iproclozide, iproniazid, isocarboxazid, mebanazine, moclobemide, nialamide, pargyline, phenelzine, pheniprazine, pirlindole, safrazine, selegiline, toloxatone, and tranlcypromine.

Atypical antidepressants include, e.g., amesergide, aminepatine, benactyzine, bupropion, clozapine, fezolamine, levoprotiline, lithium, medifoxamine, mianserin, minaprine, olanzapine, oxaflozane, oxitriptan, roliprám, teniloxazine, tofenacin, trazodone, tryptophan, and viloxazine.

3. Antiepileptics

The anticonvulsants, also called anti-epileptic drugs (AEDs) are a diverse group of drugs used in prevention of the occurrence of epileptic seizures and bipolar disorders. AEDs suppress the rapid and excessive firing of neurons that begins a seizure and/or prevents the spread of the seizure within the brain and offer protection against possible excitotoxic effects that may result in brain damage. Many anticonvulsants block sodium channels, calcium channels, AMPA receptors, or NMDA receptors.

Anti-epileptic agents include, but are not limited to, benzodiazepines, barbituates, valproates, GABA agents, iminostilibenes, hydantoins, NMDA antagonists, sodium channel blockers and succinamides.

Benzodiazepines include, e.g., alprazolam, chlordiazepoxide, cholrazepate, clobazam, clonazepam, diazepam, halazepam, lorazepam, oxazepam, and prazepam.

Barbiturates used as anti-epileptics include, e.g., amobarbital, mepobarbital, methylphenobarbital, pentobarbital, phenobarbital, and primidone.

Valproates used as anti-epileptics include, e.g., sodium valporate, valproic acid, valproate semisodium, and valpromide.

Anti-epileptic GABA agents include, e.g., gabapentin, losigamone, pregabalin, retigabine, rufinamide, and vigabatrin.

Carbamazepine and oxcarbazepine are examples of iminostilbenes.

Hydantoins include, e.g., fosphenyloin sodium, mephenyloin, and phenyloin sodium.

NMDA antagonists such as harkoseramide are used as anti-epileptics.

Sodium channel blockers such as lamotrigine are also anti-epileptic agents.

Succinimides include, e.g., ethosuximide, methsuximide, and phensuximide.

Other anti-epileptic drugs include acetazolamide, briveracetam, CBD cannabis derivative, clomthiazole edisilate, divalproex sodium, felbamate, isovaleramide, lacosamide, lamotrigine, levetiracetam, methanesulphonamide, talampanel, tiagabine, topiramate, safinamide, seletracetam, soretolide, stiripentol, sultiam, valrocemide, and zonisamide.

4. Antiemetics

Antiemetics are drugs effective against vomiting and nausea. Antiemetics are typically used to treat motion sickness and the side effects of opioid analgesics, general anaesthetics, and chemotherapy.

Classifications of antiemetics include, e.g., 5-hydroxytryptamine 3 (5-HT3) receptor antagonists, histamine receptor antagonists, dopamine receptor antagonists, muscarinic receptor antagonists, acetyl choline receptor antagonists, cannabinoid receptor antagonists, limbic system inhibitors, NK-1 receptor antagonists, corticosteroids, tachykinin antagonists, GABA agonists, cannabinoids, benzodiazepines, anticholinergics, and substance P inhibitors.

5-HT3 receptor antagonists include, e.g., alosetron, azasetron, bemesetron, cilansetron, dolasetron, granisetron, indisetron, itasetron, ondansetron, palonosetron, propisetron, ramosetron, renzapride, tropisetron, and zatosetron.

Coritcosteroid antiemetics include dexamethasone and methylprednisolone.

Lymbic system inhibitors include alprazolam, lorazepam, and midazolam.

Dopamine receptor antagonists include diphenhydramine, dronabinol, haloperidol, metoclopramide, and prochlorperazine.

NK-1 receptor antagonists used as an antiemetic include aprepitant and morpholine, and an example of a GABA agonist is propofol.

Thiethylperazine is a type of histamine receptor antagonist.

Cannabinoid receptor antagonists or agonists used as antiemetics include dronabinol, nabilone, rimonabant, tanarabout, and tetrahydrocannabinol.

Examples of other antiemetics include acetylleucine, monoethanolamine, alizapride, benzquinamide, bietanautine, bromopride, buclizine, chlorpromazine, clebopride, cyclizine, dimenhydrinate, dipheniodol, domperidone, dranisetron, meclizine, methalltal, metopimazine, oxypendyl, pipamazine, piprinhydrinate, scopolamine, thioproperzaine, and trimethobenzamide.

5. Cannabinoid Receptor Antagonists

The cannabinoid receptors are a class of the G-protein coupled receptor superfamily. Their ligands are known as cannabinoids. There are currently two known subtypes, CB1 which is expressed mainly in the brain, but also in the lungs, liver, and kidney, and CB2, which is mainly expressed in the immune system and in hematopoietic cells. It is also believed that there are novel cannabinoid receptors that is, non-CB1 and non-CB2, which are expressed in endothelial cells and in the CNS. Cannabinoid receptor antagonists may be selective for either the CB1 or CB2 receptor. The present invention contemplates the use of either or both CB1 and CB2 receptor antagonists.

Addictive agents (e.g., alcohol, opiates, Delta(9)-tetrahydrocannabinol (Delta(9)-THC) and psychostimulants, including nicotine) elicit a variety of chronically relapsing disorders by interacting with endogenous neural pathways in the brain. In particular, they share the common property of activating mesolimbic dopamine brain reward systems, and virtually all abused drugs elevate dopamine levels in the nucleus accumbens. Cannabinoid-1 (CB1) receptors are expressed in this brain reward circuit and modulate the dopamine-releasing effects of Delta(9)-THC and nicotine.

Rimonabant (SR141716), a CB1 receptor antagonist, blocks both the dopamine-releasing and the discriminative and rewarding effects of Delta(9)-THC in animals. Although CB1 receptor blockade is generally ineffective in reducing the self-administration of cocaine in rodents and primates, it reduces the reinstatement of extinguished cocaine-seeking behavior produced by cocaine-associated conditioned stimuli and cocaine priming injections. Similarly, CB1 receptor blockade is effective in reducing nicotine-seeking behavior induced by re-exposure to nicotine-associated stimuli. In human clinical trials, rimonabant was shown to block the subjective effects of Delta(9)-THC in humans and prevents relapse to smoking in ex-smokers.

Other examples of cannabinoid receptor CB1 antagonists include SR141716A (rimonabant), rosanabant, taranabant and CP-945598.

6. Dopaminergic Agents

Drug addiction is a chronic, relapsing disease characterized by a loss of control over drug use, compulsive drug seeking and craving for a substance, use that persists despite negative consequences, and physical and/or psychological dependence on the substance. A fundamental role in the pathogenesis of addiction has been attributed to dopamine. Dopamine, in fact, has permeated the natural history of drug addiction at all levels, from its involvement in shaping individual response to vulnerability factors (i.e., genetics, environmental and stress) to its role in the mechanism of action of the drugs of abuse.

The mesocorticolimbic dopamine system originates in the ventral tegmental area (VTA), which prominently projects to the nucleus accumbens (NAc) and the prefrontal cortex (PPC). It is a defining commonality of all addictive drugs that at least initially they stimulate dopamine transmission in the terminal areas of the mesolimbic system and in particular in the nucleus NAc shell. Nestler, E. J., "is there a common molecular pathway for addiction?" *Nat Neurosci* 8:1445-1449 (2005); Pierce, R. C., et al., "The mesolimbic dopamine system: The final common pathway for the reinforcing effect of drugs of abuse?" *Neurosci Biobehav Rev* 30:215-238 (2006). Brain imaging studies have extended these observations to humans. Drevets, W. C., et al., "Amphetamine-induced dopamine release in human ventral striatum correlates with euphoria," *Biol Psychiatry* 49:81-96 (2001); Brody A. L., et al., "Smoking-induced ventral striatum dopamine release," *Am J Psychiatry* 161:1211-1218 (2004). The release of dopamine from these projections is thought to play an important role in mediating drug reward, reinforcement and in the induction of compulsive addictive behaviour. Although dopamine is involved in the predisposition and in the initial stages of the development of drug addiction, this condition, once established, is associated with long-lasting changes related to the chronic exposure to the drugs themselves.

These changes are collectively indicated as "neuroadaptive" and are thought to be the substrate of behavioural sensitization, a long-lasting increase in the sensitivity to the behavioural stimulant properties of drugs and of changes in the baseline of hedonic state (hedonic allostasis). Berridge K. C., et at, "What is the role of dopamine in reward: Hedonic impact, reward learning, or incentive salience?" *Brain Res Rev* 28:309-369 (1998); Koob, G. F., et al., "Neurobiological mechanisms for opponent motivational processes in addiction," *Philos Trans R Soc. Lond B Biol Sci.* 363:3113-3123 (2008). Neuroadaptations occurs also at the level of the dopamine system, where a relative reduction in the basal level of activity of dopamine transmission in ventral striatal areas and a reduction in dopamine D2-receptor levels has been documented. Volkow, N. D., et al., "Dopamine in drug abuse and addiction: results from imaging studies and treatment implications," *Mol Psychiatry* 9:557-569 (2004); Volkow, N. D., et al., "Dopamine in drug abuse and addiction: results from imaging studies and treatment implications," *Arch Neurol* 64:1575-1579 (2007); Fehr, C. et al., "Association of low striatal dopamine d2 receptor availability with nicotine dependence similar to that seen with other drugs of abuse," *Am Psychiatry* 165:507-514 (2008).

The most common mechanism through which drugs of abuse result in dopamine neurotransmission is through modulation of VTA presynaptic γ-aminobutyric acid (GABA) activity. Lüscher, C., et al., "The mechanistic classification of addictive drugs," *PLoS Med* 3:e437 (2006). In the VTA, GABA neurons act as local inhibitory interneurons playing a tonic control on corticomesolimbic dopamine cells. Reduction in GABA neurotransmission leads to a net disinhibition of dopamine neurons and increased dopamine release in terminal areas such as the NAc and in the PFC.

A prototypical example of this mechanism is offered by opiates that following activation of μ opioid receptors located onto presynaptic GABA cells lead to a marked inhibition of GABAergic neurotransmission resulting in disinhibition of VTA dopaminergic cells. Johnson, S. W., et al., "Opioids excite dopamine neurons by hyperpolarization of local interneurons," *J Neurosci* 12:483-488 (1992). Cannabis derivatives appear to increase VIA dopamine firing rate with a similar mechanism but through selective activation of cannabinoid receptor 1 (CB1R) located on presynaptic GABA neurons. Also nicotine, increases dopamine neurotransmission but through a complex interplay of actions of nicotinic receptors on GABA and on glutamatergic inputs to dopamine neurons. Lüscher C, et al., The mechanistic classification of addictive drugs., *PLoS Med.* 3(11):e437 (2006). In fact, nicotine through β2-containing nAChRs decreases presynaptic GABA release leading to a prolonged disinhibition of dopamine, at the same time acting on homomeric α7-containing nAChRs, which are mainly expressed on synaptic terminals of excitatory glutamatergic afferents on dopamine neurons in the VTA, facilitating glutamate release. This effect may also contribute to nicotine-evoked dopamine release. Furthermore, recent evidence suggests that nicotine directly modulates dopamine release in the NAc. Ethanol and benzodiazepines also appear to stimulate VTA dopamine neurotransmission through inhibition of presynaptic GABA activity via modulation of specific GABA-A receptors subunits.

Psychostimulants like amphetamine derivatives and cocaine, comprise the only class of addictive drugs that act directly on dopaminergic terminals by inhibiting dopamine reuptake mechanisms or by facilitating dopamine release from synapses. Through these mechanisms they increase extracellular dopamine levels in terminal areas (i.e., NAc and MPF) of the brain dopamine system. Most notably, however, dopamine terminals are also present in the VTA where D1- and D2-like receptors are expressed on dopaminergic cell bodies (autoreceptors) as well as on glutamatergic and GABAergic presynaptic neurons. Direct application of cocaine in the VIA results in a reduction or to an increase (depending on the dose) of dopamine firing rate, an effect that could be potentially mediated by D1 receptors located onto presynaptic GABA and glutamate cells, respectively. Hence presynaptic modulation of VTA DA activity may play a role also in the regulation of the addictive properties of psychostimulants. Brodie, M. S., et al., "Cocaine effects in the ventral tegmental area. Evidence for an indirect dopaminergic mechanism of action" *Naunym Schmiedebergs Arch Pharmacol* 342:660-665 (1990); Bonci, A., et al., "Increased probability of GABA release during withdrawal from morphine," *J Neurosci* 17:796-803 (1997).

Accordingly, in one embodiment of the invention the additional therapeutic agent administered in combination, concurrently or sequentially with a PDE7 inhibitor is a dopaminergic agent to treat a patient suffering from an addiction or compulsive disorder. In another embodiment of the invention, the PDE7 inhibitor is administered in combination, concurrently or sequentially with a dopamine receptor agonist to treat a patient suffering from an addiction or impulse control disorder. In another embodiment of the invention, the PDE7 inhibitor is administered in combination, concurrently or sequentially with a dopamine D1 receptor agonist (i.e., a dopamine subtype D1 receptor agonist) to treat a patient suffering from an addiction or impulse control disorder.

Exemplary dopaminergic agents suitable for administration in conjunction with PDE7 inhibitors include, for example, levodopa (also referred to as "L-dopa"), carbidopa, and dopamine receptor agonists and precursors such as bromocriptine, pergolide, pramipexole, ropinirole, cabergoline, apomorphine, lisuride, rotigotine and quinagolide, as well as fenoldopam, which is selective for dopamine receptor D1.

Suitable dosages of D1 receptor agonists for administration in conjunction with a PDE7 inhibitor in accordance with the present invention may be determined by medical practitioners but may be, for example, in the range of 0.1 mg to 1,000 mg per day or biweekly, or 0.25 mg to 100 mg per day or biweekly.

C. Methods of Treating and Preventing Relapse

Relapse use, or reinstatement, refers to the process of returning to the use of alcohol or another addictive agent or the practice of an addictive behavior after a period of abstinence from, or limited or reduced use of, an addictive agent or practice of an addictive behavior. In certain situations, relapse use of an addictive agent refers to the return to use of an addictive agent by a subject who has undergone physical withdrawal from the addictive agent. Typically, the subject will have undergone physical withdrawal from the addictive agent during a period of non-use or limited or reduced use of the addictive agent. In one embodiment, relapse use occurs in a subject who has previously undergone a treatment regime with an effective amount of an anti-addiction agent to reduce or eliminate use of an addictive agent, but who is no longer using an effective amount of the anti-addiction agent. Anti-addictive agents include any and all agents used to treat or prevent addiction or withdrawal symptoms.

Alcoholism, like many other addictions, is a chronic relapsing disorder characterized by high recidivism rates. Two major factors triggering relapse behavior are stress and environmental conditioning experiences (O'Brien et al. 1997; Monti et al. 1993; Shaham et al. 1995), which probably facilitate relapse to alcohol-seeking via distinct brain mechanisms. For example, activation of the mesolimbic dopamine system via an opioid-dependent mechanism (or via direct alterations in dopamine transmission in the basolateral nucleus of amygdala) seems to mediate the effect of drug-associated cues (Liu and Wiess 2002; Ciccocioppo et al. 2001), and, extrahypothalamic CRF within the bed nucleus of the stria terminalis and median raphe nucleus is likely to mediate stress-induced reinstatement of drug-seeking behavior (Erb et al 1998; Shaham et al. 1995; Lê et al. 2000).

Several lines of evidence suggest that molecular mechanisms underlying relapse to addiction are common to different classes of drugs of abuse. Drug craving and loss of control over drug taking behavior associated to relapse are under the direct influence of stress and environmental conditioning stimuli; the two major factors affecting resumption to drug use.

Chronic drug abuse produces neuroadaptive changes not only within systems implicated in the acute reinforcing effects of ethanol, but also within other motivational systems, notably brain stress-regulatory mechanisms. Stress has an established role in the initiation and maintenance of drug abuse, and is a major determinant of relapse in abstinent individuals. (Brown, et al., *J Studies Alcohol* 56:538 (1995); Marlatt, Relapse prevention: introduction and overview of the model, in *Relapse Prevention: Maintenance Strategies in the Treatment of Addictive Behaviours*, Guilford, London, (1985); McKay, et al., *Drug Alcohol Dep.*, 38, 35, (1995); and Wallace, *J Subst Abuse Treat*, 6:95, (1989)). The significance of stress in drug-seeking behavior has also been amply documented in the animal literature. Physical, social, and emotional stress can facilitate acquisition or increase self-administration of cocaine, heroin, and ethanol in rodents and nonhuman primates. (Goeders and Guerin, *Psychopharmacology*, 114, 63, (1994); Haney, et al., *Brain Res.*, 698, 46, (1995); Ramsey and Van Ree, *Brain Res.*, 608, 216, (1993); Ahmed and Koob, *Psychopharmacology*, 132, 289, (1997); Shaham and Stewart, *Psychopharmacology* 119:334 (1995); Nash and Maickel, *Prog Neuropsychopharmacol Biol Psychiatry*, 12, 653, (1988); Mollenauer, et al., *Pharmacol. Biochem. Behav.*, 46, 35, (1993); Blanchard, et al., *Pharmacol. Biochem. Behav.* 28, 437, (1987) and Higley, et al., *Proc. Natl. Acad. Sci. USA*, 88, 7261, (1991)). Stressful stimuli have also been shown to elicit reinstatement of cocaine, heroin, and ethanol-seeking behavior in drug-free animals following extinction and these findings provide experimental support for a role of stress in relapse. (Ahmed and Koob (1997); Shaham, *Psychopharmacology*, 111, 477, (1993); and Shaham and Stewart (1995)).

Traditionally, stress-related drug-seeking behavior has been thought to be mediated via activation of the hypothalamic-pituitary-adrenal (HPA) axis. However, growing evidence suggests that the non-neuroendocrine corticotropin-releasing factor (CRF) system in the central nucleus of the amygdala (CeA) may play a significant independent role in the regulation of addictive behavior associated with stress. The CeA is rich in CRF immunoreactive cell bodies, terminals, and receptors, and this neuronal CRF system has been implicated in the mediation of behavioral and emotional responses to stressful stimuli. (Dunn and Berridge, *Brain Res Brain Res Rev*, 15, 71, (1990); and Koob et al., *Semin Neurosci* 6:221 (1994)). For example, immobilization stress elevates extracellular CRF levels in the CeA while intra-CeA injection of the CRF receptor antagonist, α-helical CRF9-41, reduces behavioral signs of anxiety produced by social and environmental stressors (Merali et al., *J. Neurosci.*, 18, 4758, (1998); Merlo Pich et al., *J. Neurosci.*, 15, 5439, (1995); Heinrichs et al., *Brain Res.*, 581, 190 (1992); Swiergiel et al., *Brain Res*, 623, 229 (1993)). Anxiety and stress-like symptoms are central to drug and alcohol withdrawal syndromes. Considering the evidence on a role of CRF neurons in the CeA in the regulation of emotional and anxiogenic effects of stress, it is likely that anxiogenic and stress-like consequences of withdrawal from drugs of abuse may be mediated by the CRF system in the CeA as well.

Changes in the regulation of the activity of the CRF system within the CeA may represent a critical neuroadaptive mechanism responsible for the development of dependence and compulsive drug-seeking behavior.

The data discussed above identify neuroadaptive changes in brain circuitries and perturbations in stress systems as an important element in compulsive drug-seeking behavior and dependence. Another important factor in the long-lasting addictive potential of drugs of abuse is the conditioning of their rewarding actions with specific environmental stimuli. Environmental cues repeatedly associated with the subjective effects of drugs of abuse including alcohol can evoke drug craving or elicit automatic behavioral responses (Miller and Gold 1994; Tiffany and Carter 1998) that ultimately may lead to relapse. (Childress et al., *Conditioned craving and arousal in cocaine addiction: A preliminary report*, in NIDA Research Monograph 81, (1988); Ehrman et al., *Psychopharmacology*, 107, 523, (1992); Monti et al., *J Stud Alcohol* 54:235-45 (1993); Pomerleau et al., *Addict. Behav.*, 8, 1, (1983); Stormark et al., *Addict. Behav.*, 20, 571, (1995); Miller and Gold *Ann. Clin. Psychiatry*, 6, 99, (1994); and Tiffany and Carter, *J. Psychopharmacol.* 12, 23, (1998)). Learned responses to drug-related stimuli may, therefore, contribute critically to the high rates of relapse associated with cocaine and other drug addiction.

Data from operant response-reinstatement models developed to investigate drug-seeking behavior associated with exposure to drug-related environmental cues in rats indicate that discriminative stimuli predictive of cocaine, ethanol, or heroin availability reliably elicit strong recovery of extinguished drug-seeking behavior in the absence of further drug availability. (Weiss et al., *Proc. Natl. Acad. Sci. USA*, 97, 4321, (2000); Katner et al., *Neuropsychopharmacology*, 20, 471, (1999); Katner and Weiss, *Alcohol Clin Exp Res.* 23:1751 (1999); and Gracy et al., *Pharmacol. Biochem. Behav.*, 65, 489, (2000)). The response-reinstating effects of these stimuli show remarkable resistance to extinction with repeated exposure and, in the case of cocaine, can still be observed after several months of forced abstinence. Additionally, in the case of ethanol, drug-seeking behavior induced by ethanol-predictive discriminative stimuli was found to be enhanced in genetically alcohol-preferring P rats compared to Alcohol Nonpreferring (NP) and nonselected Wistar rats. (Weiss and Ciccocioppo, *Soc. Neurosci. Abstr.*, 25, 1081, (1999)). This observation demonstrates that genetic predisposition toward heightened ethanol intake is reflected also by a greater susceptibility to the motivating effects of ethanol cues (i.e., enhanced drug-seeking under conditions where behavior is not directly reinforced by ethanol itself). Together, these findings strongly support the hypothesis that learned responses to drug-related stimuli are a significant factor in long-lasting vulnerability to relapse.

In humans, relapse risk involves multiple determinants that are likely to interact. For example, exposure to drug cues may augment vulnerability to relapse imparted by protracted withdrawal symptoms resulting from neuroadaptive changes in dependent individuals. Interactive effects exacerbating relapse risk may also exist between the motivating effects of stress and drug-related cues. Recent work addressing these issues has confirmed that additive interactions between the response-reinstating effects of ethanol-associated cues and stress can indeed be demonstrated, and that these effects are enhanced in rats with a history of ethanol dependence. (Liu and Weiss, *Soc. Neurosci. Abstr.* 26, 786 (2000)).

In experimental laboratories, reinstatement of drug seeking is obtained with administration of the α-2 adrenoreceptor antagonist yohimbine, which, increasing brain noradrenaline cell firing and release, acts as a pharmacological stressor. Footshock stress and yohimbine-induced reinstatement of drug-seeking behaviors both represent valid experimental models to investigate stress-induced alcohol relapse (Lee et al., *Neuropsychopharmacology* 29:686-93 (2004) and Le et al., *Psychopharmacology* 150:317-24 (2000)).

As shown in the accompanying Examples, PDE7 inhibitors significantly reduce stress-induced relapse use of an addictive agent (Example 1). These data indicate, therefore, that PDE7 inhibitors have anti-relapse properties.

Interestingly, various reports have shown that the nonselective opiate receptor antagonist naltrexone reduces the urge to drink elicited by presentation of alcohol cues in human alcoholics (Monti et al. 1993, supra) and decreases the efficacy of an alcohol cue to reinstate extinguished responding at a previously drug-paired lever in rats (Katner et al. 1999, supra). However, naltrexone does not reduce relapse behavior elicited by stress ((Le A. D. Psychopharmacology 1998).

In a related embodiment, the invention includes a method of treating or preventing relapse use of an addictive agent or practice of an addictive or compulsive behavior, comprising administering an effective amount of a PDE7 inhibitor to a subject who previously reduced or eliminated use of an addictive agent or practice of an addictive or compulsive behavior in response to exposure to an effective amount of another anti-addiction treatment, wherein the subject is no longer exposed to an effective amount of the anti-addiction treatment. The anti-addiction treatment may be an anti-addiction drug or may be a non-pharmacologic therapy such as counseling, psychotherapy or hypnosis therapy. The relapse use may be triggered by stress.

In certain embodiments, the subject is no longer exposed to an effective amount of an anti-addiction agent because the subject has become tolerant to the agent, such that the blood plasma concentration of the anti-addiction agent that was previously effective in treating the addiction is no longer effective. In other embodiments, the subject is no longer exposed to an effective amount of an anti-addiction agent because the subject is now exposed to a lower blood plasma concentration of the anti-addiction agent, and this lower blood plasma concentration is not effective.

In certain embodiments of the methods of the present invention, the subject has undergone a period of abstinence from, or limited or reduced use of, the addictive agent or practice of the addictive or compulsive behavior. This period of abstinence or limited or reduced use may be, e.g., at least 24 hours, at least 48 hours, at least 3 days, at least 5 days, at least one week, at least 2 weeks, at least 1 month, at least 2 months, at least 4 months, at least 6 months, at least 9 months, at least one year, at least 2 years, or at least 5 years.

In another embodiment, the present invention includes a method of treating or preventing relapse use of an addictive agent, comprising providing a PDE7 inhibitor and an opioid antagonist to a subject who has undergone physiological withdrawal from the addictive agent.

In a further embodiment, the present invention includes a method of treating or preventing relapse use of an addictive agent, comprising administering a PDE7 inhibitor and a CB1 antagonist, e.g., disulfuram, topiramate, levetiracetam, SSRIs, or ondansetron, to a subject who has undergone physiological withdrawal from the addictive agent.

In particular embodiments, the relapse use is triggered by stress, an environmental conditioning factor, or both.

While the methods of the present invention may be practiced in subjects addicted to a single addictive agent, they may also be used in subjects addicted to two or more addictive agents. Similarly, while these methods may be used to prevent relapse use of the addictive agent from which the subject has undergone withdrawal, they may also be adapted to prevent relapse use or the commencement of use of an addictive agent different than the one from which the subject has undergone physiological withdrawal.

D. Pharmaceutical Compositions, Routes of Administration, Unit Dosage Forms, Kits The present invention has established the efficacy of using combinations of a PDE7 inhibitor, in combination with one or more additional therapeutic agents, such as opioid antagonists, antidepressents, antiepileptics, antiemetics, and CB1 receptor antagonists. Thus, the present invention further includes compositions comprising one or more PDE7 inhibitors and one or more additional therapeutic agents, such as opioid antagonists, mixed opioid antagonists/partial agonist, antidepressants, antiepileptics, antiemetics, CRF1 receptor antagonists and CB1 receptor antagonists.

In particular embodiments, the composition comprises one PDE7 inhibitor and one additional therapeutic agent. In certain embodiments, the additional therapeutic agent is an opioid antagonist or a mixed opioid antagonist/partial agonist. In one embodiment, the opioid antagonist is naltrexone.

In another embodiment, the mixed opioid partial agonist/antagonist is buprenorphine. In certain embodiments, the additional therapeutic agent is an antidepressant. In a particular embodiment, the antidepressant is bupropion. In certain embodiments, the additional therapeutic agent is an antiepileptic, an antiemetic, or an opioid antagonist or a mixed opioid partial agonist/antagonist.

The compositions of the present invention may be administered to a subject as a pharmaceutical composition or formulation. In particular embodiments, pharmaceutical compositions of the present invention may be in any form which allows for the composition to be administered to a subject. For example, the composition may be in the form of a solid, liquid or gas (aerosol). Typical routes of administration include, without limitation, oral, topical, parenteral, sublingual, rectal, vaginal, and intranasal. The term parenteral as used herein includes subcutaneous injections, intravenous, intramuscular, epidural, intrasternal injection or infusion techniques.

Pharmaceutical compositions used according to the present invention comprise a PDE7 inhibitor, another therapeutic agent, and a pharmaceutically acceptable diluent, excipient, or carrier. "Pharmaceutically acceptable carriers" for therapeutic use are well known in the pharmaceutical art, and are described, for example, in Remingtons Pharmaceutical Sciences, Mack Publishing Co. (A. R. Gennaro edit. 1985). For example, sterile saline and phosphate buffered saline at physiological pH may be used. Preservatives, stabilizers, dyes and even flavoring agents may be provided in the pharmaceutical composition. For example, sodium benzoate, sorbic acid and esters of p hydroxybenzoic acid may be added as preservatives. Id. at 1449. In addition, antioxidants and suspending agents may be used. Id.

Pharmaceutical compositions of the invention are generally formulated so as to allow the active ingredients contained therein to be bioavailable upon administration of the composition to a subject. Compositions that will be administered to a subject may take the form of one or more dosage units, where for example, a tablet, capsule or cachet may be a single dosage unit, and a container comprising a combination of agents according to the present invention in aerosol form may hold a plurality of dosage units.

In particular embodiments, the composition comprising a PDE7 inhibitor and another therapeutic agent is administered in one or more doses of a tablet formulation, typically for oral administration. The tablet formulation may be, e.g., an immediate release formulation, a controlled-release formulation, or an extended-release formulation. In one embodiment, a tablet formulation comprises an effective amount of a composition comprising a PDE7 inhibitor and another therapeutic agent. In particular embodiments, a tablet comprises about 1, 5, 10, 20, 30, 50 100, 150, 200, 250, or 300 mg of a PDE7 inhibitor, and about 1, 5, 10, 20, 30, 50 100, 150, 200, 250, or 300 mg of another therapeutic agent.

The present invention further includes unit-dosage forms of pharmaceutical compositions comprising a PDE7 inhibitor and another therapeutic agent. Each unit-dosage form comprises a therapeutically effective amount of a pharmaceutical composition of the present invention, when used in the recommended amount. For example, a unit-dosage form may include a therapeutically effective amount in a single tablet, or a unit-dosage form may include a therapeutically effective amount in two or more tablets, such that the prescribed amount comprises a therapeutically effective amount.

In particular embodiments, a PDE7 inhibitor is provided to a subject in an amount in the range of 0.1-1000 mg/day, 1-1000 mg/day, 10-100 mg/day, or 25-50 mg/day. In one embodiment, pioglitazone is provided to a patient at about 30 mg/day.

Certain combinations of PDE7 inhibitors and other therapeutic agents may not be readily adaptable to coformulation. For example, one of the agents may be more amenable to intravenous administration, while another of the agents may be more amenable to oral administration. Or, the serum half-life of the two agents may be such that one must be administered more frequently than the other. Accordingly, the present invention contemplates kits comprising one or more unit dosage forms of a PDE7 inhibitor and one or more unit dosage forms of another therapeutic agent, such that the two unit dosage forms may be provided to a subject in a therapeutically effective manner.

In one embodiment, the present invention includes a kit comprising unit-dosage forms of a PDE7 inhibitor and unit-dosage forms of nicotine. In one embodiment, the unit dosage forms of nicotine comprise a plurality of different unit-dosage forms of nicotine, wherein the different dosage forms of nicotine represent decreasing amount that may be taken one after the other over a period of time, so as to overcome addiction and effectuate withdrawal from the nicotine. The unit-dosage forms of nicotine may be present, e.g., in the form of a transdermal patch, gum, or a lozenge.

E. PDE7 Proteins and Inhibitory Agents

Cyclic nucleotide phosphodiesterase type 7 (PDE7) is identified as a unique family based on its primary amino acid sequence and distinct enzymatic activity. The PDE genes identified as PDE7 (PDE7A and PDE7B), code for cAMP-specific PDEs. The biochemical and pharmacological characterization of PDE7 shows a high-affinity cAMP-specific PDE (Km=0.2 μM) that is not affected by cGMP nor by selective inhibitors of other PDEs. The PDE7 enzyme selectively decomposes cAMP and is characterized as an enzyme that is not inhibited by rolipram, a selective inhibitor of PDE4, which is a distinct, cAMP-specific PDE family. Two sub-types have been identified within the PDE7 family, PDE7A (Michael, T., et al., *J. Biol. Chem.* 268(17):12925-12932, 1993; Han, P., et al., *J. Biol. Chem.* 272(26):16152-16157, 1997) and PDE7B (U.S. Pat. No. 6,146,876; Gardner, C., et al., *Biochem. Biophys. Res. Commun.* 272(1):186-192, 2000; and Saski, T., et al., *Biochem. Biophys. Res. Commun.* 271(3):575-583, 2000). The two gene products exhibit 70% identity in their C-terminal catalytic domains (Hetman J. M., et al., *PNAS* 97(1):472-476 (2000).

PDE7A has three splice variants (PDE7A1, PDE7A2 and PDE7A3); these variants are generated via alternative splicing at both the N- and C-termini (Bloom, T. J., and J. A. Beavo, *Proc. Natl. Acad. Sci. USA.* 93:14188-14192, 1996). The nucleotide sequence of PDE7A, transcript variant 1, is accessible in public databases by the accession number NM_002603. Human PDE7A1 protein (SEQ ID NO: 2, encoded by SEQ ID NO:1) has 456 amino acids and migrates at an apparent molecular weight of 53-55 kDa on reduced SDS-PAGE.

The nucleotide sequence of PDE7A, transcript variant 2, is accessible in public databases by the accession number NM_002604. Human PDE7A2 protein (SEQ ID NO:4, encoded by SEQ ID NO:3) has 424 amino acids.

The PDE7A protein has a region of about 270 amino acids at the carboxy terminal end that displays significant similarity (~23% homology) to the analogous regions of other cAMP-hydrolyzing PDEs. This region serves as the catalytic domain. The amino-terminal region of this protein is divergent from that of other PDEs and presumably mediates the distinctive and regulatory properties unique to this enzyme family.

The protein sequence of human PDE7B is accessible in public databases by the accession number NM_018945, provided as SEQ ID NO:6, encoded by SEQ ID NO:5. Three splice variants of PDE7B have been reported: PDE7B1, PDE7B2 and PDE7B3. PDE7B is published in WO 01/62904, U.S. Pat. No. 6,146,876.

Both PDE7B2 and PDE7B3 possess unique N-terminal sequences. Human PDE7B gene products have an apparent molecular weight of 53-55 kDa on reduced SDS-PAGE (Sasaki, T., Kotera, J., Omori, K., *Biochemical J.* 361:211-220, 2002). As in PDE7A, the PDE7B has a significantly conserved region of about 270 amino acids common to all PDEs at the carboxy terminal, which serves as the catalytic domain. Similar to the PDE7A protein, the amino-terminal region of PDE7B protein is divergent and presumably accounts for the distinctive and regulatory properties unique to the individual PDE families. The PDE7B protein shows homology to other cAMP-dependent PDEs (23%) within the catalytic domain. The PDE7B polypeptide is 61% homologous to PDE7A, according to WO 2004/044196.

PDE7 is also uniquely localized in mammalian subjects relative to other PDE families. PDE7A expression has been detected in the majority of tissues analyzed, including the brain, heart, kidney, skeletal muscle, spleen and uterus (Bloom, et al., *PNAS* 93:14188, 1996). Within the brain, PDE7A is widely distributed in both neuronal and non-neuronal cell populations (Miro, et al., *Synapse* 40:201, 2001). PDE7A's wide expression in the brain, including the basal ganglia and substantia nigra, provides a theoretical basis for a role for PDE7A in brain functions.

In the practice of the methods of the invention, representative PDE7 inhibitory agents that inhibit the phosphodiesterase activity of PDE7 include: molecules that bind to PDE7 and inhibit the enzyme activity of PDE7 (such as small molecule inhibitors or blocking peptides that bind to PDE7 and reduce enzymatic activity), and molecules that decrease the expression of PDE7 at the transcriptional and/or translational level (such as PDE7 antisense nucleic acid molecules, PDE7 specific RNAi molecules and PDE7 ribozymes), thereby preventing PDE7 from cleaving cAMP. The PDE7 inhibitory agents can be used alone as a primary therapy or in combination with other therapeutics (such as dopamine receptor agonists) as an adjuvant therapy to enhance the therapeutic benefits, as discussed supra.

The inhibition of PDE7 is characterized by at least one of the following changes that occur as a result of administration of a PDE7 inhibitory agent in accordance with the methods of the invention: the inhibition of PDE7-dependent enzymatic cleavage of the 3'-phosphodiester bond in cAMP to form 5'-adenosine monophosphate (5'-AMP), a reduction in the gene or protein expression level of PDE7, measured, for example, by gene expression analysis (e.g., RT-PCR analysis) or protein analysis (e.g., Western blot).

In some embodiments, a PDE7 inhibitory agent is a molecule or composition that inhibits the expression of PDE7A, PDE7B, or both PDE7A and PDE7B, such as an antisense or small inhibitory nucleotide (e.g., siRNA) that specifically hybridizes with the cellular mRNA and/or genomic DNA corresponding to the gene(s) of the target PDE7 so as to inhibit their transcription and/or translation, or a ribozyme that specifically cleaves the mRNA of a target PDE7.

Potency of PDE7 Inhibitory Agents

In one embodiment, a PDE7 inhibitory agent useful in the methods of the invention is a compound that is sufficiently potent to inhibit the enzymatic activity of PDE7 (PDE7A, PDE7B, or PDE7A and PDE7B) at an $IC_{50} \leq 1$ µM, preferably less than or about 0.1 µM. In one embodiment, the PDE7 inhibitory agent is sufficiently potent to inhibit the enzymatic activity of PDE7 (PDE7A, PDE7B, or PDE7A and PDE7B) at an $IC_{50}$ of from about 0.1 to about 500 nM. In one embodiment, the PDE7 inhibitory agent is potent to inhibit the enzymatic activity of PDE7 (PDE7A, PDE7B, or PDE7A and PDE7B) at an $IC_{50}$ of from about 1 to about 100 nM.

Representative methods for determining the $IC_{50}$ for a PDE7 (PDE7A or PDE7B) inhibitory agent are well known in the art, such as the Scintillation Proximity Assay (SPA) disclosed in Bardelle et al., *Anal Biochem* 15:275(2):148-55 (1999).

PDE7A or PDE7B Selective Inhibitory Agents

In one embodiment, the PDE7 inhibitor useful in the method of the invention is a PDE7A inhibitory agent. In one embodiment, the PDE7A inhibitory agent is potent to inhibit the enzymatic activity of PDE7A at an $IC_{50}$ of from about 0.1 to about 500 nM. In one embodiment, the PDE7A inhibitor has an $IC_{50}$ of from about 1 to about 100 nM. A suitable assay for determining the $IC_{50}$ for a PDE7A inhibitor uses recombinant human PDE7A2 enzymes expressed in a baculoviral system. This assay method is a modification of the SPA assay reported by Bardelle et al. supra.

In some embodiments, the PDE7 inhibitory agent exhibits isozyme-selective activity against PDE7A. A PDE7A selective inhibitory agent reduces PDE7A activity at least two-fold more than PDE7B activity, more preferably at least 10-fold, at least 20-fold, at least 50-fold, or at least 100-fold. In some embodiments, the PDE7A inhibitory agent is an inhibitory agent that is at least 10-fold (such as at least 20-fold, or at least 50-fold or at least 100-fold) more selective for inhibiting PDE 7A activity than for the enzyme activity of any other PDE (PDE1-6, 7B, and 8-11).

In one embodiment, the PDE7B inhibitor has an $IC_{50}$ of from about 0.1 to about 500 nM. In one embodiment, the PDE7B inhibitory agent is sufficiently potent to inhibit the enzymatic activity of PDE7B at an $IC_{50}$ of from about 0.1 to about 500 nM. In one embodiment, the PDE7B inhibitor has an $IC_{50}$ of from about 1 to about 100 nM. Methods for determining the $IC_{50}$ for a PDE7B inhibitor are well known in the art, such as the assays disclosed in Bardelle et al., supra.

In some embodiments, the PDE7 inhibitor exhibits isozyme-selective activity against PDE7B. A PDE7B selective inhibitory agent reduces PDE7B activity at least two-fold more than PDE7A activity, more preferably at least 10-fold, at least 20-fold, at least 50-fold, or at least 100-fold. In some embodiments, the PDE7B inhibitory agent is an inhibitory agent that is at least 10-fold (such as at least 20-fold, or at least 50-fold or at least 100-fold) more selective for inhibiting PDE7B activity than for the enzyme activity of any other PDE (PDE1-6, 7A, and 8-11).

PDE7 Selectivity as Compared to Other PDEs

In some embodiments, the PDE7 inhibitory agent has an $IC_{50}$ for inhibiting PDE1B activity of greater than 5 times (such as at least 10-fold, at least 20-fold, or at least 50-fold or at least 100-fold) the lesser of the $IC_{50}$ for inhibiting PDE7A activity and the $IC_{50}$ for inhibiting PDE7B activity. Stated differently, the PDE7 inhibitor is more potent (by 5 times, 10 times, 20 times, 50 times or 100 times) at inhibiting the activity of PDE7A or PDE7B (whichever PDE7A or PDE7B isozyme upon which the PDE7 inhibitor has the most effect), than it is at inhibiting the activity of PDE1B. For purposes of the present specification, by way of example, this property may be still more simply stated as the PDE7 inhibitor is more potent (by 5 times, 10 times, 20 times, 50 times or 100 times) at inhibiting the activity of PDE7 than it is at inhibiting the activity of PDE1B.

Dual inhibition of both PDE7 and PDE1B may confer additional benefit in the treatment of movement disorders based on a report that deletion of the gene for PDE in mice stimulated the metabolism of dopamine and sensitized the animals to the effects of dopaminergic agonists (Siuciak, et al., *Neuropharmacology* 53(1): 113-23 (2007)).

In some embodiments, the PDE7 inhibitory agent has an $IC_{50}$ for inhibiting PDE10 activity of greater than 5 times (such as at least 10-fold, or at least 20-fold, or at least 50-fold or at least 100-fold) the lesser of the $IC_{50}$ for inhibiting PDE7A activity and the $IC_{50}$ for inhibiting PDE7B activity. Dual inhibition of both PDE7 and PDE10 may confer additional benefit in the treatment of movement disorders based on a report that selective inhibitors of PDE10 cause an increase in cAMP levels in the striatum (Siuciak J. A. et al., *Neuropharmacology* 51(2): 386-96 (2006)).

In some embodiments, the PDE7 inhibitory agent has an $IC_{50}$ for inhibiting PDE3 activity of greater than 10 times (such as at least 20-fold, at least 50-fold or at least 100-fold) the lesser of the $IC_{50}$ for inhibiting PDE7A activity and the $IC_{50}$ for inhibiting PDE7B activity. This is because the administration of selective inhibitors of PDE3 to patients in heart failure was shown to increase their rate of mortality (Packer M. et al., *N Engl J. Med.* 325(21):1468-75 (1991)).

In some embodiments, the PDE7 inhibitory agent has an $IC_{50}$ for inhibiting PDE4 activity of greater than 10 times (such as at least 20-fold, at least 50-fold or at least 100-fold) the lesser of the $IC_{50}$ for inhibiting PDE7A activity and the IC50 for inhibiting PDE7B activity. This is because deletion of one of the PDE4 genes in mice has been shown to lead to cardiac myopathy (Lehnart S. E. et al., *Cell* 123(1):25-35 (2005)).

In some embodiments, the PDE7 inhibitory agent has a half maximally effective dose ("$ED_{50}$") in an in vivo assay of PDE4 inhibition (for example, sedation or inhibition of TNF alpha levels after endotoxin treatment) of greater than 10 times (such as at least 20-fold, at least 50-fold or at least 100-fold) the lesser of the $ED_{50}$ in an in vivo assay of PDE7A and PDE7B inhibition (for example, prevention of relapse to cocaine or other psychostimulant addiction). In accordance with such embodiments, it has been determined that some compounds having dual PDE4/PDE7 inhibitory activity possess greater selectivity against PDE7 than PDE4 in vivo, as compared to the PDE4/PDE7 selectivity of the compound as determined in an in vitro assay.

In some embodiments, the PDE7 inhibitory agent has an $IC_{50}$ for inhibiting PDE3 activity and PDE4 activity of greater than 10 times (such as at least 20-fold, at least 50-fold or at least 100-fold) the lesser of the $IC_{50}$ for inhibiting PDE7A activity and the IC50 for inhibiting PDE7B activity.

In some embodiments, the PDE7 inhibitory agent has an $IC_{50}$ for inhibiting PDE8 activity of greater than 10 times (such as at least 20-fold, at least 50-fold or at least 100-fold) the lesser of the $IC_{50}$ for inhibiting PDE7A activity and the $IC_{50}$ for inhibiting PDE7B activity.

In some embodiments, the PDE7 inhibitory agent has an $IC_{50}$ for inhibiting PDE4 activity and PDE8 activity of greater than 10 times (such as at least 20-fold, at least 50-fold or at least 100-fold) the lesser of the $IC_{50}$ for inhibiting PDE7A activity and the $IC_{50}$ for inhibiting PDE7B activity. In accordance with this embodiment, it is known that the PDE families that specifically/preferentially hydrolyze cAMP include PDE4, PDE7, and PDE8.

In some embodiments, the PDE7 inhibitory agent has an $IC_{50}$ for inhibiting the activity of PDE1, PDE2, PDE3, PDE4, and PDE8, PDE10, and PDE11 of greater than 10 times the lesser of the $IC_{50}$ for inhibiting PDE7A activity and the IC50 for inhibiting PDE7B activity. In accordance with this embodiment, it is known that the PDE families that specifically/preferentially hydrolyze cAMP include PDE4, PDE7, and PDE8 and the PDE1, PDE2, PDE3, PDE10, and PDE11 families show substantial activity against both cAMP and cGMP.

In some embodiments, the PDE inhibitory agent is a selective PDE7 inhibitor for which the lesser of the $IC_{50}$ for inhibiting PDE7A activity and the IC50 for inhibiting PDE7B activity is less than one-tenth (such as one-twentieth, one-fiftieth, or one-hundredth) the $IC_{50}$ that the agent has for inhibiting any other PDE enzyme from the PDE1-6 and PDE8-11 enzyme families.

A selective PDE7 inhibitor can be identified, for example, by comparing the ability of an agent to inhibit PDE7 (PDE7A, PDE7B or PDE7A and PDE7B) enzyme activity to its ability to inhibit PDE enzymes from the other PDE families. For example, an agent may be assayed for its ability to inhibit PDE7 activity as well as PDE1, PDE2, PDE3, PDE4, PDE5, PDE6, PDE8, PDE9, PDE10, and PDE11. The ratio of the $IC_{50}$ inhibition for each of the PDE(1-6 and 8-11) isozymes to the $IC_{50}$ inhibition of PDE7 (i.e., the more sensitive of PDE7A or PDE7B) may be determined by a standard in vitro, in vivo, or ex vivo assay, such as those described herein.

In some embodiments, a PDE7 inhibitor is selective for PDE7 and substantially inactive against other PDEs (e.g., PDE1, PDE2, PDE3, PDE4, and PDE8, PDE10, and PDE11) due to targeting of the PDE7 inhibitor to one or more target tissues, such as the brain and/or skeletal muscle. As described herein, PDE7 is uniquely localized in mammalian subjects relative to other PDE families. Within the brain, PDE7A is widely distributed in both neuronal and non-neuronal cell populations, including the basal ganglia and substantia nigra (Miro et al., Synapse 40:201, 2001). PDE7B is expressed in the brain in the striatum (Reyes-Irisarri et al., Neuroscience 132:1173, 2005).

Types of PDE7 Inhibitory Agents

The PDE7 inhibitory agent can be any type of agent including, but not limited to, a chemical compound, a protein or polypeptide, a peptidomimetic, a nucleic acid molecule, or ribozyme. In some embodiments, PDE7 inhibitory agents are small molecule inhibitors including natural and synthetic substances that have a low molecular weight (i.e., less than about 450 g/mole), such as, for example, peptides, peptidomimetics and nonpeptide inhibitors such as chemical compounds.

Chemical Compounds:

The PDE7 inhibitors useful in the methods of the invention include agents that are administered by a conventional route (e.g., oral, intramuscular, subcutaneous, transdermal, transbucal, intravenous, etc.) into the bloodstream and are ultimately transported through the vascular system across the blood brain barrier to inhibit PDE7 in the brain. Accordingly, for these methods of administration, the PDE7 inhibitors have the ability to cross the blood brain barrier. Those PDE inhibitors described below that have the ability to cross the blood brain barrier (e.g., those having a molecular weight less than about 450 g/mole and that are sufficiently lipophilic) are useful in the methods of the invention when the inhibitors are administered by a route that ultimately transports the inhibitors to the brain in the bloodstream.

The following is a description of exemplary PDE7 inhibitors useful in the methods of the invention.

In one embodiment, PDE7 inhibitors useful in the methods of the invention are selected from those compounds generally or specifically disclosed in EP 1 454 897, WO 2003/053975, and US 20050148604, each expressly incorporated herein by reference in its entirety. In one embodiment, PDE7 inhibitors useful in the methods of the invention have the formulas:

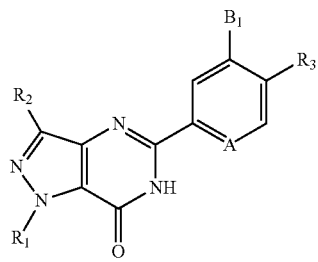

(1A)

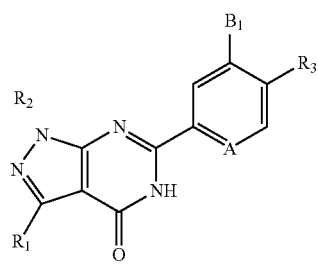

(1B)

The substituents for the above compounds are defined as follows:

A represents N or $CR_4$,

B represents a hydrogen atom or a halogen atom, $R_1$ represents optionally substituted $C_{3-7}$ cycloalkyl or tert-butyl, $R_2$ represents hydrogen, methyl, or ethyl, $R_3$ represents a hydrogen, nitro, cyano or halogen atom, $NR_5R_6$, $C(=X)R_7$, $SO_2NR_5R_6$, $OR_8$, $NR_8CONR_5R_6$, $NR_8SO_2R_9$, $NR_8CO_2R_9$, a heteroaryl group, optionally substituted $C_{1-3}$ alkyl, optionally substituted $C_{1-6}$ alkenyl, or optionally substituted saturated or unsaturated heterocycloalkyl, $R_4$ represents hydrogen, or $C_{1-3}$ alkoxy substituted, if desired, by one or more fluorine atoms, $R_5$ and $R_6$ are the same or different, and represent a hydrogen atom, optionally substituted $C_{1-6}$ alkyl, optionally substituted heterocycloalkyl, or optionally substituted acyl or, together with the nitrogen atom which they are bound to, form azetidinyl, pyrrolidinyl, piperidinyl, morpholino, thiomorpholino, piperazinyl, or homopiperazinyl, each of these groups being optionally substituted by optionally substituted $C_{1-4}$ alkyl, OH, $C_{1-3}$ alkoxy, $CO_2H$, $NR_5R_6$, an oxo group, $NR_9COR_7$, or $C(=O)R_7$, $R_7$ represents optionally substituted $C_{1-6}$ alkyl, OH, $OR_8$, or $NR_5R_6$, $R_8$ represents hydrogen, an optionally substituted $C_{1-6}$ alkyl group, or optionally substituted heterocycloalkyl, $R_9$ represents an optionally substituted $C_{1-6}$ alkyl group, and X represents O, S, or NH.

In regard to the above compounds, "optionally substituted" refers to optionally substituted linear, branched or cyclic alkyl group such as methyl, ethyl, propyl or cyclohexyl; a hydroxyl group; a cyano group; an alkoxy group such as methoxy or ethoxy; an optionally substituted amino group such as amino, methylamino or dimethylamino; an optionally substituted acyl group such as acetyl or propionyl; a carboxyl group; an optionally substituted aryl group such as phenyl or naphthyl; an optionally substituted heteroaryl group such as pyridinyl, thiazolyl, imidazolyl or pyrazyl; an optionally substituted saturated or unsaturated heterocycloalkyl group such as piperazinyl or morphonyl; an optionally substituted carbamoyl group; an optionally substituted amido group; a halogen atom such as chlorine, fluorine or bromine; a nitro group; an optionally substituted sulfone group; an optionally substituted sulfonylamido group; an oxo group; a urea group; and an optionally substituted linear, branched or cyclic alkenyl group such as ethenyl, propenyl or cyclohexenyl.

Examples of the heteroaryl group as $R^3$ include a 5- to 7-membered monocyclic heteroaryl group having 2 to 8 carbon atoms and containing 1 to 4 hetero atoms consisting of oxygen atoms, nitrogen atoms or sulfur atoms, and a polycyclic heteroaryl group comprising two or more such identical or different monocyclic compounds fused together, examples of the monocyclic and polycyclic heteroaryl groups being pyrrole, furyl, thienyl, imidazolyl, thiazolyl, pyridyl, pyrazyl, indolyl, quinolyl, isoquinolyl, and tetrazolyl.

In one embodiment, a PDE7 inhibitor useful in the invention has the formula:

Compound 1

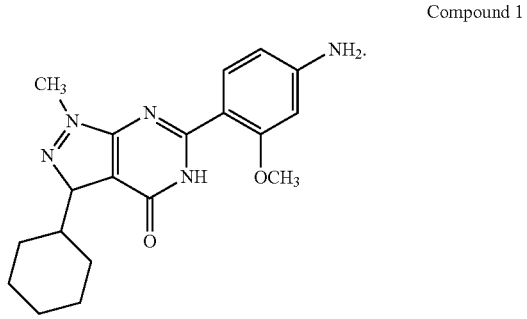

In others embodiments, PDE7 inhibitors useful in the methods of the invention have the formulas:

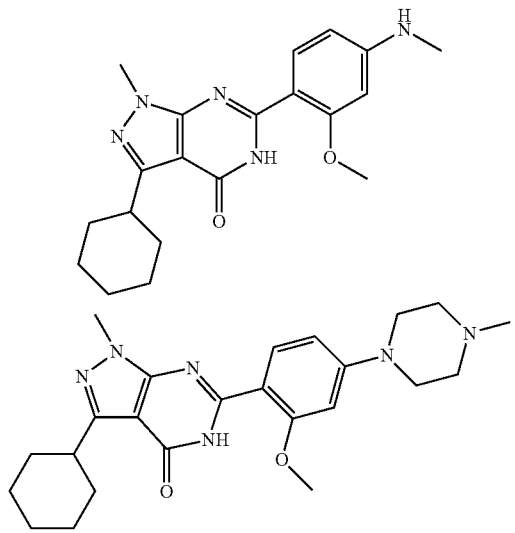

-continued

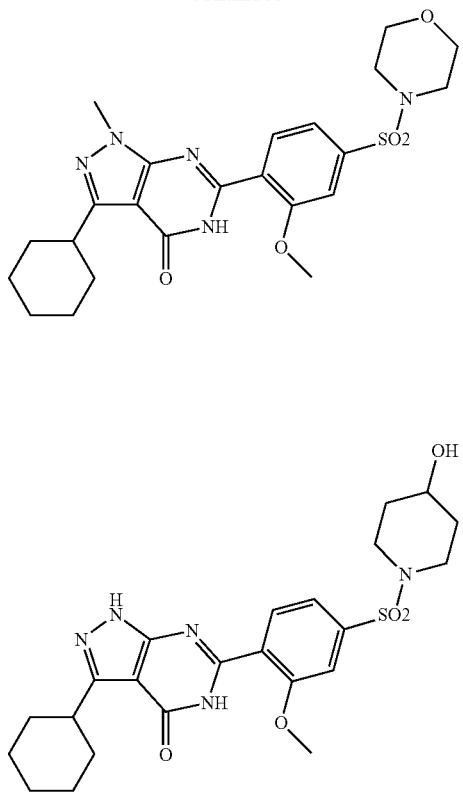

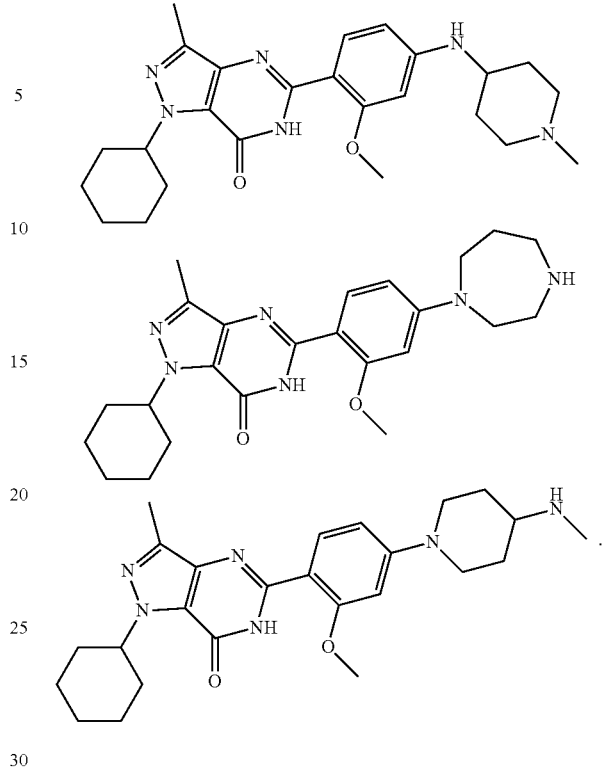

The preparation of the above compounds is described in EP 1 454 897, WO 2003/053975, and US 20050148604.

In another embodiment, PDE7 inhibitors useful in the methods of the invention are selected from those compounds generally or specifically disclosed in US 2002/0198198, WO 2002/076953, WO 2002/074754, WO 2006/092691, *Bioorganic & Medicinal Chemistry Letters* 14 (2004) 4623-4626, and *Bioorganic & Medicinal Chemistry Letters* 14 (2004) 4627-4631, each expressly incorporated herein by reference in its entirety. In one embodiment, PDE7 inhibitors useful in the methods of the invention have the formulas:

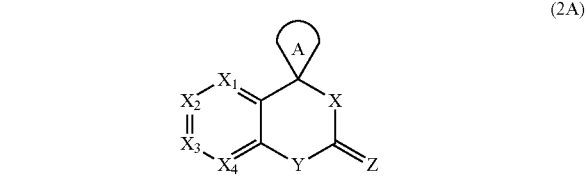
(2A)

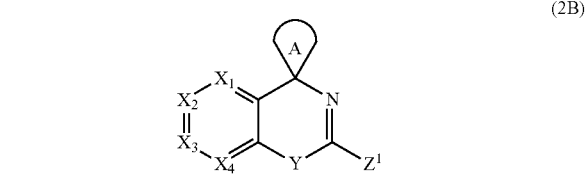
(2B)

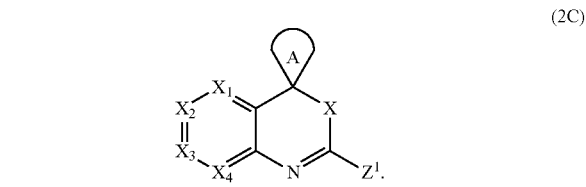
(2C)

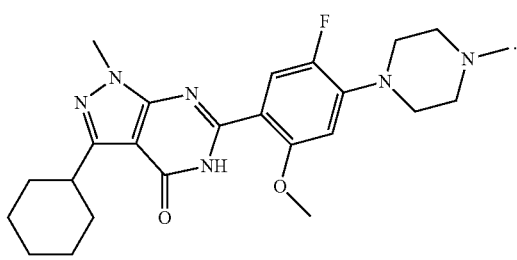

In another embodiment, a PDE7 inhibitor useful in the methods of the invention has the formula:

Compound 2

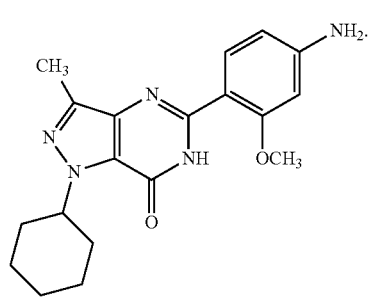

In other embodiments, PDE7 inhibitors useful in the methods of the invention have the formulas:

The substituents for the above compounds are defined as follows:

(a) $X_1$, $X_2$, $X_3$, and $X_4$ are the same or different and are selected from:

N, provided that not more than two of the groups $X_1$, $X_2$, $X_3$, and $X_4$ simultaneously represent a nitrogen atom, or, C—$R_1$, in which $R_1$ is selected from:

$Q_1$, or lower alkyl, lower alkenyl, or lower alkynyl, these groups being unsubstituted or substituted with one or several groups $Q_2$;

the group $X_5$—$R_5$ in which, $X_5$ is selected from:

a single bond, lower alkylene, lower alkenylene, or lower alkynylene; optionally interrupted with 1 or 2 heteroatoms chosen from O, S, S(=O), $SO_2$, or N, the carbon atoms of these groups being unsubstituted or substituted with one or several groups, identical or different, selected from $SR_6$, $OR_6$, $NR_6R_7$, =O, =S, or =$NR_6$ in which $R_6$ and $R_7$ are the same or different and are selected from hydrogen or lower alkyl, and, $R_5$ is selected from aryl, heteroaryl, cycloalkyl optionally interrupted with C(=O) or with 1, 2, or 3 heteroatoms chosen from O, S, S(=O), $SO_2$, or N, cycloalkenyl optionally interrupted with C(=O) or with 1, 2, or 3 heteroatoms chosen from O, S, S(=O), $SO_2$ or N, or a bicyclic group, these groups being unsubstituted or substituted with one or several groups selected from $Q_3$, heteroaryl, or lower alkyl optionally substituted with $Q_3$;

in which $Q_1$, $Q_2$, and $Q_3$ are the same or different and are selected from:

hydrogen, halogen, CN, $NO_2$, $SO_3H$, P(=O)(OH)$_2$, $OR_2$, OC(=O)$R_2$, C(=O)$OR_2$, $SR_2$, S(=O)$R_2$, $NR_3R_4$, Q-$R_2$, Q-$NR_3R_4$, $NR_2$-Q-$NR_3R_4$, or $NR_3$-Q-$R_2$ in which Q is selected from C(=NR), C(=O), C(=S), or $SO_2$, R is selected from hydrogen, or lower alkyl, and $R_2$, $R_3$, and $R_4$ are the same or different and are selected from:

hydrogen, lower alkyl optionally interrupted with C(=O), $(CH_2)_n$-aryl, $(CH_2)_n$-heteroaryl, $(CH_2)_n$-cycloalkyl optionally interrupted with C(=O) or with 1 or 2 heteroatoms chosen from O, S, S(=O), $SO_2$, or N, in which n is an integer selected from 0, 1, 2, 3 or 4;

these groups being unsubstituted or substituted with one or several groups selected from lower alkyl, halogen, CN, $CH_3$, $SO_3H$, $SO_2CH_3$, $CF_3$, C(=O)NHSO$_2$CH$_3$, $OR_6$, COOR$_6$, C(=O)$R_6$, $NR_6R_7$, C(=O)$NR_6R_7$, or $SO_2NR_6R_7$, in which $R_6$ and $R_7$ are the same or different and are selected from hydrogen or lower alkyl optionally substituted with one or two groups selected from OR, COOR or NRR$_8$ in which R and $R_8$ are hydrogen or lower alkyl, and, $R_6$ and $R_7$, and/or, $R_3$ and $R_4$, together with the nitrogen atom to which they are linked, can form a 4- to 8-membered heterocyclic ring, which may contain one or two heteroatoms selected from O, S, S(=O), $SO_2$, or N, and which may be substituted with, a 4- to 8-membered heterocyclic ring, which may contain one or two heteroatoms selected from O, S, or N, and which may be substituted with a lower alkyl, or, a lower alkyl optionally substituted with OR', NR'R", C(=O)NR'R" or COOR' in which R' and R" are the same or different and are selected from H, lower alkyl optionally substituted with OR or COOR in which R is hydrogen or lower alkyl, and R' and R" together with the nitrogen atom to which they are linked, can form a 4- to 8-membered heterocyclic ring, which may contain one or two heteroatoms selected from O, S, or N; or, (b) X is O, S, or $NR_9$, in which $R_9$ is selected from hydrogen, CN, OH, $NH_2$, lower alkyl, lower alkenyl, or lower alkynyl, these groups being unsubstituted or substituted with cycloalkyl optionally interrupted with 1 or 2 heteroatoms chosen from O, S, S(=O), $SO_2$, or N, cycloalkenyl optionally interrupted with 1 or 2 heteroatoms chosen from O, S, S(=O), $SO_2$, or N, aryl, heteroaryl, $OR_{10}$, or $NR_{10}R_{11}$ in which $R_{10}$ and $R_{11}$ are the same or different and are selected from hydrogen or lower alkyl;

(c) Y is selected from O, S, or N—$R_{12}$, in which $R_{12}$ is selected from hydrogen, CN, OH, $NH_2$, lower alkyl, lower alkenyl, or lower alkynyl, these groups being unsubstituted or substituted with cycloalkyl optionally interrupted with 1 or 2 heteroatoms chosen from O, S, S(=O), $SO_2$, or N, cycloalkenyl optionally interrupted with 1 or 2 heteroatoms chosen from O, S, S(=O), $SO_2$, or N, aryl, heteroaryl, $OR_{10}$, or $NR_{10}R_{11}$ in which $R_{10}$ and $R_{11}$ are the same or different and are selected from hydrogen or lower alkyl;

(d) Z is chosen from CH—$NO_2$, O, S, or $NR_{13}$ in which $R_{13}$ is selected from hydrogen, CN, OH, $NH_2$, aryl, heteroaryl, cycloalkyl optionally interrupted with one or several heteroatoms chosen from O, S, S(=O), $SO_2$, or N, cycloalkenyl optionally interrupted with one or several heteroatoms chosen from O, S, S(=O), $SO_2$, or N, C(=O)$R_{14}$, C(=O)$NR_{14}R_{15}$, $OR_{14}$, or, lower alkyl, unsubstituted or substituted with one or several groups which are the same or different and which are selected $OR_{14}$ or $NR_{14}R_{15}$;

$R_{14}$ and $R_{15}$ being independently selected from hydrogen or lower alkyl, or, $R_{14}$ and $R_{15}$, together with the nitrogen atom to which they are linked, can form a 4- to 8-membered heterocyclic ring which may contain one or two heteroatoms chosen from O, S, or N, and which may be substituted with a lower alkyl;

(e) $Z_1$ is chosen from H, $CH_3$, or $NR_{16}R_{17}$ in which $R_{16}$ and $R_{17}$ are the same or different and are selected from hydrogen, CN, aryl, heteroaryl, cycloalkyl optionally interrupted with one or several heteroatoms chosen from O, S, S(=O), $SO_2$, or N, cycloalkenyl optionally interrupted with one or several heteroatoms chosen from O, S, S(=O), $SO_2$, or N, C(=O)$R_{14}$, C(=O)$NR_{14}R_{15}$, $OR_{14}$, or, lower alkyl unsubstituted or substituted with one or several groups selected from $OR_{14}$ or $NR_{14}R_{15}$, $R_{14}$ and $R_{15}$ being chosen from hydrogen or lower alkyl, and, $R_{14}$ and $R_{15}$, and/or, $R_{16}$ and $R_{17}$, together with the nitrogen atom to which they are linked, can form a 4- to 8-membered heterocyclic ring which may contain one or two heteroatoms chosen from P, S, or N, and which may be substituted with a lower alkyl;

(f) A is a cycle selected from:

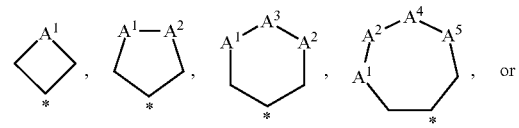

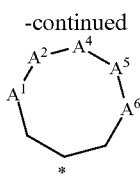

in which $A_1, A_2, A_3, A_4, A_5$, and $A_6$ are the same or different and are selected from O, S, C, C(=O), SO, $SO_2$, or $NR_{18}$ in which $R_{18}$ is selected from hydrogen, aryl, heteroaryl, cycloalkyl optionally interrupted with one or several heteroatoms chosen from O, S, S(=O), $SO_2$, or N, cycloalkenyl optionally interrupted with one or several heteroatoms chosen from O, S, S(=O), $SO_2$, or N, lower alkyl unsubstituted or substituted with aryl, heteroaryl, cycloalkyl optionally interrupted with one or several heteroatoms chosen from O, S, S(=O), $SO_2$, or N, cycloalkenyl optionally interrupted with one or several heteroatoms chosen from O, S, S(=O), $SO_2$, or N, CN, $NR_{19}R_{20}$, C(=O)$NR_{19}R_{20}$, $OR_{19}$, C(=O)$R_{19}$ or C(=O)$OR_{19}$ in which $R_{19}$ and $R_{20}$ are identical or different and are selected from hydrogen or lower alkyl;

* represents the carbon atom which is shared between the cycle A and the backbone cycle containing X and/or Y;

each carbon atom of the cycle A is unsubstituted or substituted with 1 or 2 groups, identical or different, selected from lower alkyl optionally substituted with $OR_{21}$, $NR_{21}R_{22}$, $COOR_{21}$, or $CONR_{21}R_{22}$, lower haloalkyl, CN, F, =O, $SO_2NR_{19}R_{20}$, $OR_{19}$, $SR_{19}$, C(=O)$OR_{19}$, C(=O)$NR_{19}R_{20}$, or $NR_{19}R_{20}$ in which $R_{19}$ and $R_{20}$ are identical or different and are selected from hydrogen or lower alkyl optionally substituted with $OR_{21}$, $NR_{21}R_{22}$, $COOR_{21}$, or $CONR_{21}R_{22}$, in which $R_{21}$ and $R_{22}$ are identical or different and are selected from hydrogen or lower alkyl, and, $R_{19}$ and $R_{20}$, and/or, $R_{21}$ and $R_{22}$, together with the nitrogen atom to which they are linked, can form a 4- to 8-membered heterocyclic ring;

two atoms of the cycle A, which are not adjacent, may be linked by a 2, 3 or 4 carbon atom chain which may be interrupted with 1 heteroatom chosen from O, S or N; provided that not more than two of the groups $A_1, A_2, A_3, A_4, A_5$, and $A_6$ simultaneously represent a heteroatom; and their tautomeric forms, their racemic forms, their isomers, and their pharmaceutically acceptable derivatives;

In regard to the above compounds, halogen includes fluoro, chloro, bromo, and iodo. Preferred halogens are F and Cl. Lower alkyl includes straight and branched carbon chains having from 1 to 6 carbon atoms. Examples of such alkyl groups include methyl, ethyl, isopropyl, and tert-butyl. Lower alkenyl includes straight and branched hydrocarbon radicals having from 2 to 6 carbon atoms and at least one double bond. Examples of such alkenyl groups are ethenyl, 3-buten-1-yl, 2-ethenylbutyl, and 3-hexen-1-yl. Lower alkynyl includes straight and branched hydrocarbon radicals having from 2 to 6 carbon atoms and at least one triple bond. Examples of such alkynyl groups are ethynyl, 3-butyn-1-yl, propynyl, 2-butyn-1-yl, and 3-pentyn-1-yl. Lower haloalkyl includes a lower alkyl as defined above, substituted with one or several halogens. An example of haloalkyl is trifluoromethyl. Aryl is understood to refer to an aromatic carbocycle containing between 6 and 10 carbon atoms. An example of an aryl group is phenyl. Heteroaryl includes aromatic cycles which have from 5 to 10 ring atoms, from 1 to 4 of which are independently selected from the group consisting of O, S, and N. Representative heteroaryl groups have 1, 2, 3 or 4 heteroatoms in a 5- or 6-membered aromatic ring. Examples of such groups are tetrazole, pyridyl, and thienyl. Representative cycloalkyl contain from 3 to 8 carbon atoms. Examples of such groups are cyclopropyl, cyclobutyl, cyclopentyl, cyclohexyl, cycloheptyl and cyclooctyl. The term "interrupted" means that in a backbone chain, a carbon atom is replaced by an heteroatom or a group as defined herein. For example, in "cycloalkyl or cycloalkenyl optionally interrupted with C(=O) or with 1 heteroatom chosen from O, S, S(=O), $SO_2$ or N", the term "interrupted" means that C(=O) or a heteroatom can replace a carbon atom of the ring. Example of such groups are morpholine or piperazine. Cycloalkenyl includes 3- to 10-membered cycloalkyl containing at least one double bond. Heterocyclic rings include heteroaryl as defined above and cycloalkyl or cycloalkenyl, as defined above, interrupted with 1, 2 or 3 heteroatoms chosen from O, S, S(=O), $SO_2$, or N. Bicyclic substituents refer to two cycles, which are the same or different and which are chosen from aryl, heterocyclic ring, cycloalkyl or cycloalkenyl, fused together to form said bicyclic substituents. An example of a bicyclic substituent is indolyl.

In one embodiment, a PDE7 inhibitor useful in the methods of the invention has the formula:

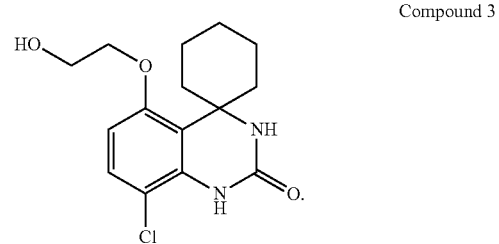 [SMILES: O=C1Nc2c(Cl)ccc(OCCO)c2C2(CCCCC2)N1]

Compound 3

In other embodiments, PDE7 inhibitors useful in the methods of the invention have the formulas:

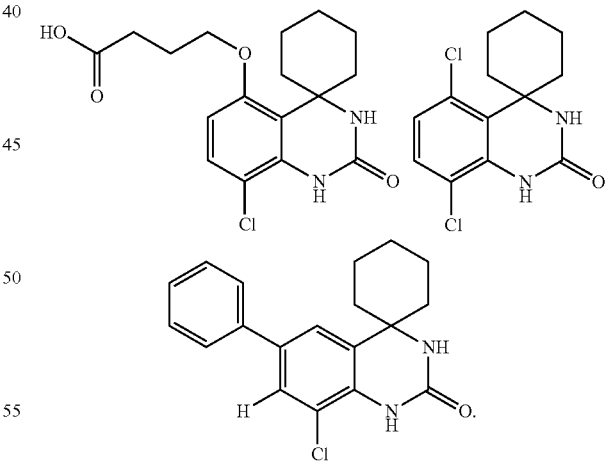

The preparation of the above compounds is described in US 2002/0198198, WO 2002/076953, WO 2002/074754, WO 2006/092691, *Bioorganic & Medicinal Chemistry Letters* 14 (2004) 4623-4626, and *Bioorganic & Medicinal Chemistry Letters* 14 (2004) 4627-4631.

In another embodiment, PDE7 inhibitors useful in the methods of the invention are selected from those compounds generally or specifically disclosed in EP 1 193 261, WO 2002/28847, US 20030045557, U.S. Pat. No. 7,122,565,

*Bioorganic & Medicinal Chemistry Letters* 14 (2004) 4607-4613, and *Bioorganic & Medicinal Chemistry Letters* 14 (2004) 4615-4621, each expressly incorporated herein by reference in its entirety. In one embodiment, PDE7 inhibitors useful in the methods of the invention have the formula:

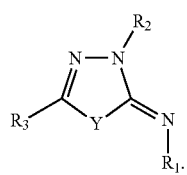

(3)

The substituents for the above compounds are defined as follows:

Y is S or O;

$R_1$ is $C_1$-$C_{10}$ alkyl, $C_2$-$C_{10}$ alkenyl, $C_2$-$C_{10}$ alkynyl, cycloalkyl, cycloalkenyl, heterocycle, aryl, or a polycyclic group; each optionally substituted with one or several groups $X_1$—$R_4$, identical or different, in which $X_1$ is a single bond, lower alkylene, $C_2$-$C_6$ alkenylene, cycloalkylene, arylene, or divalent heterocycle, and $R_4$ is:

(1) H, =O, $NO_2$, CN, halogen, lower haloalkyl, lower alkyl, carboxylic acid bioisostere;

(2) $COOR_5$, $C(=O)R_5$, $C(=S)R_5$, $SO_2R_5$, $SOR_5$, $SO_3R_5$, $SR_5$, $OR_5$;

(3) $C(=O)NR_7R_8$, $C(=S)NR_7R_8$, $C(=CH-NO_2)NR_7R_8$, $C(=N-CN)NR_7R_8$, $C(=N-SO_2NH_2)NR_7R_8$, $C(=NR_7)NHR_8$, $C(=NR_7)R_8$, $C(=NR_9)NHR_8$, $C(=NR_9)R_8$, $SO_2NR_7R_8$, or $NR_7R_8$, wherein $R_7$ and $R_8$ are the same or different and are selected from OH, $R_5$, $R_6$, $C(=O)NR_5R_6$, $C(=O)R_5$, $SO_2R_5$, $C(=NR_9)NHR_{10}$, $C(=NR_9)R_{10}$, $C(=CH-NO_2)NR_9R_{10}$, $C(=N-SO_2NH_2)NR_9R_{10}$, $C(=N-CN)NR_9R_{10}$, or $C(=S)NR_9R_{10}$;

$R_2$ is lower alkyl, $C_2$-$C_{10}$ alkenyl, $C_2$-$C_{10}$ alkynyl, cycloalkyl, cycloalkenyl, heterocycle, aryl; each optionally substituted with one or several groups which are the same or different and which are selected from:

(1) H, carboxylic acid bioisostere, lower haloalkyl, halogen, (2) $COOR_5$, $OR_5$, $SO_2R_5$, (3) $SO_2NR_{11}R_{12}$, $C(=O)NR_{11}R_{12}$, $NR_{11}R_{12}$, wherein $R_{11}$ and $R_{12}$ are the same or different and are selected from OH, $R_5$, $R_6$, $C(=O)NR_5R_6$, $C(=O)R_5$, $SO_2R_5$, $C(=S)NR_9R_{10}$, $C(=CH-NO_2)NR_9R_{10}$, $C(=N-CN)NR_9R_{10}$, $C(=N-SO_2NH_2)NR_9R_{10}$, $C(=NR_9)NHR_{10}$, or $C(=NR_9)R_{10}$;

$R_3$ is $X_2$—$R'_3$, wherein $X_2$ is a single bond or, a group selected from $C_1$-$C_4$ alkylene, $C_2$-$C_6$ alkenylene, $C_2$-$C_6$ alkynylene, each optionally substituted with one or several groups which are the same or different and which are selected from:

(1) H, $C_1$-$C_3$ alkyl, $C_3$-$C_4$ cycloalkyl, aryl, heterocycle, =O, CN, (2) $OR_5$, =$NR_5$; or (3) $NR_{13}R_{14}$, wherein $R_{13}$ and $R_{14}$ are the same or different and are selected from $R_5$, $R_6$, $C(=O)NR_5R_6$, $C(=O)R_5$, $SO_2R_5$, $C(=S)NR_9R_{10}$, $C(=CH-NO_2)NR_9R_{10}$, $C(=NR_9)NHR_{10}$, or $C(=NR_9)R_{10}$;

$R'_3$ is cycloalkyl, cycloalkenyl, aryl, heterocycle, or a polycyclic group; each optionally substituted with one or several groups $X_3$—$R_{17}$ wherein $X_3$ is a single bond, lower alkylene, $C_2$-$C_6$ alkenylene, $C_2$-$C_6$ alkynylene, cycloalkylene, arylene, divalent heterocycle or a divalent polycyclic group, and, $R_{17}$ is:

(1) H, =O, $NO_2$, CN, lower haloalkyl, halogen, carboxylic acid bioisostere, cycloalkyl, (2) $COOR_5$, $C(=O)R_5$, $C(=S)R_5$, $SO_2R_5$, $SOR_5$, $SO_3R_5$, $SR_5$, $OR_5$;

(3) $C(=O)NR_{15}R_{16}$, $C(=S)NR_{15}R_{16}$, $C(=N-CN)NR_{15}R_{16}$, $C(=N-SO_2NH_2)NR_{15}R_{16}$, $C(=CH-NO_2)NR_{15}R_{16}$, $SO_2NR_{15}R_{16}$, $C(=NR_{15})NHR_{16}$, $C(=NR_{15})R_{16}$, $C(=NR_9)NHR_{16}$, $C(=NR_9)R_{16}$, or $NR_{15}R_{16}$ wherein $R_{15}$ and $R_{16}$ are the same or different and are selected from OH, $R_5$, $R_6$, $C(=O)NR_5R_6$, $C(=O)R_5$, $SO_2R_5$, $C(=S)NR_9R_{10}$, $C(=CH-NO_2)NR_9R_{10}$, $C(=N-CN)NR_9R_{10}$, $C(=N-SO_2NH_2)NR_9R_{10}$, $C(=NR_9)NHR_{10}$ or $C(=NR_9)R_{10}$, (4) heterocycle optionally substituted with one or several groups $R_5$;

wherein $R_5$ and $R_6$ are the same or different and are selected from H, lower alkyl, $C_2$-$C_6$ alkenyl, $C_2$-$C_6$ alkynyl, $X_4$-cycloalkyl, $X_4$-cycloalkenyl, $X_4$-aryl, $X_4$-heterocycle or $X_4$-polycyclic group, wherein $X_4$ is a single bond, lower alkylene, or $C_2$-$C_6$ alkenylene; each optionally substituted with one or several groups that are the same or different and selected from halogen, =O, $COOR_{20}$, CN, $OR_{20}$, O-lower alkyl optionally substituted with $OR_{20}$, $C(=O)$-lower alkyl, lower haloalkyl,

in which $X_5$ is a single bond or lower alkylene and $R_{18}$, $R_{19}$, and $R_{20}$, are the same or different and are selected from H or lower alkyl;

$X_6$-heterocycle, $X_6$-aryl, $X_6$-cycloalkyl, $X_6$-cycloalkenyl, or $X_6$-polycyclic group, wherein $X_6$ is a single bond or lower alkylene, these groups being optionally substituted with one or several groups, identical or different, selected from halogens, $COOR_{21}$, $OR_{21}$, or $(CH_2)_n NR_{21}R_{22}$ in which n is 0, 1, or 2 and $R_{21}$ and $R_{22}$ are the same or different and are selected from H or lower alkyl;

$R_9$ is selected from H, CN, OH, lower alkyl, O-lower alkyl, aryl, heterocycle, $SO_2NH_2$, or

in which $X_5$ is a single bond or lower alkylene and $R_{18}$ and $R_{19}$ are the same or different and are selected from H or lower alkyl;

$R_{10}$ is selected from hydrogen, lower alkyl, cyclopropyl, or heterocycle;

or their pharmaceutically acceptable derivatives.

In regard to the above compounds, aryl refers to an unsaturated carbocycle, exclusively comprising carbon atoms in the cyclic structure, the number of which is between 5 and 10, including phenyl, naphthyl, or tetrahydronaphthyl. Heterocycle refers to a nonsaturated or saturated monocycle containing between 1 and 7 carbon atoms in the cyclic structure and at least one heteroatom in the cyclic structure, such as nitrogen, oxygen, or sulfur, preferably from 1 to 4 heteroatoms, identical or different, selected from nitrogen, sulfur and oxygen atoms. Suitable heterocycles include morpholinyl, piperazinyl, pyrrolidinyl, piperidinyl, pyrimidinyl, 2- and 3-furanyl, 2- and 3-thienyl, 2-pyridyl, 2- and 3-pyranyl, hydroxypyridyl, pyrazolyl, isoxazolyl, tetrazole, imidazole, triazole, and the like. Polycyclic groups include at least two cycles, identical or different, selected from aryl, heterocycle, cycloalkyl, cycloalkenyl groups fused together to form said polycyclic group such as 2- and 3-benzothienyl, 2- and 3-benzofuranyl, 2-indolyl, 2- and 3-quinolinyl, acridinyl, quinazolinyl, indolyl benzo[1,3]dioxolyl, and 9-thioxantanyl. Bicyclic groups refer to two cycles, which are the same or different and which are chosen from aryl, heterocycle, cycloalkyl or cycloalkenyl, fused together to form said bicyclic groups. Halogen refers to fluorine, chlorine, bromine, or iodine. Lower alkyl refers to an alkyl is linear or branched and contains 1 to 6 carbon atoms. Examples of lower alkyl groups include methyl, ethyl, propyl, butyl, isopropyl, tert-butyl, isobutyl, n-butyl, pentyl, hexyl and the like. Alkenyl refers to a linear or branched unsaturated carbon atom chain, comprising one or several double bonds, preferably one or two double bonds. Alkynyl refers to a linear or branched unsaturated carbon atom chain, comprising one or several triple bonds, preferably one or two triple bonds. Lower haloalkyl refers to a lower alkyl substituted with one or several halogens; preferred lower haloalkyl groups include perhaloalkyl groups such as $CF_3$. Cycloalkyl refers to saturated monocarbocyle containing from 3 to 10 carbon atoms; including cyclopropyl, cyclobutyl, cyclopentyl, cyclohexyl, and cycloheptyl. Cycloalkenyl refers to unsaturated monocarbocyle containing from 3 to 10 carbon atoms. Examples of suitable cycloalkenyl are 3-cyclohexene, and 3-cycloheptene. Carboxylic acid bioisostere has the classical meaning; common carboxylic acid bioisostere are tetrazole-5-yl, C(=O)N(H)OH, isoxazol-3-yl, hydroxythiadiazolyl, sulfonamido, sulfonylcarboxamido, phosphonic acid, phosphonamido, phosphinic acid, sulfonic acids, acyl sulfonamido, mercaptoazole, acyl cyanamides.

In one embodiment, a PDE7 inhibitor useful in the methods of the invention has the formula:

Compound 4

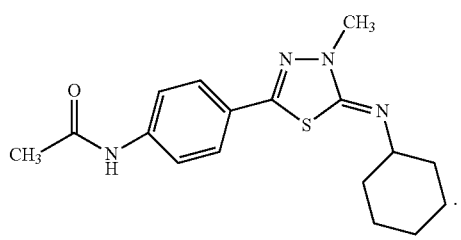

In other embodiments, PDE7 inhibitors useful in the methods of the invention have the formulas:

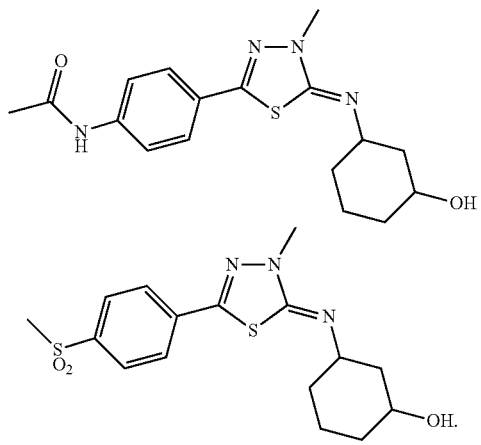

The preparation of the above compounds is described in EP 1 193 261, WO 02/28847, US 20030045557, U.S. Pat. No. 7,122,565, *Bioorganic & Medicinal Chemistry Letters* 14 (2004) 4607-4613, and *Bioorganic & Medicinal Chemistry Letters* 14 (2004) 4615-4621.

In another embodiment, PDE7 inhibitors useful in the methods of the invention are selected from those compounds generally or specifically disclosed in WO 2004/111054, US 20060128728, and US 20070270419, each expressly incorporated herein by reference in its entirety. In one embodiment, PDE7 inhibitors useful in the methods of the invention have the formulas:

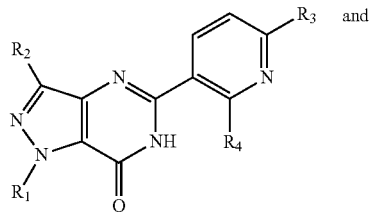
(4A)

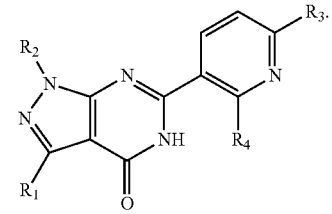
(4B)

The substituents for the above compounds are defined as follows:

$R_1$ is a substituted or unsubstituted $C_{3-8}$ cycloalkyl group or tert-butyl group;

$R_2$ is a hydrogen atom or $C_{1-3}$ alkyl group;

$R_3$ is a group: $NR_5R_6$, $C(=O)R_7$, or $S(O)_{0-2}R_8$;

$R_4$ is a hydrogen atom or $C_{1-3}$ alkoxyl group which is unsubstituted or substituted by one or more fluorine atom(s);

$R_5$ and $R_6$ are, same or different from each other, a hydrogen atom, substituted or unsubstituted $C_{1-6}$ alkyl group, substituted or unsubstituted acyl group, substituted or unsubstituted heterocycloalkyl group, and substituted or unsubstituted heterocycloalkyl ring formed with a nitrogen atom which is binding $R_5$ and $R_6$;

$R_7$ is a group: $OR_9$ or $NR_5R_6$;

$R_8$ is a hydrogen atom, a halogen atom, a group: $NR_5R_6$, substituted or unsubstituted $C_{1-6}$ alkyl group, or substituted or unsubstituted aryl group;

$R_9$ is a hydrogen atom or substituted or unsubstituted $C_{1-6}$ alkyl group;

or pharmaceutically acceptable salts or solvates thereof.

In regard to the above compounds, the term "$C_1$-$C_3$ alkyl group" includes a straight or branched-chained alkyl group having 1 to 3 carbon atoms. The term "$C_3$-$C_8$ cycloalkyl group" includes a cycloalkyl group having 3 to 8 carbon atoms such as cyclopropyl, cyclobutyl, cyclopentyl, cyclohexyl and cyclooctyl. The term "heterocycloalkyl group" is 3 to 7 membered heterocyclic group containing the same or different 1 to 4 hetero atom(s) such as oxygen, nitrogen or sulfur atom(s), and examples may include pyrrolidinyl, piperidinyl, piperazinyl, homopiperazinyl, tetrahydrofuryl, tetrahydrophyranyl, morpholinyl and azetidinyl. The term "$C_1$-$C_3$ alkoxy group" means alkoxy group having 1 to 3 carbon atoms. The term "acyl group" means acyl group having 1 to 8 carbon atoms. The term "aryl group" is phenyl, naphthyl, biphenyl group, having 6 to 12 carbon atoms, and the term "heteroaryl group" is 5 to 7 membered monocyclic or polycyclic group thereof containing 2 to 8 carbon atoms and the same or different 1 to 4 hetero atom(s) such as oxygen, nitrogen, sulfur atom(s). The examples include pyrrole, furyl, thienyl, imidazolyl, thiazolyl, pyrazinyl, indolyl, quinolinyl, isoquinolinyl, tetrazolyl, pyridinyl, pyrazolyl pyridazinyl and pyrimidinyl. Examples of suitable substituent of "substituted or unsubstituted $C_1$-$C_6$ alkyl group" include hydroxyl group and halogen atom, and examples of suitable substituent of "substituted or unsubstituted acyl group" include halogen atom and nitro group. Further, examples of suitable substituent of "substituted or unsubstituted aryl group" include $C_1$-$C_3$ alkyl, halogen atom, amino group, acyl group, amide group, hydroxyl group, acylamino group, carboxyl group and sulfonyl group. Examples of suitable substituent of "substituted or unsubstituted $C_3$-$C_8$ cycloalkyl group" is $C_1$-$C_3$ alkyl, hydroxyl group and oxo group, and examples of suitable substituent of "substituted or unsubstituted heterocycloalkyl group" may include carboxy group, acyl group, alkoxy group, amino group, alkylamino group, acylamino group, hydroxyl group, oxo group, ethylenedioxy group, methyl group, ethyl group and hydroxyethyl group.

In other embodiments, PDE7 inhibitors useful in the methods of the invention have the formulas:

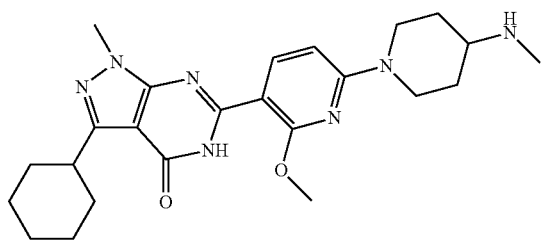

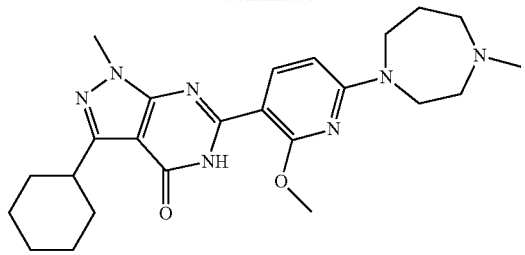

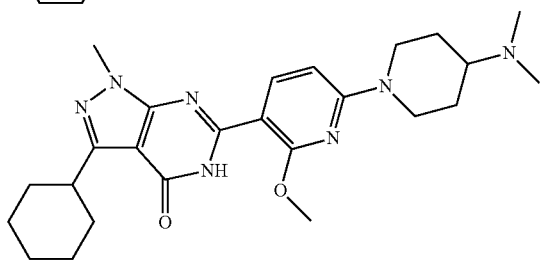

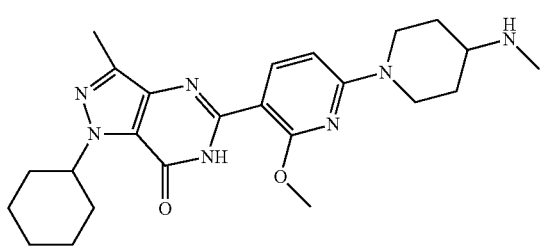

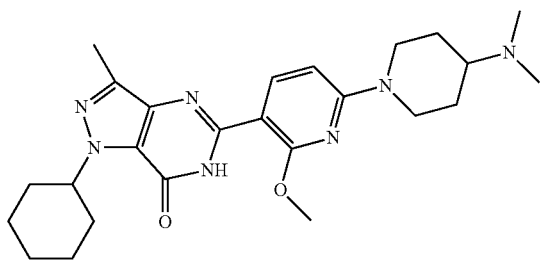

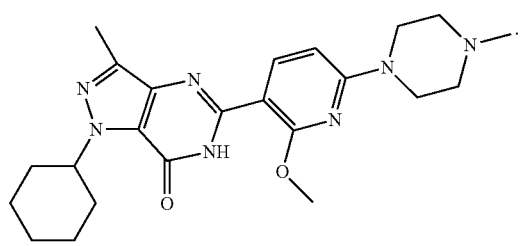

The preparation of the above compounds is described in WO 2004/111054, US 20060128728, and US 20070270419.

In another embodiment, PDE7 inhibitors useful in the methods of the invention are selected from those compounds generally or specifically disclosed in U.S. Pat. No. 6,903,109, US 20040082578, WO 2003/088963, and US 20060154949, each expressly incorporated herein by reference in its entirety. In one embodiment, PDE7 inhibitors useful in the methods of the invention have the formula:

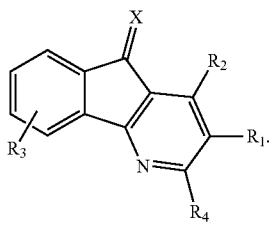

(5)

The substituents for the above compounds are defined as follows:

(a) $R_1$ is selected from the group consisting of:
(i) $COR_5$, wherein $R_5$ is selected from H, optionally substituted $C_{1-8}$ straight or branched chain alkyl, optionally substituted aryl and optionally substituted arylalkyl; wherein the substituents on the alkyl, aryl and arylalkyl group are selected from $C_{1-8}$ alkoxy, phenylacetyloxy, hydroxy, halogen, p-tosyloxy, mesyloxy, amino, cyano, carboalkoxy, or $NR_2OR_{21}$ wherein $R_{20}$ and $R_{21}$ are independently selected from the group consisting of hydrogen, $C_{1-8}$ straight or branched chain alkyl, $C_{3-7}$ cycloalkyl, benzyl, or aryl;
(ii) $COOR_6$, wherein $R_6$ is selected from H, optionally substituted $C_{1-8}$ straight or branched chain alkyl, optionally substituted aryl and optionally substituted arylalkyl; wherein the substituents on the alkyl, aryl and arylalkyl group are selected from C1-8 alkoxy, phenylacetyloxy, hydroxy, halogen, p-tosyloxy, mesyloxy, amino, cyano, carboalkoxy, or $NR_2OR_{21}$ wherein $R_{20}$ and $R_{21}$ are independently selected from the group consisting of hydrogen, $C_{1-8}$ straight or branched chain alkyl, $C_{3-7}$ cycloalkyl, benzyl, or aryl;
(iii) cyano;
(iv) a lactone or lactam formed with $R_4$;
(v) $CONR_7R_8$ wherein $R_7$ and $R_8$ are independently selected from H, $C_{1-8}$ straight or branched chain alkyl, $C_{3-7}$ cycloalkyl, trifluoromethyl, hydroxy, alkoxy, acyl, alkylcarbonyl, carboxyl, arylalkyl, aryl, heteroaryl, and heterocyclyl; wherein the alkyl, cycloalkyl, alkoxy, acyl, alkylcarbonyl, carboxyl, arylalkyl, aryl, heteroaryl, and heterocyclyl groups may be substituted with carboxyl, alkyl, aryl, substituted aryl, heterocyclyl, substituted heterocyclyl, heteroaryl, substituted heteroaryl, hydroxamic acid, sulfonamide, sulfonyl, hydroxy, thiol, alkoxy, or arylalkyl;
or $R_7$ and $R_8$ taken together with the nitrogen to which they are attached form a heterocyclyl or heteroaryl group;
(vi) a carboxylic ester or carboxylic acid bioisostere including optionally substituted heteroaryl groups;
(b) $R_2$ is selected from the group consisting of optionally substituted alkyl, optionally substituted aryl, optionally substituted heteroaryl, optionally substituted $C_{3-7}$ cycloalkyl, optionally substituted heterocyclyl, wherein the heterocyclyl is 1,3-dioxolane or furan, or $R_2$ is

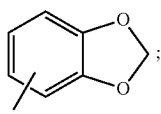

(c) $R_3$ is from one to four groups independently selected from the group consisting of:

(i) hydrogen, halo, $C_{1-8}$ straight or branched chain alkyl, arylalkyl, $C_{3-7}$ cycloalkyl, $C_{1-8}$ alkoxy, cyano, $C_{1-4}$ carboalkoxy, trifluoromethyl, $C_{1-8}$ alkylsulfonyl, halogen, nitro, hydroxy, trifluoromethoxy, $C_{1-8}$ carboxylate, aryl, heteroaryl, and heterocyclyl;
(ii) $NR_{10}R_{11}$ wherein $R_{10}$ and $R_{11}$ are independently selected from H, $C_{1-8}$ straight or branched chain alkyl, arylalkyl, $C_{3-7}$ cycloalkyl, carboxyalkyl, aryl, heteroaryl, or heterocyclyl, or $R_{10}$ and $R_{11}$ taken together with the nitrogen to which they are attached form a heterocyclyl or heteroaryl group;
(iii) $NR_{12}COR_{13}$ wherein $R_{12}$ is selected from hydrogen or alkyl and $R_{13}$ is selected from hydrogen, alkyl, substituted alkyl, $C_{1-3}$ alkoxyl, carboxyalkyl, $R_{30}R_{31}N(CH_2)_p$, $R_3OR_{31}NCO(CH_2)_p$, aryl, arylalkyl, heteroaryl, or heterocyclyl, or $R_{12}$ and $R_{13}$ taken together with the carbonyl group form a carbonyl containing heterocyclyl group, wherein $R_{30}$ and $R_{31}$ are independently selected from H, OH, alkyl, and alkoxy, and p is an integer from 1-6, wherein the alkyl group may be substituted with carboxyl, alkyl, aryl, substituted aryl, heterocyclyl, substituted heterocyclyl, heteroaryl, substituted heteroaryl, hydroxamic acid, sulfonamide, sulfonyl, hydroxy, thiol, alkoxy, or arylalkyl;
(d) $R_4$ is selected from the group consisting of (i) hydrogen, (ii) $C_{1-3}$ straight or branched chain alkyl, (iii) benzyl, and (iv) $NR_{13}R_{14}$, wherein $R_{13}$ and $R_{14}$ are independently selected from hydrogen and $C_{1-6}$ alkyl; wherein the $C_{1-3}$ alkyl and benzyl groups are optionally substituted with one or more groups selected from $C_{3-7}$ cycloalkyl, $C_{1-8}$ alkoxy, cyano, $C_{1-4}$ carboalkoxy, trifluoromethyl, $C_{1-8}$ alkylsulfonyl, halogen, nitro, hydroxy, trifluoromethoxy, $C_{1-8}$ carboxylate, amino, $NR_{13}R_{14}$, aryl, and heteroaryl; and
(e) X is selected from S and O;
and the pharmaceutically acceptable salts, esters and prodrug forms thereof.

In an alternative embodiment, $R_1$, $R_3$, and $R_4$ are as above and $R_2$ is $NR_{15}R_{16}$, where $R_{15}$ and $R_{16}$ are independently selected from hydrogen, $C_{1-8}$ straight or branched chain alkyl, arylalkyl, $C_{3-7}$ cycloalkyl, aryl, heteroaryl, and heterocyclyl, or $R_{15}$ and $R_{16}$ taken together with the nitrogen to which they are attached form a heterocyclyl or heteroaryl group.

In regard to the above compounds, "alkyl" refers to straight, cyclic and branched-chain alkyl. The alkyl group may be optionally substituted with one or more groups such as halogen, OH, CN, mercapto, nitro, amino, $C_1$-$C_8$-alkyl, $C_1$-$C_8$-alkoxyl, $C_1$-$C_8$-alkylthio, $C_1$-$C_8$-alkyl-amino, di($C_1$-$C_8$-alkyl)amino, (mono-, di-, tri-, and per-) halo-alkyl, formyl, carboxy, alkoxycarbonyl, $C_1$-$C_8$-alkyl-CO—O—, $C_1$-$C_8$-alkyl-CO—NH—, carboxamide, hydroxamic acid, sulfonamide, sulfonyl, thiol, aryl, aryl($C_1$-$C_8$)alkyl, heterocyclyl, and heteroaryl. The term "bioisostere" is defined as "groups or molecules which have chemical and physical properties producing broadly similar biological properties." (Burger's Medicinal Chemistry and Drug Discovery, M. E. Wolff, ed. Fifth Edition, Vol. 1, 1995, Pg. 785). The term "acyl" as used herein, whether used alone or as part of a substituent group, means an organic radical having 2 to 6 carbon atoms (branched or straight chain) derived from an organic acid by removal of the hydroxyl group. "Aryl" or "Ar," whether used alone or as part of a substituent group, is a carbocyclic aromatic radical including, but not limited to, phenyl, 1- or 2-naphthyl and the like. The carbocyclic aromatic radical may be substituted by independent replacement of 1 to 5 of the hydrogen atoms thereon with halogen, OH, CN, mercapto, nitro, amino, $C_1$-$C_8$-alkyl, $C_1$-$C_8$-alkoxyl, $C_1$-$C_8$-alkylthio, $C_1$-$C_8$-alkyl-amino, di($C_1$-$C_8$-alkyl)amino, (mono-, di-, tri-, and per-) halo-alkyl, formyl, carboxy, alkoxycarbonyl, $C_1$-$C_8$-alkyl-CO—O—, $C_1$-$C_8$-alkyl-CO—NH—, or carboxamide. Illustrative aryl radicals include, for example, phenyl, naphthyl, biphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl and the like. The term "heteroaryl" refers to a cyclic, fully unsaturated radical having from five to ten ring atoms of which one ring atom is selected from S, O, and N; 0-2 ring atoms are additional heteroatoms independently selected from S, O, and N; and the remaining ring atoms are carbon. The radical may be joined to the rest of the molecule via any of the ring atoms. The terms "heterocycle," "heterocyclic," and "heterocycle" refer to an optionally substituted, fully or partially saturated cyclic group which is, for example, a 4- to 7-membered monocyclic, I-5 to 11-membered bicyclic, or 10- to 15-membered tricyclic ring system, which has at least one heteroatom in at least one carbon atom containing ring. Each ring of the heterocyclic group containing a heteroatom may have 1, 2, or 3 heteroatoms selected from nitrogen atoms, oxygen atoms, and sulfur atoms, where the nitrogen and sulfur heteroatoms may also optionally be oxidized. The nitrogen atoms may optionally be quaternized. The heterocyclic group may be attached at any heteroatom or carbon atom.

In other embodiments, PDE7 inhibitors useful in the methods of the invention have the formulas:

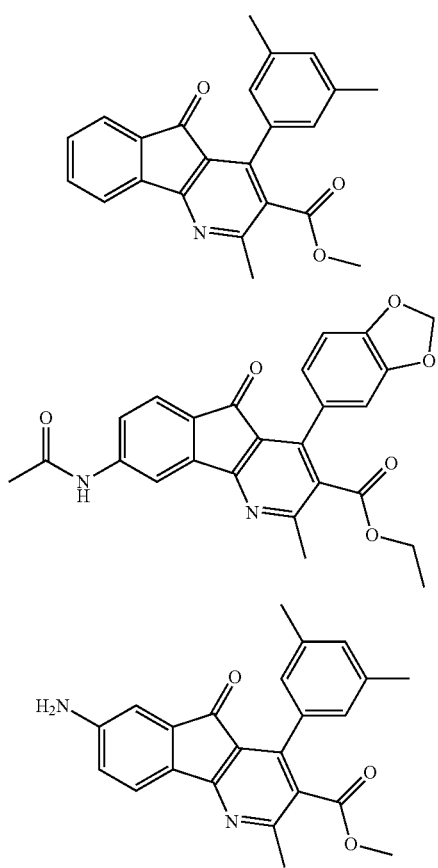

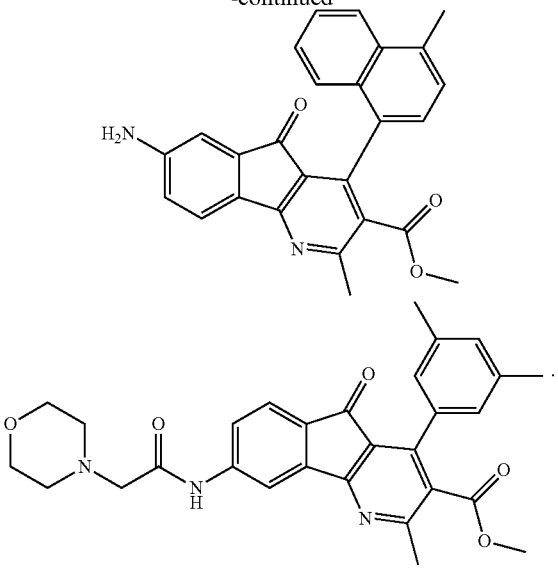

The preparation of the above compounds is described in U.S. Pat. No. 6,903,109, US 20040082578, WO 2003/088963, and US 20060154949.

In another embodiment, PDE7 inhibitors useful in the methods of the invention are selected from those compounds generally or specifically disclosed in U.S. Pat. No. 6,958,328, WO 2002/085894, and US 20030212089, each expressly incorporated herein by reference in its entirety. These PDE7 inhibitors have the same formula as those described above (e.g., U.S. Pat. No. 6,903,109), except that $R_1$ is not a carboxylic ester or carboxylic acid bioisostere. The preparation of these compounds is described in U.S. Pat. No. 6,958,328, US 20030212089, and WO 2002/085894.

In another embodiment, PDE7 inhibitors useful in the methods of the invention are selected from those compounds generally or specifically disclosed in WO 2006/004040 and EP 1 775 298, each expressly incorporated herein by reference in its entirety. In one embodiment, PDE7 inhibitors useful in the methods of the invention have the formula:

(6)

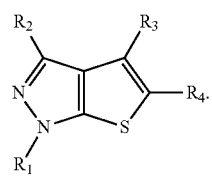

The substituents for the above compounds are defined as follows:

$R_1$ is substituted or unsubstituted $C_{3-8}$ alkyl group, substituted or unsubstituted cycloalkyl group, or substituted or unsubstituted heterocycloalkyl group (e.g., cyclohexyl, cycloheptyl, or tetrahydropyranyl);

$R_2$ is a hydrogen atom or substituted or unsubstituted $C_{1-3}$ alkyl group (e.g., methyl);

$R_3$ is a hydrogen atom, substituted or unsubstituted $C_{1-3}$ alkyl group, or a halogen atom; and $R_4$ is substituted or unsubstituted aryl group, substituted or unsubstituted heteroaryl group, or a group $CONR_5R_6$, or $CO_2R_7$, wherein $R_5$ and $R_6$ are, same or different from each other, a hydrogen atom; $C_{1-6}$ alkyl group which may be substituted by a halogen atom, substituted or unsubstituted aryl group, substituted or unsubstituted heteroaryl group, substituted or unsubstituted heterocycloalkyl group, substituted or unsubstituted cycloalkyl group, a group $NR_7COR_8$, $COR_5$, $NR_9R_{10}$; substituted or unsubstituted cycloalkyl group; substituted or unsubstituted heterocycloalkyl group; substituted or unsubstituted aryl group; substituted or unsubstituted heteroaryl group; or substituted or unsubstituted heterocycloalkyl group in which the ring is formed together with the nitrogen atom binding $R_5$ and $R_6$;

wherein $R_7$ is a hydrogen atom or substituted or unsubstituted $C_{1-3}$ alkyl group;

wherein $R_8$ is substituted or unsubstituted heterocycloalkyl group, or a group OH, $OR_7$, or $NR_9R_{10}$;

wherein $R_9$ and $R_{10}$ are, same or different from each other, a hydrogen atom; substituted or unsubstituted $C_{1-3}$ alkyl group, substituted or unsubstituted heterocycloalkyl group; substituted or unsubstituted acyl; a group $SO_2R_7$, or substituted or unsubstituted heterocycloalkyl group in which the ring is formed together with the nitrogen atom binding $R_5$ and $R_6$;

or pharmaceutically acceptable salts or solvates thereof.

In regard to the above compounds, the term "cycloalkyl group" means cycloalkyl group having 3 to 8 carbon atoms. The term "heterocycloalkyl group" may be 3 to 7 membered monocyclic or polycyclic heterocyclic group containing the same or different 1 to 4 hetero atom(s) such as oxygen, nitrogen or sulfur atom(s), and examples may include piperidinyl, pyrrolidinyl, piperazinyl, tetrahydrofuryl, tetrahydropyranyl, morpholinyl, azetidinyl, imidazolidinyl, oxazolidinyl, hexahydropyrrolidinyl, octahydroindolidinyl, octahydroquinolidinyl, octahydroindolyl, and oxo-derivatives thereof. The term "aryl group" may be aromatic hydrocarbon group, which consists of mono-benzene ring, or binding or condensed benzene ring, such as phenyl, naphthyl, biphenyl and the like; and dicyclic or tricyclic group, which consists of benzene ring condensed with cycloalkyl or heterocyclic ring, such as 1,2,3,4-tetrahydronaphthalene, 2,3-dihydroindene, indoline, coumarone and the like. The term "heteroaryl group" may be 5 to 7 membered monocyclic heteroaryl group or polycyclic heteroaryl group, and having 2 to 8 carbon atoms with 1 to 4 hetero atom(s) such as oxygen, nitrogen, sulfur atom(s), in which the polycyclic heteroaryl group has condensed ring system by the same or different mono cyclic heteroaryl or benzene ring each other; or polycyclic group which is consisted of heteroaryl group condensed with cycloalkyl or heterocycloalkyl ring. Examples of suitable substituent of the present invention may include straight, branched-chained or cyclic $C_1$-$C_8$ alkyl group, which may be substituted by one or more methyl, ethyl, propyl, isopropyl, n-butyl, t-butyl, cyclohexyl, cycloheptyl, methoxymethyl, hydroxymethyl, trifluoromethyl, $C_1$-$C_3$ alkoxy group, halogen atom, and hydroxyl group; hydroxyl group; cyano group; substituted or unsubstituted alkoxy group such as methoxy, ethoxy group; amino group which may be substituted by $C_1$-$C_6$ alkyl group or acyl group such as amino, methylamino, ethylamino, dimethylamino, acylamino and the like; carboxylic group; substituted or unsubstituted ester group; phosphate group; sulfonic group; substituted or unsubstituted aryl group; substituted or unsubstituted heteroaryl group; saturated or unsaturated heterocycloalkyl group which may be substituted; substituted or unsubstituted carbamoyl group; substituted or unsubstituted amide group; substituted or unsubstituted thioamide group; halogen atom; nitro group; substituted or unsubstituted sulfone group; substituted or unsubstituted sulfonylamide group; oxo group; substituted or unsubstituted urea group; straight, branched-chained or cyclic alkenyl group such as ethenyl, propenyl, cyclohexenyl and the like.

In other embodiments, PDE7 inhibitors useful in the methods of the invention have the formulas:

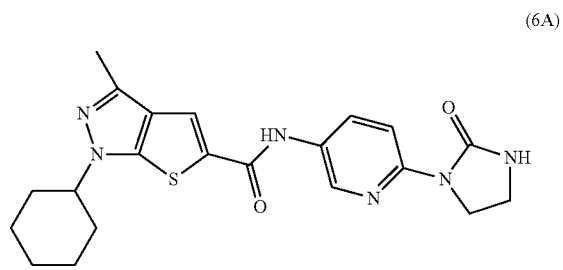

(6A)

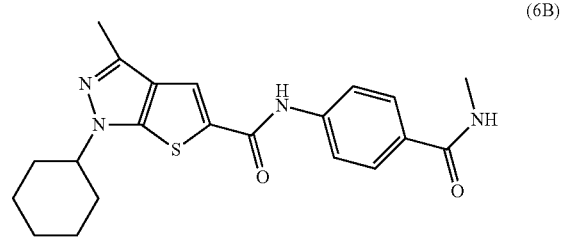

(6B)

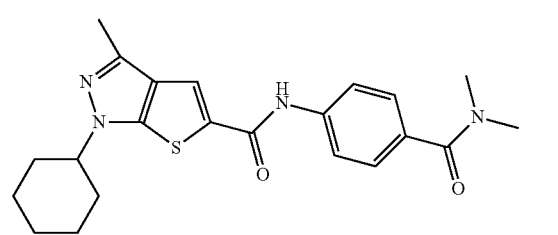

(6C)

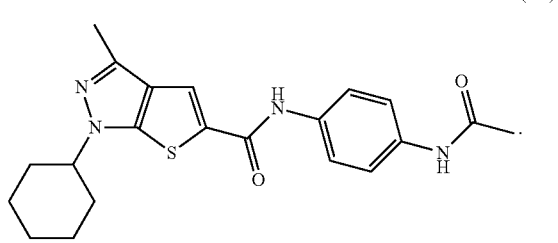

(6D)

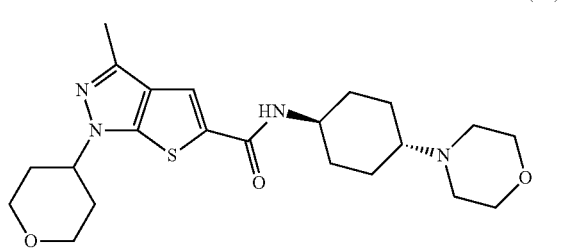

(6E)

-continued (6F)
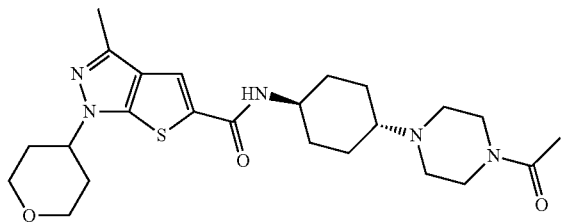

(6G)
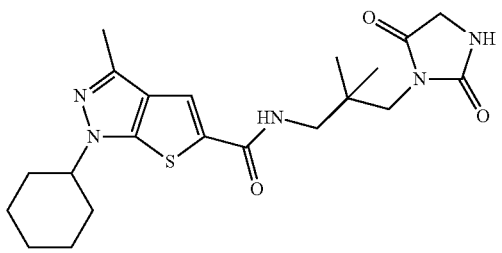

(6H)
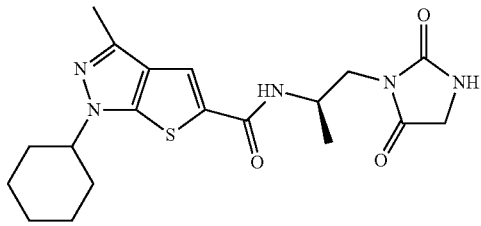

The preparation of the above compounds is described in EP 1 775 298 and WO 2006/004040.

In another embodiment, PDE7 inhibitors useful in the methods of the invention are selected from those compounds generally or specifically disclosed in WO 2004/111053 and US 20060128707, each expressly incorporated herein by reference in its entirety. In one embodiment, PDE7 inhibitors useful in the methods of the invention have the formulas:

(7A)
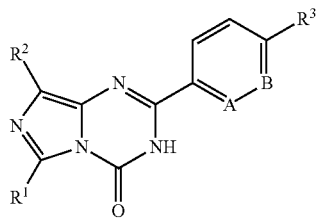

(7B)
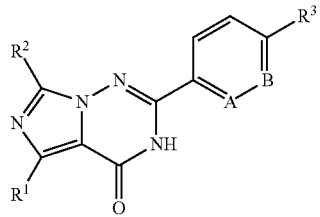

The substituents for the above compounds are defined as follows:

A is N or $CR_4$;

B is N or CH;

$R_1$ is substituted or unsubstituted $C_{3-8}$ cycloalkyl group or tert-butyl group;

$R_2$ is a hydrogen atom or $C_{1-6}$ alkyl group;

$R_3$ is a hydrogen atom; nitro group; cyano group; a halogen atom; heteroaryl group; substituted or unsubstituted $C_{1-6}$ alkyl group; substituted or unsubstituted $C_{2-6}$ alkenyl group; saturated or unsaturated heterocycloalkyl group which is substituted or unsubstituted; a group: $NR_5R_6$, $C(O)R_7$, $SO_2R_7$, $OR_8$, $NR_8COR_7$, $NR_8SO_2R_7$;

$R_4$ is a hydrogen atom or $C_{1-3}$ alkoxy group which is unsubstituted or substituted by one or more fluorine atom(s);

$R_5$ and $R_6$ are, same or different from each other, a hydrogen atom; substituted or unsubstituted $C_{1-6}$ alkyl group; substituted or unsubstituted acyl group; or substituted or unsubstituted heterocycloalkyl group;

$R_7$ is a hydrogen atom; substituted or unsubstituted $C_{1-6}$ alkyl group; substituted or unsubstituted heterocycloalkyl group; OH; $OR_8$ or $NR_5R_6$;

$R_8$ is a hydrogen atom, substituted or unsubstituted $C_{1-6}$ alkyl group; or substituted or unsubstituted heterocycloalkyl group;

or pharmaceutically acceptable salts or solvates thereof.

In regard to the above compounds, the term "$C_1$-$C_6$ alkyl group" refers to a straight or branched-chained alkyl group having 1 to 6 carbon atoms, and the term "$C_2$-$C_6$ alkenyl group" refers to a straight or branched-chained alkenyl group having 2 to 6 carbon atoms. The term "cycloalkyl group" refers to a cycloalkyl group having 3 to 8 carbon atoms such as cyclopropyl, cyclobutyl, cyclopentyl, cyclohexyl, cycloheptyl, and cyclooctyl. The term "heterocycloalkyl group" is 3 to 7 membered heterocyclic group containing the same or different 1 to 4 hetero atom(s) such as oxygen, nitrogen or sulfur atom(s), and examples may include piperidinyl, pyrrolidinyl, piperazinyl, tetrahydrofuryl, tetrahydropyranyl, morpholinyl, azetidinyl, and homopiperazinyl. The term "heteroaryl group" is 5 to 7 membered monocyclic or polycyclic group thereof containing 2 to 8 carbon atoms and the same or different 1 to 4 hetero atom(s) such as oxygen, nitrogen or sulfur atom(s). The examples include pyrrole, furyl, thienyl, imidazolyl, thiazolyl, pyrazinyl, indolyl, quinolinyl, isoquinolinyl, tetrazolyl, pyridinyl, pyrazolyl, pyridazinyl, and pyrimidinyl. The "halogen atom" includes fluorine, chlorine, bromine and iodine. Examples of the suitable substituent of "substituted or unsubstituted $C_1$-$C_6$ alkyl group", "substituted or unsubstituted $C_3$-$C_8$ cycloalkyl group", "substituted or unsubstituted alkenyl group", "substituted or unsubstituted heterocycloalkyl group" and "substituted or unsubstituted acyl group" include a straight or branched-chained, or substituted or unsubstituted alkyl group such as methyl, ethyl, propyl, isopropyl, n-butyl, tert-butyl, substituted or unsubstituted cycloalkyl group such as cyclopropyl, cyclobutyl, cyclopentyl, cyclohexyl, and cycloheptyl; hydroxyl group; cyano group; alkoxy group such as methoxy and ethoxy; substituted or unsubstituted amino group such as amino, methylamino, ethylamino, and dimethylamino; substituted or unsubstituted acyl group such as acetyl, and propionyl; substituted or unsubstituted aryl group; substituted or unsubstituted heteroaryl group; saturated or unsaturated heterocycloalkyl group which is substituted or unsubstituted; substituted or unsubstituted carbamoyl group; substituted or unsubstituted amide group; halogen atom; nitro group; substituted or unsubstituted sulfone group; oxo group; urea group; a straight or branched-chained, or cyclic alkenyl group which is substituted or unsubstituted such as ethenyl, propenyl, and cyclohexenyl.

In other embodiments, PDE7 inhibitors useful in the methods of the invention have the formulas:

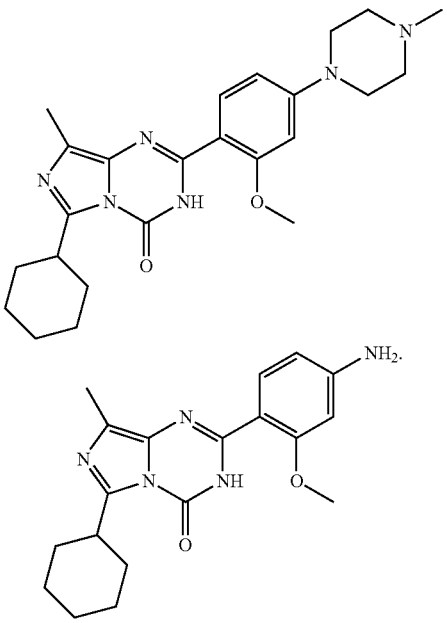

The preparation of the above compounds is described in US 20060128707 and WO 2004/111053.

In another embodiment, PDE7 inhibitors useful in the methods of the invention are selected from those compounds generally or specifically disclosed in U.S. Pat. No. 6,617,357, US 20020156064, and *Molecular Pharmacology*, 66:1679-1689, 2004, each expressly incorporated herein by reference in its entirety. In one embodiment, PDE7 inhibitors useful in the methods of the invention have the formula:

(8)

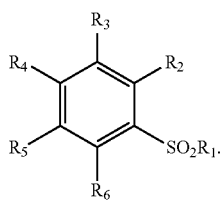

The substituents for the above compounds are defined as follows:

$R_1$ is $NR_aR_b$ where $R_a$ and $R_b$ are independently H or $C_{1-6}$ alkyl, or represents a 5 to 7 member ring comprised of carbon or carbon and one or more additional heteroatoms selected from O, N, or S;

$R_2$ is H, $C_{1-8}$ alkyl, $C_{1-3}$ alkyl-Ar, $C_{1-3}$ alkyl-$C_{3-6}$ cycloalkyl, $C_{2-8}$ alkenyl, $C_{2-4}$ alkenyl-Ar, or $C_{2-4}$ alkenyl-$C_{3-6}$ cycloalkyl, wherein Ar is substituted or unsubstituted phenyl;

$R_3$ is $NO_2$, halo, CN, C(O)$OR_7$, $COR_1$, or $NR_aR_b$ where $R_a$ and $R_b$ are independently H or $C_{1-6}$ alkyl;

$R_4$ is H, $OC_{1-6}$ alkyl, halo, C(O)$NR_aR_b$, C(O)$OR_7$, $C_{1-8}$ alkyl, $OCHF_2$, $CH_2OR_8$, $OC_{1-3}$ alkyl-Ar, or $CH_2NHC(O)CH_3$;

$R_5$ is H, halo, or alkyl;

$R_6$ is $C_{1-8}$ alkyl, $OC_{1-4}$ alkyl, or halo;

$R_7$ is hydrogen or an ester or amide-forming group;

$R_8$ is hydrogen or $C_{1-6}$ alkyl;

or a pharmaceutically acceptable salt or solvate thereof.

In one embodiment, a PDE7 inhibitor useful in the methods of the invention has the formula:

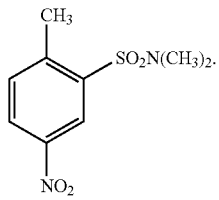

The preparation of the above compounds is described in U.S. Pat. No. 6,617,357, US 20020156064, and *Molecular Pharmacology*, 66:1679-1689, 2004.

In another embodiment, PDE7 inhibitors useful in the methods of the invention are selected from those compounds generally or specifically disclosed in U.S. Pat. No. 6,852,720, EP 1 348 433, and WO 2003/082277, each expressly incorporated herein by reference in its entirety. In one embodiment, PDE7 inhibitors useful in the methods of the invention have the formula:

(9)

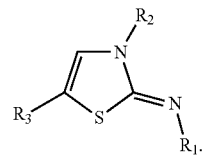

The substituents for the above compounds are defined as follows:

$R_1$ is a group selected from cycloalkyl, heterocycloalkyl, aryl and heteroaryl, those groups being optionally substituted by one or more groups, identical or different, selected independently of each other from halogen, trifluoromethyl, nitro, cyano, oxo, $NR_4R_5$, $CO_2R_4$, $CONR_4R_5$, $OR_4$, $S(O)_nR_4$, $S(O)_n NR_4R_5$, tetrazolyl and ($C_1$-$C_6$) alkyl which is optionally substituted by 1 to 3 groups, identical or different, selected independently of each other from $OR_4$, $NR_4R_5$, and $CO_2R_4$; wherein n is an integer from 0 to 2 inclusive, $R_4$ and $R_5$ are identical or different and independently of each other are a hydrogen atom or a group of formula $X_1$—$R_a$, wherein $X_1$ is a single bond or a ($C_1$-$C_6$) alkylene group, and $R_a$ is a group selected from ($C_1$-$C_6$) alkyl, cycloalkyl, heterocycloalkyl, aryl, and heteroaryl, $R_2$ is a group selected from ($C_1$-$C_6$) alkyl, ($C_2$-$C_6$) alkenyl, ($C_2$-$C_6$) alkynyl, aryl, and cycloalkyl, $R_3$ is a group selected from cycloalkyl, heterocycloalkyl, aryl and heteroaryl, these groups being optionally substituted by one or more groups, identical or different, selected independently of each other from halogen, nitro, cyano, trifluoromethyl, oxo, ($C_1$-$C_6$) alkyl, $OR_6$, $NR_6R_7$, $COR_6$, $CO_2R_6$, CONHOH, $CONR_6R_7$, $S(O)_mR_6$, $S(O)_mNR_6R_7$, $NR_6COR_7$, $NR_6SO_2R_7$, $N(SO_2R_7)_2$, $NR_6CONR_7R_8$, C(=NCN)$NR_6R_7$, $NR_8C$(=NCN)$NR_6R_7$, and tetrazolyl optionally substituted with a ($C_1$-$C_4$) alkyl, wherein m is an integer from 0 to 2 inclusive, $R_6$ and $R_7$ are identical or different and independently of each other are a hydrogen atom or a group of formula $X_2R_b$, wherein $X_2$ is a single bond or a ($C_1$-$C_6$) alkylene group, $R_b$ is a group selected from ($C_1$-$C_6$) alkyl, cycloalkyl, heterocycloalkyl, aryl and heteroaryl, these groups being optionally substituted by 1 to 3 groups, identical or different, selected independently of each other from hydroxy, $(C_1-C_6)$ alkoxy, $(C_1-C_6)$ alkyl, amino, mono$(C_1-C_6)$ alkylamino, di$(C_1-C_6)$ alkylamino (each alkyl amino being identical or different, independently of each other), carboxy, $(C_1-C_6)$ alkoxycarbonyl, and benzyl, and $R_8$ represents a hydrogen atom or a $(C_1-C_6)$ alkyl group;

a racemic form thereof, an isomer thereof, an N-oxide thereof, or a pharmaceutically acceptable acid or base salt thereof.

The preparation of the above compounds is described in U.S. Pat. No. 6,852,720, EP 1 348 433, and WO 2003/082277.

In another embodiment, PDE7 inhibitors useful in the methods of the invention are selected from those compounds generally or specifically disclosed in U.S. Pat. No. 6,753,340, US 20030191167, EP 1 348 701, and WO 2003/082839, each expressly incorporated herein by reference in its entirety. In one embodiment, PDE7 inhibitors useful in the methods of the invention have the formula:

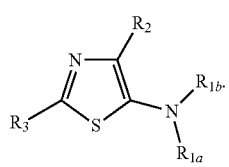

(10)

The substituents for the above compounds are defined as follows:

$R_{1a}$ is a group selected from hydrogen, $(C_1-C_6)$ alkyl and aryl$(C_1-C_6)$ alkyl, $R_{1b}$ is a group selected from cycloalkyl, heterocycloalkyl, aryl and heteroaryl, those groups being optionally substituted by one or more groups, identical or different, selected independently of each other from halogen, trifluoromethyl, nitro, cyano, oxo, $NR_4R_5$, $CO_2R_4$, $CONR_4R_5$, $OR_4$, $S(O)_nR_4$, $S(O)_n NR_4R_5$, tetrazolyl, and $(C_1-C_6)$ alkyl which is optionally substituted by 1 to 3 groups, identical or different, selected independently of each other from $OR_4$, $NR_4R_5$, and $CO_2R_4$, wherein n is an integer from 0 to 2 inclusive, $R_4$ and $R_5$ are identical or different and independently of each other are a hydrogen atom or a group of formula $X_1$—$R_a$, wherein $X_1$ is a single bond or a $(C_1-C_6)$ alkylene group, and $R_a$ is a group selected from $(C_1-C_6)$ alkyl, cycloalkyl, heterocycloalkyl, aryl and heteroaryl, $R_2$ is a group selected from $(C_1-C_6)$ alkyl, $(C_2-C_6)$ alkenyl, $(C_2-C_6)$ alkynyl, aryl and cycloalkyl, $R_3$ is a group selected from cycloalkyl, heterocycloalkyl, aryl and heteroaryl, these groups being optionally substituted by one or more groups, identical or different, selected independently of each other from halogen, nitro, cyano, trifluoromethyl, oxo, $(C_1-C_6)$ alkyl, $OR_6$, $NR_6R_7$, $COR_6$, $CO_2R_6$, CONHOH, $CONR_6R_7$, $S(O)_mR_6$, $S(O)_mNR_6R_7$, $NR_6COR_7$, $NR_6SO_2R_7$, $N(SO_2R_7)_2$, $NR_6CONR_7R_8$, $C(=N-CN)NR_6R_7$, $NR_8C(=N-CN)NR_6R_7$, and tetrazolyl optionally substituted with a $(C_1-C_4)$ alkyl, wherein m is an integer from 0 to 2 inclusive, $R_6$ and $R_7$ are identical or different and independently of each other are a hydrogen atom or a group of formula $X_2$—$R_b$, wherein $X_2$ is a single bond or a $(C_1-C_6)$ alkylene group, $R_b$ is a group selected from $(C_1-C_6)$ alkyl, cycloalkyl, heterocycloalkyl, aryl and heteroaryl, these groups being optionally substituted by 1 to 3 groups, identical or different, selected independently of each other from hydroxy, $(C_1-C_6)$ alkoxy, $(C_1-C_6)$ alkyl, amino, mono$(C_1-C_6)$ alkylamino, di$(C_1-C_6)$ alkylamino (each alkyl amino being identical or different, independently of each other), carboxy, $(C_1-C_6)$ alkoxycarbonyl, and benzyl, and $R_8$ is a hydrogen atom or a $(C_1-C_6)$ alkyl group, or a racemic form thereof, an isomer thereof, an N-oxide thereof or a pharmaceutically acceptable acid or base salt thereof.

The preparation of these compounds is described in U.S. Pat. No. 6,753,340, US 20030191167, EP 1 348 701, and WO 2003/082839.

In another embodiment, PDE7 inhibitors useful in the methods of the invention are selected from those compounds generally or specifically disclosed in U.S. Pat. No. 6,849,638, US 20030119829, and WO 2002/088138, each expressly incorporated herein by reference in its entirety. In one embodiment, PDE7 inhibitors useful in the methods of the invention have the formula:

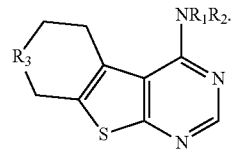

(11)

The substituents for the above compounds are defined as follows:

$R_1$ and $R_2$ are independently selected from the group consisting of hydrogen, alkyl of 1-8 carbon atoms, alkenyl of 2-8 carbon atoms, alkynyl of 2-8 carbon atoms, cycloalkyl of 3-7 carbon atoms, fully saturated heterocycle of 2-6 carbon atoms and 1-2 heteroatoms selected from NH, S and O, aryl of 6-12 carbon atoms, that may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms or heteroaryl of 4-11 carbon atoms and 1, 2 heteroatoms selected from N, S, and O, heteroaryl of 4-11 carbon atoms and 1-2 heteroatoms selected from N, S and O, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms or heteroaryl of 4-11 carbon atoms and 1-2 heteroatoms selected from N, S and O, and $R_4$-$R_5$, or $R_1$ and $R_2$ combine to form, together with the nitrogen atom to which they are attached, a 5-7 membered saturated ring which may contain 1-2 additional heteroatoms selected from the group consisting of NH, $NR_8$, S and O, or combine to form, together with the nitrogen atom to which they are attached, a 5-7 membered unsaturated ring that may contain 1-2 additional heteroatoms selected from the group consisting of N, S and O, wherein said saturated or unsaturated ring may be substituted with 1-2 substituents selected from the group consisting of OH, alkyl of 1-6 carbon atoms, alkenyl of 2-6 carbon atoms, alkynyl of 2-6 carbon atoms, cycloalkyl of 3-7 carbon atoms, fully saturated heterocycle of 2-6 carbon atoms and 1-2 heteroatoms selected from NH, S, and O, halogen, haloalkyl of 1-2 carbon atoms and a number of halogen atoms up to the perhalo level, alkoxy of 1-6 carbon atoms, haloalkoxy of 1-6 carbon atoms and a number of halogen atoms up to the perhalo level, and $R_9$-$R_{10}$; or $R_1$ and $R_2$ combine to form, together with the nitrogen atom to which they are attached, an 8-10 membered bicyclic saturated ring;

$R_3$ is selected from the group consisting of NH, S, S(=O)$_2$, and O;

$R_4$ is selected from alkyl of 1-8 carbon atoms, alkenyl of 2-8 carbon atoms, alkynyl of 2-8 carbon atoms, C(=C), S(=O)$_2$, and C(=O)O;

$R_5$ is selected from hydrogen, OH, alkyl of 1-8 carbon atoms, alkenyl of 2-8 carbon atom, alkynyl of 2-8 carbon atoms, alkoxy of 1-8 carbon atoms, aryl of 6-12 carbon atoms, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkyl of 1-6 carbon atoms and a number of halogen atoms up to the perhalo level, aryl of 6-12 carbon atoms and heteroaryl of 4-11 carbon atoms and 1-2 heteroatoms selected from N, S, and O, heteroaryl of 4-11 carbon atoms and 1-2 heteroatoms selected from N, S, and O, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms and heteroaryl of 4-11 carbon atoms and 1-2 heteroatoms selected from N, S, and O, cycloalkyl of 3-7 carbon atoms, fully saturated heterocycle of 2-6 carbon atoms and 1-2 heteroatoms selected from NH, S and O, and NR$_6$R$_7$, $R_6$ and $R_7$ are independently selected from hydrogen, alkyl of 1-8 carbon atoms, alkenyl of 2-8 carbon atoms, and alkynyl of 2-8 carbon atoms, or $R_6$ and $R_7$ combine together with the nitrogen atom to which they are attached to form a 5-7 membered, unsaturated ring which may contain 1-2 additional heteroatoms selected from N, S and O or to form a 5-7 membered, saturated ring which may contain 1-2 additional heteroatoms selected from NH, S, and O;

$R_8$ is selected from alkyl of 1-8 carbon atoms, alkenyl of 2-8 carbon atoms, alkynyl of 2-8 carbon atoms, $R_{11}$-$R_{12}$, cycloalkyl of 3-7 carbon atoms, fully saturated heterocycle of 2-6 carbon atoms and 1-2 heteroatoms selected from NH, S, and O, aryl of 6-12 carbon atoms, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms or heteroaryl of 4-11 carbon atoms and 1-2 heteroatoms selected from N, S, and O, heteroaryl of 4-11 carbon atoms and 1-2 heteroatoms selected from N, S, and O, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms or heteroaryl of 4-11 carbon atoms and 1-2 heteroatoms selected from N, S, and O;

$R_9$ is selected from alkyl of 1-8 carbon atoms, alkenyl of 2-8 carbon atoms, and alkynyl of 2-8 carbon atoms, $R_{10}$ is selected from OH, aryl of 6-12 carbon atoms, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms or heteroaryl of 4-11 carbon atoms and 1-2 heteroatoms selected from N, S, and O, and heteroaryl of 4-11 carbon atoms and 1-2 heteroatoms selected from N, S, and O, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms or heteroaryl of 4-11 carbon atoms and 1-2 heteroatoms selected from N, S, and O;

$R_{11}$ is selected from alkyl of 1-8 carbon atoms, alkenyl of 2-8 carbon atoms, and alkynyl of 2-8 carbon atoms; and $R_{12}$ is selected from cycloalkyl of 3-7 carbon atoms, fully saturated heterocycle of 2-6 carbon atoms and 1-2 heteroatoms selected from NH, S, and O, aryl of 6-12 carbon atoms, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms or heteroaryl of 4-11 carbon atoms and 1-2 heteroatoms selected from N, S, and O, and heteroaryl of 4-11 carbon atoms and 1-2 heteroatoms selected from N, S and O, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms or heteroaryl of 4-11 carbon atoms and 1-2 heteroatoms selected from N, S and O;

and pharmaceutically acceptable salts thereof.

The preparation of these compounds is described in U.S. Pat. No. 6,849,638, US 20030119829, and WO 2002/088138.

In another embodiment, PDE7 inhibitors useful in the methods of the invention are selected from those compounds generally or specifically disclosed in US 2005222138 and WO 2003/064389, each expressly incorporated herein by reference in its entirety. In one embodiment, PDE7 inhibitors useful in the methods of the invention have the formula:

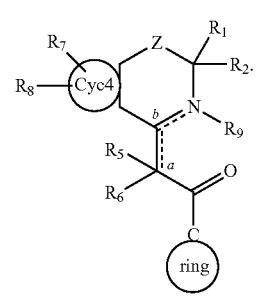

(12)

The substituents for the above compounds are defined as follows:

$R_1$ and $R_2$ are each independently, (1) hydrogen atom, or (2) $C_{1-8}$ alkyl, or $R_1$ and $R_2$ may be taken together with the carbon atom to which they are attached to form Cyc1, wherein $R_1$ and $R_2$ do not represent hydrogen atom at the same time;

Z is (1) $CR_3R_4$, (2) O, (3) S, or (4) a bond;

$R_3$ and $R_4$ are each independently, (1) hydrogen atom, (2) $C_{1-8}$ alkyl, (3) $C_{1-8}$ alkoxy, or (4) hydroxy, or $R_3$ and $R_4$ may be taken together with the carbon atom to which they are attached to form Cyc1 or C(O);

$R_5$ and $R_6$ are each independently, (1) hydrogen atom, or (2) $C_{1-8}$ alkyl, or $R_5$ and $R_6$ may be taken together with the carbon atom to which they are attached to form Cyc1;

Cyc1, which is represented by $R_1$ and $R_2$, $R_3$ and $R_4$, $R_5$ and $R_6$ is, each independently, (1) $C_{3-10}$ cycloalkyl, or (2) 3-10 membered monocyclic hetero-ring comprising 1-2 of heteroatom selected from oxygen, nitrogen and sulfur, and Cyc1 may be substituted with $R_{10}$;

$R_{10}$ is (1) $C_{1-8}$ alkyl, (2) $C_{1-8}$ alkoxy, (3) hydroxy, (4) $COOR_{11}$, (5) oxo, (6)$SO_2R_{12}$, or (7) $COR_{13}$;

$R_{11}$ is hydrogen atom, or $C_{1-8}$ alkyl;

$R_{12}$ and $R_{13}$ are (1) $C_{1-8}$ alkyl, or (2) phenyl which may be substituted with $C_{1-8}$ alkyl;

$R_7$ and $R_8$ are each independently, (1) hydrogen atom, (2) $C_{1-8}$ alkyl, (3) $C_{1-8}$ alkoxy, (4) hydroxy, (5) cyano, (6) halogen atom, (7) $COOR_{14}$, (8) $CONR_{15}R_{16}$, (9) Cyc2, (10) $C_{2-8}$ alkenyl, (11) $C_{2-8}$ alkynyl, (12) $NR_{51}R_{52}$, (13) nitro, (14) formyl, (15) $C_{2-8}$ acyl, (16) $C_{1-8}$ alkyl substituted with hydroxy, $C_{1-8}$ alkoxy, Cyc2, $NR_{51}R_{52}$, or $NR_{53}$-Cyc2, (17) $NR_{54}COR_{55}$, (18) $NR_{56}SO_2R_{57}$, (19) $SO_2NR_{58}R_{59}$, (20) $C_{2-8}$ alkenyl substituted with $COOR_{14}$, (21) CH=N—OH, (22) $C_{1-8}$ alkylene-$NR_{60}$—($C_{1-8}$ alkylene)-$R_{61}$, (23) $C_{1-8}$ alkylthio, (24) $C_{1-8}$ alkyl substituted with 1-3 of halogen atom, (25) $C_{1-8}$ alkoxy substituted with 1-3 of halogen atom, (26) $C_{1-8}$ alkoxy substituted with Cyc2, (27) O—Cyc2, (28) $OSO_2R_{65}$, or (29) CH=N—$OR_{137}$;

$R_{14}$ is hydrogen atom, or $C_{1-8}$ alkyl;

$R_{15}$ and $R_{16}$ are each independently hydrogen atom or $C_{1-8}$ alkyl;

$R_{51}$ and $R_{52}$, $R_{58}$ and $R_{59}$ are each independently, hydrogen atom, or $C_{1-8}$ alkyl;

$R_{53}$, $R_{54}$, $R_{56}$, and $R_{60}$ are each independently, hydrogen atom, or $C_{1-8}$ alkyl;

$R_{55}$ is hydrogen atom, $C_{1-8}$ alkyl, or $C_{1-8}$ alkoxy; $R_{57}$ is $C_{1-8}$ alkyl;

$R_{61}$ is $NR_{62}R_{63}$ or hydroxy;

$R_{62}$ and $R_{63}$ are each independently, hydrogen atom, or $C_{1-8}$ alkyl;

$R_{65}$ is $C_{1-8}$ alkyl;

$R_{137}$ is $C_{1-8}$ alkyl;

(hereinafter it is abbreviated as ring) is Cyc2 wherein the group which attaches to carbonyl is carbon;

$R_7$, $R_8$, and Cyc2 represented by ring are each independently, (1) $C_{3-15}$ mono-, bi- or tri-cyclic (fused or spiro)carboring, or (2) 3-15 membered mono-, bi- or tri-cyclic (fused or spiro)heteroring comprising 1-4 of heteroatom selected from oxygen, nitrogen and sulfur;

Cyc2 may be substituted with 1-5 of $R_{17}$ or $R_{17'}$;

$R_{17}$ is (1) $C_{1-8}$ alkyl, (2) $C_{2-8}$ alkenyl, (3) $C_{2-8}$ alkynyl, (4) $C_{1-8}$ alkoxy, (5) $C_{1-8}$ alkylthio, (6) hydroxy, (7) halogen atom, (8) nitro, (9) oxo, (10) carboxy, (11) formyl, (12) cyano, (13) $NR_{18}R_{19}$, (14) phenyl, phenoxy or phenylthio, which may be substituted with 1-5 of $R_{20}$, (15) $C_{1-8}$ alkyl, $C_{2-8}$ alkenyl, $C_{1-8}$ alkoxy or $C_{1-8}$ alkylthio, which may be substituted with 1-5 of $R_{21}$ (16) $OCOR_{22}$, (17) $CONR_{23}R_{24}$, (18) $SO_2NR_{25}R_{26}$ (19) $COOR_{27}$, (20) $COCOOR_{28}$, (21) $COR_{29}$, (22) $COCOR_{30}$, (23) $NR_{31}COR_{32}$, (24) $SO2R_{33}$, (25) $NR_{34}SO_2R_{35}$, or (26) $SOR_{64}$;

$R_{18}$ and $R_{19}$, $R_{31}$ and $R_{34}$ are each independently, hydrogen atom, or $C_{1-8}$ alkyl;

$R_{20}$ and $R_{21}$ are $C_{1-8}$ alkyl, $C_{1-8}$ alkoxy, hydroxy, halogen atom, nitro, or $COOR_{36}$;

$R_{22}$ and $R_{64}$ are each independently $C_{1-8}$ alkyl;

$R_{23}$, $R_{24}$, $R_{25}$ and $R_{26}$ are each independently hydrogen atom, $C_{1-8}$ alkyl, or phenyl;

$R_{27}$, $R_{28}$, $R_{29}$, $R_{30}$, $R_{32}$, $R_{33}$ and $R_{35}$ are (1) $C_{1-8}$ alkyl, (2) $C_{2-8}$ alkenyl, (3) $C_{1-8}$ alkyl substituted with 1-5 of $R_{37}$, (4) diphenylmethyl, (5) triphenylmethyl, (6) Cyc3, (7) $C_{1-8}$ alkyl or $C_{2-8}$ alkenyl substituted with Cyc3, (8) $C_{1-8}$ alkyl substituted with O-Cyc3, S-Cyc3 or $SO_2$-Cyc3;

$R_{36}$ is hydrogen atom, or $C_{1-8}$ alkyl;

$R_{37}$ is $C_{1-8}$ alkoxy, $C_{1-8}$ alkylthio, benzyloxy, halogen atom, nitro or $COOR_{38}$;

$R_{38}$ is hydrogen atom, $C_{1-8}$ alkyl or $C_{2-8}$ alkenyl;

Cyc3 is (1) $C_{3-15}$ mono-, bi- or tri-cyclic (fused or spiro) carboring, or (2) 3-15 membered mono-, bi- or tri-cyclic (fused or spiro)heteroring comprising 1-4 of heteroatom selected from oxygen, nitrogen and sulfur;

Cyc3 may be substituted with 1-5 of $R_{39}$;

$R_{39}$ is (1) $C_{1-8}$ alkyl, (2) $C_{2-8}$ alkenyl, (3) $C_{2-8}$ alkynyl, (4) $C_{1-8}$ alkoxy, (5) $C_{1-8}$ alkylthio, (6) hydroxy, (7) halogen atom, (8) nitro, (9) oxo, (10) cyano, (11) benzyl, (12) benzyloxy, (13) $C_{1-8}$ alkyl, $C_{1-8}$ alkoxy or $C_{1-8}$ alkylthio substituted with 1-5 of $R_{40}$, (14) phenyl, phenoxy, phenylthio, phenylsulfonyl or benzoyl which may be substituted with 1-5 of $R_{41}$, (15) $OCOR_{42}$, (16) $SO_2R_{43}$, (17) $NR_{44}COR_{45}$, (18) $SO_2NR_{46}R_{47}$, (19) $COOR_{48}$, or (20) $NR_{49}R_{50}$;

$R_{40}$ is halogen atom;

$R_{41}$ is $C_{1-8}$ alkyl, $C_{1-8}$ alkoxy, halogen atom, or nitro;

$R_{42}$, $R_{43}$ and $R_{45}$ are $C_{1-8}$ alkyl;

$R_{44}$ and $R_{48}$ are hydrogen atom or $C_{1-8}$ alkyl;

$R_{46}$ and $R_{47}$, $R_{49}$ and $R_{50}$ are each independently, hydrogen atom or $C_{1-8}$ alkyl;

$R_{17'}$ is (1) SH, (2) $NR_{66}$CHO, (3) Cyc5, (4) $C_{1-8}$ alkyl, $C_{2-8}$ alkenyl or $C_{2-8}$ alkynyl substituted with Cyc5, (5) CO—(NH-amino acid residue-CO)$_n$—OH, (6) $NR_{67}CONR_{68}R_{69}$, (7) $CONR_{70}NR_{71}R_{72}$, (8) $CONR_{73}OR_{74}$, (9) $CONR_{75}COR_{76}$, (10) $C(S)NR_{77}R_{78}$, (11) $CONR_{79}C(S)COOR_{80}$, (12) $NR_{81}COCOOR_{82}$, (13) $NR_{83}COOR_{84}$, (14) $CONR_{85}C(S)R_{86}$, (15) $OCOR_{87}$, (16) $SOR_{88}$, (17) $CONR_{89}R_{90}$, (18) $SO_2NR_{91}R_{92}$, (19) $COOR_{93}$, (20) $COCOOR_{94}$, (21) $COR_{95}$, (22) $COCOR_{96}$, (23) $NR_{97}COR_{98}$, (24) $SO_2R_{99}$, (25) $NR_{100}SO_2R_{101}$, or (26) $NR_{102}R_{103}$;

n is an integer of 1 or 2;

$R_{66}$, $R_{73}$, $R_{75}$, $R_{77}$, $R_{79}$, $R_{81}$, $R_{83}$, $R_{85}$, $R_{97}$, $R_{100}$ and $R_{102}$ are hydrogen atom, or $C_{1-8}$ alkyl;

$R_{67}$ and $R_{68}$, $R_{70}$ and $R_{71}$ are each independently, hydrogen atom, or $C_{1-8}$ alkyl;

$R_{89}$ and $R_{91}$ are (1) hydrogen atom, (2) $C_{1-8}$ alkyl, (3) phenyl, or (4) $C_{1-8}$ alkyl substituted with cyano or $C_{1-8}$ alkoxy;

$R_{103}$ is Cyc6;

$R_{69}$, $R_{72}$, $R_{74}$, $R_{76}$, $R_{78}$, $R_{80}$, $R_{82}$, $R_{84}$, $R_{86}$, $R_{87}$, $R_{88}$, $R_{90}$ and $R_{92}$ are (1) hydrogen atom, (2) $C_{1-8}$ alkyl, (3) $C_{2-8}$ alkenyl, (4) $C_{2-8}$ alkynyl, (5) $C_{1-8}$ alkyl substituted with 1-5 of $R_{104}$, (6) diphenylmethyl, (7) triphenylmethyl, (8) Cyc6, (9) $C_{1-8}$ alkyl or $C_{2-8}$ alkenyl substituted with Cyc6, or (10) $C_{1-8}$ alkyl substituted with O-Cyc6, S-Cyc6 or $SO_2$-Cyc6;

$R_{104}$ is (1) $C_{1-8}$ alkoxy, (2) $C_{1-8}$ alkylthio, (3) benzyloxy, (4) halogen atom, (5) nitro, (6) $COOR_{105}$, (7) cyano, (8)

NR$_{106}$R$_{107}$, (9) N$_{108}$COR$_{109}$, (10) hydroxy, (11) SH, (12) SO$_3$H, (13) S(O)OH, (14) OSO$_3$H, (15) C$_{2-8}$ alkenyloxy, (16) C$_{2-8}$ alkynyloxy, (17) COR$_{110}$, (18) SO$_2$R$_{111}$, or (19) C$_{1-8}$ alkoxy or C$_{1-8}$ alkylthio substituted with hydroxy;

R$_{105}$ is hydrogen atom, C$_{1-8}$ alkyl, or C$_{2-8}$ alkenyl;

R$_{106}$ and R$_{107}$ are each independently, hydrogen atom, or C$_{1-8}$ alkyl;

R$_{108}$ is hydrogen atom, or C$_{1-8}$ alkyl;

R$_{109}$ and R$_{111}$ are C$_{1-8}$ alkyl;

R$_{110}$ is C$_{1-8}$ alkyl, or halogen atom;

R$_{93}$, R$_{94}$, R$_{95}$, R$_{96}$, R$_{98}$, R$_{99}$ and R$_{101}$ are (1) C$_{2-8}$ alkynyl, (2) C$_{1-8}$ alkyl substituted with R$_{128}$ which may be substituted with 1-4 of R$_{29}$, (3) Cyc8, (4) C$_{1-8}$ alkyl or C$_{2-8}$ alkenyl substituted with Cyc8, or (5) C$_{1-8}$ alkyl substituted with O-Cyc8, S-Cyc8 or SO$_2$-Cyc8; R$_{128}$ is (1) cyano, (2) NR$_{106}$R$_{107}$, (3) NR$_{108}$COR$_{109}$, (4) hydroxy, (5) SH, (6) SO$_3$H, (7) S(O)OH, (8) OSO$_3$H, (9) C$_{2-8}$ alkenyloxy, (10) C$_{2-8}$ alkynyloxy, (11) COR$_{110}$, (12) SO$_2$R$_{111}$, or (13) C$_{1-8}$ alkoxy or C$_{1-8}$ alkylthio substituted with hydroxy;

R$_{129}$ has the same meaning as R$_{104}$;

Cyc5 and Cyc6 may be substituted with 1-5 of R$_{112}$;

R$_{112}$ is (1) C$_{1-8}$ alkyl, (2) C$_{2-8}$ alkenyl, (3) C$_{2-8}$ alkynyl, (4) C$_{1-8}$ alkoxy, (5) C$_{1-8}$ alkylthio, (6) hydroxy, (7) halogen atom, (8) nitro, (9) oxo, (10) cyano, (11) benzyl, (12) benzyloxy, (13) C$_{1-8}$ alkyl, C$_{1-8}$ alkoxy or C$_{1-8}$ alkylthio substituted with 1-5 of R$_{113}$, (14) phenyl, phenoxy, phenylthio or benzoyl, which may be substituted with 1-5 of R$_{114}$, (15) COR$_{115}$, (16) SO$_2$R$_{116}$, (17) NR$_{117}$COR$_{118}$, (18) SO$_2$NR$_{119}$R$_{120}$, (19) COOR$_{121}$, (20) NR$_{122}$R$_{123}$, (21) COR$_{124}$, (22) CONR$_{125}$R$_{126}$, (23) SH, (24) C$_{1-8}$ alkyl substituted with hydroxy or NR$_{127}$-benzoyl, or (25) Cyc7;

R$_{113}$ is halogen atom;

R$_{114}$ is C$_{1-8}$ alkyl, C$_{1-8}$ alkoxy, halogen atom, or nitro;

R$_{115}$, R$_{116}$ and R$_{118}$ are C$_{1-8}$ alkyl;

R$_{117}$, R$_{121}$, R$_{124}$ and R$_{127}$ are hydrogen atom, or C$_{1-8}$ alkyl;

R$_{119}$ and R$_{120}$, R$_{122}$ and R$_{123}$, R$_{125}$ and R$_{126}$ are each independently, hydrogen atom or C$_{1-8}$ alkyl;

Cyc7 may be substituted with 1-5 group selected from (1) C$_{1-8}$ alkyl, (2) C$_{1-8}$ alkoxy, (3) halogen atom, or (4) nitro;

Cyc8 may be substituted with R$_{130}$, and it further may be substituted with 1-4 of R$_{131}$;

R$_{130}$ is (1) COR$_{124}$, (2) CONR$_{125}$R$_{126}$, (3) SH, (4) C$_{1-8}$ alkyl substituted with hydroxy or NR$_{127}$-benzoyl, or (5) Cyc7;

R$_{131}$ has the same meaning as R$_{112}$;

Cyc5, Cyc6, Cyc7 and Cyc8 are (1) C$_{3-15}$ mono-, bi- or tri-cyclic (fused or spiro)carboring, or (2) 3-15 membered mono-, bi- or tri-cyclic (fused or spiro)heteroring comprising 1-4 of heteroatom selected from 1-4 of oxygen, nitrogen or sulfur;

wherein when R$_{17'}$ is Cyc5, Cyc5 is not phenyl which may be substituted with 1-5 selected from C$_{1-8}$ alkyl, C$_{1-8}$ alkoxy, hydroxy, halogen atom, nitro, COOH, or COO(C$_{1-8}$ alkyl);

wherein Cyc7 is not phenyl;

Cyc4 is (1) C$_{5-7}$ monocyclic carboring, or (2) 5-7 membered monocyclic heteroring comprising 1-2 of heteroatom selected from oxygen, nitrogen and sulfur; (abbreviated as dashed line a hereafter;) and (abbreviated as dashed line b hereafter;) are (1) a bond, or (2) a double bond;

R$_9$ (1) absent or (2) is hydrogen atom;
wherein
(1) when dashed line a is a bond, dashed line b is a double bond, and R$_9$ is absent,
(2) when dashed line a is a double bond, dashed line b is a bond, and R$_9$ is hydrogen atom and R$_6$ is absent, and (3) 2-(3,3-dimethyl-3,4-dihydro-(2H)-isoquinolin-1-ylidene)-1-phenylethan-1-one is excluded, or a pharmacologically acceptable salt thereof.

The preparation of these compounds is described in US 2005222138 and WO 2003/064389.

In another embodiment, PDE7 inhibitors useful in the methods of the invention are selected from those compounds generally or specifically disclosed in WO 2003/057149, expressly incorporated herein by reference in its entirety. In one embodiment, PDE7 inhibitors useful in the methods of the invention have the formula:

(13)

The substituents for the above compounds are defined as follows:

(1) X is selected from halogen and NR$_1$R$_2$, (2) Y is selected from NR$_3$, S, and O, with the proviso that Y is not S when X is Cl, (3) R$_1$ and R$_2$ are independently selected from hydrogen, alkyl of 1-8 carbon atoms, alkenyl of 2-8 carbon atoms, alkynyl of 2-8 carbon atoms, cycloalkyl of 3-7 carbon atoms, polycycloalkyl of 5-9 carbon atoms, heterocycloalkyl of 2-6 carbon atoms and 1-2 heteroatoms selected from NH, S, and O, aryl of 6-12 carbon atoms, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms, or heteroaryl of 4-11 carbon atoms and 1-2 heteroatoms selected from N, S, and O, heteroaryl of 4-11 carbon atoms and 1-2 heteroatoms selected from N, S and O, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms, or heteroaryl of 4-11 carbon atoms and 1-2 heteroatoms selected from N, S, and O, and R$_4$R$_5$, or R$_1$ and R$_2$ combine to form, together with the nitrogen atom to which they are attached, a 5-7 membered monocyclic saturated ring, which optionally contains 1-2 additional heteroatoms selected from the group consisting of NH, NR$_6$, S, and O, or combine to form, together with the nitrogen atom to which they are attached, a 6-10 membered fused polycyclic saturated ring, which optionally contains 1-2 additional heteroatoms selected from the group consisting of NH, NR$_6$, S, and O, or combine to form, together with the nitrogen atom to which they are attached, a 5-7 membered unsaturated ring, which optionally contains 1-2 additional heteroatoms selected from the group consisting of N, S, and O, wherein said monocyclic saturated ring, polycyclic saturated ring or unsaturated ring may be substituted with 1-2 substituents selected from the group consisting of OH, alkyl of 1-6 carbon atoms, alkenyl of 2-6 carbon atoms, alkynyl of 2-6 carbon atoms, cycloalkyl of 3-7 carbon atoms, heterocycloalkyl of 2-6 carbon atoms and 1-2 heteroatoms selected from NH, S, and O, halogen, haloalkyl of 1-2 carbon atoms and a number of halogen atoms up to the perhalo level, alkoxy of 1-6 carbon atoms, haloalkoxy of 1-6 carbon atoms and a number of halogen atoms up to the perhalo level, and R₇R₈, (4) R₃ is selected from hydrogen, alkyl of 1-8 carbon atoms, alkenyl of 2-8 carbon atoms, alkynyl of 2-8 carbon atoms, cycloalkyl of 3-7 carbon atoms, and heteroaryl of 4-11 carbon atoms and 1-2 heteroatoms selected from N, S, and O, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atom sup to the perhalo level, haloalkoxy of 1-6 carbon atoms and a number of halogen atoms up to the perhalo level, aryl of 6-12 carbon atoms, or heteroaryl of 4-11 carbon atoms and 1-2 heteroatoms selected from N, S, and O, (5) R₄ is selected from alkyl of 1-8 carbon atoms, alkenyl of 2-8 carbon atoms, alkynyl of 2-8 carbon atoms, C(=O), S(=O)₂, and C(=O)O, (6) R₅ is selected from hydrogen, OH, alkyl of 1-8 carbon atoms, alkenyl of 2-8 carbon atoms, alkynyl of 2-8 carbon atoms, alkoxy of 1-8 carbon atoms, thioxy of 1-8 carbon atoms, aryl of 6-12 carbon atoms, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms, or heteroaryl of 4-11 carbon atoms and 1-2 heteroatoms selected from N, S, and O, heteroaryl of 4-11 carbon atoms and 1-2 heteroatoms selected from N, S, and O, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms, or heteroaryl of 4-11 carbon atoms and 1-2 heteroatoms selected from N, S, and O, cycloalkyl of 3-7 carbon atoms, heterocycloalkyl of 2-6 carbon atoms and 1-2 heteroatoms selected from NH, S, and O, and NR₉R₁₀, (7) R₆ and R₇ are independently selected from alkyl of 1-8 carbon atoms, alkenyl of 2-8 carbon atoms, and alkynyl of 2-8 carbon atoms, (8) R₈ is selected from OH, aryl of 6-12 carbon atoms, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms or heteroaryl of 4-11 carbon atoms and 1-2 heteroatoms selected from N, S, and O, and heteroaryl of 4-11 carbon atoms and 1-2 heteroatoms selected from N, S, and O, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, aryl of 6-12 carbon atoms or heteroaryl of 4-11 carbon atoms and 1-2 heteroatoms selected from N, S, and O;

(9) R₉ and R₁₀ are independently selected from hydrogen, alkyl of 1-8 carbon atoms, alkenyl of 2-8 carbon atoms, and alkynyl of 2-8 carbon atoms, or R₉ and R₁₀ combine together with the nitrogen atom to which they are attached to form a 5-7 membered, unsaturated ring which may contain 1-2 additional heteroatoms selected from N, S, and O, or to form a 5-7 membered, saturated ring which may contain 1-2 additional heteroatoms selected from NH, NR₁₁, S, and O;

(10) R₁ is selected from alkyl of 1-8 carbon atoms, alkenyl of 2-8 carbon atoms, and alkynyl of 2-8 carbon atoms, and pharmaceutically acceptable salts thereof.

The preparation of these compounds is described in WO 2003/057149.

In another embodiment, PDE7 inhibitors useful in the methods of the invention are selected from those compounds generally or specifically disclosed in US 20030092721, U.S. Pat. No. 7,022,849, WO 2002/102315, and US 2006116516, each expressly incorporated herein by reference in its entirety. In one embodiment, PDE7 inhibitors useful in the methods of the invention have the formula:

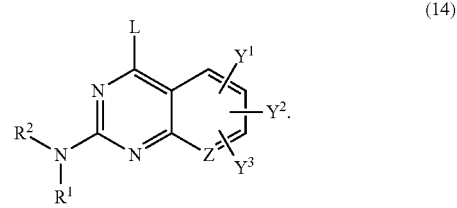

(14)

The substituents for the above compounds are defined as follows: R₁ is H or alkyl;

R₂ is (a) heteroaryl or heterocyclo, either of which may be optionally substituted with one to three groups T1, T2, T3; or (b) aryl fused to a heteroaryl or heterocyclo ring wherein the combined ring system may be optionally substituted with one to three groups T1, T2, T3;

L is (a) OR₄, C(O)R₄, C(O)OR₄, SR₄, NR₃R₄, C(O)NR₃R₄, NR₃SO₂R₄ᵦ, halogen, nitro, or haloalkyl; or (b) alkyl, aryl, heteroaryl, heterocyclo, or cycloalkyl any of which may be optionally substituted with one to three groups T1a, T2a and/or T3a;

Y₁, Y₂ and Y₃ are independently (a) hydrogen, halo, or —OR₄ₐ; or (b) alkyl, alkenyl, or alkynyl, any of which may be optionally substituted with one to three groups T1b, T2b and/or T3b;

R₃ and R₄ are independently H, alkyl, alkenyl, aryl, (aryl) alkyl, heteroaryl, (heteroaryl) alkyl, cycloalkyl, (cycloalkyl) alkyl, heterocyclo, or (heterocyclo) alkyl, any of which may be optionally substituted with one to three groups T1a, T2a and/or T3a; or R₃ and R₄ together with the nitrogen atom to which they are attached may combine to form a 4- to 8-membered heterocyclo ring optionally substituted with one to three groups T1a, T2a and/or T3a;

R₄ₐ is hydrogen, alkyl, alkenyl, aryl, heteroaryl, (aryl) alkyl, (heteroaryl) alkyl, heterocyclo, (heterocyclo) alkyl, cycloalkyl, or (cycloalkyl) alkyl, any of which may be optionally substituted with one to three groups T1b, T2b and/or T3b;

R₄ᵦ is alkyl, alkenyl, aryl, (aryl) alkyl, heteroaryl, (heteroaryl) alkyl, cycloalkyl, (cycloalkyl) alkyl, heterocyclo, or (heterocyclo) alkyl, any of which may be optionally substituted with one to three groups T1a, T2a and/or T3a;

Z is N or CH;

T1-1b, T2-2b, and T3-3b are each independently;

(1) hydrogen or T6, where T6 is (i) alkyl, (hydroxy)alkyl, (alkoxy)alkyl, alkenyl, alkynyl, cycloalkyl, (cycloalkyl) alkyl, cycloalkenyl, (cycloalkenyl)alkyl, aryl, (aryl)alkyl, heterocyclo, (heterocyclo)alkyl, heteroaryl, or (heteroaryl) alkyl; (ii) a group (i) which is itself substituted by one or more of the same or different groups (i); or (iii) a group (i) or (ii)

which is independently substituted by one or more of the following groups (2) to (13) of the definition of T1-1b, T2-2b and T3-3b;

(2) —OH or —OT6;

(3) —SH or —ST6;

(4) —C(O)$_t$H, —C(O)$_t$T6, or —O—C(O)T6, where t is 1 or 2;

(5) —SO$_3$H, —S(O)$_t$T6, or S(O)$_t$N(T9)T6;

(6) halo;

(7) cyano;

(8) nitro;

(9) -T4-NT7T8;

(10) -T4-N(T9)-T5-NT7T8;

(11) -T4-N(T10)-T5-T6;

(12) -T4-N(T10)-T5-H; and

(13) oxo;

T4 and T5 are each independently a single bond, T11S(O)$_t$T12-, T11C(O)T12-, T11C(S)T12, T11OT12, T11ST12, T11OC(O)T12, T11C(O)OT12, T11C(=NT9a)T12, or T11C(O)C(O)T12;

T7, T8, T9, T9a and T10 are:

(1) each independently hydrogen or a group provided in the definition of T6, or (2) T7 and T8 may together be alkylene or alkenylene, completing a 3- to 8-membered saturated or unsaturated ring together with the atoms to which they are attached, which ring is unsubstituted or substituted with one or more groups listed in the description of T1-1b, T2-2b and T3-3b, or (3) T7 or T8, together with T9, may be alkylene or alkenylene completing a 3- to 8-membered saturated or unsaturated ring together with the nitrogen atoms to which they are attached, which ring is unsubstituted or substituted with one or more groups listed in the description of T1-1b, T2-2b and T3-3b, or (4) T7 and T8 or T9 and T10 together with the nitrogen atom to which they are attached may combine to form a group N=CT13T14 where T13 and T14 are each independently H or a group provided in the definition of T6; and T11 and T12 are each independently a single bond, alkylene, alkenylene, or alkynylene.

The preparation of these compounds is described in US 20030092721, U.S. Pat. No. 7,022,849, WO 2002/102315, and US 2006116516.

In another embodiment, PDE7 inhibitors useful in the methods of the invention are selected from those compounds generally or specifically disclosed in U.S. Pat. No. 6,838,559, U.S. 20030100571, and WO 2002/102314, each expressly incorporated herein by reference in its entirety. In one embodiment, PDE7 inhibitors useful in the methods of the invention have the formulas:

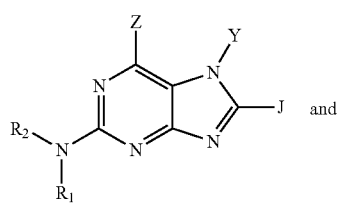

(15A)

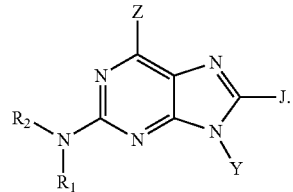

(15B)

The substituents for the above compounds are defined as follows:

$R_1$ is H or alkyl;

$R_2$ is (a) heteroaryl, or heterocyclo, either of which may be optionally substituted with one to three groups T1, T2, T3; (b) aryl substituted with one to three groups T1, T2, T3 provided that at least one of T1, T2, T3 is other than H; or (c) aryl fused to a heteroaryl or heterocyclo ring wherein the combined ring system may be optionally substituted with one to three groups T1, T2, T3;

Y is alkyl, alkenyl, alkynyl, cycloalkyl, aryl, heterocyclo, heteroaryl, (aryl)alkyl or (heteroaryl) alkyl any of which may be optionally substituted with one to three groups T1a, T2a, T3a;

J is (a) hydrogen, halo, or OR$_4$, or (b) alkyl, alkenyl, alkynyl, aryl, heteroaryl, heterocyclo, or, cycloalkyl any of which may be optionally substituted with one to three groups T1b, T2b, T3b;

Z is (a) OR$_4$, SR$_4$, NR$_3$R$_4$, NR$_3$SO$_2$R$_{4a}$ halogen, nitro, haloalkyl; or (b) alkyl, aryl, heteroaryl, heterocyclo, or cycloalkyl any of which may be optionally substituted with one to three groups T1c, T2c, T3c;

$R_3$ is H, alkyl, alkenyl, aryl, (aryl)alkyl, heteroaryl, (heteroaryl)alkyl, cycloalkyl, (cycloalkyl)alkyl, heterocyclo or (heterocyclo)alkyl any of which may be optionally independently substituted where valance allows with one to three groups T1c, T2c, T3c;

$R_4$ is alkyl, alkenyl, aryl, (aryl)alkyl, heteroaryl, (heteroaryl)alkyl, cycloalkyl, (cycloalkyl)alkyl, heterocyclo or (heterocyclo)alkyl any of which may be optionally independently substituted where valance allows with one to three groups T1d, T2d, or T3d; or $R_3$ and $R_4$ together with the nitrogen atom to which they are attached may combine to form a 4 to 8 membered heterocyclo ring optionally substituted with one to three groups T1c, T2c, or T3c;

$R_{4a}$ is hydrogen, alkyl, alkenyl, aryl, heteroaryl, (aryl)alkyl, (heteroaryl)alkyl, heterocyclo, (heterocyclo)alkyl, cycloalkyl or (cycloalkyl)alkyl any of which may be optionally substituted with one to three groups T1d, T2d or T3d;

T1, T1a, T1b, T1c, T1d, T2, T2a, T2b, T2c, T2d, T3, T3a, T3b, T3c, and T3d (hereinafter abbreviated as T1-1d, T2-2d, and T3-3d) are independently (1) hydrogen or T6, where T6 is
  (a) alkyl, (hydroxy) alkyl, (alkoxy) alkyl, alkenyl, alkynyl, cycloalkyl, (cycloalkyl) alkyl, cycloalkenyl, (cycloalkenyl) alkyl, aryl, (aryl) alkyl, heterocyclo, (heterocyclo) alkyl, heteroaryl, or (heteroaryl) alkyl;
  (b) a group (a) which is itself substituted by one or more of the same or different groups (a); or
  (c) a group (a) or (b) which is independently substituted by one or more (preferably 1 to 3) of the following groups (2) to (13) of the definition of T1-1d, T2-2d and T3-3d, (2) OH or OT6, (3) SH or ST6, (4) C(O)t H, C(O)t T6, or OC(O)T6, where t is 1 or 2;

(5) SO3H, S(O)tT6, or S(O)t N(T9)T6, (6) halo, (7) cyano, (8) nitro, (9) T4NT7 T8,

(10) T4N(T9)-T5NT7 T8,

(11) T4N(T10)-T5-T6,

(12) T4N(T10)-T5H,

(13) oxo,

T4 and T5 are each independently a single bond, T11-S(O)$_t$-T12, T11-C(O)-T12, T11-C(S)-T12, T11-O-T12, -T11S-T12, -T11OC(O)-T12, -T11-C(O)O-T12, -T11C(=NT9a)-T12, or T11-C(O)—C(O)-T12;

T7, T8, T9, T9a and T10 are (1) each independently hydrogen or a group provided in the definition of T6, or (2) T7 and T8 may together be alkylene or alkenylene, completing a 3- to 8-membered saturated or unsaturated ring together with the atoms to which they are attached, which ring is unsubstituted or substituted with one or more groups listed in the description of T1-1d, T2-2d and T3-3d, or (3) T7 or T8, together with T9, may be alkylene or alkenylene completing a 3- to 8-membered saturated or unsaturated ring together with the nitrogen atoms to which they are attached, which ring is unsubstituted or substituted with one or more groups listed in the description of T1-1d, T2-2d and T3-3d, or (4) T7 and T8 or T9 and T10 together with the nitrogen atom to which they are attached may combine to form a group N=CT13 T14 where T13 and T14 are each independently H or a group provided in the definition of T6; and T11 and T12 are each independently a single bond, alkylene, alkenylene, or alkynylene.

The preparation of these compounds is described in U.S. Pat. No. 6,838,559, U.S. 20030100571, and WO 2002/102314.

In another embodiment, PDE7 inhibitors useful in the methods of the invention are selected from those compounds generally or specifically disclosed in U.S. Pat. No. 7,087,614, U.S. 20030162802, and WO 2002/102313, each expressly incorporated herein by reference in its entirety. In one embodiment, PDE7 inhibitors useful in the methods of the invention have the formula:

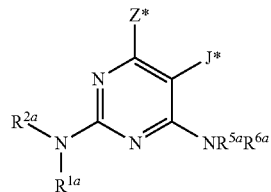

(16)

The substituents for the above compounds are described below.

In a related embodiment, PDE7 inhibitors useful in the methods of the invention have the formula:

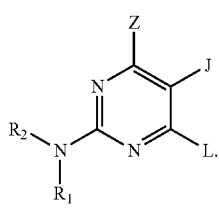

(16a)

The substituents for the above compounds are defined as follows:

$R_{1a}$ is hydrogen or alkyl; $R_{2a}$ is

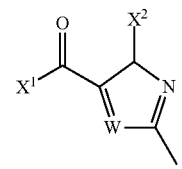

W is S; $X_1$ is alkoxy; and $X_2$ is alkyl;

Z* is halogen, haloalkyl, oxazolyl, $NR_{3a}R_{4a}$, C(O)—N(H)-alkylene-COOH, or phenyl which is unsubstituted or substituted with heteroaryl, $CO_tH$, or $CO_tT_6$;

$R_{3a}$ is hydrogen or alkyl;

$R_{4a}$ is alkyl, alkoxy, unsubstituted or substituted (heteroaryl) alkyl, unsubstituted or substituted heterocyclo, unsubstituted or substituted (heterocyclo) alkyl, or (aryl) alkyl wherein the aryl group is substituted with one or two groups T1 and/or T2 and/or further substituted with a group T3; or $R_{3a}$ and $R_{4a}$ together with the nitrogen atom to which they are attached combine to form an unsubstituted or substituted heterocyclo ring;

$R_{5a}$ is an unsubstituted or substituted (heteroaryl) alkyl, or (aryl) alkyl wherein the aryl group is substituted with one or two groups T1 and/or T2 and/or further substituted with a group T3; or $R_{5a}$ and $R_{6a}$ together with the nitrogen atom to which they are attached combine to form an unsubstituted or substituted heterocyclo ring; $R_{6a}$ is hydrogen or alkyl; J* is hydrogen or alkyl; T1 and T2 are independently alkoxy, alkoxycarbonyl, heteroaryl, $SO_3H$, or $SO_2R_{8a}$ where $R_{8a}$ is alkyl, amino, alkylamino or dialkylamino; or T1 and T2 together with the aryl ring to which they are attached combine to form a bicyclic ring; T3 is H, alkyl, halo, haloalkyl, or cyano; t is 1 or 2; and T6 is alkyl, haloalkyl, cycloalkyl, alkoxy, or heteroaryl.

The preparation of these compounds is described in U.S. Pat. No. 7,087,614, U.S. 20030162802, and WO 2002/102313.

In another embodiment, PDE7 inhibitors useful in the methods of the invention are selected from those compounds generally or specifically disclosed in US 20030104974, WO 2002/088080, and WO 2002/088079, each expressly incorporated herein by reference in its entirety. In one embodiment, PDE7 inhibitors useful in the methods of the invention have the formulas:

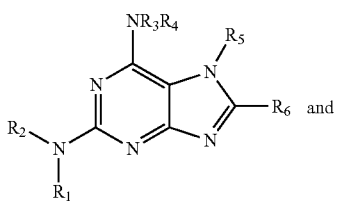
(17A)

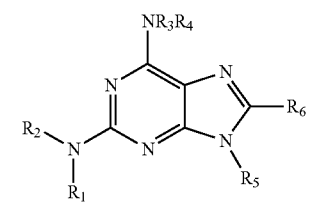
(17B)

The substituents for the above compounds are defined as follows:

$R_1$ is H or alkyl; $R_2$ is optionally substituted heteroaryl, or 4-substituted aryl; $R_3$ is hydrogen or alkyl; $R_4$ is alkyl, optionally substituted (aryl)alkyl, optionally substituted (heteroaryl)alkyl, optionally substituted heterocyclo, or optionally substituted (heterocyclo)alkyl; or $R_3$ and $R_4$ together with the nitrogen atom to which they are attached may combine to form an optionally substituted heterocyclo ring; $R_5$ is alkyl, optionally substituted (aryl)alkyl, or optionally substituted (heteroaryl)alkyl; and $R_6$ is hydrogen or alkyl.

In a related embodiment, PDE7 inhibitors useful in the methods of the invention have the formula:

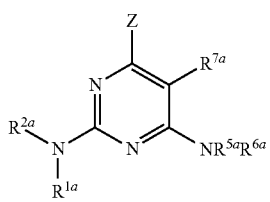

wherein $R_{1a}$ is H or alkyl; $R_{2a}$ is optionally substituted heteroaryl; Z is halogen, alkyl, substituted alkyl, haloalkyl, or $NR_{3a}R_{4a}$; $R_{3a}$ is hydrogen or alkyl; $R_{4a}$ is alkyl, optionally substituted (heteroaryl) alkyl, optionally substituted heterocyclo, optionally substituted (heterocyclo) alkyl, or (aryl) alkyl wherein the aryl group is substituted with one or two groups T1 and T2 and optionally further substituted with a group T3; or $R_{3a}$ and $R_{4a}$ together with the nitrogen atom to which they are attached may combine to form an optionally substituted heterocyclo ring; $R_{5a}$ is (aryl) alkyl wherein the aryl group is substituted with one or two groups T1 and T2 and optionally further substituted with a group T3; $R_{6a}$ is hydrogen or alkyl; $R_{7a}$ is hydrogen or alkyl; T1 and T2 are independently alkoxy, alkoxycarbonyl, heteroaryl or $SO_2R_{8a}$ where $R_{8a}$ is alkyl, amino, alkylamino or dialkylamino; or T1 and T2 together with the atoms to which they are attached may combine to form a ring (e.g., benzodioxole); T3 is H, alkyl, halo, haloalkyl or cyano.

In another related embodiment, PDE7 inhibitors useful in the methods of the invention have the formula:

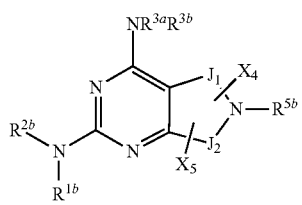

wherein $R_{1b}$ is H or alkyl; $R_{2b}$ is optionally substituted heteroaryl; $R_{3b}$ is H or alkyl; $R_{4b}$ is optionally substituted (aryl)alkyl; $R_{5b}$ is H, alkyl, or $C(O)(CH_2)_v OYR_{6b}$, where Y is a bond or C(O), $R_{6b}$ is hydrogen or alkyl, and v is an integer from 0 to 2; $J_1$ and $J_2$ are independently optionally substituted $C_{1-13}$ alkylene, provided that $J_1$ and $J_2$ are not both greater than $C_2$ alkylene; $X_4$ and $X_5$ are optional substituents bonded to any available carbon atom in one or both of $J_1$ and $J_2$, independently selected from hydrogen, $OR_7$, $NR_8R_9$, alkyl, substituted alkyl, alkenyl, substituted alkenyl, alkynyl, substituted alkynyl, cycloalkyl, substituted cycloalkyl, aryl, substituted aryl, heterocycloalkyl, or heteroaryl; R7 is hydrogen, alkyl, substituted alkyl, alkenyl, alkynyl, cycloalkyl, substituted cycloalkyl, C(O)alkyl, C(O)substituted alkyl, C(O)cycloalkyl, C(O) substituted cycloalkyl, C(O)aryl, C(O)substituted aryl, C(O)O-alkyl, C(O)O-substituted alkyl, C(O) heterocycloalkyl, C(O)heteroaryl, aryl, substituted aryl, heterocycloalkyl and heteroaryl; and $R_8$ and $R_9$ are independently selected from the group consisting of hydrogen, alkyl, substituted alkyl, cycloalkyl, substituted cycloalkyl, alkenyl, alkynyl, C(O) alkyl, C(O) substituted alkyl, C(O) cycloalkyl, C(O)substituted cycloalkyl, C(O)aryl, C(O)substituted aryl, C(O)O alkyl, C(O)O substituted alkyl, C(O) heterocycloalkyl, C(O) heteroaryl, $S(O)_2$alkyl, $S(O)_2$ substituted alkyl, $S(O)_2$ cycloalkyl, $S(O)_2$ substituted cycloalkyl, $S(O)_2$ aryl, $S(O)_2$substituted aryl, $S(O)_2$ heterocycloalkyl, $S(O)_2$ heteroaryl, aryl, substituted aryl, heterocycloalkyl, and heteroaryl, or $R_8$ and $R_9$ taken together with the nitrogen atom to which they are attached complete an optionally substituted heterocycloalkyl or heteroaryl ring.

In a further related embodiment, PDE7 inhibitors useful in the methods of the invention have the formula:

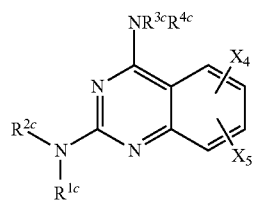

wherein $R_{1c}$ is H or alkyl; $R_{2c}$ is optionally substituted heteroaryl; $R_{3c}$ is H or alkyl; $R_{4c}$ is optionally substituted (aryl)alkyl; and $X_4$ and $X_5$ are optional substituents bonded to any available carbon atom in one or both of $J_1$ and $J_2$, independently selected from hydrogen, $OR_7$, $NR_8R_9$, alkyl, substituted alkyl, alkenyl, substituted alkenyl, alkynyl, substituted alkynyl, cycloalkyl, substituted cycloalkyl, aryl, substituted aryl, heterocycloalkyl, or heteroaryl.

The preparation of these compounds is described in US 20030104974, WO 2002/088080, and WO 2002/088079.

In another embodiment, PDE7 inhibitors useful in the methods of the invention are selected from those compounds generally or specifically disclosed in US 20030092908 and WO 2002/087513, each expressly incorporated herein by reference in its entirety. In one embodiment, PDE7 inhibitors useful in the methods of the invention have the formula:

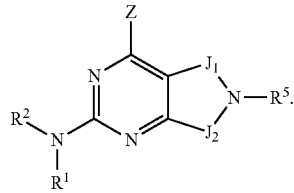
(18)

The substituents for the above compounds are defined as follows:

$R_1$ is hydrogen or alkyl;

$R_2$ is (a) heteroaryl, or heterocyclo, either of which may be optionally substituted with one to three groups T1, T2, T3; (b) aryl substituted with one to three groups T1, T2, T3 provided that at least one of T1, T2, T3 is other than H; or (c) aryl fused to a heteroaryl or heterocyclo ring wherein the combined ring system may be optionally substituted with one to three groups T1, T2, T3;

Z is $NR_3R_4$, $NR_3SO_2R_{4a}$, $OR_4$, $SR_4$, haloalkyl, or halogen;

$R_3$ and $R_4$ are independently H, alkyl, alkenyl, aryl, (aryl)alkyl, heteroaryl, (heteroaryl)alkyl, cycloalkyl, (cycloalkyl)alkyl, heterocyclo or (heterocyclo)alkyl any of which may be optionally independently substituted where valance allows with one to three groups T1a, T2a, or T3a; or $R_3$ and $R_4$ may be taken together with the nitrogen atom to which they are attached to form a heterocyclo or heteroaryl ring optionally independently substituted where valance allows with one to three groups T1a, T2a, or T3a;

$R_{4a}$ is alkyl, alkenyl, aryl, (aryl)alkyl, heteroaryl, (heteroaryl)alkyl, cycloalkyl, (cycloalkyl)alkyl, heterocyclo or (heterocyclo)alkyl any of which may be optionally independently substituted where valance allows with one to three groups T1a, T2a, or T3a;

$R_{3b}$ and $R_{4b}$ are independently H, alkyl, alkenyl, aryl, (aryl)alkyl, heteroaryl, (heteroaryl)alkyl, cycloalkyl, (cycloalkyl)alkyl, heterocyclo or (heterocyclo)alkyl;

$R_5$ is
(1) hydrogen, or cyano;
(2) alkyl, alkenyl, alkynyl, cycloalkyl, (cycloalkyl)alkyl, aryl, (aryl)alkyl, heterocyclo, (heterocyclo)alkyl, heteroaryl or (heteroaryl)alkyl, any of which may be optionally independently substituted where valance allows with one to three groups T1b, T2b, or T3b; or
(3) $C(O)R_6$, $C(O)OR_6$, $C(O)$—$C(O)OR$, or $SO_2R_{6a}$;

$R_6$ is H, alkyl, alkenyl, $NR_{3b}R_{4b}$, heterocyclo, (heterocyclo)alkyl, (hydroxy)alkyl, (alkoxy)alkyl, (aryloxy)alkyl, $(NR_{3b}R_{4b})$alkyl, heteroaryl, aryl or (aryl)alkyl, any of which may be optionally independently substituted where valance allows with one to three groups T1b, T2b, or T3b;

$R_{6a}$ is alkyl, alkenyl, $NR_{3b}R_{4b}$, heterocyclo, (heterocyclo)alkyl, (hydroxy)alkyl, (alkoxy)alkyl, (aryloxy)alkyl, $(NR_{3b}R_{4b})$alkyl, heteroaryl, aryl or (aryl)alkyl, any of which may be optionally independently substituted where valance allows with one to three groups T1b, T2b, or T3b;

$J_1$ and $J_2$ are independently optionally substituted $C_{1-3}$ alkylene, provided that $J_1$ and $J_2$ are not both greater than $C_2$ alkylene; and T1-1b, T2-2b, and T3-3b are each independently
(1) hydrogen or T6, where T6 is (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl) alkyl, heterocyclo, (heterocyclo)alkyl, heteroaryl, or (heteroaryl)alkyl; (ii) a group (i) which is itself substituted by one or more of the same or different groups (i); or (iii) a group (i) or (ii) which is independently substituted by one or more (preferably 1 to 3) of the following groups (2) to (13) of the definition of T1-1b, T2-2b, and T3-3b,
(2) OH or OT6,
(3) SH or ST6,
(4) $C(O)tH$, $C(O)_tT6$, or $OC(O)T6$, where t is 1 or 2,
(5) $SO_3H$, $S(O)_tT6$, or $S(O)_tN(T9)T6$,
(6) halo,
(7) cyano,
(8) nitro,
(9) T4-NT7T8,
(10) T4-N(T9)-T5-NT7T8,
(11) T4-N(T10)-T5-T6,
(12) T4-N(T10)-T5H,
(13) oxo, T4 and T5 are each independently (1) a single bond, (2) T1'-S(O)$_t$-T12, (3) T11-C(O)-T12, (4) T11-C(S)-T12, (5)-T11-O-T12, (6) T11-S-T12, (7) T11-O—C(O)-T12, (8) T11-C(O)—O-T12, (9) T11-C(=NT9a)-T12, or (10) T11-C(O)—C(O)-T12, T7, T8, T9, T9a and T10,
(1) are each independently hydrogen or a group provided in the definition of T6, or
(2) T7 and T8 may together be alkylene or alkenylene, completing a 3- to 8-membered saturated or unsaturated ring together with the atoms to which they are attached, which ring is unsubstituted or substituted with one or more groups listed in the description of T1-1b, T2-2b, and T3-3b, or
(3) T7 or T8, together with T9, may be alkylene or alkenylene completing a 3- to 8-membered saturated or unsaturated ring together with the nitrogen atoms to which they are attached, which ring is unsubstituted or substituted with one or more groups listed in the description of T1-1b, T2-2b, and T3-3b, or
(4) T7 and T8 or T9 and T10 together with the nitrogen atom to which they are attached may combine to form a group N=CT13T14 where T13 and T14 are each independently H or a group provided in the definition of T6; and T11 and T12 are each independently a single bond, alkylene, alkenylene, or alkynylene.

The preparation of these compounds is described in US 20030092908 and WO 2002/087513.

In another embodiment, PDE7 inhibitors useful in the methods of the invention are selected from those compounds generally or specifically disclosed in US 20040127707 and WO 2002/085906, each expressly incorporated herein by reference in its entirety. In one embodiment, PDE7 inhibitors useful in the methods of the invention have the formula:

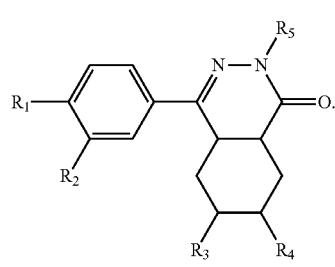
(19)

The substituents for the above compounds are defined as follows:

$R_1$ is 1-2C-alkoxy or 1-2C-alkoxy which is completely or predominantly substituted by fluorine, $R_2$ is fluorine, bromine, or chlorine, $R_3$ and $R_4$ are both hydrogen or together form an additional bond, $R_5$ is $R_6$, $C_mH_{2m}$—$R_7$, $C_nH_{2n}$—$C(O)R_8$, $CH(R_9)_2$, $C_pH_{2p}$—Y-Aryl1, $R_{12}$ or $R_{26}$, wherein $R_6$ 1-8C-alkyl, 3-10C-cyclo, 3-7C-cycloalkylmethyl, 3-7C-alkenyl, 3-7C-alkinyl, phenyl-3-4C-alkenyl, 7-10C-polycycloalkyl, naphthyl, pyridyl, pyrazinyl, pyridazinyl, pyrimidyl, quinazolinyl, quinoxalinyl, cinnolinyl, isoquinolinyl, quinolinyl, indanyl, indazolyl, benzoxazolyl, benzothiazolyl, oxazolyl, thiazolyl, N-methylpiperidyl, tetrahydropyranyl, 6-methyl-3-trifluoromethyl-pyridin-2-yl, 1,3,4-trimethyl-1H-pyrazolo[3,4-b)]pyridin-6-yl, 3-thiophen-2-yl [1,2,4]thiadiazol-5-yl, 1,1-dioxide-tetrahydrothiophen-3-yl, 1-oxo-1,3-dihydro-isobenzofuran-5-yl, 4-(4-yl-but-1-oxy) benzoic acid, or an unsubstituted or by $R_{61}$ and/or $R_{62}$ substituted phenyl radical, wherein $R_{61}$ is hydroxyl, 1-4C-alkyl, 1-4C-alkoxy, nitro, cyano, halogen, carboxyl, hydroxycarbonyl-1-4C-alkyl, 1-4C-alkoxycarbonyl, hydroxy-1-4C-alkyl, amino, mono- or di-1-4C-alkylamino, 1-4C-alkylcarbonylamino, aminocarbonyl, mono- or di-1-4C-alkylaminocarbon-yl, aminosulfonyl, mono- or di-1-4C-alkylaminosulfonyl, 4-methylphenylsulfonamido, imidazolyl; tetrazol-5-yl, 2-(1-4C-alkyl)tetrazol-5-yl or 2-benzyltetrazol-5-yl and $R_{62}$ is 1-4C-alkyl, 1-4C-alkoxy, nitro, or halogen, $R_7$ is hydroxyl, halogen, cyano, nitro, nitroxy(O—$NO_2$), carboxyl, carboxyphenyloxy, phenoxy, 1-4C-alkoxy, 3-7C-cydoalkoxy, 3-7C-cycloalkylmethoxy, 1-4C-alkylcarbonyl, 1-4C-alkylcarbonyloxy, 1-4C-alkylcarbonylamino, 1-4C-alkoxycarbonyl, aminocarbonyl, mono- or di-1-4C-alkylaminocarbonyl, amino, mono- or di-1-4C-alkylamino, or an unsubstituted or by $R_{71}$ and/or $R_{72}$ substituted piperidyl, piperazinyl, pyrrolidinyl or morpholinyl radical, wherein $R_{71}$ is hydroxyl, 1-4C-alkyl, hydroxy-1-4C-alkyl or 1-4C-alkoxycarbonyl, and $R_{72}$ is 1-4C-alkyl, carboxyl, aminocarbonyl or 1-4C-alkoxycarbonyl, $R_8$ is an unsubstituted or by $R_{81}$ and/or $R_{82}$ substituted phenyl, naphthyl, phenanthrenyl or anthracenyl radical, wherein $R_{81}$ is hydroxyl, halogen, cyano, 1-4C-alkyl, 1-4C-alkoxy, carboxyl, aminocarbonyl, mono- or di-1-4C-alkylaminocarbonyl, 1-4C-alkylcarbonyloxy, 1-4C-alkoxycarbonyl, amino, mono- or di-1-4C-alkylamino, 1-4C-alkylcarbonylamino, or 1-4C-alkoxy which is completely or predominantly substituted by fluorine, and $R_{82}$ is hydroxyl, halogen, 1-4C-alkyl, 1-4C-alkoxy or 1-4C-alkoxy which is completely or predominantly substituted by fluorine, $R_9$ is $C_qH_{2q}$-phenyl, Y is a bond or O (oxygen), Aryl$_1$ is an unsubstituted phenyl, naphthyl, pyridyl, pyrazinyl, pyridazinyl, pyrimidinyl, quinazolinyl, quinoxalinyl, cinnolinyl, isoquinolyl, quinolyl, coumarinyl, benzimidazolyl, benzoxazolyl, benzothiazolyl, benzotriazolyl, N-benzosuccinimidyl, imidazolyl, pyrazolyl, oxazolyl, thiazolyl, furyl, thienyl, pyrrolyl, a 2-(1-4C-alkyl)-thiazol-4-yl radical, or a phenyl radical substituted by $R_{10}$ and/or $R_{11}$, wherein $R_{10}$ is hydroxyl, halogen, nitro, cyano, 1-4C-alkyl, trifluoromethyl, 1-4C-alkoxy, carboxyl, hydroxycarbonyl-1-4C-alkyl, 1-4C-alkylcarbonyloxy, 1-4C-alkoxycarbonyl, amino, mono- or di-1-4C-alkylamino, 1-4C-alkylcarbonylamino, aminocarbonyl, mono- or di-1-4C-alkylamino-carbonyl, imidazolyl or tetrazolyl, and $R_{11}$ is hydroxyl, halogen, nitro, 1-4C-alkyl or 1-4C-alkoxy, m is an integer from 1 to 8, n is an integer from 1 to 4, p is an integer from 1 to 6, q is an integer from 0 to 2, $R_{12}$ is a radical of formula

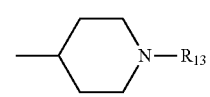

(a)

wherein $R_{13}$ is $S(O)_2$—$R_{14}$, $S(O)_2$—$(CH_2)_r$—$R_{15}$, $(CH_2)_s$—$S(O)_2R_{16}$, $C(O)R_{17}$, $C(O)$—$(CH_2)_r$—$R_{18}$, $(CH_2)_s$—$C(O)$—$R_{19}$, Hetaryl1, Aryl$_2$ or Aryl$_3$-1-4C-alkyl, $R_{14}$ is 1-4C-alkyl, 5-dimethylaminonaphthalin-1-yl, $N(R_{20})R_{21}$, phenyl or phenyl substituted by $R_{22}$ and/or $R_{23}$, $R_{15}$ is $N(R_{20})R_{21}$, $R_{16}$ is $N(R_{20})R_{21}$, $R_{17}$ is 1-4C-alkyl, hydroxycarbonyl-1-4C-alkyl, phenyl, pyridyl, 4-ethyl-piperazin-2,3-dion-1-yl, 2-oxo-imidazolidin-1-yl or $N(R_{20})R_{21}$, $R_{18}$ is $N(R_{20})R_{21}$, $R_{19}$ is $N(R_{20})R_{21}$ phenyl, phenyl substituted by $R_{22}$ and/or $R_{23}$ and/or $R_{24}$, $R_{20}$ and $R_{21}$ are independent from each other hydrogen, 1-7C-alkyl, 3-7C-cycloalkyl, 3-7C-cycloalkylmethyl or phenyl, or $R_{20}$ and $R_{21}$ together and with inclusion of the nitrogen atom to which they are bonded, form a 4-morpholinyl-ring, 1-pyrrolidinyl-ring, 1-piperidinyl-ring, 1-hexahydroazepino-ring or a 1-piperazinyl-ring of formula

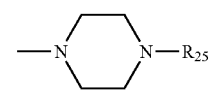

(b)

wherein $R_{25}$ is pyrid-4-yl, pyrid4-ylmethyl, 1-4C-alkyl-dimethylamino, dimethylaminocarbonylmethyl, N-methyl-piperidin-4-yl, 4-morpholino-ethyl or tetrahydrofuran-2-yl-methyl-, $R_{22}$ is halogen, nitro, cyano, carboxyl, 1-4C-alkyl, trifluoromethyl, 1-4C-alkoxy, 1-4C-alkoxycarbonyl, amino, mono- or di-1 4C-alkylamino, aminocarbonyl 1-4C-alkylcarbonylamino or mono- or di-1-4C-alkylaminocarbon-yl, $R_{23}$ is halogen, amino, nitro, 1-4C-alkyl or 1-4C-alkoxy, $R_{24}$ is halogen, Hetaryl$_1$ is pyrimidin-2-yl, thieno-[2,3-d]pyrimidin-4-yl, 1-methyl-1H-pyrazolo-[3,4-d]pyrimidin-4-yl, thiazolyl, imidazolyl or furanyl, Aryl$_2$ is pyridyl, phenyl or phenyl substituted by $R_{22}$ and/or $R_{23}$, Aryl$_3$ is pyridyl, phenyl, phenyl substituted by $R_{22}$ and/or $R_{23}$, 2-oxo-2H-chromen-7-yl or 4-(1,2,3-thiadiazol-4-yl)phenyl, r is an integer from 1 to 4, s is an integer from 1 to 4, $R_{26}$ is a radical of formula

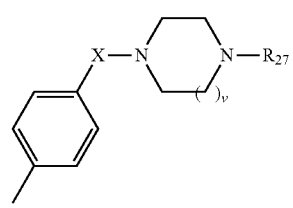

(c)

wherein R$_{27}$ is C(O)R$_{28}$, (CH$_2$)$_t$—C(O)R$_{29}$, (CH$_2$)$_u$R$_{30}$, Aryl$_4$, Hetaryl$_2$, phenylprop-1-en-3-yl or 1-methylpiperidin-4-yl, R$_{28}$ hydrogen, 1-4C-alkyl, OR$_{31}$, furanyl, indolyl, phenyl, pyridyl, phenyl substituted by R$_{34}$ and/or R$_{35}$ or pyridyl substituted by R$_{36}$ and/or R$_{37}$, R$_{29}$ is N(R$_{32}$)R$_{33}$, R$_{30}$ is N(R$_{32}$)R$_{33}$, tetrahydrofuranyl or pyridinyl, R$_{31}$ is 1-4C-alkyl, R$_{32}$ is hydrogen, 1-4C-alkyl, 3-7C-cycloalkyl or 3-7C-cycloalkylmethyl, R$_{33}$ is hydrogen, 1-4C-alkyl, 3-7C-cycloalkyl or 3-7C-cycloalkylmethyl, or R$_{32}$ and R$_{33}$ together and with inclusion of the nitrogen atom to which they are bonded, form a 4-morpholinyl-, 1-pyrrolidinyl-, 1-piperidinyl- or 1-hexahydroazepinyl-ring, Aryl$_4$ is phenyl, pyridyl, pyrimidinyl, phenyl substituted by R$_{34}$ and/or R$_{35}$, pyridyl substituted by R$_{36}$ and/or R$_{37}$, R$_{34}$ is halogen, nitro, 1-4C-alkyl, trifluoromethyl or 1-4C-alkoxy, R$_{35}$ is halogen or 1-4C-alkyl, R$_{36}$ is halogen, nitro, 1-4C-alkyl, trifluoromethyl or 1-4C-alkoxy, R$_{37}$ is halogen or 1-4C-alkyl, Hetaryl$_2$ is indol-4-yl, 2-methyl-quinolin-4-yl, 5-chloro-6-oxo-1-phenyl-1,6-dihydro-pyridazin-4-y-1,3-phenyl-1,2,4-thiadiazol-5-yl or 3-o-tolyl-1,2,4-thiadiazol-5-yl, t is an integer from 1 to 4, u is an integer from 1 to 4, v is an integer from 1 to 2, X is —C(O)— or —S(O)$_2$—, and the salts of these compounds.

The preparation of these compounds is described in US 20040127707 and WO 2002/085906.

In another embodiment, PDE7 inhibitors useful in the methods of the invention are selected from those compounds generally or specifically disclosed in U.S. Pat. No. 6,818,651, US 20040044212, and WO 2002/040450, each expressly incorporated herein by reference in its entirety. In one embodiment, PDE7 inhibitors useful in the methods of the invention have the formula:

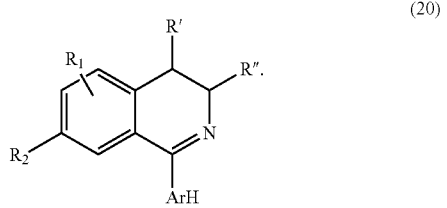

(20)

The substituents for the above compounds are defined as follows:

either R$_1$ denotes hydrogen, and R$_2$ denotes fluorine, chlorine, bromine, cyano, trifluoromethyl or phenoxy, or R$_1$ denotes hydrogen, fluorine, chlorine, bromine, trifluoromethyl or cyano, and R$_2$ denotes hydrogen, R' and R" both denote hydrogen or together represent a bond, and Ar represents a phenyl radical of the formulae IIa, IIb, or IIc

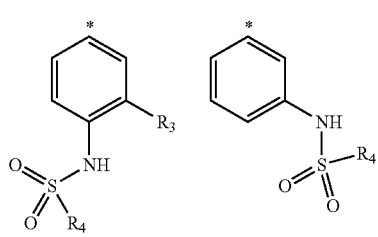

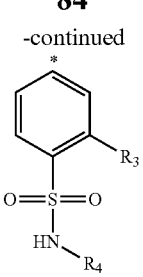

wherein R$_3$ denotes hydrogen, hydroxyl, nitro, amino, carboxyl, aminocarbonyl, 1-4C-alkoxy, trifluoromethoxy, 1-4C-alkoxycarbonyl or mono- or di-1-4C-alkylaminocarbonyl, R$_4$ represents 1-4C-alkyl, naphthalenyl, 5-dimethylaminonaphthalen-1-yl, phenylethen-2-yl, 3,5-dimethylisoxazol-4-yl, 5-chloro-3-methylbenzo[b]thiophen-2-yl, 6-chloroimidazo[2,1b]-thiazol-5-yl, or represents a phenyl or thiophene radical which is unsubstituted or is substituted by one or more identical or different radicals selected from the group halogen, cyano, 1-4C-alkyl, trifluoromethyl, 1-4C-alkoxy which is substituted entirely or mainly by fluorine, 1-4C-alkoxy, 1-4C-alkylcarbonylamino, 1-4C-alkoxycarbonyl, phenylsulfonyl or isoxazolyl, or a hydrate, solvate, salt, hydrate of a salt, or solvate of a salt thereof.

The preparation of these compounds is described in U.S. Pat. No. 6,818,651, US 20040044212, and WO 2002/040450.

In another embodiment, PDE7 inhibitors useful in the methods of the invention are selected from those compounds generally or specifically disclosed in WO 2002/040449, expressly incorporated herein by reference in its entirety. In one embodiment, PDE7 inhibitors useful in the methods of the invention have the formula:

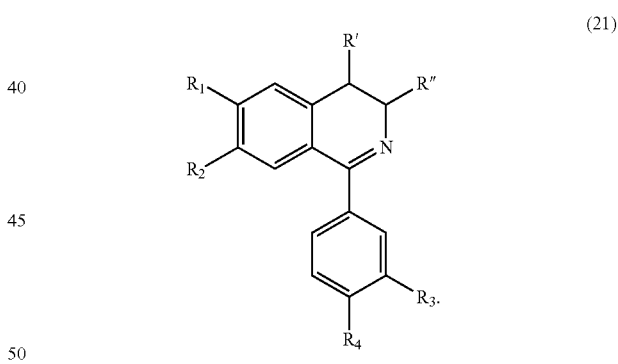

(21)

The substituents for the above compounds are defined as follows:

either R$_1$ denotes hydrogen and R$_2$ denotes fluorine, chlorine, bromine, cyano, trifluoromethyl or phenoxy, or R$_1$ denotes hydrogen, fluorine, chlorine, bromine, trifluoromethyl or cyano and R$_2$ denotes hydrogen, R' and R" both denote hydrogen or together represent a bond, R$_3$ denotes hydrogen, hydroxyl, nitro, amino, carboxyl, aminocarbonyl, 1-4C-alkoxy, trifluoromethoxy, 1-4C-alkoxycarbonyl or mono- or di-1-4C-alkylaminocarbonyl and R$_4$ denotes C(O)—X—R$_5$, N(H)—C(O)—R$_6$ or N(H)—C(O)—N(H)—R$_2$, wherein X denotes 0 or N(H), R$_5$ denotes hydrogen, 1-4C-alkyl, 3-7C-cycloalkylmethyl, 6,6-dimethylbicyclo[3,3,I]hept-2-yl, 3-7C-alkynyl, 1-4C- alkylcarbonyl-1-4C-alkyl, aminocarbonyl-1-4C-alkyl, furan-2-ylmethyl, 2-pyridin-2-yleth-1-yl, 2-pyridin-3-ylmethyl, N-methylpiperidin-3-yl, 1-benzylpiperidin-4-yl, morpholin-4-yl-eth-2-yl, morpholin-4-yl-eth-1-yl, 2-benzo[1,3]dioxol-4-yl-eth-1-yl, chroman-4-yl, 1-methoxycarbonyl-2-indol-3-yl-eth-1-yl, 1,3-bis-methoxycarbonylprop-1-yl, 1-methoxycarbonyl-3-methylsulfanyl-eth-1-yl, 1-methoxycarbonyl-2-thiazol-2-yl-eth-1-yl, or 4-methylthiazol-5-yl-eth-2-yl, or represents a benzyl-, phenyl-eth-1-yl or 1-methoxycarbonyl-2-phenyl-eth-2-yl radical which is unsubstituted or substituted by one or more radicals selected from the group halogen, trifluoromethyl and phenyl, $R_6$ denotes 2,4-dichlorophenoxymethyl, 2-tert-butoxycarbonylamino-eth-1-yl, 1-acetylpiperidin-4-yl, Ar1 or Ar2-CH=CH—, where Ar1 represents 3-chlorophenyl, 4-trifluoromethoxyphenyl, 3-phenoxyphenyl, indol5-yl, 2-methylpyridin-5-yl, quinolin-6-yl or 2-benzothiazol-6-yl, Ar2 represents furan-2-yl, furan-3-yl, thiophen-2-yl, indol-3-yl, 3-trifluoromethylphenyl, 3-methoxyphenyl or pyridin-3-yl, $R_7$ represents 1-4C-alkyl, 3-7C-alkenyl, 3-7C-cycloalkyl, 1-ethoxycarbonyl-2-phenyl-eth-1-yl, thiophen-2-yleth-1-yl or a phenyl radical which is unsubstituted or substituted by one or more radicals selected from the group halogen, cyano, 1-4C-alkyl, trifluoromethyl, 1-4C-alkylthio, 1-4C-alkoxy, 1-4C-alkoxy which is entirely or predominantly substituted by fluorine, 1-4C-alkylcarbonyl and phenoxy, or a salt thereof.

The preparation of these compounds is described in WO 2002/040449.

In another embodiment, PDE7 inhibitors useful in the methods of the invention are selected from those compounds generally or specifically disclosed in WO 2001/098274, expressly incorporated herein by reference in its entirety. In one embodiment, PDE7 inhibitors useful in the methods of the invention have the formula:

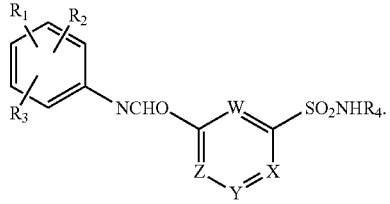

(22)

The substituents for the above compounds are defined as follows:

W, X, Y and Z, which may be the same or different, each represents a nitrogen atom or a $C(R^5)$ group [wherein $R_5$ is a hydrogen or halogen atom or an alkyl, haloalkyl, alkoxy, haloalkoxy, hydroxy, —$NO_2$ or —CN group] provided that two or more of W, X, Y, and Z are $C(R_5)$ groups;

$R_1$, $R_2$ and $R_3$, which may be the same or different, each is an atom or group -$L_1(Alk_1)_rL_2(R_6)_s$ wherein $L_1$ and $L_2$, which may be the same or different, is each a covalent bond or a linker atom or group, r is zero or the integer 1, $Alk_1$ is an aliphatic or heteroaliphatic chain, s is an integer 1, 2 or 3 and $R_6$ is a hydrogen or halogen atom or a group selected from alkyl, —$OR_7$ [where $R_7$ is a hydrogen atom or an optionally substituted alkyl group], —$SR_7$, $NR_7R_8$ [where $R_8$ is as just defined for $R_7$ and may be the same or different], —$NO_2$, CN, $CO_2R_7$, $SO_3H$, $S(O)R_7$, $SO_2R_7$, $OCO_2R_7$, $CONR_7R_8$, $OCONR_7R_8$, $CSNR_7R_8$, $OCR_7$, $OCOR_7$, $N(R_7)COR_8$, $N(R_7)CSR_8$, $S(O)NR_7R_8$, $SO_2NR_7R_8$, $N(R_7)SO_2R_8$, $N(R_7)CON$ $(R_8)(R_9)$ [where $R_9$ is a hydrogen atom or an optionally substituted alkyl group], $N(R_7)CSN(R_8)(R_9)$, $N(R_7)SO_2N(R_8)$ $(R_9)$, $C(R_7)$=$NO(R_8)$, cycloaliphatic, heterocycloaliphatic, aryl or heteroaryl group]; provided that one or more of $R_1$, $R_2$, or $R_3$ is a substituent other than a hydrogen atom;

$R_4$ represents an optionally substituted phenyl, 1- or 2-naphthyl, pyridyl, pyrimidinyl, pyridazinyl, or pyrazinyl group; and the salts, solvates, hydrates and N-oxides thereof.

The preparation of these compounds is described in WO 2001/098274.

In another embodiment, PDE7 inhibitors useful in the methods of the invention are selected from those compounds generally or specifically disclosed in WO 2001/074786, expressly incorporated herein by reference in its entirety. In one embodiment, PDE7 inhibitors useful in the methods of the invention have the formula:

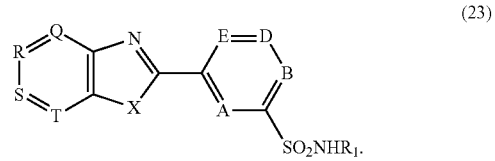

(23)

The substituents for the above compounds are defined as follows:

$R_1$ represents an aryl or heteroaryl group;

A, B, P, and E, which may be the same or different, each represents a nitrogen atom or a $C(R_2)$ group [wherein $R_2$ is a hydrogen or halogen atom or an alkyl, haloalkyl, alkoxy, haloalkoxy, hydroxy, —$NO_2$ or —CN group] provided that two or more of A, B, D, and E are $C(R_2)$ groups; X represents an oxygen or sulphur atom or a $N(R_3)$ group wherein $R_3$ is a hydrogen atom or an alkyl group;

Q, R, S, and T, which may be the same or different each represents a nitrogen atom or a group $C(R_4)$ [wherein $R_4$ is an atom or group -$L_1(Alk_1)_rL_2(R_5)$s wherein $L_1$ and $L_2$, which may be the same or different, is each a covalent bond or a linker atom or group, r is zero or the integer 1, Alkyl is an aliphatic or heteroaliphatic chain, s is an integer 1, 2 or 3 and $R_5$ is a hydrogen or halogen atom or a group selected from alkyl, $OR_6$ [where $R_6$ is a hydrogen atom or an optionally substituted alkyl group], $SR_6$, $NR_6R_7$ [where $R_7$ is as just defined for $R_6$ and may be the same or different], $NO_2$, CN, $CO_2R_6$, $SO_3H$, $S(O)R_6$, $SO_2R_6$, $OCO_2R_6$, $CONR_6R_7$, $OCONR_6R_7$, $CSNR_7R_7$, $OCR_6$, $OCOR_6$, $N(R_6)COR_7$, $N(R_6)$ $CSR_7$, $S(O)NR_6R_7$, $SO_2NR_6R_7$, $N(R_6)SO_2R_7$; $N(R_6)CON$ $(R_7)(R_8)$ [where $R_8$ is a hydrogen atom or an optionally substituted alkyl group], $N(R_6)CSN(R_7)(R_8)$, $N(R_6)SO_2N(R_7)$ $(R_8)$, $C(R_6)$=$NO(R_7)$ cycloaliphatic, heterocycloaliphatic, aryl or heteroaryl group] provided that two or more of Q, R, S, and T are $C(R_4)$ groups; and the salts, solvates, hydrates and N-oxides thereof.

The preparation of these compounds is described in WO 2001/074786.

In another embodiment, PDE7 inhibitors useful in the methods of the invention are selected from those compounds generally or specifically disclosed in WO 2000/068230, expressly incorporated herein by reference in its entirety. In one embodiment, PDE7 inhibitors useful in the methods of the invention have the formula:

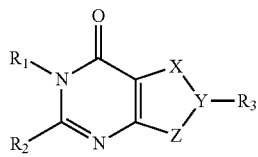

(24)

The substituents for the above compounds are defined as follows:

X—Y—Z represents $NR_4$—C=N or N=C—$NR_4$;

$R_1$ represents H, alkyl, cycloalkyl, cycloalkylalkyl, arylalkyl, heteroarylalkyl or heterocycloalkyl;

$R_2$ represents $OR_8$, $NR_8R_9$, $SR_{13}$, alkyl or $CF_3$;

$R_3$ represents halogen, alkyl, $CF_3$ or $OR_8$;

$R_4$, which can be attached to either X or Z, is a residue selected from

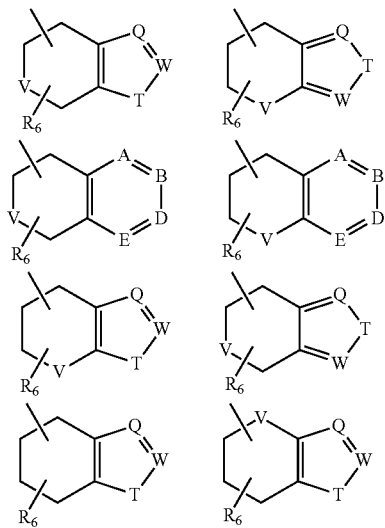

wherein attachment is through any position on the saturated ring, provided the attachment is not at a position adjacent to V, and the saturated ring may be substituted at any position with one or more $R_6$;

A, B, D, and E are the same or different and each represents $Cl_nR_5$, N or N—O;

V represents O, S, $NR_7$ or $C(L^1_m R_{14})(L^2_n R_{14})$;

Q and W are the same or different and each represents $CL_nR_5$ or N;

T represents O, S or $NR_7$;

$L^1$ and $L^2$ are the same or different and each represents $C(R_{15})_2$;

m and n are the same or different and each represents 0, 1, 2, 3, 4 or 5;

the $R_5$s are the same or different and each represents H, halogen, alkyl, cycloalkyl, $OR_8$, $NR_8R_9$, $CO_2R_{10}$, $CONR_{11}R_{12}$, CONHOH, $SO_2NR_{11}R_{12}$, $SON_{11}R_{12}$, $COR_{13}$, $SO_2R_{13}$, $SOR_{13}$, $SR_{13}$, $CF_3$, $NO_2$ or CN;

$R_6$ represents H, alkyl, cycloalkyl, $OR_8$, $NR_8R_9$, $CO_2R_{10}$, $CONR_{11}R_{12}$, $SO_2NR_{11}R_{12}$, $SON_{11}R_{12}$, $COR_{13}$, $SO_2R_{13}$, $SOR_{13}$, $SR_{13}$, $CF_3$, CN or =O;

$R_7$ represents H or alkyl;

$R_8$ represents H, alkyl, cycloalkyl, cycloalkylalkyl, aryl, arylalkyl, heteroaryl, heteroarylalkyl, heterocyclo or heterocycloalkyl;

$R_9$ represents $R_8$ or alkylcarbonyl, alkoxycarbonyl, alkylsulphonyl, cycloalkylcarbonyl, cycloalkoxycarbonyl, cycloalkylsulphonyl, cycloalkylalkylcarbonyl, cycloalkylalkoxycarbonyl, cycloalkylalkylsulphonyl, arylcarbonyl, arylsulphonyl, heteroarylcarbonyl, heteroarylsulphonyl, heterocyclocarbonyl, heterocyclosulphonyl, arylalkylcarbonyl, arylalkoxycarbonyl, arylalkylsulphonyl, heteroarylalkylcarbonyl, heteroarylalkoxycarbonyl, heteroarylsulphonyl, heterocycloalkylcarbonyl, heterocycloalkoxycarbonyl or heterocycloalkylsulphonyl; or $NR_8R_9$ represents a heterocyclic ring such as morpholine;

$R_{10}$ represents H, alkyl, cycloalkyl, cycloalkylalkyl, arylalkyl, heteroarylalkyl or heterocycloalkyl;

$R_{11}$ and $R_{12}$ are the same or different and are each $R_8$, or $NR_{11}R_{12}$ represents a heterocyclic ring such as morpholine;

$R_{13}$ represents alkyl, cycloalkyl, cycloalkylalkyl, aryl, arylalkyl, heteroaryl, heteroarylalkyl, heterocyclo or heterocycloalkyl;

the $R_{14}$s are the same or different and are each selected from H, alkyl, cycloalkyl, $OR_8$, $NR_8R_9$, $CO_2R_{10}$, $CONR_{11}R_{12}$, CONHOH, $SO_2NR_{11}R_{12}$, $SON_{11}R_{12}$, $COR_{13}$, $SO_2R_{13}$, $SOR_{13}$, $SR_{13}$, $CF_3$, $NO_2$ and CN, provided that when both m and n represent 0, if one $R_{14}$ is $OR_8$, $NR_8R_9$ or $SR_{13}$, the other is not $OR_8$, $NR_8R_9$ or $SR_{13}$; and $R_{15}$ represents H, alkyl or F; or a pharmaceutically acceptable salt thereof.

The preparation of these compounds is described in WO 2000/068230, incorporated herein by reference in its entirety.

In another embodiment, PDE7 inhibitors useful in the methods of the invention are selected from those compounds generally or specifically disclosed in US 20040106631, EP 1 400 244, and WO 2004/026818, each expressly incorporated herein by reference in its entirety. In one embodiment, PDE7 inhibitors useful in the methods of the invention have the formula:

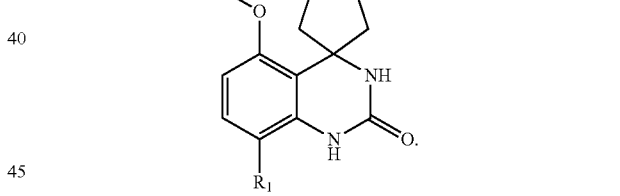

(25)

The substituents for the above compounds are defined as follows:

m is 1, 2 or 3; $R_1$ is methyl, chloro, bromo or fluoro; $R_2$ is $-Q^1-Q^2-Q^3-Q^4$ or ($C_1$-$C_6$) alkyl, said ($C_1$-$C_6$) alkyl is substituted with one to three $OR_4$, $COOR_4$, $NR_4R_5$, NRC(=O)$R_4$, C(=O)$NR_4R_5$ or $SO_2NR_4R_5$;

$R_4$ is ($C_1$-$C_6$) alkyl substituted with one to three F, CN, S(=O)$R_6$, $SO_3H$, $SO_2R_6$, $SR_7$, C(=O)—NH—$SO_2$—$CH_3$, C(=O)$R_7$, NR'C(=O)$R_7$, NR'$SO_2R_6$, C(=O)$NR_7R_8$, O—C(=O)$NR_7R_8$ or $SO_2NR_7R_8$;

$R_5$ is H or ($C_1$-$C_6$) alkyl optionally substituted with one to three F, CN, S(=O)$R_6$, $SO_3H$, $SO_2R_6$, $SR_7$, C(=O)—NH—$SO_2$—$CH_3$, C(=O)$R_7$, NR'C(=O)$R_7$, NR'$SO_2R_6$, C(=O)$NR_7R_8$, O—C(=O)$NR_7R_8$ or $SO_2NR_7R_8$; or said ($C_1$-$C_6$) alkyl is (1) substituted with one to three OC(=O)$R_{4a}$, $SR_{4a}$, S(=O)$R_3$, C(=$NR_9$)$R_{4a}$, C(=$NR_9$)—$NR_{4a}R_{5a}$, NR—C(=$NR_9$)—$NR_{4a}R_{5a}$, NRCOOR$_{4a}$, NR—C(=O)$NR_{4a}R_{5a}$, NR—$SO_2$—$NR_{4a}R_{5a}$, NR—C(=$NR_9$)—$R_{4a}$ or NR—$SO_2$—$R_3$; and (2) optionally substituted with one or two $OR_{4a}$, $COOR_{4a}$, $C(=O)—R_{4a}$, $NR_{4a}R_{5a}$, $NRC(=O)R_{4a}$, $C(=O)NR_4R_{5a}$ or $SO_2NR_{4a}R_{5a}$;

$R_9$ is H, CN, OH, $OCH_3$, $SO_2CH_3$, $SO_2NH_2$ or $(C_1-C_6)$ alkyl; and $R_3$ is $(C_1-C_6)$ alkyl optionally substituted with one to three F, CN, $S(=O)R_6$, $SO_3H$, $SO_2R_6$, $C(=O)—NH—SO_2—CH_3$, $OR_7$, $SR_7$, $COOR_5$, $C(=O)R_7$, $O—C(=O)NR_7R_8$, $NR_7R_8$, $NR'C(=O)R_7$, $NR'SO_2R_6$, $C(=O)NR_7R_8$ or $SO_2NR_7R_8$;

$R_{4a}$ and $R_{5a}$ are the same or different and are H or $(C_1-C_6)$ alkyl optionally substituted with one to three F, CN, $S(=O)R_6$, $SO_3H$, $SO_2R_6$, $C(=O)—NH—SO_2—CH_3$, $OR_7$, $SR_5$, $COOR_5$, $C(=O)R_7$, $O—C(=O)NR_7R_8$, $NR_7R_8$, $NR'C(=O)R_7$, $NR'SO_2R_6$, $C(=O)NR_7R_8$ or $SO_2NR_7R_8$;

$Q^1$ is a single bond or $(C_1-C_6)$ alkylene; $Q^2$ is a saturated 4- to 6-membered heterocyclyl comprising one or two O or N; $Q^3$ is $(C_1-C_6)$ alkylene; $Q^4$ is a 4 to 8-membered, aromatic or non aromatic, heterocyclyl comprising 1 to 4 O, S, $S(=O)$, $SO_2$, or N, said heterocyclyl being optionally substituted with one to three OR, NRR', —CN or $(C_1-C_6)$ alkyl;

R is H or $(C_1-C_6)$ alkyl;

$R_6$ is $(C_1-C_6)$ alkyl optionally substituted with one or two OR';

$R_7$ and $R_8$ are the same or different and are H or $(C_1-C_6)$ alkyl optionally substituted with one or two OR';

$R_9$ is H, CN, OH, $OCH_3$, $SO_2CH_3$, $SO_2NH_2$ or $(C_1-C_6)$ alkyl;

R' is H or $(C_1-C_6)$ alkyl; and R" is H or $(C_1-C_6)$ alkyl;

provided that (1) the atom of $Q^2$ bound to $Q^1$ is a carbon atom; and (2) the atom of $Q^4$ bound to $Q^3$ is a carbon atom;

or a racemic form, isomer, pharmaceutically acceptable derivative thereof.

The preparation of these compounds is described in US 20040106631, EP 1 400 244, and WO 2004/026818.

In another embodiment, PDE7 inhibitors useful in the methods of the invention are selected from those compounds generally or specifically disclosed in U.S. Pat. No. 6,936,609 and US 20040249148, each expressly incorporated herein by reference in its entirety. In one embodiment, PDE7 inhibitors useful in the methods of the invention have the formula:

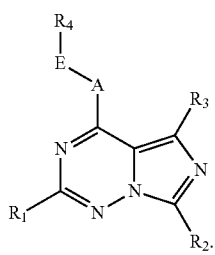

(26)

The substituents for the above compounds are defined as follows:

$R_1$ represents $(C_6-C_{10})$-aryl, which is optionally identically or differently substituted by radicals selected from the group consisting of halogen, formyl, carbamoyl, cyano, hydroxyl, trifluoromethyl, trifluoromethoxy, nitro, $(C_1-C_6)$-alkyl or $(C_1-C_6)$-alkoxy, and optionally by a radical of the formula $SO_2NR_5R_6$, wherein $R_5$ and $R_6$ independently of one another denote hydrogen or $(C_1-C_6)$-alkyl, or $NR_5R_6$ denotes 4- to 8-membered heterocyclyl, bonded via a nitrogen atom, optionally identically or differently substituted by radicals selected from the group consisting of oxo, halogen, $(C_1-C_6)$-alkyl and $(C_1-C_6)$-acyl, $R_2$ represents a saturated or partially unsaturated hydrocarbon radical having 1 to 10 carbon atoms, $R_3$ represents methyl or ethyl, A represents O, S, or $NR_5$, wherein $R_7$ denotes hydrogen or $(C_1-C_6)$-alkyl optionally substituted by $(C_1-C_3)$-alkoxy, E represents a bond or $(C_1-C_3)$-alkanediyl, $R_4$ represents $(C_6-C_{10})$-aryl or 5- to 10-membered heteroaryl, where aryl and heteroaryl are optionally identically or differently substituted by radicals selected from the group consisting of halogen, formyl, carboxyl, carbamoyl, —$SO_3H$, aminosulphonyl, cyano, hydroxyl, trifluoromethyl, trifluoromethoxy, nitro, $(C_1-C_6)$-alkyl, $(C_1-C_6)$-alkoxy, 1,3-dioxa-propane-1,3-diyl, $(C_1-C_6)$-alkylthio, $(C_1-C_6)$-alkylsulphinyl and $(C_1-C_6)$-alkylsulphonyl, —$NR_8R_9$ end optionally methyl-substituted, 5- to 6-membered heteroaryl or phenyl, wherein $R_8$ and $R_9$ independently of one another denote hydrogen, $(C_1-C_6)$-alkyl or $(C_1-C_6)$-acyl, or salt thereof.

The preparation of these compounds is described in U.S. Pat. No. 6,936,609 and US 20040249148.

In another embodiment, PDE7 inhibitors useful in the methods of the invention are selected from those compounds generally or specifically disclosed in WO 2006/092692, expressly incorporated herein by reference in its entirety. In one embodiment, PDE7 inhibitors useful in the methods of the invention have the formulas:

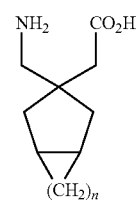

(27A)

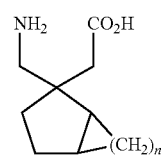

(27B)

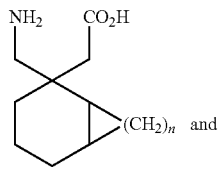

(27C)

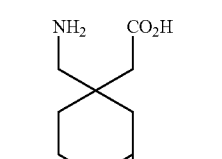

(27D)

wherein n is an integer of from 1 to 4, and where there are stereocenters, each center may be independently R or S.

The preparation of these compounds is described in WO 2006/092692.

In another embodiment, PDE7 inhibitors useful in the methods of the invention are selected from those compounds generally or specifically disclosed in US 2006229306 and WO 2004/065391, each expressly incorporated herein by reference in its entirety. In one embodiment, PDE7 inhibitors useful in the methods of the invention have the formula:

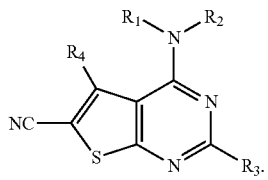
(28)

The substituents for the above compounds are defined as follows:

$R_1$ and $R_2$ either (1) independently represent:
(a) a hydrogen atom;
(b) a group selected from alkyl, alkenyl and alkynyl groups, wherein each alkyl, alkenyl and alkynyl group is independently optionally substituted by one or more substituents selected from halogen atoms, hydroxy, alkoxy, aryloxy, alkylthio, hydroxycarbonyl, alcoxycarbonyl, mono- and di-alkylaminoacyl, oxo, amino, and mono- and di-alkylamino groups; or
(c) a group of formula $(CH_2)_n$—$R_6$, wherein n is an integer from 0 to 4 and $R_6$ represents a cycloalkyl or cycloalkenyl group;

(2) $R_1$ and $R_2$ form, together with the nitrogen atom to which they are attached, a 3- to 8-membered ring comprising from 1 to 4 heteroatoms selected from nitrogen, oxygen and sulphur, which ring is saturated or unsaturated and optionally substituted by one or more substituents selected from halogen atoms, alkyl, hydroxy, alkoxy, acyl, hydroxycarbonyl, alkoxycarbonyl, alkylenedioxy, amino, mono- and di-alkylamino, mono- and di-alkylaminoacyl, nitro, cyano and trifluoromethyl groups;

$R_3$ is a group of formula $(CH_2)_{n\text{-}G}$, wherein n is an integer from 0 to 4 and G represents a monocyclic or bicyclic aryl or heteroaryl group comprising from zero to four heteroatoms which group is optionally substituted by one or more substituents selected from:
(1) halogen atoms;
(2) alkyl and alkylene groups, wherein each alkyl and alkylene group is independently optionally substituted by one or more substituents selected from halogen atoms; and
(3) phenyl, hydroxy, hydroxyalkyl, alkoxy, alkylenedioxy, aryloxy, alkylthio, amino, mono- and di-alkylamino, acylamino, nitro, acyl, hydroxycarbonyl, alkoxycarbonyl, cyano, difluoromethoxy and trifluoromethoxy groups;

$R_4$ represents a hydrogen atom, an alkyl or an aryl group.

The preparation of these compounds is described in US 2006229306 and WO 2004/065391.

Other compounds useful in the methods of the invention include imidazopyridine derivatives (WO 2001/34601), dihydropurine derivatives (WO 2000/68203), pyrrole derivatives (WO 2001/32618), benzothiopyranoimidazolone derivatives (DE 19950647), heterocyclic compounds (WO 2002/87519), guanine derivatives (*Bioorg. Med. Chem. Lett.* 11:1081-1083, 2001), and benzothienothiadiazine derivatives (*Eur. J. Med. Chem.* 36:333, 2001). The disclosure of each published patent application and journal article listed above is expressly incorporated herein by reference in its entirety.

In another embodiment, PDE7 inhibitors useful in the methods of the invention are selected from those compounds generally or specifically disclosed in WO 2008/130619, expressly incorporated herein by reference in its entirety. In one embodiment, PDE7 inhibitors useful in the methods of the invention have the formula:

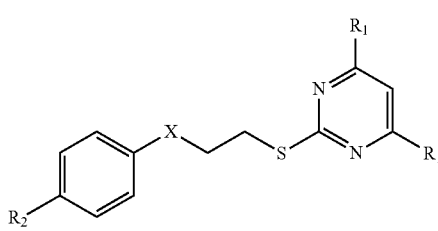
(29)

The substituents for the above compounds are defined as follows:

X is SO, or $SO_2$,

R1 is H, or alkyl,

R2 is alkyl, or halogen.

In specific embodiments, R1 is Me. In other specific embodiments R1 is F. In certain embodiments R2 is t-Bu. In specific embodiments, R1 is methyl. In more specific embodiments, the compounds are selected from:

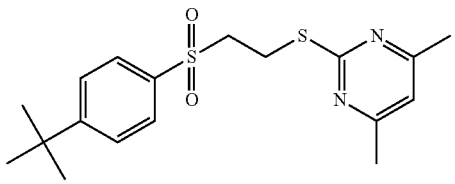

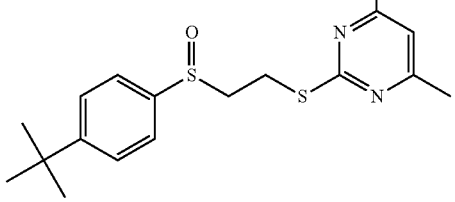

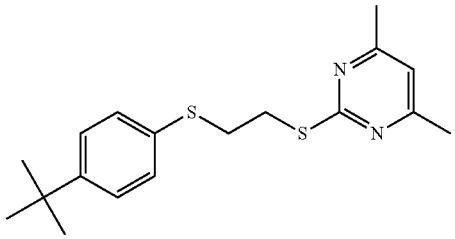

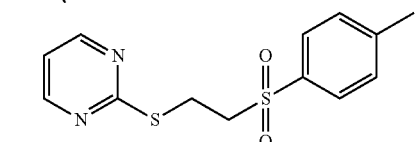

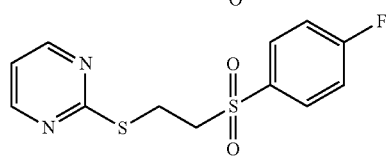

In a related embodiment, PDE7 inhibitors useful in the methods of the invention have the formula:

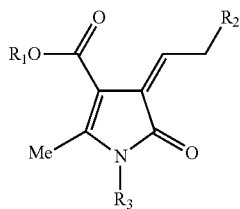
(30)

wherein

R1 is alkyl,

R2 is aryl or heteroaryl,

R3 is alkyl, aryl, cycloakyl, or alkylaryl.

In specific embodiments, R1 is methyl. In certain embodiments R2 is furanyl or thiophenyl. In other specific embodiments, R2 is substituted phenyl or benzyl. In preferred embodiments, R3 is iso-butyl. In more specific embodiments, the compounds are selected from:

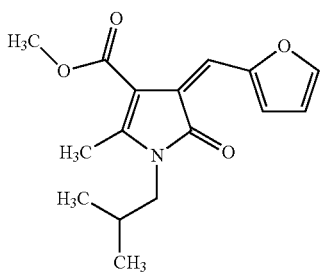

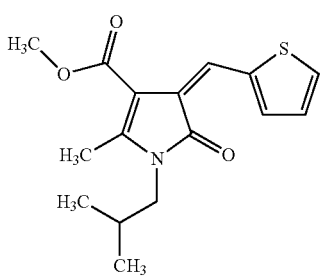

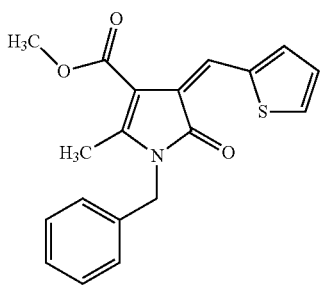

-continued

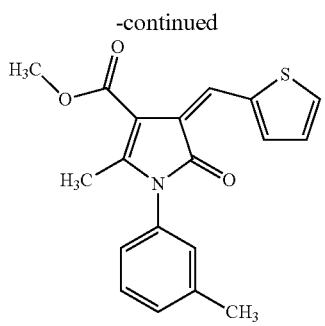

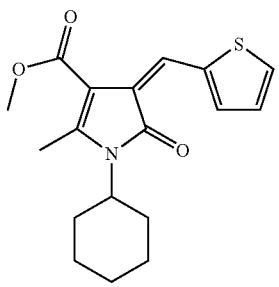

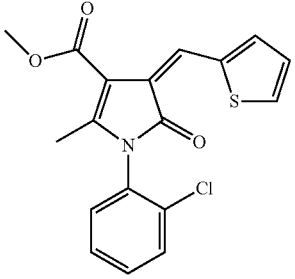

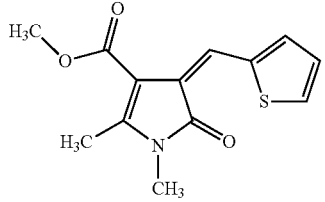

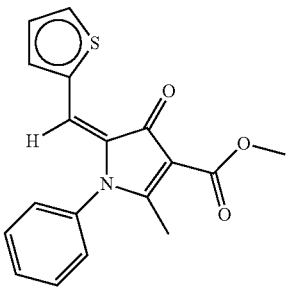

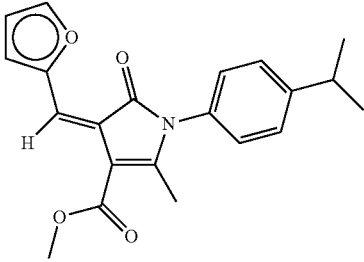

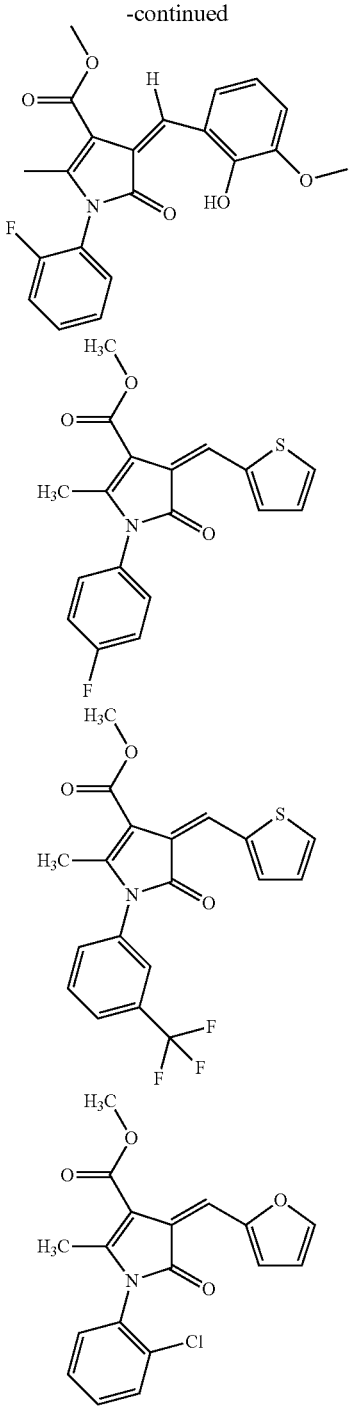

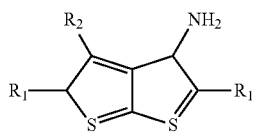

In another related embodiment, PDE7 inhibitors useful in the methods of the invention have the formula:

wherein
R1 is nitrile, or alkylcarboxylate,
R2 is alkyl, aryl, or heteroaryl.

In specific embodiments, R1 is nitrile or methylcarboxylate. In certain embodiments, R2 is a five membered heteroaryl. In more specific embodiments, R2 is furanyl, or thienyl. In other embodiments, R2 is a six membered aryl. In more specific embodiments, R2 is substituted phenyl.

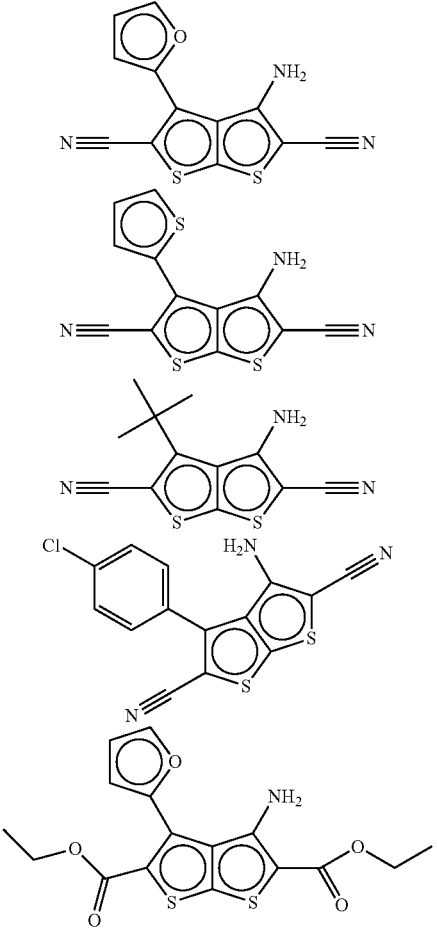

In another related embodiment, PDE7 inhibitors useful in the methods of the invention have the formula:

(32)

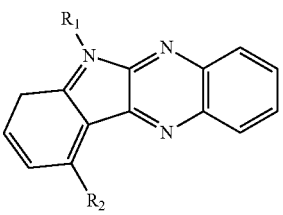

wherein
R1 is alkyl, alkenyl, or alkylcarboxylic acid,
R2 is halogen.

In certain embodiments R1 is butyl. In other embodiments R1 is terminal alkenyl. In more specific embodiments R1 is allyl, or vinyl. In other embodiments, R1 is $C_{1-4}$ alkyl. In specific embodiments R1 is methylcarboxylic acid. In certain embodiments R2 is Cl, or Br. In more specific embodiments, the compounds are selected from:

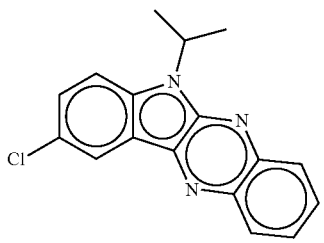
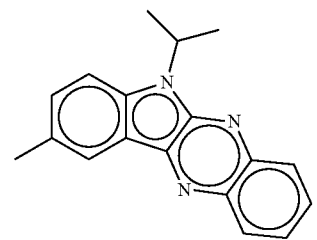
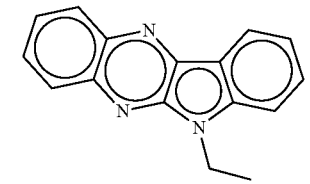
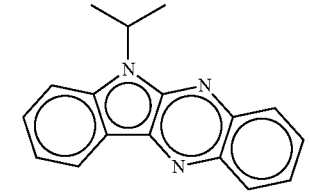
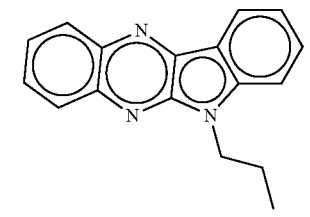
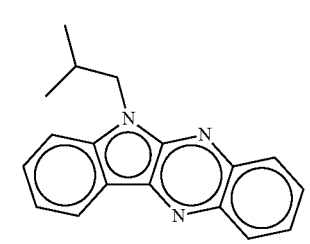
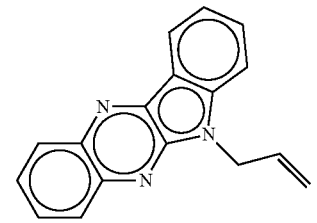

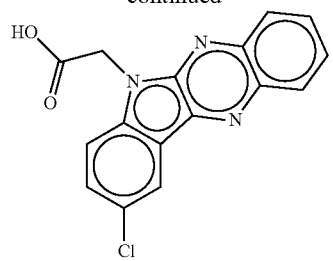
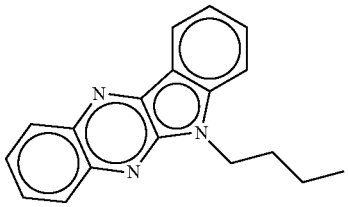
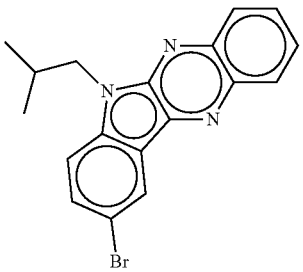
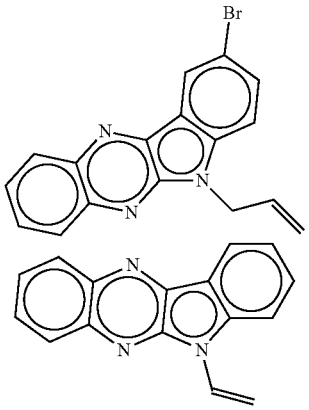

In other related embodiments, PDE7 inhibitors useful in the methods of the invention have the formula:

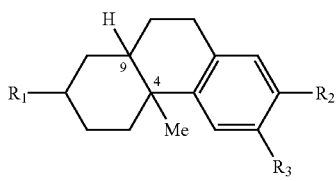

(33)

wherein

R1 is CO, or alkylalcohol, R2 is alkyl, R3 is alkoxy, and the C4 and C9 stereocenters are independently (R) or (S).

In certain embodiments R1 is carbonyl, or 2-methylpropan-1-ol. In specific embodiments R2 is methyl. In certain embodiments, R3 is methoxy. In more specific embodiments the compounds are selected from:

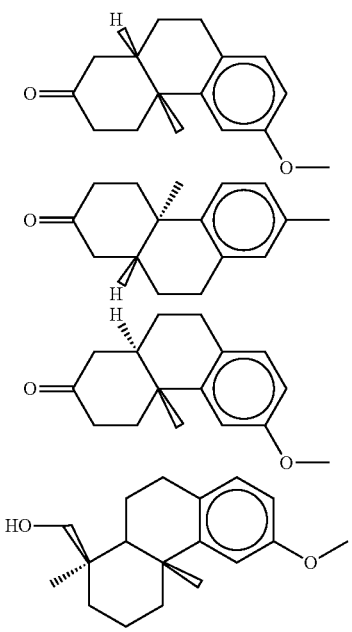

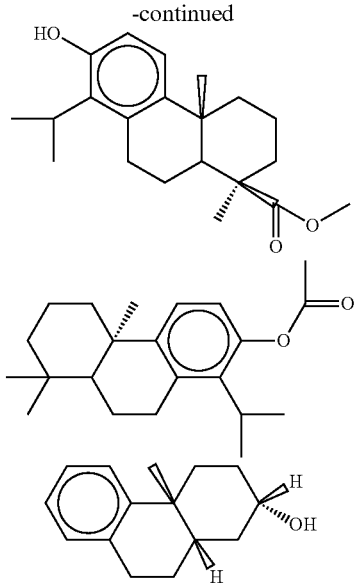

In another related embodiment, PDE7 inhibitors useful in the methods of the invention have the formula:

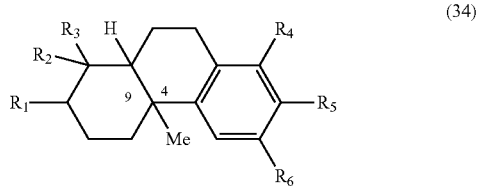

(34)

wherein

R1 is hydrogen, hydroxyl, carbonyl, or alkylalcohol,

R2 and R3 are independently selected from hydrogen, alkyl, alkylcarboxylate, or carboxylic acid, R4 is hydrogen, or alkyl, R5 is hydrogen, alkyl, hydroxyl, or acetate, R6 is hydrogen, or alkoxy, and the C4 and C9 stereocenters are independently (R) or (S).

In certain embodiments R1 is 2-methylpropan-1-ol. In specific embodiments R2 is methyl. In certain embodiments, R2 is methylcarboxylate. In specific embodiments R2 and R3 are both methyl. In other embodiments, R2 is methyl, and R3 is methylcarboxylate. In specific embodiments R4 is iso-propyl. In specific embodiments, R5 is methyl. In certain embodiments, R6 is methoxy. In more specific embodiments the compounds are selected from:

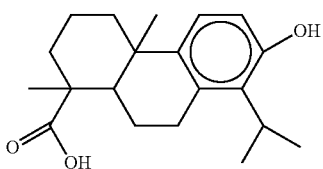

In regards to the above compounds, the terms "alkyl", "alkenyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms. Preferred groups have a total of up to 10 carbon atoms. Cyclic groups can be monocyclic or polycyclic and preferably have from 3 to 10 ring carbon atoms. Exemplary cyclic groups include cyclopropyl, cyclopentyl, cyclohexyl, cyclopropylmethyl, adamantly, norbornane, and norbornee. This is also true of groups that include the prefix "alkyl-", such as alkylcarboxylic acid, alkyl alcohol, alkylcarboxylate, alkylaryl, and the like. Examples of suitable alkylcarboxylic acid groups are methylcarboxylic acid, ethylcarboxylic acid, and the like. Examples of suitable alkylalcohols are methylalcohol, ethylalcohol, isopropylalcohol, 2-methylpropan-1-ol, and the like. Examples of suitable alkylcarboxylates are methylcarboxylate, ethylcarboxylate, and the like. Examples of suitable alkyl aryl groups are benzyl, phenylpropyl, and the like.

The term "aryl" as used herein includes carbocyclic aromatic rings or ring systems. Examples of aryl groups include phenyl, naphthyl, biphenyl, fluorenyl and indenyl. The term "heteroaryl" includes aromatic rings or ring systems that contain at least one ring hetero atom (e.g., O, S, N). Suitable heteroaryl groups include furyl, thienyl, pyridyl, quinolinyl, isoquinolinyl, indolyl, isoindolyl, thiazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, and so on.

The aryl, and heteroaryl groups can be unsubstituted or substituted by one or more substituents independently selected from the group consisting of alkyl, alkoxy, methylenedioxy, ethylenedioxy, alkylthio, haloalkyl, haloalkoxy, haloalkylthio, halogen, nitro, hydroxy, mercapto, cyano, carboxy, formyl, aryl, aryloxy, arylthio, arylalkoxy, arylalkylthio, heteroaryl, heteroaryloxy, heteroarylalkoxy, heteroarylalkylthio, amino, alkylamino, dialkylamino, heterocyclyl, heterocycloalkyl, alkylcarbonyl, alkenylcarbonyl, alkoxycarbonyl, haloalkylcarbonyl, haloalkoxycarbonyl, alkylthiocarbonyl, arylcarbonyl, heteroarylcarbonyl, aryloxycarbonyl, heteroaryloxycarbonyl, arylthiocarbonyl, heteroarylthiocarbonyl, alkanoyloxy, alkanoylthio, alkanoylamino, arylcarbonyloxy, arylcarbonylthio, alkylaminosulfonyl, alkylsulfonyl, arylsulfonyl, heteroarylsulfonyl, aryldiazinyl, alkylsulfonylamino, arylsulfonylamino, arylalkylsulfonylamino, alkylcarbonylamino, alkenylcarbonylamino, arylcarbonylamino, arylalkylcarbonylamino, arylcarbonylaminoalkyl, heteroarylcarbonylatnino, heteroarylalkycarbonylamino, alkylsulfonylamino, alkenylsulfonylamino, arylsulfonylamino, arylalkylsulfonylamino, heteroarylsulfonylamino, heteroarylalkylsulfonylamino, alkylaminocarbonylamino, alkenylaminocarbonylamino, arylaminocarbonylamino, arylalkylaminocarbonylamino, heteroarylaminocarbonylamino, heteroarylalkylaminocarbonylamino and, in the case of heterocyclyl, oxo. If other groups are described as being "substituted" or "optionally substituted," then those groups can also be substituted by one or more of the above enumerated substituents.

In another embodiment, PDE7 inhibitors useful in the methods of the invention are selected from those compounds generally or specifically disclosed in WO 2008/142550, expressly incorporated herein by reference in its entirety. In one embodiment, PDE7 inhibitors useful in the methods of the invention have the formula:

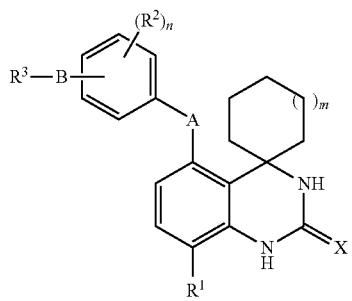

(35)

The substituents for the above compounds are defined as follows:

m is 0, 1 or 2, n is 0, 1, 2 or 3,
X is O, S or N—CN,
$R^1$ is halogen or CN,
A is a single bond, $CH_2$, O or S,
B is a single bond, $CH_2$ or $OCH_2$, each $R^2$ is independently halogen, $(C_{1-6})$alkyl (optionally substituted by 1 to 3 fluorine atoms), OH, $(C_{1-6})$alkylthio or CN,
$R^3$ is selected from the following groups (i) to (x):

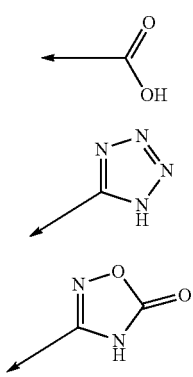

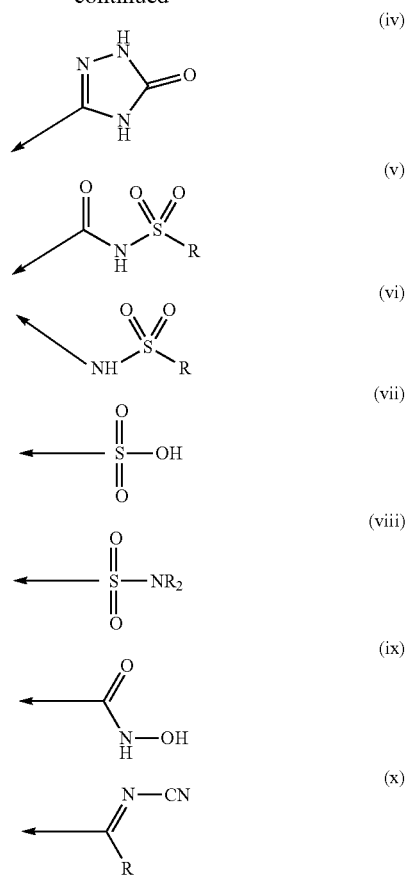

R is H or $(C_{1-6})$alkyl (optionally substituted by 1 to 3 fluorine atoms), R' is $(C_{1-6})$alkyl (optionally substituted by 1 to 3 fluorine atoms), or a pharmaceutically acceptable salt, solvate, polymorph or prodrug thereof.

In regard to the above compounds, the term "alkyl" denotes a monovalent, straight or branched, saturated hydrocarbon chain containing 1 to 6 carbon atoms Examples of alkyl groups include methyl, ethyl, n-propyl, isopropyl, n-butyl, isobutyl, sec-butyl, tert-butyl, n-pentyl, 2-methylbutyl, 3-methylbutyl, neopentyl, n-hexyl, 2-methylpentyl, 3-methylpentyl, 4-methylpentyl, 2-ethylbutyl and 2,2-dimethylbutyl. Preferred alkyl groups are particularly methyl and ethyl, especially methyl.

Where stated, alkyl groups may be substituted by 1 to 3 fluorine atoms. The substitution may be at any position on the alkyl chain. Preferably, such fluorinated alkyl groups have 1 to 4 carbon atoms, more preferably 1 or 2 carbon atoms. Mono-, di- and trifluoromethyl groups (especially trifluoromethyl), and mono-, di- and trifluoroethyl groups (especially 2,2,2-trifluoroethyl) are especially preferred.

The term "alkoxy" denotes "alkyl-O—", wherein "alkyl" is as defined above, either in its broadest aspect or a preferred aspect. Preferred alkoxy groups are groups, particularly methoxy and ethoxy. The term "alkylthio" denotes "alkyl-S—", wherein "alkyl" is as defined above, either in its broadest aspect or a preferred aspect. Preferred alkylthio groups are $(C_{1-4})$alkylthio groups, particularly methylthio and ethylthio. The term "halogen" denotes fluoro, chloro, bromo or iodo. Preferred halogen groups are fluoro and chloro.

Preferably, m is 0 or 1, more preferably 1.
Preferably, n is 0 or 1, more preferably 0.

Preferably, X is O or N—CN, more preferably O.
Preferably, R¹ is F or Cl, more preferably Cl.
Preferably, A is a single bond or O, more preferably O.
When the group B is OCH₂, the oxygen atom is bonded to the benzene ring and the methylene group to the group R³.
Preferably, B is a single bond.
Preferably, R² is F or Cl, more preferably F.
Preferably, R³ is a group (i), (ii), (iii), (iv), (v) or (vi), more preferably a group (i) or (ii), and especially a group (ii).

In one embodiment, the group —B—R³ is present at the 2-position of the phenyl ring (the position of the group A being the 1-position). In other embodiments, the group —B—R³ is present at the 3-position In further embodiments, the group —B—R³ is present at the 4-position.

PDE7 inhibitors useful in the methods of the invention include those in which each variable in the above formula is selected from the suitable and/or preferred groups for each variable. Even more preferred PDE7 inhibitors useful in the methods of the invention include those where each variable in the above formula is selected from the more preferred or most preferred groups for each variable.

In a related embodiment, the following PDE7 inhibitors are useful in the methods of the invention:

5-[(8'-chloro-2'-oxo-2',3'-dihydro-1'H-spiro[cyclohexane-1,4'-quinazolin]-5'-yl)]-2-fluorobenzoic acid,
3-(8'-chloro-2-oxo-2',3'-dihydro-1'H-spiro[cyclohexane-1,4'-quinazolin]-5'-ylbenzoic acid,
5-[(8'-chloro-2'-oxo-2',3'-dihydro-1'H-spiro[cyclohexane-1,4'-quinazolin]-4'-yl)]-2-fluorobenzoic acid,
8-chloro-5'-[4-fluoro-3-(2H-tetrazol-5-yl)phenyl]-1'H-spiro[cyclohexane-1,4'-quinazolin]-2'(3'H)-one,
[3-(8'-chloro-2'-oxo-2',3'-dihydro-1'H-spiro[cyclohexane-1,4'-quinazolin]-5'-yl)phenoxy]acetic acid,
2-{(8'-chloro-2'-oxo-2,3'-dihydro-1'H-spiro[cyclohexane-1,4'-quinazolin]-5'-yl)oxy}-3-fluorobenzoic acid,
2-{(8'-chloro-2'-oxo-2',3'-dihydro-1'H-spiro[cyclopentane-1,4'-quinazolin]-5'-oxy}-3-fluorobenzoic acid,
3-chloro-2-{(8'-chloro-2'-oxo-2',3'-dihydro-1'H-spiro[cyclohexane-1,4'-quinazolin]-5'-yl)oxy}benzoic acid,
3-chloro-2-{(8'-fluoro-2'-oxo-2',3'-dihydro-1'H-spiro[cyclohexane-1,4'-quinazolin]-5'-yl)oxy}benzoic acid,
8'-chloro-5'-[2-fluoro-6-(2H-tetrazol-5-yl)phenoxy]-1'H-spiro[cyclohexane-1,4'-quinazolin]-2'(3'H)-one,
8'-chloro-5'-[4-fluoro-2-(1H-tetrazol-5-yl)phenoxy]-1'H-spiro[cyclohexane-1,4'-quinazolin]-2'(3'H)-one,
8'-chloro-5'-[6-fluoro-2-(1H-tetrazol-5-yl)phenoxy]-1'H-spiro[cyclohexane-1,4'-quinazolin]-2'(3'H)-one,
8'-chloro-5'-[4-fluoro-2-(1H-tetrazol-5-yl)phenoxy]-1'H-spiro[cyclopentane-1,4'-quinazolin]-2'(3'H)-one,
8'-chloro-5'-[6-fluoro-2-(1H-tetrazol-5-yl)phenoxy]-1'H-spiro[cyclopentane-1,4'-quinazolin]-2'(3'H)-one,
8'-chloro-5'-[6-chloro-2-(1H-tetrazol-5-yl)phenoxy]-1'H-spiro[cyclopentane-1,4'-quinazolin]-2'(3'H)-one,
8'-chloro-5'-[2-(1H-tetrazol-5-yl)phenoxy]-1'H-spiro[cyclopentane-1,4'-quinazolin]-2'(3'H)-one,
8'-chloro-5'-[2-(1H-tetrazol-5-yl)phenoxy]-1'H-spiro[cyclohexane-1,4'-quinazolin]-2'(3'H)-one,
8'-chloro-5'-[2-fluoro-6-(5-oxo-4,5-dihydro-1,2,4-oxadiazol-3-yl)phenoxy]-1'H-spiro[cyclohexane-1,4'-quinazolin]-2'(3'H)-one,
8'-chloro-5'-[2-fluoro-6-(5-oxo-4,5-dihydro-1H-1,2,4-triazol-3-yl)phenoxy]-1'H-spiro[cyclohexane-1,4'-quinazolin]-2'(3'H)-one,
2-[(8'-chloro-2'-oxo-2',3'-dihydro-1'H-spiro[cyclohexane-1,4'-quinazolin]-5'-yl)oxy]-3-fluoro-N-(methylsulfonyl)benzamide,
N-{2-[(8'-chloro-2'-oxo-2',3'-dihydro-1'H-spiro[cyclohexane-1,4'-quinazolin]-5'-yl)oxy]-3-fluorophenyl}-1,1,1-trifluoromethanesulfonamide,
{2-[(8'-chloro-2'-oxo-2',3'-dihydro-1'H-spiro[cyclohexane-1,4'-quinazolin]-5'-yl)oxy]-3-fluorophenyl}acetic acid,
{2-[(8'-chloro-2'-oxo-2',3'-dihydro-1'H-spiro[cyclohexane-1,4'-quinazolin]-5'-yl)oxy]phenoxy}acetic acid,
{4-[(8'-chloro-2'-oxo-2',3'-dihydro-1'H-spiro[cyclohexane-1,4'-quinazoline-5'-yl)oxy]phenoxy}acetic acid,
methyl 2-[(8'-chloro-2'-oxo-2',3'-dihydro-1'H-spiro[cyclohexane-1,4'-quinazolin]-5'-yl)oxy]-3-fluorobenzoate,
and pharmaceutically acceptable salts, solvates and prodrugs thereof.

In another related embodiment, the following PDE7 inhibitors are useful in the methods of the invention:

8'-chloro-5'-[2-fluoro-6-(2H-tetrazol-5-yl)phenoxy]-1'H-spirocyclohexane-1,4'-quinazolin]-2'(3'H)-one,
8'-chloro-5'-[4-fluoro-2-(1H-tetrazol-5-yl)phenoxy]-1'H-spiro[cyclohexane-1,4'-quinazolin]-2'(3'H)-one,
8'-chloro-5'-[6-fluoro-2-(1H-tetrazol-5-yl)phenoxy]-1'H-spiro[cyclohexane-1,4'-quinazolin]-2'(3'H)-one,
8'-chloro-5'-[4-fluoro-2-(1H-tetrazol-5-yl)phenoxy]-1'H-spiro[cyclopentane-1,4'-quinazolin]-2'(3'H)-one,
8'-chloro-5'-[6-fluoro-2-(1H-tetrazol-5-yl)phenoxy]-1'H-spiro[cyclopentane-1,4'-quinazolin]-2'(3'H)-one,
8'-chloro-5'-[6-chloro-2-(1H-tetrazol-5-yl)phenoxy]-1'H-spiro[cyclopentane-1,4'-quinazolin]-2'(3'H)-one,
8'-chloro-5'-[2-(1H-tetrazol-5-yl)phenoxy]-1'H-spiro[cyclopentane-1,4'-quinazolin]-2'(3'H)-one,
8'-chloro-5'-[2-(1H-tetrazol-5-yl)phenoxy]-1'H-spiro[cyclohexane-1,4'-quinazolin]-2'(3'H)-one,
and pharmaceutically acceptable salts, solvates and prodrugs thereof.

The following compounds are most preferred:
8'-chloro-5'-[2-fluoro-6-(2H-tetrazol-5-yl)phenoxy]-1'H-spiro[cyclohexane-1,4'-quinazolin]-2'(3'H)-one,
8'-chloro-5'-[4-fluoro-2-(1H-tetrazol-5-yl)phenoxy]-1'H-spiro[cyclohexane-1,4'-quinazolin]-2'(3'H)-one,
8'-chloro-5'-[6-fluoro-2-(1H-tetrazol-5-yl)phenoxy]-1'H-spiro[cyclopentane-1,4'-quinazolin]-2'(3'H)-one,
8'-chloro-5'-[2-(1H-tetrazol-5-yl)phenoxy]-1'H-spiro[cyclohexane-1,4'-quinazolin]-2'(3'H)-one,
and pharmaceutically acceptable salts, solvates and prodrugs thereof.

The preparation of these compounds is described in WO 2008/142550.

In another embodiment, PDE7 inhibitors useful in the methods of the invention are selected from those compounds generally or specifically disclosed in U.S. Pat. No. 7,498,334, US 2005/0059686 and WO 2003/055882, each expressly incorporated herein by reference in its entirety. In one embodiment, PDE7 inhibitors useful in the methods of the invention have the formula:

(36)

The substituents for the above compounds are defined as follows:

X is phenyl or Het, each of which is unsubstituted or monosubstituted or polysubstituted by R1 and/or R2, R1 and R2 are each, independently of one another, A, OH, OA, SA, SOA, SO2A, SO2NH2, SO2NHA, SO2AA', CN, NO2, NH2, NHA, NAA', NHCOA, NHCOOA, COOH, COOA, CONH2, CONHA, CONAA' or Hal, R' and R2 together are alternatively —OCH2O— or —OCH2CH2O—, R3 is A, OH, OA, SA, SOA, SO2A, SO2NH2, SO2NHA, SO2AA', CN, NO2, NH2, NHA, NHB, NAA', NHCOA, NHCOOA, NHCOB, NHCOOB, COOH, COOA, COOB, CONH2, CONHA, CONHB, CONAA' or Hal, R4 is branched or unbranched alkyl or alkenyl having up to 10 carbon atoms, which may be substituted by from 1 to 5 F and/or Cl atoms and/or in which one or more CH2 groups may be replaced by O, S, SO, SO2, NH, NA, NHCO, NACO, NHCOO or NACOO, or cycloalkyl or cycloalkenyl having from 3 to 7 carbon atoms, in which one or two CH2 groups may be replaced by O, S, SO, SO2, SO2NH, SO2NA, NH, NHA, NHCONH, NACONH, NACONA, NHCO, NACO, NHCOO or NACOO, R5 is OH, OA, SA, SOA, SO2A, SO2NH2, SO2NHA, SO2AA', CN, NO2, NH2, NHA, NAA', NHCOA, NHCOOA, COOH, COOA, CONH2, CONHA, CONAA' or Hal, R6 is H, OH, OA, SA, SOA, SO2A, SO2NH2, SO2NHA, SO2AA', CN, NO2, NH2, NHA, NAA', NHCOA, NHCOOA, COOH, COOA, CONH2, CONHA, CONAA' or Hal, A and A' are each, independently of one another, branched or unbranched alkyl or alkenyl having up to 10 carbon atoms, which may be substituted by from 1 to 5 F and/or Cl atoms and/or in which one or more CH2 groups may be replaced by O, S, SO, SO2, NH, NR7, NHCO, NR7CO, NHCOO or NR7COO. A and A' together are alternatively alkylene having from 3 to 7 carbon atoms, in which one or two CH2 groups may be replaced by CHR7, CHR7R8, O, S, SO, SO2, NH, NR7, NHCO, NR7CO, NHCOO or NR7COO. B is phenyl or Het, each of which is unsubstituted or monosubstituted or polysubstituted by R1 and/or R2, Het is an aromatic 5- or 6-membered heterocyclic ring having 1-3 N, O and/or S atoms which is unsubstituted or monosubstituted, disubstituted or trisubstituted by A", Hal or CF3, R7 and R8 are each, independently of one another, branched or unbranched alkyl or alkenyl having up to 5 carbon atoms, which may be substituted by from 1 to 5 F and/or Cl atoms and/or in which one or more CH2 groups may be replaced by O, S, SO, SO2 or NH, A" is alkyl having from 1 to 6 carbon atoms, and Hal is F, Cl, Br or I, and pharmaceutically usable derivatives, solvates and stereoisomers thereof, including mixtures thereof in all ratios.

In a related embodiment, PDE7 inhibitors useful in the methods of the invention include compounds of the above formula in which R5 is OH may also be in the form of their tautomers of the formula:

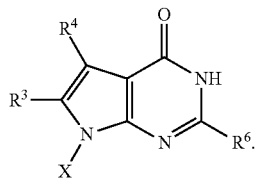

In regard to the above compounds, PDE7 inhibitors useful in methods of the invention include the optically active forms (stereo-isomers), the enantiomers, the racemates, the diastereomers and the hydrates and solvates of these compounds. The term solvates of the compounds is taken to mean adductions of inert solvent molecules onto the compounds which form owing to their mutual attractive force. Solvates are, for example, monohydrates, dihydrates or alcoholates.

In regards to the above compounds, the term pharmaceutically usable derivatives is taken to mean, for example, the salts of the above compounds and so-called prodrug compounds. The term prodrug derivatives is taken to mean, for example, the above compounds which have been modified, for example, with alkyl or acyl groups, sugars or oligopeptides and which are rapidly cleaved in the organism and thus release the active compounds. These also include biodegradable polymer derivatives of the above compounds, as described, for example, in *Int. J. Pharm.* 115, 61-67 (1995).

In regard to the above compounds, the meanings of all radicals which occur more than once are in each case independent of one another.

A and A' are preferably alkyl, furthermore preferably alkyl which is substituted by from 1 to 5 fluorine and/or chlorine atoms, furthermore preferably alkenyl.

In the above formulae, alkyl is preferably unbranched and has 1, 2, 3, 4, 5, 6, 7, 8, 9 or 10 carbon atoms, preferably 1, 2, 3, 4, 5 or 6 carbon atoms, and is preferably methyl, ethyl, trifluoromethyl, pentafluoroethyl or propyl, furthermore preferably isopropyl, butyl, isobutyl, sec-butyl or tert-butyl, but also n-pentyl, neopentyl, isopentyl or n-hexyl. Particular preference is given to methyl, ethyl, trifluoromethyl, propyl, isopropyl, butyl, n-pentyl, n-hexyl or n-decyl.

A" is preferably alkyl having 1, 2, 3, 4, 5 or 6 carbon atoms, for example methyl, ethyl or propyl, furthermore preferably isopropyl, butyl, isobutyl, sec-butyl or tert-butyl, but also n-pentyl, neopentyl, isopentyl or n-hexyl. Particular preference is given to methyl, ethyl, propyl, isopropyl or butyl.

Cycloalkyl preferably has 3-7 carbon atoms and is preferably cyclopropyl or cyclobutyl, furthermore preferably cyclopentyl or cyclohexyl, furthermore also cycloheptyl; particular preference is given to cyclopentyl.

Alkenyl is preferably vinyl, allyl, 2- or 3-butenyl, isobutenyl or sec-butenyl; preference is furthermore given to 4-pentenyl, isopentenyl or 5-hexenyl.

Alkylene is preferably unbranched and is preferably methylene or ethylene, furthermore preferably propylene or butylene.

Hal is preferably F, Cl or Br, furthermore also I.

The radicals R1 and R2 may be identical or different and are preferably in the 2- or 4-position of the phenyl ring. They are, for example, independently of one another, A or Hal, or together are methylenedioxy.

However, they are preferably each methyl, ethyl, propyl, methoxy, ethoxy, propoxy, isopropoxy, benzyloxy, but also fluoro-, difluoro- or trifluoro-methoxy, or 1-fluoro-, 2-fluoro-, 1,2-difluoro-, 2,2-difluoro-, 1,2,2-trifluoro- or 2,2,2-trifluoroethoxy, furthermore fluorine or chlorine.

R1 is particularly preferably fluorine, chlorine, methyl, ethyl or propyl.

R2 is particularly preferably fluorine, chlorine, methyl, ethyl or propyl.

X is preferably a phenyl radical which is monosubstituted by R1 or is unsubstituted Het.

X is particularly preferably 2-chlorophenyl, 2-fluorophenyl, 4-methyl-phenyl, 3-chlorophenyl or 4-chlorophenyl.

Het is preferably, for example, unsubstituted 2- or 3-furyl, 2- or 3-thienyl, 1-, 2- or 3-pyrrolyl, 1-, 2-, 4- or 5-imidazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, or 1,2,3-thia-diazol-4- or -5-yl.

R3 is preferably, for example, COOA" or COOH.

R4 is preferably, for example, unbranched or branched alkyl having 1, 2, 3, 4, 5 or 6 carbon atoms, which may be substituted by 1-5 F or Cl atoms, preferably methyl, ethyl, trifluoromethyl, pentafluoroethyl or propyl, furthermore preferably isopropyl, butyl, isobutyl, sec-butyl or tert-butyl, but also n-pentyl, neopentyl, isopentyl or n-hexyl. Particular preference is given to methyl, ethyl, trifluoromethyl, propyl, isopropyl, butyl, n-pentyl, n-hexyl or n-decyl.

R5 is preferably Cl or OH.

R6 is preferably H.

In regard to the above compounds, at least one of the said radicals has one of the preferred meanings indicated above.

In a related embodiment, PDE7 inhibitors useful in the methods of the invention include the following compounds, wherein X is a phenyl radical which is monosubstituted by R1, or is unsubstituted Het; R1 is A or Hal; R3 is COOA" or COOH; R4 is unbranched or branched alkyl having 1, 2, 3, 4, 5 or 6 carbon atoms, which may be substituted by 1-5 F or Cl atoms; R5 is Cl or OH; and R6 is H;

In other related embodiments, PDE7 inhibitors useful in the methods of the invention include the following compounds, wherein X is a phenyl radical which is monosubstituted by R1, or is unsubstituted Het, R1 is A or Hal, R3 is COOA" or COOH, R4 is unbranched or branched alkyl having 1, 2, 3, 4, 5 or 6 carbon atoms, which may be substituted by 1-5 F or Cl atoms, R5 is Cl or OH, R6 is H, Het is furyl, thienyl, pyrrolyl, imidazolyl, pyridyl or pyrimidinyl, A and A" are each, independently of one another, unbranched or branched alkyl having 1, 2, 3, 4, 5 or 6 carbon atoms, which may be substituted by 1-5 F or Cl atoms, Hal is F, Cl or Br, and pharmaceutically usable derivatives, solvates and stereoisomers thereof, including mixtures thereof in all ratios.

The preparation of the above compounds and also the starting materials for their preparation are described in the literature (for example in the standard works, such as Houben-Weyl, *Methoden der organischen Chemie [Methods of Organic Chemistry]*, Georg-Thieme-Verlag, Stuttgart), to be precise under reaction conditions which are known and suitable for the said reactions. Use can also be made here of variants which are known per se, but are not mentioned here in greater detail.

In another related embodiment, PDE7 inhibitors useful in the methods of the invention include:

ethyl 5-isopropyl-4-oxo-7-p-tolyl-4,7-dihydro-3H-pyrrolo[2,3-d]-pyrimidine-6-carboxylate, ethyl 5-methyl-4-oxo-7-(3-chlorophenyl)-4,7-dihydro-3H-pyrrolo[2,3-d]pyrimidine-6-carboxylate, ethyl 5-methyl-4-oxo-7-(2-chlorophenyl)-4,7-dihydro-3H-pyrrolo[2,3-d]pyrimidine-6-carboxylate, ethyl 5-methyl-4-oxo-7-(2-fluorophenyl)-4,7-dihydro-3H-pyrrolo[2,3-d]pyrimidine-6-carboxylate, ethyl 5-propyl-4-oxo-7-(2-chlorophenyl)-4,7-dihydro-3H-pyrrolo[2,3-d]pyrimidine-6-carboxylate, ethyl 5-methyl-4-oxo-7-(4-chlorophenyl)-4,7-dihydro-3H-pyrrolo[2,3-d]pyrimidine-6-carboxylate, ethyl 5-methyl-4-oxo-7-p-tolyl-4,7-dihydro-3H-pyrrolo[2,3-d]-pyrimidine-6-carboxylate, methyl 5-methyl-4-oxo-7-(2-chlorophenyl)-4,7-dihydro-3H-pyrrolo[2,3-d]pyrimidine-6-carboxylate, methyl 5-methyl-4-oxo-7-phenyl-4,7-dihydro-3H-pyrrolo[2,3-d]-pyrimidine-6-carboxylate, methyl 5-methyl-4-oxo-7-(2-thienyl)-4,7-dihydro-3H-pyrrolo[2,3-d]-pyrimidine-6-carboxylate, and pharmaceutically usable derivatives, solvates and stereoisomers thereof, including mixtures thereof in all ratios.

The preparation of the above compounds is described in U.S. Pat. No. 7,498,334 and WO 2003/055882.

In another embodiment, PDE7 inhibitors useful in the methods of the invention are selected from those compounds generally or specifically disclosed in U.S. Pat. No. 6,884,800 and WO 01/36425, each expressly incorporated herein by reference in its entirety. In one embodiment, PDE7 inhibitors useful in the methods of the invention have the formula:

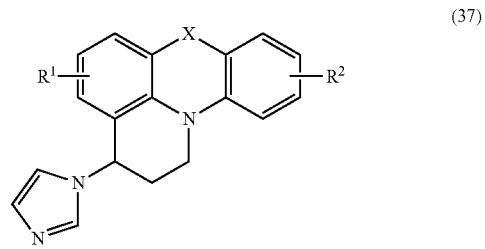

(37)

The substituents for the above compounds are defined as follows:

R1 and R2, independently of one another, each denote A1, OA1, SA1 or Hal, A1 denotes H, A, alkenyl, cycloalkyl or alkylenecycloalkyl, A denotes alkyl having 1-10 carbon atoms, Hal denotes F, Cl, Br or I, and x denotes O, S, SO or SO2, and their physiologically acceptable salts and/or solvates.

In regards to the above compounds, A denotes alkyl having 1-10 carbon atoms and has 1, 2, 3, 4, 5, 6, 7, 8, 9 or 10 carbon atoms and preferably denotes methyl, ethyl or propyl, furthermore preferably isopropyl, butyl, isobutyl, sec-butyl or tert-butyl, but also n-pentyl, neopentyl, isopentyl or hexyl. In these radicals, 1-7H atoms may also be replaced by F and/or Cl. A therefore also denotes, for example, trifluoromethyl or pentafluoroethyl. Cycloalkyl has 3-9 carbon atoms and preferably denotes, for example, cyclopentyl or cyclohexyl. Alkenyl has 2-10 carbon atoms, is linear or branched and preferably denotes vinyl, propenyl or butenyl. Alkylenecycloalkyl has 4-10 carbon atoms and denotes, for example, methylenecyclopentyl, ethylenecyclopentyl, methylenecyclohexyl or ethylenecyclohexyl. R1 and R2 preferably denote, in each case independently of one another, H, fluorine, chlorine, methyl, ethyl, propyl, methoxy, ethoxy, propoxy, methylthio, cyclopentyl or cyclohexyl.

In a related embodiment, PDE7 inhibitors useful in the methods of the invention include the following compounds, wherein X is S;
X is S, R1 is H;
X is S, R1 is F or Cl;
X is S, R2 is H;
X is S, R2 is F or Cl;
X is S, R1 is H, R2 is F or Cl;
X is S, R1 is F or Cl, R2 is H;
X is S; A1 is H or A, A is alkyl having 1, 2, 3 or 4 carbon atoms;
X is S, R1 and R2, independently of one another, each denote A1 or Hal, A1 is H or A, A is alkyl having 1, 2, 3 or 4 carbon atoms, Hal is F or Cl;
and their physiologically acceptable salts and solvates.

In another related embodiment, PDE7 inhibitors useful in the methods of the invention include the following compounds:

10-Chloro-3-imidazol-1-yl-2,3-dihydro-1H-pyrido[3,2,1-kl]phenothiazine, 4-chloro-3-imidazol-1-yl-2,3-dihydro-1H-pyrido[3,2,1-kl]phenothiazine, 10-methoxy-3-imidazol-1-yl-2,3-dihydro-1H-pyrido[3,2,1-kl]phenothiazine, 10-propoxy-3-imidazol-1-yl-2,3-dihydro-1H-pyrido[3,2,1-kl]phenothiazine, 10-methylthio-3-imidazol-1-yl-2,3-dihydro-1H-pyrido[3,2,1-kl]phenothiazine, 10-fluoro-3-imidazol-1-yl-2,3-dihydro-1H-pyrido[3,2,1-kl]phenothiazine, 4,10-dichloro-3-imidazol-1-yl-2,3-dihydro-1H-pyrido[3,2,1-kl]phenothiazine, 10-trifluoromethyl-3-imidazol-1-yl-2,3-dihydro-1H-pyrido[3,2,1-kl]phenothiazine, 4-cyclopentoxy-3-imidazol-1-yl-2,3-dihydro-1H-pyrido[3,2,1-kl]phenothiazine, 10-chloro-3-imidazol-1-yl-2,3-dihydro-1H-7-oxa-11b-azabenzo[de]-anthracene, and 10-chloro-3-imidazol-1-yl-2,3-dihydro-1H-pyrido[3,2,1-kl]phenothiazine 7,7-dioxide.

The preparation of these compounds is described in U.S. Pat. No. 6,884,800 and WO 01/36425.

In another embodiment, PDE7 inhibitors useful in the methods of the invention are selected from those compounds generally or specifically disclosed in U.S. Pat. No. 6,531,498 and WO 01/32175, each expressly incorporated herein by reference in its entirety. In one embodiment, PDE7 inhibitors useful in the methods of the invention have the formula:

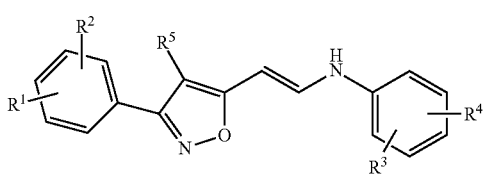

(38)

The substituents of the above compounds are defined as follows:
R1, R2, R3, R4 are each, independently of one another, Hal, OA1, SA1, A, H, COOA1, CN or CONA1A2,
R5 is COOA1, CN or CONA1A2,
A1, A2 are each, independently of one another, H, A, alkenyl, cycloalkyl or alkylenecycloalkyl,
A is alkyl having 1 to 10 C atoms,
Hal is F, Cl, Br or I,
and their physiologically acceptable salts and/or solvates.

In regard to the above compounds, A is alkyl having 1-10 C atoms and has 1, 2, 3, 4, 5, 6, 7, 8, 9 or 10 C atoms and is preferably methyl, ethyl or propyl, also preferably isopropyl, butyl, isobutyl, sec-butyl or tert-butyl, but is also n-pentyl, neopentyl, isopentyl or hexyl. It is also possible for 1-7H atoms in the radicals to be replaced by F and/or Cl. A is therefore also, for example, trifluoromethyl or pentafluoroethyl.

Cycloalkyl has 3-9 C atoms and is preferably, for example, cyclopentyl or cyclohexyl. Alkenyl has 2-10 C atoms, is linear or branched and is preferably vinyl, propenyl or butenyl.

Alkylenecycloalkyl has 4-10 C atoms and is, for example methylenecyclopentyl, ethylenecyclopentyl, methylenecyclohexyl or ethylenecyclohexyl.

In a related embodiment, PDE7 inhibitors useful in the methods of the invention include the compounds wherein
R1 is H;
R1 and R2 are H;
R1 is H and R2 is F or Cl;
R1, R2 are each, independently of one another, H or Hal;
R1, R2 are each, independently of one another, H or Hal, A1, A2 are each, independently of one another, H or A;
A1, A2 are each, independently of one another, H or A;
R1, R2 are each, independently of one another, H or Hal, A1, A2 are each, independently of one another, H or A, A is alkyl having 1, 2, 3 or 4 C atoms, Hal is F or Cl.

In another related embodiment, PDE7 inhibitors useful in the methods of the invention include the compounds:
5-[2-(2-Fluoro-4-hydroxyphenylamino)vinyl]-4-cyano-3-phenylisoxazole,
5-[2-(2,4-Difluorophenylamino)vinyl]-4-cyano-3-phenylisoxazole,
5-[2-(3-Methylthiophenylamino)vinyl]-4-cyano-3-phenylisoxazole,
5-[2-(2,4-Dimethoxyphenylamino)vinyl]-4-cyano-3-(2-chlorophenyl)isoxazole,
5-(2-Amino-2-phenylvinyl)-4-methylaminocarbonyl-3-phenylisoxazole,
5-(2-Phenylaminovinyl)-4-methoxycarbonyl-3-phenylisoxazole,
5-[2-(4-Carboxyphenylamino)vinyl]-4-cyano-3-phenylisoxazole,
5-[2-(4-Carboxyphenylamino)vinyl]-4-methoxycarbonyl-3-phenylisoxazole,
5-[2-(5-Chloro-2-hydroxyphenylamino)vinyl]-4-cyano-3-phenylisoxazole,
5-[2-(3,4-Dimethylphenylamino)vinyl]-4-cyano-3-(2-chlorophenyl)isoxazole,
5-[2-(4-Chlorophenylamino)vinyl]-4-cyano-3-(2-chlorophenyl)isoxazole,
5-(2-Phenylaminovinyl)-4-cyano-3-(2-chlorophenyl)isoxazole,
5-[2-(4-Methoxyphenylamino)vinyl]-4-cyano-3-(2-chlorophenyl)isoxazole,
5-[2-(4-Carboxyphenylamino)vinyl]-4-cyano-3-(2-chlorophenyl)isoxazole,
5-[2-(2-Fluoro-4-hydroxyphenylamino)vinyl]-4-cyano-3-(2-chlorophenyl)isoxazole,
5-[2-(4-Fluorophenylamino)vinyl]-4-cyano-3-(2-chlorophenyl)isoxazole,
5-[2-(3,5-Dichlorophenylamino)vinyl]-4-cyano-3-(2-chlorophenyl)isoxazole,
5-[2-(3-Chlorophenylamino)vinyl]-4-cyano-3-(2-chlorophenyl)isoxazole,
5-(2-Phenylaminovinyl)-4-cyano-3-(2,6-dichlorophenyl)isoxazole,
5-[2-(4-Chlorophenylamino)vinyl]-4-cyano-3-(2,6-dichlorophenyl)isoxazole,
5-(2-Phenylaminovinyl)-4-methoxycarbonyl-3-(2,6-dichlorophenyl)isoxazole,
5-[2-(4-Chlorophenylamino)vinyl]-4-methoxycarbonyl-3-(2,6-dichlorophenyl)isoxazole,
5-[2-(4-Carboxyphenylamino)vinyl]-4-methoxycarbonyl-3-(2,6-dichlorophenyl)isoxazole,
5-[2-(2,4-Difluorophenylamino)vinyl]-4-cyano-3-(2,6-dichlorophenyl)isoxazole,
5-[2-(2,4-Dichlorophenylamino)vinyl]-4-cyano-3-(2,6-dichlorophenyl)isoxazole,
5-[2-(4-Carboxyphenylamino)vinyl]-4-cyano-3-(2,6-dichlorophenyl)isoxazole,
5-[2-(3,5-Dichlorophenylamino)vinyl]-4-cyano-3-(2,6-dichlorophenyl)isoxazole,
5-[2-(4-Methoxyphenylamino)vinyl]-4-cyano-3-(2,6-dichlorophenyl)isoxazole,
5-[2-(2,4-Dimethoxyphenylamino)vinyl]-4-cyano-3-(2,6-dichlorophenyl)isoxazole,
5-[2-(2-Phenylphenylamino)vinyl]-4-cyano-3-(2,6-dichlorophenyl)isoxazole,
5-[2-(4-Methylphenylamino)vinyl]-4-cyano-3-(2,6-dichlorophenyl)isoxazole,
5-(2-Phenylaminovinyl)-4-cyano-3-(2-chloro-6-fluorophenyl)isoxazole, 5-[2-(4-Carboxyphenylamino)vinyl]-4-cyano-3-(2-chloro-6-fluorophenyl)isoxazole,
5-[2-(4-Chlorophenylamino)vinyl]-4-cyano-3-(2-chloro-6-fluorophenyl)isoxazole,
5-[2-(3-Methoxyphenylamino)vinyl]-4-cyano-3-(2-chloro-6-fluorophenyl)isoxazole,
5-[2-(4-Chlorophenylamino)vinyl]-4-methoxycarbonyl-3-(2-chloro-6-fluorophenyl)isoxazole,
5-(2-Phenylaminovinyl)-4-methoxycarbonyl-3-(2-chloro-6-fluorophenyl)isoxazole,
5-[2-(2,4-Dichlorophenylamino)vinyl]-4-methoxycarbonyl-3-(2-chloro-6-fluorophenyl)isoxazole,
5-(2-Phenylaminovinyl)-4-cyano-3-phenylisoxazole,
5-[2-(3-Trifluoromethoxyphenylamino)vinyl]-4-cyano-3-phenylisoxazole,
5-[2-(4-Methoxyphenylamino)vinyl]-4-cyano-3-phenylisoxazole,
5-[2-(4-Methoxyphenylamino)vinyl]-4-methoxycarbonyl-3-(2-chloro-6-fluorophenyl)isoxazole,
5-[2-(3-Methylthiophenylamino)vinyl]-4-cyano-3-phenylisoxazole,
5-[2-(2,4-Difluorophenylamino)vinyl]-4-cyano-3-phenylisoxazole,
5-[2-(2-Fluoro-4-hydroxyphenylamino)vinyl]-4-cyano-3-phenylisoxazole.

The preparation of these compounds is described in U.S. Pat. No. 6,531,498 and WO 01/32175.

In another embodiment, PDE7 inhibitors useful in the methods of the invention are selected from those compounds generally or specifically disclosed in U.S. Pat. No. 7,491,742 and WO 2001/29049, each expressly incorporated by reference in its entirety. In one embodiment, PDE7 inhibitors useful in the methods of the invention have the formula:

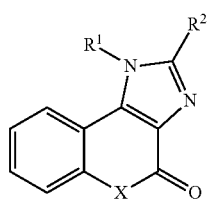

(39)

The substituents of the above compounds are defined as follows:

R1 is H, A, benzyl, indan-5-yl, 1,2,3,4-tetrahydronaphthalen-5-yl, dibenzothien-2-yl, or phenyl which is unsubstituted or mono-, di- or trisubstituted by Hal, A, A-CO—NH, benzyloxy, alkoxy, COOH or COOA, R2 is H or A, X is O or S, Hal is F, Cl, Br or I, A is alkyl with 1 to 6 C atoms, and the physiologically acceptable salts and/or solvates thereof.

In regard to the above compounds, A is alkyl with 1-6 C atoms and has 1, 2, 3, 4, 5 or 6 C atoms and is preferably methyl, ethyl or propyl, also preferably isopropyl, butyl, isobutyl, sec-butyl or tert-butyl, but also n-pentyl, neopentyl, isopentyl or hexyl. A is also cycloalkyl such as, for example, cyclohexyl. Alkoxy is preferably methoxy, ethoxy, propoxy or butoxy. Hal is preferably F or Cl. A-CO—NH is preferably acetamido.

In a related embodiment, PDE7 inhibitors useful in the methods of the invention are selected from the following compounds:

1-Phenyl-[1]benzopyrano[3,4-d]imidazol-4-(1H)-one, 1-Benzyl-[1]benzopyrano[3,4-d]imidazol-4-(1H)-one, 1-Cyclohexyl-[1]benzopyrano[3,4-d]imidazol-4-(1H)-one, 1-Cyclopentyl-[1]benzopyrano[3,4-d]imidazol-4-(1H)-one, 1-Butyl-[1]benzopyrano[3,4-d]imidazol-4-(1H)-one, 1-Isopropyl-[1]benzopyrano[3,4-d]imidazol-4-(1H)-one, 1-Propyl-[1]benzopyrano[3,4-d]imidazol-4-(1H)-one, 1-Ethyl-[1]benzopyrano[3,4-d]imidazol-4-(1H)-one, 1-Methyl-[1]benzopyrano[3,4-d]imidazol-4-(1H)-one, [1]Benzopyrano[3,4-d]imidazol-4-(1H)-one, 2-Methyl-[1]benzopyrano[3,4-d]imidazol-4-(1H)-one, 1-Phenyl-[1]benzothiopyrano[3,4-d]imidazol-4-(1H)-one, 1-Benzyl-[1]benzothiopyrano[3,4-d]imidazol-4-(1H)-one, 1-Cyclohexyl-[1]benzothiopyrano[3,4-d]imidazol-4-(1H)-one, 1-Cyclopentyl-[1]benzothiopyrano[3,4-d]imidazol-4-(1H)-one, 1-Butyl-[1]benzothiopyrano[3,4-d]imidazol-4-(1H)-one, 1-Isopropyl-[1]benzothiopyrano[3,4-d]imidazol-4-(1H)-one, 1-Propyl-[1]benzothiopyrano[3,4-d]imidazol-4-(1H)-one, 1-Ethyl-[1]benzothiopyrano[3,4-d]imidazol-4-(1H)-one, 1-Methyl-[1]benzothiopyrano[3,4-d]imidazol-4-(1H)-one, [1]Benzothiopyrano[3,4-d]imidazol-4-(1H)-one, 2-Methyl-[1]benzothiopyrano[3,4-d]imidazol-4-(1H)-one, 1-(2-Chlorophenyl-[1]benzopyrano[3,4-d]imidazol-4-(1H)-one, 1-(4-Methyl-phenyl)-[1]benzopyrano[3,4-d]imidazol-4-(1H)-one, 1-(4-Fluorophenyl)-[1]benzopyrano[3,4-d]imidazol-4-(1H)-one, 1-(2,4-Dimethyl-phenyl)-[1]benzopyrano[3,4-d]imidazol-4-(1H)-one, 1-(3-Chlorophenyl)-[1]benzopyrano[3,4-d]imidazol-4-(1H)-one, 1-(2,4-Dichlorophenyl)-[1]benzopyrano[3,4-d]imidazol-4-(1H)-one, 1-(2,5-Dichlorophenyl)-[1]benzopyrano[3,4-d]imidazol-4-(1H)-one, 1-(4-Acetamido-phenyl)-[1]benzopyrano[3,4-d]imidazol-4-(1H)-one, 1-(2-Fluorophenyl)-[1]benzopyrano[3,4-d]imidazol-4-(1H)-one, 1-(3-Fluorophenyl)-[1]benzopyrano[3,4-d]imidazol-4-(1H)-one, 1-(2-Benzyloxyphenyl)-[1]benzopyrano[3,4-d]imidazol-4-(1H)-one, 1-(2,6-Dimethyl-phenyl)-[1]benzopyrano[3,4-d]imidazol-4-(1H)-one, 1-(Indan-5-yl)-[1]benzopyrano[3,4-d]imidazol-4-(1H)-one, 1-(2-Methoxy-phenyl)-[1]benzopyrano[3,4-d]imidazol-4-(1H)-one, 1-(2,3-Dimethyl-phenyl)-[1]benzopyrano[3,4-d]imidazol-(1H)-4-one, 1-(2,3-Dichlorophenyl)-[1]benzopyrano[3,4-d]imidazol-4-(1H)-one, 1-(3-Chloro-4-methyl-phenyl)-[1]benzopyrano[3,4-d]imidazol-4-(1H)-one, 1-(2,5-Dimethyl-phenyl)-[1]benzopyrano[3,4-d]imidazol-4-(1H)-one, 1-(4-Chlorophenyl)-[1]benzopyrano[3,4-d]imidazol-4-(1H)-one, 1-(1,2,3,4-Tetrahydronaphthalen-5-yl)-[1]benzopyrano-[3,4-d]imidazol-4-(1-H)-one, 1-(Dibenzothien-2-yl)-[1]benzopyrano[3,4-d]imidazol-4-(1H)-one, 1-(3-Methoxy-phenyl)-[1]benzopyrano[3,4-d]imidazol-4-(1H)-one, 1-(4-Carboxy-2-methyl-phenyl)-[1]benzopyrano[3,4-d]imidazol-4-(1H)-one, and their physiologically acceptable salts and/or solvates thereof.

In another embodiment, PDE7 inhibitors useful in the methods of the invention are selected from those compounds generally or specifically disclosed in U.S. Pat. No. 6,737,436 and WO 01/32618, expressly incorporated herein by reference in its entirety. In one embodiment, PDE7 inhibitors useful in the methods of the invention have the formula:

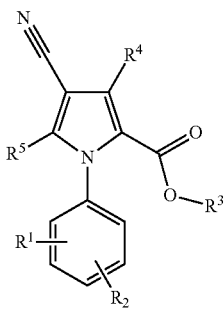

(40)

The substituents for the above compounds are defined as follows:

R1 and R2, independently of one another, each denote H, A, OA, SA or Hal,

R3 denotes H or A,

R4 denotes A or NH2,

R5 denotes H, NH2, NHA or NA2,

A denotes alkyl having 1 to 10 carbon atoms, alkenyl, cycloalkyl or alkylenecycloalkyl, Hal denotes F, Cl, Br or I, and their physiologically acceptable salts and/or solvates.

In regard to the above compounds, A denotes alkyl having 1-10 carbon atoms and has 1, 2, 3, 4, 5, 6, 7, 8, 9 or 10 carbon atoms and preferably denotes methyl, ethyl or propyl, furthermore preferably isopropyl, butyl, isobutyl, sec-butyl or tert-butyl, but also n-pentyl, neopentyl, isopentyl or hexyl. In these radicals, 1-7H atoms may also be replaced by F and/or Cl. A therefore also denotes, for example, trifluoromethyl or pentafluoroethyl.

A also denotes cycloalkyl having 3-8 carbon atoms and preferably denotes, for example, cyclopentyl or cyclohexyl.

A also denotes alkenyl. Alkenyl has 2-10 carbon atoms, is linear or branched and denotes, for example, vinyl, propenyl or butenyl. A furthermore denotes alkylenecycloalkyl. Alkylenecycloalkyl has 4-10 carbon atoms and preferably denotes, for example, methylenecyclopentyl, ethylenecyclopentyl, methylenecyclohexyl or ethylenecyclohexyl.

R1 and R2 preferably each denote, independently of one another, H, methyl, ethyl, propyl, butyl, isopropyl, tert-butyl, methoxy, ethoxy, propoxy, isopropoxy, butoxy, S-methyl, S-ethyl, F or Cl.

R3 preferably denotes H, methyl or ethyl.

R4 preferably denotes methyl, ethyl, propyl, butyl or NH2.

R5 preferably denotes H, amino, methylamino, ethylamino, dimethylamino or diethylamino.

In a related embodiment, PDE7 inhibitors useful in the methods of the invention include compounds of the above formula wherein R1 and R2 are not both H and wherein when one of R1 or R2 is H, the other cannot be CH3, OCH3 or Cl.

In another related embodiment, PDE7 inhibitors useful in the methods of the invention include compounds wherein R1, R2, R3 and R5 are H and R4 is methyl;

R1 is 4-Cl, R2 is H, R3 is ethyl, R4 is amino and R5 is H;

R1 and R2 are H, R3 is ethyl, R4 is methyl and R5 is amino;

R1 and R2 are H, R3 is ethyl, R4 is amino and R5 is H;

R1 and R2 are H, R3 is ethyl, R4 is H and R5 is amino;

R1 is 3-Cl, R2 is 4-O-methyl, R3 is ethyl, R4 is amino and R5 is H;

R1 is 3-Cl, R2 is 4-O-methyl, R3 is ethyl, R4 is methyl and R5 is amino;

R1 is 4-OCF3, R2 is H, R3 is ethyl, R4 is amino and R5 is H;

R1 is 3-Cl, R2 is 4-O-methyl, R3 is ethyl, R4 is amino and R5 is H;

R1 is 3-Cl, R2 is 4-O-methyl, R3 is ethyl, R4 is methyl and R5 is amino;

R1 is 4-OCF3, R2 is H, R3 is ethyl, R4 is amino and R5 is H.

In another embodiment, PDE7 inhibitors useful in the methods of the invention are selected from those compounds generally or specifically disclosed in U.S. Pat. No. 6,613,778 and WO 01/34601, expressly incorporated herein by reference in its entirety. In one embodiment, PDE7 inhibitors useful in the methods of the invention have the formula:

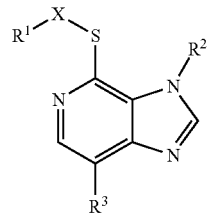

(41)

The substituents for the above compounds are defined as follows:

R1 denotes CONR4R5,

R2 denotes H or A,

R4 and R5, independently of one another, each denote H or A1,

R3 denotes Hal,

Hal denotes F, Cl, Br or I,

A denotes alkyl having 1-4 carbon atoms,

A1 denotes alkyl having 1-10 carbon atoms,

X denotes alkylene having 1-4 carbon atoms, in which an ethylene group may also be replaced by a double or triple bond, and their physiologically acceptable salts and/or solvates.

In regard to the above compounds, A denotes alkyl having 1-4 carbon atoms and has 1, 2, 3 or 4 carbon atoms and preferably denotes methyl, ethyl or propyl, furthermore preferably isopropyl, butyl, isobutyl, sec-butyl or tert-butyl. 1-7H atoms in the radicals may also be replaced by F and/or Cl. A therefore also denotes, for example, trifluoromethyl or pentafluoroethyl.

A1 denotes alkyl having 1-10 carbon atoms and has 1, 2, 3, 4, 5, 6, 7, 8, 9 or 10 carbon atoms and preferably denotes methyl, ethyl or propyl, furthermore preferably isopropyl, butyl, isobutyl, sec-butyl or tert-butyl, but also n-pentyl, neopentyl, isopentyl or hexyl. 1-7H atoms in the radicals may also be replaced by F and/or Cl. A1 therefore also denotes, for example, trifluoromethyl or pentafluoroethyl.

X denotes alkylene having 1-4 carbon atoms, preferably methylene, ethylene, propylene or butylene, in which one ethylene group may also be replaced by a double or triple bond. X therefore also denotes, for example, —CH2-CH=CH—H2- or —C≡—C—.

In a related embodiment, PDE7 inhibitors useful in the methods of the invention include the following compounds:

2-(3-Butyl-7-chloro-3H-imidazo[4,5-c]pyridin-4-ylsulfanyl)-N,N-dimethylacetamide

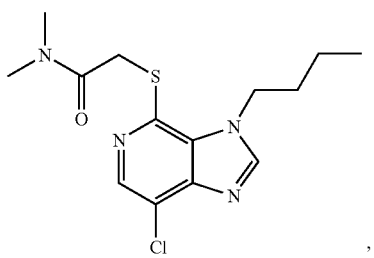 [SMILES: CCCCn1cnc2c(Cl)cnc(SCC(=O)N(C)C)c21]

2-(3-butyl-7-chloro-3H-imidazo[4,5-c]pyridin-4-ylsulfanyl) acetamide,
2-(3-butyl-7-chloro-3H-imidazo[4,5-c]pyridin-4-ylsulfanyl) propionamide,
2-(3-butyl-7-chloro-3H-imidazo[4,5-c]pyridin-4-ylsulfanyl) butyramide,
2-(3-butyl-7-chloro-3H-imidazo[4,5-c]pyridin-4-ylsulfanyl)-N-hexylacetamide,
2-(3-butyl-7-chloro-3H-imidazo[4,5-c]pyridin-4-ylsulfanyl)-N-octylacetamide,
4-(3-butyl-7-chloro-3H-imidazo[4,5-c]pyridin-4-ylsulfanyl)-but-2-enoic acid dimethylamide.

In another related embodiment, PDE7 inhibitors useful in the methods of the invention include the following compounds, wherein
R3 is Cl;
R3 is Cl, and X is alkylene having 1-4 carbon atoms;
R3 is Cl, X is alkylene having 1, 2, 3 or 4 carbon atoms, and A1 is alkyl having 1, 2, 3 or 4 carbon atoms.

The preparation of these compounds is described in U.S. Pat. No. 6,613,778 and WO 01/34601.

In another embodiment, PDE7 inhibitors useful in the methods of the invention are selected from those compounds generally or specifically disclosed in WO 2008/113881 and ES P 200700762, each expressly incorporated herein by reference in its entirety. In one embodiment, PDE7 inhibitors useful in the methods of the invention have the formula:

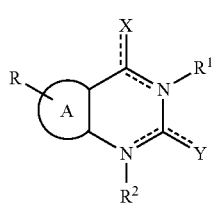

(42)

The substituents for the above compounds are defined as follows:

A is fused carbocyclo or heterocyclo of 5, 6 or 7 members and may be saturated or unsaturated; the dashed lines represent, independently, a single or double bond; X and Y are chosen independently from the group consisting of alkyl, hydrogen, =O, =S, —N (alkyl), —N(aryl), aryl, O-alkyl, O-aryl, alkyl-S and —S-aryl; and R1 and R2 are chosen independently from the group consisting of hydrogen, halogen, alkyl, haloalkyl, aryl, cycloalkyl, $(Z)_n$-aryl, heteroaryl, —OR3; —C(O)OR3, —$(Z)_n$—C(O)OR3 and —S(O), or a pharmaceutically acceptable salt, derivative, prodrug, solvate or stereoisomer of the same.

Exception: when A is unsubstituted benzene, X=O, Y=S, when A is unsubstituted benzene, X=O, Y=O, when A is unsubstituted benzene, X=O, Y=S-Me, when A is unsubstituted thiophene, X=O, Y=S, and when A is unsubstituted benzothiophene, X=O, Y=S.

In related embodiments, the above compounds constitute a useful pharmaceutical composition that includes a therapeutically effective amount of the above compounds, or mixtures of the same, a salt, derivative, prodrug, solvate or pharmaceutically acceptable stereoisomer of the same along with a carrier, adjuvant or pharmaceutically acceptable vehicle, for IV administration to patient.

In other related embodiments, the PDE7 inhibitors useful in the methods of the present invention include the following compound: 4-oxo-2-dioxo-1,2,3,4-tetrahydroquinazoline, and derivatives thereof selected from the following group:

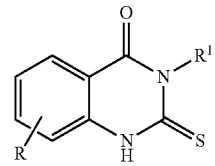

6-Bromo-2,3,4-tetrahydroquinazoline, 6-Bromo-(2,6-difluorophenyl)-4-oxo-2-dioxo-1,2,3,4-tetrahydroquinazoline, 6-Bromo-(2,3,4-trifluorophenyl)-4-oxo-2-dioxo-1,2,3,4-tetrahydroquinazoline, 6-Bromo-(2-bromophenyl)-4-oxo-2-dioxo-1,2,3,4-tetrahydroquinazoline, 3-(2,6-Difluorophenyl)-8-methyl-4-oxo-2-dioxo-1,2,3,4-tetrahydroquinazoline, 3-(2,3,4-Trifluorophenyl)-8-methyl-4-oxo-2-dioxo-1,2,3,4-tetrahydroquinazoline, and 3-(2-Bromophenyl)-8-methyl-4-oxo-2-dioxo-1,2,3,4-tetrahydroquinazoline.

In a further related embodiment, the PDE7 inhibitors useful in the methods of the present invention include the following compound: 2-methylthio-4-oxo-3,4-dihydroquinazoline and derivatives thereof selected from the following group:

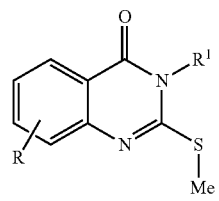

6-Bromo-(2,6-difluorophenyl)-2-methylthio-4-oxo-3,4-dihydroquinazoline, 6-Bromo-(2,3,4-trifluorophenyl)-2-methylthio-4-oxo-3,4-dihydroquinazoline, 6-Bromo-(2-bromophenyl)-2-methylthio-4-oxo-3,4-dihydroquinazoline, 3-Phenyl-8-methyl-2-methylthio-4-oxo-3,4-dihydroquinazoline, 3-(2,6-Difluorophenyl)-8-methyl-2-methylthio-4-oxo-3,4-dihydroquinazoline, 3-(2,3,4-Trifluorophenyl)-8-methyl-2-methylthio-4-oxo-3,4-dihydroquinazoline, and 3-(2-Bromophenyl)-8-methyl-2-methylthio-4-oxo-3,4-dihydroquinazoline.

In another related embodiment, the PDE7 inhibitors useful in the methods of the present invention include the following compound: 2,4-dithioxo-1,2,3,4-tetrahydroquinazoline, and derivatives thereof selected from the following group:

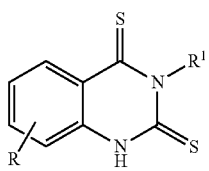

3-Phenyl-2,4-dithioxo-1,2,3,4-tetrahydroquinazo, 3-(2,6-Difluorophenyl)-2,4-dithioxo-1,2,3,4-tetrahydroquinazo, and 3-(2,3,4-Trifluorophenyl)-2,4-dithioxo-1,2,3,4-tetrahydroquinazoline.

In another related embodiment, PDE7 inhibitors useful in the methods of the present invention include the following compound: (2-methylthio-4-thioxo-3,4-dihydroquinazoline) and derivatives thereof selected from the following group:

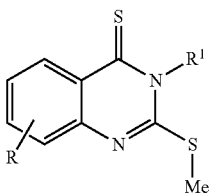

3-Phenyl-2-methylthio-4-thioxo-3,4-dihydroquinazoline, 3-(2,6-Difluorophenyl)-2-methylthio-4-thioxo-3,4-dihydroquinazoline, 3-(2,3,4-Trifluorophenyl)-2-methylthio-4-thioxo-3,4-dihydroquinazoline, and 3-(2-Bromophenyl)-2-methylthio-4-tioxo-3,4-dihydroquinazoline.

The preparation of the above compounds is described in WO 2008/113881.

In a related embodiment, PDE7 inhibitors useful in the methods of the invention are described in ES P 200700762, expressly incorporated by reference herein in its entirety. In one embodiment, PDE7 inhibitors useful in the methods of the invention have the formulas:

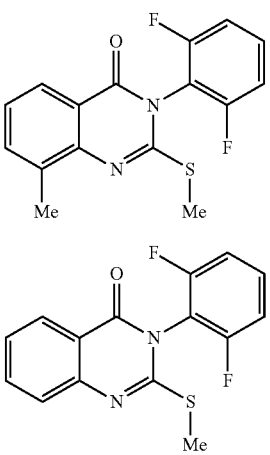

In another embodiment, PDE7 inhibitors useful in the methods of the invention are selected from those compounds generally or specifically disclosed in U.S. Pat. No. 7,214,676, and U.S. 2007/0049558, each expressly incorporated herein by reference in its entirety. In one embodiment, PDE7 inhibitors useful in the methods of the invention include the following compounds:

Spiro[cyclohexane-1-4'-(3',4'-dihydro)quinazolin]-2'(1'H)-one, 6'-Methoxyspiro[cyclohexane-1-4'-(3',4'-dihydro)quinazolin]-2'(1'H)-one, Spiro[cycloheptane-1-4'-(3',4'-dihydro)quinazolin]-2'(1'H)-one, 7'-Methoxyspiro[cyclohexane-1-4'-(3',4'-dihydro)quinazolin]-2'(1'H)-one, 6'-Phenylspiro[cycloheptane-1-4'-(3',4'-dihydro)quinazolin]-2'(1'H)-one, 8'-Methoxyspiro[cyclohexane-1-4'-(3',4'-dihydro)quinazolin]-2'(1'H)-one, 8'-Chlorospiro[cyclohexane-1-4'-(3',4'-dihydro)quinazolin]-2'(1'H)-one, 7'-chlorospiro[cyclohexane-1-4'-(3',4'-dihydro)quinazolin]-2'(1'H)-one, 5'-chlorospiro[cyclohexane-1-4'-(3',4'-dihydro)quinazolin]-2'(1'H)-one, 8'-methylspiro[cyclohexane-1-4'-(3',4'-dihydro)quinazolin]-2'(1'H)-one, 6'-chlorospiro[cyclohexane-1-4'-(3',4'-dihydro)quinazolin]-2'(1'H)-one, 8'-bromospiro[cyclohexane-1-4'-(3',4'-dihydro)quinazolin]-2'(1'H)-one, 8'-fluorospiro[cyclohexane-1-4'-(3',4'-dihydro)quinazolin]-2'(1'H)-one, 6'-methylspiro[cyclohexane-1-4'-(3',4'-dihydro)quinazolin]-2'(1'H)-one, 5',8'-dichlorospiro[cyclohexane-1-4'-(3',4'-dihydro)quinazolin]-2'(1'H)-one, 6',7'-dichlorospiro[cyclohexane-1-4'-(3',4'-dihydro)quinazolin]-2'(1'H)-one, 5',6'-dichlorospiro[cyclohexane-1-4'-(3',4'-dihydro)quinazolin]-2'(1'H)-one, 6'-phenylspiro[cyclohexane-1-4'-(3',4'-dihydro)quinazolin]-2'(1'H)-one, 8'-iodospiro[cyclohexane-1-4'-(3',4'-dihydro)quinazolin]-2'(1'H)-one, 8'-Bromospiro[cyclobutane-1-4'-(3',4'-dihydro)quinazolin]-2'(1'H)-one, 8'-Bromospiro[cycloheptane-1-4'-(3',4'-dihydro)quinazolin]-2'(1'H)-one, 8'-Bromo-4-methylspiro[cyclohexane-1-4'-(3',4'-dihydro)quinazolin]-2'(1'H)-one, 8'-Bromospiro[bicyclo[3,2,1]octane-2-4'-(3',4'-dihydro)quinazolin]-2'(1'H)-one, 6',8'-dichlorospiro[cyclohexane-1-4'-(3',4'-dihydro)quinazolin]-2'(1'H)-one, 8'-chloro-6'-iodospiro[cyclohexane-1-4'-(3',4'-dihydro)quinazolin]-2'(1'H)-one, 8'-chloro-6'-methoxyspiro[cyclohexane-1-4'-(3',4'-dihydro)quinazolin]-2'(1'H)-one, 8'-chloro-6'-phenylspiro[cycloheptane-1-4'-(3',4'-dihydro)quinazolin]-2'(1'H)-one, 8'-chloro-6'-phenylspiro[cyclohexane-1-4'-(3',4'-dihydro)quinazolin]-2'(1'H)-one, 8'-chloro-6'-methylspiro[cyclohexane-1-4'-(3',4'-dihydro)quinazolin]-2'(1'H)-one, 8'-chloro-6'-(3-pyridyl)spiro[cyclohexane-1-4'-(3',4'-dihydro)quinazolin]-2'(1'H)-one, 8'-chloro-6'-(4-pyridyl)spiro[cyclohexane-1-4'-(3',4'-dihydro)quinazolin]-2'(1'H)-one, 6'-(4-carboxyphenyl)-8'-chlorospiro[cyclohexane-1-4'-(3',4'-dihydro)quinazolin]-2'(1'H)-one, 6'-(3-carboxyphenyl)-8'-chlorospiro(cyclohexane-1-4'-(3',4'-dihydro)-quinazolin]-2'(1'H)-one, 8'-chloro-6'-(1H-indol-5yl)spiro[cyclohexane-1-4'-(3',4'-dihydro)quinazolin]-2'(1'H)-one, 8'-chloro-6'-(2-pyridyl)spiro[cyclohexane-1-4'-(3',4'-dihydro)quinazolin]-2'(1'H)-one, 8'-chloro-6'-(3-dimethylamino-prop-1-ynyl)spiro[cyclohexane-1-4'-(3',4'-dihydro)-quinazolin]-2'(1'H)-one, 8'-chloro-6'-(3-methylamino-prop-1-ynyl)spiro[cyclohexane-1-4'-(3',4'-dihydro)quinazolin]-2'(1'H)-one, 8'-chloro-6'-[4-(4-methyl-piperazine-1-carbonyl)phenyl]spiro[cyclohexane-1-4'-(3',4'-dihydro)quinazolin]-2'(1'H)-one, 8'-chloro-6'-[4-(3-N-dimethylamino-propylcarboxamide)phenyl]-spiro-[cyclohexane-1-4'-(3',4'-dihydro)quinazolin]-2'(1'H)-one, 8'-chloro-6'-[4-(2-N-dimethylamino-ethylcarboxamide)phenyl]-spiro-[cyclohexane-1-4'-(3',4'-dihydro)quinazolin]-2'(1'H)-one, 8'-chloro-6'-[3-(3-N-dimethylamino-propylcarboxamide)phenyl]-spiro-[cyclohexane-1-4'-(3',4'-dihydro)quinazolin]-2'(1'H)-one, 8'-chloro-6'-[3-(4-methyl-piperazine-1-carbonyl)-phenyl]spiro-[cyclohexane-1-4'-(3',4'-dihydro)quinazolin]-2'(1'H)-one, 8'-chloro-6'-[3-(2-N-dimethylamino-ethylcarboxamide)phenyl]Spiro-[cyclohexane-1-4'-(3',4'-dihydro)quinazolin]-2'(1'H)-one, 8'-Chlorospiro[cyclohexane-1-4'-(3',4'-dihydro)quinazolin]-2'(1'H)-thione, 8'-Chloro-2'-cyanoiminospiro[cyclohexane-1-4'-(3',4'-dihydro)

quinazoline, 8'-chloro-6'-[4-(4-pyrimidin-2-yl-piperazine-1-carbonyl)phenyl]spiro[-cyclohexane-1-4'-(3',4'-dihydro)quinazolin]-2'(1'H)-one, 8'-chloro-6'-[4-(4-(2-morpholin-4-yl-ethyl)-piperazine-1-carbonyl)-phenyl]Spiro[-cyclohexane-1-4'-(3',4'-dihydro)quinazolin]-2'(1'H)-one, 8'-chloro-6'-[4-(4-(2-morpholin-4-yl-2-oxo-ethyl)-piperazine-1-carbonyl)-phenyl]spiro[-cyclohexane-1-4'-(3',4'-dihydro)quinazolin]-2'(1'H)-one, 8'-chloro-6'-[4-(4-(2-hydroxy-ethoxy)-ethyl)-piperazine-1-carbonyl)-phenyl]spiro[-cyclohexane-1-4'-(3',4'-dihydro)quinazolin]-2'(1'H)-one, Spiro[cyclohexane-1-9'-(8',9'-dihydro)-pyrazolo[4',3'-f]quinazolin]-7'(6'H)-one, 8'-Chloro-5'-methoxyspiro[cyclohexane-1-4'-(3',4'-dihydro)quinazolin]-2'(1'H)-one, 5',8'-difluorospiro[cyclohexane-1-4'-(3',4'-dihydro)quinazolin]-2'(1'H)-one, 8'-Chloro-5'-methylspiro[cyclohexane-1-4'-(3',4'-dihydro)quinazolin]-2'(1'H)-one, 8'-Chloro-6'-(morpholin-4-yl)methylspiro[cyclohexane-1-4'-(3',4'-dihydro)quinazolin]-2'(1'H)-one, 8'-Chloro-5'-hydroxyspiro[cyclohexane-1-4'-(3',4'-dihydro)quinazolin]-2'(1'H)-one, 8'-Chloro-5'-hydroxy-6'-iodo-spiro[cyclohexane-1-4'-(3',4'-dihydro)quinazolin]-2'(1'H)-one, 8'-Chloro-6'-iodo-5'-methoxy-spiro[cyclohexane-1-4'-(3',4'-dihydro)quinazolin]-2'(1'H)-one, 8'-Chloro-6'-cyano-5'-methoxy-spiro[cyclohexane-1-4'-(3',4'-dihydro)quinazolin]-2'(1'H)-one, 8'-Chloro-5'-[2-(4-morpholino)ethoxy]spiro[cyclohexane-1-4'-(3',4'-dihydro)quinazolin]-2'(1'H)-one, 8'-Chloro-5'-[2-dimethylaminoethoxy]spiro[cyclohexane-1-4'-(3',4'-dihydro)quinazolin]-2'(1'H)-one, 8'-Chloro-5'-(2-aminoethoxy)-spiro[cyclohexane-1-4'-(3',4'-dihydro)quinazolin]-2'(1'H)-one, 8'-Chloro-5'-[2-(methylamino)ethoxy]-Spiro[cyclohexane-1-4'-(3',4'-dihydro)quinazolin]-2'(1'H)-one, 8'-Chloro-5'-[2-(2-aminoethoxy)ethoxy]spiro[cyclohexane-1-4'-(3',4'-dihydro)quinazolin]-2'(1'H)-one, 8'-Chloro-5'-[3-dimethylaminopropoxy]spiro[cyclohexane-1-4'-(3',4'-dihydro)quinazolin]-2'(1'H)-one, 8'-Chloro-5'-ethoxycarbonylmethoxyspiro[cyclohexane-1-4'-(3',4'-dihydro)quinazolin]-2'(1'H)-one, 5'-carboxymethoxy-8'-chloro-spiro[cyclohexane-1-4'-(3',4'-dihydro)quinazolin]-2'(1'H)-one, 5'-carboxypropoxy-8'-chloro-spiro[cyclohexane-1-4'-(3',4'-dihydro)quinazolin]-2'(1'H)-one, 8'-chloro-5'-(3-sulphopropoxy)-spiro[cyclohexane-1-4'-(3',4'-dihydro)quinazolin]-2'(1'H)-one, 8'-Chloro-5'-[2-(tetrahydro-pyran-2-yloxy)-ethoxy]-spiro[cyclohexane-1-4'-(3',4'-dihydro)quinazolin]-2'(1'H)-one, 8'-Chloro-5'-(2-hydroxy-ethoxy)-spiro[cyclohexane-1-4'-(3',4'-dihydro)quinazolin]-2'(1'H)-one, 8'-Chloro-5'-(5-ethoxycarbonyl-furan-2-ylmethoxy)-spiro[cyclohexane-1-4'-(3',4'-dihydro)quinazolin]-2'(1'H)-one, 8'-Chloro-5'-(5-carboxy-furan-2-ylmethoxy)-spiro[cyclohexane-1-4'-(3',4'-dihydro)quinazolin]-2'(1'H)-one, 8'-Chloro-5'-cyanomethoxyspiro[cyclohexane-1-4'-(3',4'-dihydro)quinazolin]-2'(1'H)-one, 8'-Chloro-5'-(1H-tetrazol-5-ylmethoxy)-spiro[cyclohexane-1-4'-(3',4'-dihydro)quinazolin]-2'(1'H)-one, 8'-Chloro-5'-(5-hydroxy-[1,2,4]oxadiazol-3-ylmethoxy)-spiro[cyclohexane-1-4'-(3',4'-dihydro)quinazolin]-2'(1'H)-one, 8'-Chloro-6'-iodo-5'-[2-dimethylamino-ethoxy]spiro[cyclohexane-1-4'-(3',4'-dihydro)quinazolin]-2'(1'H)-one, 6'-(4-carboxyphenyl)-8'-chloro-5'-methoxyspiro[cyclohexane-1-4'-(3',4'-dihydro)quinazolin]-2'(1'H)-one, 6'-(3-carboxyphenyl)-8'-chloro-5'-methoxyspiro[cyclohexane-1-4'-(3',4'-dihydro)quinazolin]-2'(1'H)-one, 8'-chloro-6'-[2-(4-methyl-piperazine-1-carbonyl)phenyl]spiro[cyclohexane-1-4'-(3',4'-dihydro)quinazolin]-2'(1'H)-one, 8'-chloro-6'-[2-methyl-4-(4-methyl-piperazine-1-carbonyl)phenyl]spiro[cyclohexane-1-4'-(3',4'-dihydro)quinazolin]-2'(1'H)-one, 8'-chloro-6'-[4-(piperazine-1-carbonyl)phenyl]spiro[cyclohexane-1-4'-(3',4'-dihydro)quinazolin]-2'(1'H)-one, 8'-chloro-6'-[4-carbamoyl-phenyl]spiro[cyclohexane-1-4'-(3',4'-dihydro)quinazolin]-2'(1'H)-one, 8'-chloro-6'-[4-((1-methyl-piperidin-4-yl)-piperazine-1-carbonyl)phenyl]spiro[cyclohexane-1-4'-(3',4'-dihydro)quinazolin]-2'(1'H)-one, 8'-chloro-5'-methoxy-6-[4-(4-methyl-piperazine-1-carbonyl)phenyl]spiro[cyclohexane-1-4'-(3',4'-dihydro)quinazolin]-2'(1'H)-one, 8'-Trifluoromethylspiro[cyclohexane-1-4'-(3',4'-dihydro)quinazolin]-2'(1'H)-one, 8'-Chloro-6'-cyanomethylspiro[cyclohexane-1-4'-(3',4'-dihydro)quinazolin]-2'(1'H)-one, 8'-Chloro-5'-(3-dimethylamino-2-hydroxy-propoxy)-spiro[cyclohexane-1-4'-(3',4'-dihydro)quinazolin]-2'(1'H)-one, 8'-Chloro-5'-(3-methylamino-2-hydroxy-propoxy)-spiro[cyclohexane-1-4'-(3',4'-dihydro)quinazolin]-2'(1'H)-one, 8'-Chloro-5'-[2-(ethoxycarbonylmethyl-amino)-ethoxy]-spiro[cyclohexane-1-4'-(3',4'-dihydro)quinazolin]-2'(1'H)-one, 8'-Chloro-5'-[2-(carboxymethyl-amino)-ethoxy]-spiro[cyclohexane-1-4'-(3',4'-dihydro)quinazolin]-2'(1'H)-one hydrochloride, 8'-Chloro-5'-(2-methanesulfonylamino-2-oxo-ethoxy)-spiro[cyclohexane-1-4'-(3',4'-dihydro)quinazolin]-2'(1'H)-one, 8'-Chloro-5'-(2-[(5-methyl-isoxazol-3-ylmethyl)-amino]ethoxy)-spiro[cyclohexane-1-4'-(3',4'-dihydro)quinazolin]-2'(1'H)-one.

Preparation of these compounds is described in U.S. Pat. No. 7,087,614, U.S. 2007/0049558 and WO 2002/074754.

In another embodiment, PDE7 inhibitors and dual PDE4/7 inhibitors useful in the methods of the invention are selected from those compounds generally or specifically disclosed in U.S. Pat. No. 7,087,614, US 2003/0162802 and WO 2002/102313, each expressly incorporated herein by reference in its entirety. In one embodiment, PDE7 inhibitors useful in the methods of the invention have the formula:

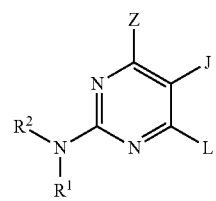

(54)

The PDE7 inhibitors useful in the methods of the invention include enantiomers, diastereomers, tautomers, and pharmaceutically acceptable salts, prodrugs, and solvates of the compounds of the above formula.

The substituents for the above compounds are defined as follows:

R1 is H or alkyl;

R2 is (a) heteroaryl, or heterocyclo, either of which may be optionally substituted with one to three groups T1, T2, T3; (b) aryl substituted with one to three groups T1, T2, T3 provided that at least one of T1, T2, T3 is other than H; or (c) aryl fused to a heteroaryl or heterocyclo ring wherein the combined ring system may be optionally substituted with one to three groups T1, T2, T3;

Z is (a) —OR4, —C(O)R4, —C(O)OR4, —SR4, —NR3R4, —C(O)NR3R4, —NR3SO2R4c, halogen, nitro, haloalkyl; or (b) alkyl, aryl, heteroaryl, heterocyclo, or cycloalkyl any of which may be optionally substituted with one to three groups T1a, T2a T3a;

J is (a) hydrogen, halo, —OR4a, or (b) alkyl, alkenyl, or alkynyl any of which may be optionally substituted with one to three groups T1b, T2b or T3b;

L is (a) hydrogen, —OR4b, —C(O)R4b, —C(O)OR4b, —SR4b, —NR5R6, —C(O)NR5R6, —NR5SO2R4d, halogen, haloalkyl, nitro, or (b) alkyl, aryl, heteroaryl, heterocylo, or cycloalkyl any of which may be optionally substituted with one to three groups T1c, T2c or T3c;

R3 and R4 are independently H, alkyl, alkenyl, aryl, (aryl)alkyl, heteroaryl, (heteroaryl)alkyl, cycloalkyl, (cycloalkyl)alkyl, heterocylo or (heterocyclo)alkyl any of which may be optionally substituted with one to three groups T1a, T2a or T3a;

or R3 and R4 together with the nitrogen atom to which they are attached may combine to form a 4 to 8 membered heterocyclo ring optionally substituted with one to three groups T1a, T2a or T3a;

R4a is hydrogen, alkyl, alkenyl, aryl, heteroaryl, (aryl)alkyl, (heteroaryl)alkyl, heterocylo, (heterocyclo)alkyl, cycloalkyl or (cycloalkyl)alkyl any of which may be optionally substituted with one to three groups T1b, T2b or T3b;

R4b is hydrogen, alkyl, alkenyl, aryl, heteroaryl, (aryl)alkyl, (heteroaryl)alkyl, heterocylo, (heterocyclo)alkyl, cycloalkyl or (cycloalkyl)alkyl any of which may be optionally substituted with one to three groups T1c, T2c or T3c;

R4c and R4d are independently alkyl, alkenyl, aryl, (aryl)alkyl, heteroaryl, (heteroaryl)alkyl, cycloalkyl, (cycloalkyl)alkyl, heterocylo or (heterocyclo)alkyl any of which may be optionally substituted with one to three groups T1a, T2a or T3a;

R5 and R6 are independently H, alkyl, alkenyl, aryl, (aryl)alkyl, heteroaryl, (heteroaryl)alkyl, cycloalkyl, (cycloalkyl)alkyl, heterocylo or (heterocyclo)alkyl any of which may be optionally independently substituted where valance allows with one to three groups T1c, T2c or T3c;

or R5 and R6 together with the nitrogen atom to which they are attached may combine to form a 4 to 8-membered heterocyclo ring optionally substituted with one to three groups T1c, T2c or T3c;

T1-1c T2-2c, and T3-3c are each independently (1) hydrogen or T6, where T6 is (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl; (ii) a group (i) which is itself substituted by one or more of the same or different groups (i); or (iii) a group (i) or (ii) which is independently substituted by one or more (preferably 1 to 3) of the following groups (2) to (13) of the definition of T1-1c, T2-2c and T3-3c (2) —OH or —OT6, (3) —SH or —ST6, (4) —C(O)tH, —C(O)tT6, or —O—C(O)T6, where t is 1 or 2; (5) —SO3H, —S(O)T6, or S(O)tN(T9)T6, (6) halo, (7) cyano, (8) nitro, (9) -T4-NT7T8, (10) -T4-N(T9)-T5-NT7T8, (11) -T4-N(T10)-T5-T6, (12) -T4-N(T10)-T5-H, (13) oxo, T4 and T5 are each independently (1) a single bond, (2) -T11-S(O)t-T12-, (3) -T11-C(O)-T12-, (4) -T11-C(S)-T12-, (5) -T11-O-T12-, (6) -T11-S-T12-, (7) -T11-O—C(O)-T12-, (8) -T11-C(O)—O-T12-, (9) -T11-C(=NT9a)-T12-, or (10) -T11-C(O)—C(O)-T12, T7, T8, T9, T9a and T10 (1) are each independently hydrogen or a group provided in the definition of T6, or (2) T7 and T8 may together be alkylene or alkenylene, completing a 3- to 8-membered saturated or unsaturated ring together with the atoms to which they are attached, which ring is unsubstituted or substituted with one or more groups listed in the description of T1-1c, T2-2c and T3-3c, or (3) T7 or T8, together with T9, may be alkylene or alkenylene completing a 3- to 8-membered saturated or unsaturated ring together with the nitrogen atoms to which they are attached, which ring is unsubstituted or substituted with one or more groups listed in the description of T1-1c, T2-2c and T3-3c, or (4) T7 and T8 or T9 and T10 together with the nitrogen atom to which they are attached may combine to form a group-N=CT13T14 where T13 and T14 are each independently H or a group provided in the definition of T6;

and T11 and T12 are each independently (1) a single bond, (2) alkylene, (3) alkenylene, or (4) alkynylene.

In a related embodiment, PDE7 inhibitors useful in the methods of the present invention include the above compounds, wherein:

Z is (a) halogen, alkoxy, haloalkyl, —NR3R4, —C(O)OR4, —C(O)NR3R4; (b) aryl or heteroaryl either of which may be optionally substituted with one or more T1a, T2a, T3a (especially cyano, optionally substituted alkyl, (hydroxy)alkyl, —OH, —OT6, —ST6, —SOtT6, —COtH, —COtT6, -T4NT7T8, or -T4N(T10)-T5-T6); (c) optionally substituted alkyl (especially substituted with one or more —OH, —COtH, —COtT6, -T4-NT7T8, -T4-N(T10)-T5-H, or -T4-N(T10)-T5-T6);

J is (a) H, or (b) alkyl or alkenyl either of which may be optionally substituted (especially with one or more —OH, —OT6, —COtH, or —COtT6);

L is (a) H; (b) halogen, alkoxy, haloalkyl, —NR5R6, —C(O)OR4b, —C(O)NR5R6; (c) aryl or heteroaryl either of which may be optionally substituted with one or more T1c, T2c, T3c (especially cyano, optionally substituted alkyl, (hydroxy)alkyl, —OH, —OT6, —ST6, —SOtT6, —COtH, —COtT6, -T4NT7T8, or -T4N(T10)-T5-T6); or (d) optionally substituted alkyl (especially substituted with one or more —OH, —COtH, —COtT6, -T4-NT7T8, -T4-N(T10)-T5-H, or; -T4-N(T10)-T5-T6);

R1 is H or alkyl;

R2 is (a) heteroaryl (more preferably thiazolyl or oxazolyl) optionally substituted with one to three groups T1, T2, T3, preferably including H, alkyl, haloalkyl, halo, heteroaryl, cyano, C(O) tT6, OT6, -T4NT7T8; (b) aryl substituted with one to three groups T1, T2, T3 (preferably including heteroaryl (preferably, imidazolyl, oxazolyl, or thiazolyl any of which may be further optionally substituted), cyano, C(O) tT6, S(O)tN(T9)T6, halo alkyl, and haloalkyl); or (c) aryl fused to a heterocyclo ring (e.g., 2,3-dihydro-1H-indole bound through the aryl ring, quinolyl bound through the aryl ring (especially quinol-6-yl), quinazolinyl bound through the aryl ring (especially quinazolin-7-yl), cinnolinyl bound through the aryl ring (especially cinnolin-6-yl), isoquinolinyl bound through the aryl ring (especially isoquinol-6-yl), and phthalazinyl bound through the aryl ring (especially phthalazin-6-yl)) wherein the combined ring system may be optionally substituted with one to three groups T1, T2, T3 (especially halo, OH, OT6, alkyl, —COtH, —COtT6, or —C(O)NT7T8);

R3 is H or optionally substituted alkyl (especially substituted with one or more —OH, or —OT6);

R4 is (a) hydrogen; (b) (aryl)alkyl where the aryl group is optionally independently substituted with one or more groups T1a, T2a, T3a (especially optionally substituted alkyl, halo, cyano, nitro, (hydroxy)alkyl, —OH, —OT6, —ST6, —COtH, —COtT6, —SO3H, —SOtT6, —SOtN(T9)(T6), -T4NT7T8, -T4-N(T10)-T5-T6, heterocyclo, or heteroaryl); (c) (heteroaryl)alkyl where the heteroaryl group is optionally independently substituted with one or more groups T1a, T2a, T3a (especially optionally substituted alkyl, halo, cyano, nitro, (hydroxy)alkyl, —OH, —OT6, —ST6, —COtH, —COtT6, —SO3H, —SOtT6, —SOtN(T9)(T6), -T4NT7T8, -T4-N(T10)-T5-T6, heterocyclo, or heteroaryl); (d) (heterocyclo)alkyl where the heterocyclo group is optionally independently substituted with one or more groups T1a, T2a, T3a (especially optionally substituted alkyl, halo, cyano, nitro, oxo, (hydroxy)alkyl, —OH, —OT6, —ST6, —COtH, —COtT6, —SO3H, —SOtT6, —SOtN(T9)(T6), -T4NT7T8, -T4-N(T10)-T5-T6, heterocyclo, or heteroaryl); (e) alkyl optionally independently substituted with one or more groups T1a, T2a, T3a (especially —OH, —OT6, —COtH, —COtT6, -T4NTT8 or -T4-N(T10)-T5-T6); (f) heterocyclo optionally independently substituted with one or more groups T1a, T2a, T3a (especially optionally substituted alkyl, optionally substituted aryl, optionally substituted heteroaryl, optionally substituted aralkyl, optionally substituted heterocyclo, cyano, —OH, —OT6, —COtH, —COtT6, oxo, hydroxy(alkyl), (alkoxy)alkyl, -T4-N(T10)-T5-T6, or -T4-NT2T8);

or R3 and R4 together with the nitrogen atom to which they are attached combine to form a 4 to 8-membered heterocyclo ring (especially pyrrolidinyl, piperadinyl, piperazinyl, morpholinyl, diazapanyl or 1,4-dioxa-8-azaspiro[4.5]decan-8-yl) optionally substituted with one to three groups T1a, T2a, T3a (especially optionally substituted alkyl, optionally substituted aryl, optionally substituted heteroaryl, optionally substituted aralkyl, optionally substituted heterocyclo, cyano, —OH, —OT6, —COtH, —COtT6, oxo, hydroxy(alkyl), (alkoxy)alkyl, -T4-N(T10)-T5-T6, or -T4-NT7T8);

R5 is hydrogen or alkyl;

R6 is (a) hydrogen; (b) (aryl)alkyl where the aryl group is optionally independently substituted with one or more groups T1c, T2c, T3c (especially optionally substituted alkyl, halo, cyano, nitro, (hydroxy)alkyl, —OH, —OT6, —ST6, —COtH, —COtT6, —SO3H, —SOtT6, —SOtN(T9)(T6), -T4-N(T10)-T5-T6, heterocyclo, or heteroaryl); (c) (heteroaryl)alkyl where the heteroaryl group is optionally independently substituted with one or more groups T1c, T2c, T3c (especially optionally substituted alkyl, halo, cyano, nitro, (hydroxy)alkyl, —OH, —OT6, —ST6, —COtH, —COtT6, —SO3H, —SOtT6, —SOtN(T9)(T6), -T4-N(T10)-T5-T6, heterocyclo, or heteroaryl); (d) (heterocyclo)alkyl where the heterocyclo group is optionally independently substituted with one or more groups T1c, T2c, T3c (especially optionally substituted alkyl, halo, cyano, nitro, oxo, (hydroxy)alkyl, —OH, —OT6, —ST6, —COtH, —COtT6, —SO3H, —SOtT6, —SOtN(T9)(T6), -T4-N(T10)-T5-T6, heterocyclo, or heteroaryl); (e) alkyl optionally independently substituted with one or more groups T1c, T2c, T3c (especially —OH, —OT6, —COtH, —COtT6, -T4NT7T8 or -T4-N(T10)-T5-T6); (f) heterocyclo optionally independently substituted with one or more groups T1c, T2c, T3c (especially optionally substituted alkyl, optionally substituted aryl, optionally substituted heteroaryl, optionally substituted aralkyl, optionally substituted heterocyclo, cyano, —OH, —OT6, —COtH, —COtT6, oxo, hydroxy(alkyl), (alkoxy)alkyl, -T4-N(T10)-T5-T6, or -T4-NT7T8);

or R5 and R6 together with the nitrogen atom to which they are attached combine to form a 4 to 8-membered heterocyclo ring (especially pyrrolidinyl, piperadinyl, piperazinyl, morpholinyl, diazapanyl or 1,4-dioxa-8-azaspiro[4.5]decan-8-yl) optionally substituted with one to three groups T1c, T2c, T3c (especially optionally substituted alkyl, optionally substituted aryl, optionally substituted heteroaryl, optionally substituted aralkyl, optionally substituted heterocyclo, cyano, —OH, —OT6, —COtH, —COtT6, oxo, hydroxy(alkyl), (alkoxy)alkyl, -T4-N(T10)-T5-T6, or -T4-NT7T8).

In another related embodiment, PDE7 inhibitors useful in the methods of the present invention include the above compounds, wherein:

Z is (a) halogen, alkoxy, haloalkyl, —NR3R4, —C(O)OR4, —C(O)NR3R4; (b) aryl or heteroaryl either of which may be optionally substituted with one or more T1a, T2a, T3a selected from cyano, optionally substituted alkyl, (hydroxy)alkyl, —OH, —OT6, —ST6, —SOtT6, —COtH, —COtT6, -T4NT7T8, -T4N(T10)-T5-T6, where T4 is a bond or —C(O)—; T5 is —C(O)—, or —C(O)O—; T6 is alkyl or haloalkyl; T7 and T8 are independently H; alkyl optionally substituted with cycloalkyl, heteroaryl, hydroxy or —NT7T8 cycloalkyl; or aryl optionally substituted with halogen; or T7 and T8 together with the nitrogen atom to which they are attached combine to form a heterocyclo ring optionally substituted with (hydroxy)alkyl, COtH or COtT6, T10 is hydrogen; (c) alkyl optionally substituted with one or more —OH, —COtH, —COtT6, -T4-NT7T8, -T4-N(T10)-T5-H, or -T4-N(T10)-T5-T6 where T4 is —C(O)—; T5 is -alkylene-O—; T6 is alkyl; T7 and T8 are independently H, alkyl, cycloalkyl, aryl, (aryl)alkyl (optionally substituted as described in the definition of R4), or heterocyclo (optionally substituted as described in the definition of R3 and R4 combining to form a heterocyclo ring); and T10 is H;

J is (a) H, or (b) alkyl or alkenyl either of which may be optionally substituted with one or more —OH, —OT6, —COtH, or —COtT6, where T6 is alkyl;

L is (a) H; (b) halogen, alkoxy, haloalkyl, —NR5R6, —C(O)OR4b, —C(O)NR5R6; (c) aryl or heteroaryl either of which may be optionally substituted with one or more T1c, T2c, T3c selected from cyano, optionally substituted alkyl (especially substituted with COtH or COtT6), (hydroxy)alkyl, —OH, —OT6, —ST6, —SOtT6, —COtH, —COtT6, -T4NT7T8, or -T4N(T10)-T5-T6, where T4 is a bond or —C(O)—; T5 is —C(O)—, or —C(O)O—; T6 is alkyl or haloalkyl; T7 and T8 are independently H; alkyl optionally substituted with cycloalkyl, heteroaryl, hydroxy or —NT7T8; cycloalkyl; or aryl optionally substituted with halogen; or T7 and T8 together with the nitrogen atom to which they are attached combine to form a heterocyclo ring optionally substituted with (hydroxy)alkyl, COtH or COtT6; T10 is hydrogen; (d) alkyl optionally substituted with one or more —OH, —COtH, —COtT6, -T4-NT7T8, -T4-N(T10)-T5-H, or -T4-N(T10)-T5-T6 where T4 is —C(O)—; T5 is -alkylene-O—; T6 is alkyl; T7 and T8 are independently H, alkyl, cycloalkyl, aryl, (aryl)alkyl (optionally substituted as described in the definition of R4), or heterocyclo (optionally substituted as described in the definition of R3 and R4 combining to form a heterocyclo ring); and T10 is H;

R1 is H or alkyl;

R2 is (a) heteroaryl (more preferably thiazolyl or oxazolyl) optionally substituted with one to three groups T1, T2, T3, preferably including H, alkyl, haloalkyl, halo, heteroaryl, cyano, C(O) tT6, OT6, -T4NT7T8; (b) aryl substituted with one to three groups T1, T2, T3 (preferably including heteroaryl (preferably, imidazolyl, oxazolyl, or thiazolyl any of which may be further optionally substituted), cyano, C(O) tT6, S(O)tN(T9)T6, halo alkyl, and haloalkyl); or (c) aryl fused to a heterocyclo ring (e.g., 2,3-dihydro-1H-indole bound through the aryl ring) wherein the combined ring system may be optionally substituted with one to three groups T1, T2, T3 (especially halo, —OH, —OT6, alkyl, —COtH, —COtT6, or —C(O)NT7T8);

R3 is H or optionally substituted alkyl (especially substituted with one or more —OH, or —OT6);

R4 is (a) hydrogen; (b) (aryl)alkyl where the aryl group is optionally independently substituted with one or more groups T1a, T2a, T3a selected from optionally substituted alkyl, halo, cyano, nitro, (hydroxy)alkyl, —OH, —OT6, —ST6, —COtH, —COtT6, —SO3H, —SOtT6, —SOtN(T9)(T6), -T4NT7T8, -T4N(T10)-T5-T6, heterocyclo, or heteroaryl) where T4 is a bond, —SO2-, or —C(O)—; T5 is —SO2-, or -alkylene-O—; T6 is alkyl, or cycloalkyl; T7 and T8 are independently H or alkyl; and T9 and T10 are hydrogen; (c) (heteroaryl)alkyl where the heteroaryl group is optionally independently substituted with one or more groups T1a, T2a, T3a selected from optionally substituted alkyl, halo, cyano, nitro, oxo, (hydroxy)alkyl, —OH, —OT6, —ST6, —COtH, —COtT6, —SO3H, —SOtT6, —SOtN(T9)(T6), -T4NT7T8, -T4-N(T10)-T5-T6, heterocyclo, or heteroaryl) where T4 is a bond, —SO2-, or —C(O)—; T5 is —SO2-, or -alkylene-O—; T6 is alkyl, or cycloalkyl; T7 and T8 are independently H or alkyl; and T9 and T10 are hydrogen; (d) (heterocyclo)alkyl where the heterocyclo group is optionally independently substituted with one or more groups T1a, T2a, T3a selected from optionally substituted alkyl, halo, cyano, nitro, (hydroxy)alkyl, —OH, —OT6, —ST6, —COtH, —COtT6, —SO3H, —SOtT6, -T4NT7T8, -T4-N(T10)-T5-T6, heterocyclo, or heteroaryl) where T4 is a bond, —SO2-, or —C(O)—; T5 is —SO2-, or -alkylene-O—; T6 is alkyl, or cycloalkyl; T7 and T8 are independently H or alkyl; and T9 and T10 are hydrogen; (e) alkyl optionally independently substituted with one or more groups T1a, T2a T3a selected from —OH, —OT6, —COtH, —COtT6, -T4NT7T8 or -T4-N(T10)-T5-T6) where T4 is a bond; T5 is —C(O)—; T6 is alkyl; T7 and T8 are independently H or alkyl; and T10 is hydrogen; heterocyclo optionally independently substituted with one or more groups T1a, T2a, T3a selected from optionally substituted alkyl (especially substituted with -T4NT7T8), optionally substituted aryl (especially substituted with halogen or haloalkyl), cyano, —OH, —OT6, —COtH, —COtT6, oxo, hydroxy(alkyl), (alkoxy)alkyl, -T4-N(T10)-T5-T6, or -T4-NT7T8 where T4 is a bond or —C(O)—; T5 is —C(O)—, —SO2-, or -alkylene-C(O)O—; T6 is alkyl, alkoxy, or heteroaryl; T7 and T8 are independently H, alkyl, or cycloalkyl; or T7 and T8 together with the nitrogen atom to which they are attached combine to form an optionally substituted heterocyclo ring;

or R3 and R4 together with the nitrogen atom to which they are attached combine to form a heterocyclo ring selected from pyrrolidinyl, piperadinyl, piperazinyl, morpholinyl, diazapanyl or 1,4-dioxa-8-azaspiro[4.5]decan-8-yl), any of which are optionally independently substituted with one to three groups T1a, T2a, T3a selected from optionally substituted alkyl (especially substituted with -T4NT7T8), optionally substituted aryl (especially substituted with halogen or haloalkyl), cyano, —OH, —OT6, —COtH, —COtT6, oxo, hydroxy(alkyl), (alkoxy)alkyl, -T4-N(T10)-T5-T6, or -T4-NT7T8) where T4 is a bond or —C(O)—; T5 is —C(O)—, —SO2-, or -alkylene-C(O)O—; T6 is alkyl, alkoxy, or heteroaryl; T7 and T8 are independently H, alkyl, or cycloalkyl; or T7 and T8 together with the nitrogen atom to which they are attached combine to form an optionally substituted heterocyclo ring;

R5 is hydrogen or alkyl;

R6 is (a) hydrogen; (b) (aryl)alkyl where the aryl group is optionally independently substituted with one or more groups T1c, T2c, T3c selected from optionally substituted alkyl, halo, cyano, nitro, (hydroxy)alkyl, —OH, —OT6, —ST6, —COtH, —COtT6, —SO3H, —SOtT6, —SOtN(T9)(T6), -TNT7T8, -T4-N(T10)-T5-T6, heterocyclo, or heteroaryl) where T4 is a bond, —SO2-, or —C(O)—; T5 is —SO2-, or -alkylene-O—; T6 is alkyl, or cycloalkyl; T7 and T8 are independently H or alkyl; and T9 and T10 are hydrogen; (c) (heteroaryl)alkyl where the heteroaryl group is optionally independently substituted with one or more groups T1c, T2c, T3c selected from optionally substituted alkyl, halo, cyano, nitro, oxo, (hydroxy)alkyl, —OH, —OT6, —ST6, —COtH, —COtT6, —SO3H, —SOtT6, —SOtN(T9)(T6), -T4NT7T8, -T4-N(T10)-T5-T6, heterocyclo, or heteroaryl) where T4 is a bond, —SO2-, or —C(O)—; T5 is —SO2-, or -alkylene-O—; T6 is alkyl, or cycloalkyl; T7 and T8 are independently H or alkyl; and T9 and T10 are hydrogen; (d) (heterocyclo)alkyl where the heterocyclo group is optionally independently substituted with one or more groups T1c, T2c, T3c selected from optionally substituted alkyl, halo, cyano, nitro, (hydroxy)alkyl, —OH, —OT6, —ST6, —COtH, —COtT6, —SO3H, —SOtT6, -T4NT7T8, -T4-N(T10)-T5-T6, heterocyclo, or heteroaryl) where T4 is a bond, —SO2-, or —C(O)—; T5 is —SO2-, or -alkylene-O—; T6 is alkyl, or cycloalkyl; T7 and T8 are independently H or alkyl; and T9 and T10 are hydrogen; (e) alkyl optionally independently substituted with one or more groups T1c, T2c, T3c selected from —OH, —OT6, —OCtH, —COtT6, -T4NT7T8 or -T4-N(T10)-T5-T6) where T4 is a bond; T5 is —C(O)—; T6 is alkyl; T7 and T8 are independently H or alkyl; and T10 is hydrogen; heterocyclo optionally independently substituted with one or more groups T1c, T2c, T3c selected from optionally substituted alkyl (especially substituted with -T4NT7T8), optionally substituted aryl (especially substituted with halogen or haloalkyl), cyano, —OH, —OT6, —COtH, —COtT6, oxo, hydroxy(alkyl), (alkoxy)alkyl, -T4-N(T10)-T5-T6, or -T4-NT7T8, where T4 is a bond or —C(O)—; T5 is —C(O)—, —SO2-, or -alkylene-C(O)O—; T6 is alkyl, alkoxy, or heteroaryl; T7 and T8 are independently H, alkyl, or cycloalkyl; or T7 and T8 together with the nitrogen atom to which they are attached combine to form an optionally substituted heterocyclo ring;

or R5 and R6 together with the nitrogen atom to which they are attached combine to form a heterocyclo ring selected from pyrrolidinyl, piperadinyl, piperazinyl, morpholinyl, diazapanyl or 1,4-dioxa-8-azaspiro[4.5]decan-8-yl), any of which are optionally independently substituted with one to three groups T1a, T2a, T3a selected from optionally substituted alkyl (especially substituted with -T4NT7T8), optionally substituted aryl (especially substituted with halogen or haloalkyl), cyano, —OH, —OT6, —COtH, —COtT6, oxo, hydroxy(alkyl), (alkoxy)alkyl, -T4-N(T10)-T5-T6, or -T4-NT7T8 where T4 is a bond or —C (O)—; 5 is —C(O)—, —SO2-, or -alkylene-C(O)O—; T6 is alkyl, alkoxy, or heteroaryl; T7 and T8 are independently H, alkyl, or cycloalkyl; or T7 and T8 together with the nitrogen atom to which they are attached combine to form a an optionally substituted heterocyclo ring.

In a further related embodiment, PDE7 inhibitors useful in the methods of the present invention include the following compounds:

2-[[4-[[[4-(Aminosulfonyl)phenyl]methy]amino]-6-(4-methyl-1-piperazinyl)-2-pyrimidinyl]amino]-4-methyl-5-thiazolecarboxylic acid ethyl ester; 2-[[4-[[(3,4-Dimethoxyphenyl)methyl]amino]-6-(1-piperazinyl)-2-pyrimidinyl]amino]-4-methyl-5-thiazolecarboxylic acid ethyl ester trifluoroacetate salt; 2-[[4-[[[4-(Aminosulfonyl)phenyl]methyl]amino]-6-(1-piperazinyl)-2-pyrimidinyl]amino]-4-methyl-5-thiazolecarboxylic acid ethyl ester; 4-Methyl-2-[[4-[[[4-(methylsulfonyl)phenyl]methyl]amino]-6-(1-piperazinyl)-2-pyrimidinyl]amino]-5-thiazolecarboxylic acid ethyl ester; 2-[[4-[[(4-Methoxyphenyl)methyl]amino]-6-(1-piperazinyl)-2-pyrimidinyl]amino]-4-methyl-5-thiazolecarboxylic acid ethyl ester; 2-[[4-[[(3-Methoxyphenyl)methyl]amino]-6-(1-piperazinyl)-2-pyrimidinyl]amino]-4-methyl-5-thiazolecarboxylic acid ethyl ester; 2-[[4-[[(2-Methoxyphenyl)methyl]amino]-6-(1-piperazinyl)-2-pyrimidinyl]amino]-4-methyl-5-thiazolecarboxylic acid ethyl ester; 4-Methyl-2-[[4-(1-piperazinyl)-6-[[(3,4,5-trimethoxyphenyl)methyl]amino]-2-pyrimidinyl]amino]-5-thiazolecarboxylic acid ethyl ester; 2-[[4-[[(2-Ethoxyphenyl)methyl]amino]-6-(1-piperazinyl)-2-pyrimidinyl]amino]-4-methyl-5-thiazolecarboxylic acid ethyl ester; 2-[[4-[[(2,5-

Dimethoxyphenyl)methyl]amino]-6-(1-piperazinyl)-2-pyrimidinyl]amino]-4-methyl-5-thiazolecarboxylic acid ethyl ester; 2-[[4-[[(3,5-Dimethoxyphenyl)methyl]amino]-6-(1-piperazinyl)-2-pyrimidinyl]amino]-4-methyl-5-thiazolecarboxylic acid ethyl ester; 2-[[4-[[(2,6-Dimethylphenyl)methyl]amino]-6-(1-piperazinyl)-2-pyrimidinyl]amino]-4-methyl-5-thiazolecarboxylic acid ethyl ester; 2-[[4-[[[4-(Methoxycarbonyl)phenyl]methyl]amino]-6-(1-piperazinyl)-2-pyrimidinyl]amino]-4-methyl-5-thiazolecarboxylic acid ethyl ester; 2-[[4-[[(3-Bromophenyl)methyl]amino]-6-(1-piperazinyl)-2-pyrimidinyl)amino]-4-methyl-5-thiazolecarboxylic acid ethyl ester; 2-[[4-[(1,3-Benzodioxol-5-ylmethyl)amino]-6-(1-piperazinyl)-2-pyrimidinyl]amino]-4-methyl-5-thiazolecarboxylic acid ethyl ester; 4-Methyl-2-[[4-[methyl(3-pyridinylmethyl)amino]-6-(1-piperazinyl)-2-pyrimidinyl]amino]-5-thiazolecarboxylic acid ethyl ester; 4-Methyl-2-[[4-(1-piperazinyl)-6-[[[4-(1,2,3-thiadiazol-4-yl)phenyl]methyl]amino]-2-pyrimidinyl]amino]-5-thiazolecarboxylic acid ethyl ester; 2-[[4-[[[3-(Cyclopentyloxy)-4-methoxyphenyl]methyl]amino]-6-(1-piperazinyl)-2-pyrimidinyl]amino]-4-methyl-5-thiazolecarboxylic acid ethyl ester; 4-Methyl-2-[[4-[(phenylmethyl)amino]-6-(1-piperazinyl)-2-pyrimidinyl]amino]-5-thiazolecarboxylic acid ethyl ester; 4-Methyl-2-[[4-(4-methyl-1-piperazinyl)-6-[[(3,4,5-trimethoxyphenyl)methyl]amino]-2-pyrimidinyl]amino]-5-thiazolecarboxylic acid ethyl ester; 2-[[4-(4-Hydroxy-1-piperidinyl)-6-[[[4-(methylsulfonyl)phenyl]methyl]amino]-2-pyrimidinyl]amino]-4-methyl-5-thiazolecarboxylic acid ethyl ester; 4-Methyl-2-[[4-[[2-(1-methylethoxy)ethyl]amino]-6-[[[4-(methylsulfonyl)phenyl]methyl]amino]-2-pyrimidinyl]amino]-5-thiazolecarboxylic acid ethyl ester; 2-[[4-[3-(Aminocarbonyl)-1-piperidinyl]-6-[[[4-(methylsulfonyl)phenyl]methyl]amino]-2-pyrimidinyl]amino]-4-methyl-5-thiazolecarboxylic acid ethyl ester; 2-[[4-[[(2-(1H-imidazol-4-yl)ethyl]amino]-6-[[[4-(methylsulfonyl)phenyl]methyl]amino]-2-pyrimidinyl]amino]-4-methyl-5-thiazolecarboxylic acid ethyl ester; 4-Methyl-2-[[4-[[[4-(methylsulfonyl)phenyl]methyl]amino]-6-[[3-(4-morpholinyl)propyl]amino]-2-pyrimidinyl]amino]-5-thiazolecarboxylic acid ethyl ester; 2-[[4-[(2-Methoxy-1-methylethyl)amino]-6-[[[4-(methylsulfonyl)phenyl]methyl]amino]-2-pyrimidinyl]amino]-4-methyl-5-thiazolecarboxylic acid ethyl ester; 4-Methyl-2-[[4-[[[4-(methylsulfonyl)phenyl]methyl]amino]-6-[[(tetrahydro-2-furanyl)methyl]amino]-2-pyrimidinyl]amino]-5-thiazolecarboxylic acid ethyl ester; 2-[[4-[4-(2-Hydroxyethyl)-1-piperazinyl]-6-[[[4-(methylsulfonyl)phenyl]methyl]amino]-2-pyrimidinyl]amino]-4-methyl-5-thiazolecarboxylic acid ethyl ester; 2-[[4-[2-(Aminocarbonyl)-1-pyrrolidinyl]-6-[[[4-(methylsulfonyl)phenyl]methyl]amino]-2-pyrimidinyl]amino]-4-methyl-5-thiazolecarboxylic acid ethyl ester; 4-Methyl-2-[[4-[methyl(3-pyridinylmethyl)amino]-6-[[[4-(methylsulfonyl)phenyl]methyl]amino]-2-pyrimidinyl]amino]-5-thiazolecarboxylic acid ethyl ester; 2-[[4-[4-(Hydroxymethyl)-1-piperidinyl]-6-[[[4-(methylsulfonyl)phenyl]methyl]amino]-2-pyrimidinyl]amino]-4-methyl-5-thiazolecarboxylic acid ethyl ester; 2-[[4-[[2-(Diethylamino)ethyl]methylamino]-6-[[[4-(methylsulfonyl)phenyl]methyl]amino]-2-pyrimidinyl]amino]-4-methyl-5-thiazolecarboxylic acid ethyl ester; 4-Methyl-2-[[4-[[[4-(methylsulfonyl)phenyl]methyl]amino]-6-[[3-(2-oxo-1-pyrrolidinyl)propyl]amino]-2-pyrimidinyl]amino]-5-thiazolecarboxylic acid ethyl ester; 2-[[4-[3-(Hydroxymethyl)-1-piperidinyl]-6-[[[4-(methylsulfonyl)phenyl]methyl]amino]-2-pyrimidinyl]amino]-4-methyl-5-thiazolecarboxylic acid ethyl ester; 4-Methyl-2-[[4-(4-methyl-1-piperazinyl)-6-[[[4-(methylsulfonyl)phenyl]methyl]amino]-2-pyrimidinyl]amino]-5-thiazolecarboxylic acid ethyl ester; 2-[[4-[[2-[(Acetylamino)ethyl]amino]-6-[[[4-(methylsulfonyl)phenyl]methyl]amino]-2-pyrimidinyl]amino]-4-methyl-5-thiazolecarboxylic acid ethyl ester; 2-[[4-(4-Ethyl-1-piperazinyl)-6-[[[4-(methylsulfonyl)phenyl]methyl]amino]-2-pyrimidinyl]amino]-4-methyl-5-thiazolecarboxylic acid ethyl ester; 2-[[4-(4-Acetyl-1-piperazinyl)-6-[[[4-(methylsulfonyl)phenyl]methyl]amino]-2-pyrimidinyl]amino]-4-methyl-5-thiazolecarboxylic acid ethyl ester; 2-[[4-[[2-(Dimethylamino)ethyl]amino]-[[[4-(methylsulfonyl)phenyl]methyl]amino]-2-pyrimidinyl]amino]-4-methyl-5-thiazolecarboxylic acid ethyl ester; 2-[[4-[3-(Aminocarbonyl)-1-piperazinyl]-6-[[[4-(methylsulfonyl)phenyl]methyl]amino]-2-pyrimidinyl]amino]-4-methyl-5-thiazolecarboxylic acid ethyl ester; 2-[[4-(3-Hydroxy-1-pyrrolidinyl)-6-[[[4-(methylsulfonyl)phenyl]methyl]amino]-2-pyrimidinyl]amino]-4-methyl-5-thiazolecarboxylic acid ethyl ester; 2-[[4-[(4-Hydroxybutyl)amino]-6-[[[4-(methylsulfonyl)phenyl]methyl]amino]-2-pyrimidinyl]amino]-4-methyl-5-thiazolecarboxylic acid ethyl ester; 2-[[4-[(2,3-Dihydroxypropyl)amino]-6-[[[4-(methylsulfonyl)phenyl]methyl]amino]-2-pyrimidinyl]amino]-4-methyl-5-thiazolecarboxylic acid ethyl ester; 2-[[4-[(4-Amino-1-piperidinyl)-6-[[[4-(methylsulfonyl)phenyl]methyl]amino]-2-pyrimidinyl]amino]-4-methyl-5-thiazolecarboxylic acid ethyl ester; 2-[[4-[4-Hydroxy-3-(hydroxymethyl)-1-piperidinyl]-6-[[[4-(methylsulfonyl)phenyl]methyl]amino]-2-pyrimidinyl]amino]-4-methyl-5-thiazolecarboxylic acid ethyl ester; 2-[[4-(4-Dimethylamino-1-piperidinyl)-6-[[[4-(methylsulfonyl)phenyl]methyl]amino]-2-pyrimidinyl]amino]-4-methyl-5-thiazolecarboxylic acid ethyl ester; 2-[[4-[[[4-(Aminosulfonyl)phenyl]methyl]amino]-6-(methylamino)-2-pyrimidinyl]amino]-4-methyl-5-thiazolecarboxylic acid, ethyl ester; 2-[4,6-Bis-(4-methyl-piperazin-1-yl)-pyrimidin-2-ylamino]-4-methyl-thiazole-5-carboxylic acid ethyl ester; 2-[4-(4-Hydroxy-piperidin-1-yl)-6-(4-methyl-piperazin-1-yl)-pyrimidin-2-ylamino]-4-methyl-thiazole-5-carboxylic acid ethyl ester; 2-[4-(3-Hydroxymethyl-piperidin-1-yl)-6-(4-methyl-piperazin-1-yl)-pyrimidin-2-ylamino]-4-methyl-thiazole-5-carboxylic acid ethyl ester; 4-Methyl-2-[4-(4-methyl-piperazin-1-yl)-6-morpholin-4-yl-pyrimidin-2-ylamino]-thiazole-5-carboxylic acid ethyl ester; 2-[4-(4-Amino-piperidin-1-yl)-6-(4-methyl-piperazin-1-yl)-pyrimidin-2-ylamino]-4-methyl-thiazole-5-carboxylic acid ethyl ester; 2-[4,6-Bis-(4-hydroxy-piperidin-1-yl)-pyrimidin-2-ylamino]-4-methyl-thiazole-5-carboxylic acid ethyl ester; 2-[4-(4-oxo-piperidin-1-yl)-6-(4-methyl-piperazin-1-yl)-pyrimidin-2-ylamino]-4-methyl-thiazole-5-carboxylic acid ethyl ester; 2-[4-(4-methyl-4-hydroxy-piperidin-1-yl)-6-(4-methyl-piperazin-1-yl)-pyrimidin-2-ylamino]-4-methyl-thiazole-5-carboxylic acid ethyl ester; 2-[-(4-hydroxy-piperidin-1-yl)-6-(4-dimethylmethyl-piperazin-1-yl)-pyrimidin-2-ylamino]-4-methyl-thiazole-5-carboxylic acid ethyl ester; 2-[4-(4-hydroxymethyl-piperidin-1-yl)-6-(4-dimethylmethyl-piperazin-1-yl)-pyrimidin-2-ylamino]-4-methyl-thiazole-5-carboxylic acid ethyl ester; 2-[4-(3-hydroxymethyl-piperidin-1-yl)-6-(4-dimethylmethyl-piperazin-1-yl)-pyrimidin-2-ylamino]-4-methyl-thiazole-5-carboxylic acid ethyl ester; 2-[4-(4-hydroxymethyl-piperidin-1-yl)-6-(4-hydroxy-piperazin-1-yl)-pyrimidin-2-ylamino]-4-methyl-thiazole-5-carboxylic acid ethyl ester; 4-Methyl-2-[4-(4-hydroxy-piperazin-1-yl)-6-morpholin-4-yl-pyrimidin-2-ylamino]-thiazole-5-carboxylic acid ethyl ester; 2-[[(4-[[[4-(Methylsulfonyl)phenyl]methyl]amino]-6-chloro-2-pyrimidinyl]amino]-4-methyl-5-thiazolecarboxylic acid, ethyl ester; 2-[[4-[[[4-(Aminosulfonyl)phenyl]methyl]amino]-6-chloro-2-pyrimidinyl]amino]-4-methyl-5-thiazolecarboxylic acid, ethyl ester; 2-[[4-[4-(Dimethylamino)-1-piperidinyl]-6-[[(3,4,5-trimethoxyphenyl)methyl]amino]-2-pyrimidinyl]amino]-4-methyl-5-thiazolecarboxylic acid, ethyl ester; 2-[[4-[1-piperizinyl]-6-methyl-6-[[(3,4,5-trimethoxyphenyl)methyl]amino]-2-pyrimidinyl]amino]-4-methyl-5-thiazolecarboxylic acid, ethyl ester; 2-[[4-(4-Amino-1-piperidinyl)-6-[[[4-(methylsulfonyl)phenyl]methyl]amino]-2-pyrimidinyl]amino]-4-methyl-5-thiazolecarboxylic acid, ethyl ester; 2-[[4-[4-hydroxy-1-piperidinyl]-6-methyl-6-[[(3,4,5-trimethoxyphenyl)methyl]amino]-2-pyrimidinyl]amino]-4-methyl-5-thiazolecarboxylic acid, ethyl ester; 2-[[4-[4-(Hydroxymethyl)-1-piperidinyl]-6-methyl-6-[[(3,4,5-trimethoxyphenyl)methyl]amino]-2-pyrimidinyl]amino]-4-methyl-5-thiazolecarboxylic acid, ethyl ester; 2-[4-(4-Hydroxypiperidin-1-yl)-6-(3-oxo-piperazin-1-yl)-pyrimidin-2-ylamino]-4-methyl-thiazole-5-carboxylic acid ethyl ester; 2-[[4-[3-(Aminocarbonyl)-1-piperizinyl]-6-methyl-6-[[(3,4,5-trimethoxyphenyl)methyl]amino]-2-pyrimidinyl]amino]-4-methyl-5-thiazolecarboxylic acid, ethyl ester; 2-[[4-[1-morpholinyl]-6-methyl-6-[[(3,4,5-trimethoxyphenyl)methyl]amino]-2-pyrimidinyl]amino]-4-methyl-5-thiazolecarboxylic acid, ethyl ester; 2-[[4-[3-oxo-1-piperizinyl]-6-[[(1,1-dioxido-3-oxo-1,2-benzisothiazol-2-(3H)-yl)methyl]amino]-2-pyrimidinyl]amino]-4-methyl-5-thiazolecarboxylic acid, ethyl ester; 2-[[4-[3-oxo-1-piperizinyl]-6-[[(4-(ethylsulfonylamino)phenyl)methyl]amino]-2-pyrimidinyl]amino]-4-methyl-5-thiazolecarboxylic acid, ethyl ester; 2-[[4-[3-oxo-1-piperizinyl]-6-[[(4-(hydroxysulfonyl)phenyl)methyl]amino]-2-pyrimidinyl]amino]-4-methyl-5-thiazolecarboxylic acid, ethyl ester; 2-[4-(4-Hydroxypiperidin-1-yl)-6-(4-methyl-3-oxo-piperazin-1-yl)-pyrimidin-2-ylamino]-4-methyl-thiazole-5-carboxylic acid ethyl ester; 2-[4-(4(Dimethylamino)-piperizin-1-yl)-6-(4-((1-pyrrolidinyl)carbonylmethyl)piperazin-1-yl)-pyrimidin-2-ylamino]-4-methyl-thiazole-5-carboxylic acid ethyl ester; 2-[[4-[3-(Aminocarbonyl)-1-piperazinyl]-6-[[(3,4,5-trimethoxyphenyl)methyl]amino]-2-pyrimidinyl]amino]-4-methyl-5-thiazolecarboxylic acid, ethyl ester; 2-[[4-(4-Amino-1-piperidinyl)-6-[[(3,4,5-trimethoxyphenyl)methyl]amino]-2-pyrimidinyl]amino]-4-methyl-5-thiazolecarboxylic acid, ethyl ester; 2-[[4-[4-(Hydroxymethyl)-1-piperidinyl]-6-[4-[tetrazol-5-yl]-4-hydroxypiperidin-1-yl]2-pyrimidinyl]amino]-4-methyl-5-thiazolecarboxylic acid, ethyl ester; 2-[[4-[4-methyl-1-piperazinyl]-6-[N-methyl-N-[(3,4,5-trimethoxyphenyl)methyl]amino]-2-pyrimidinyl]amino]-4-methyl-5-thiazolecarboxylic acid, ethyl ester; 2-[[4-[4-Hydroxy-1-piperidinyl]-6-[[(4-(hydroxysulfonyl)phenyl)methyl]amino]-2-pyrimidinyl]amino]-4-methyl-5-thiazolecarboxylic acid, ethyl ester; 2-[[4-[[(4-Cyanophenyl)methyl]amino]-6-(1-piperazinyl)-2-pyrimidinyl]amino]-4-methyl-5-thiazolecarboxylic acid, ethyl ester; trifluoroacetate (1:1); 2-[[4-[[[4-(Aminosulfonyl)phenyl]methyl]amino]-6-(4-morpholinyl)-2-pyrimidinyl]amino]-4-methyl-5-thiazolecarboxylic acid, ethyl ester; 2-[[4-[4-Hydroxy-1-piperidinyl]-6-[(1-oxa-3,8-diazaspiro[4.5]decan-2,4,dion-8-yl]-2-pyrimidinyl]amino]-4-methyl-5-thiazolecarboxylic acid, ethyl ester; 2-[4-(2-(Dimethylamino)ethyl)-piperazin-1-yl)-6-(4-methylpiperazin-1-yl)-pyrimidin-2-ylamino]-4-methyl-thiazole-5-carboxylic acid ethyl ester; 2-[[4-(4-Hydroxy-1-piperidinyl]-6-[methyl(3-pyridinylmethyl)amino]-2-pyrimidinyl]amino]-4-methyl-5-thiazolecarboxylic acid, ethyl ester; 2-[[4-[4-Hydroxy-3-hydroxymethylpiperidin-1-yl]-6-[[(3,4,5-trimethoxyphenyl)methyl]amino]-2-pyrimidinyl]amino]-4-methyl-5-thiazolecarboxylic acid, ethyl ester; 2-[[4-(3,4-Dihydro-6,7-dihydroxy-2(1H)-isoquinolinyl)-6-(4-methyl-1-piperazinyl)-2-pyrimidinyl]amino]-4-methyl-5-thiazolecarboxylic acid, ethyl ester, trifluoroacetate 1:1); 2-[[4-[4-[(Methoxyacetyl)amino]-1-piperidinyl]-6-[[4-(methylsulfonyl)phenyl]methyl]amino]-2-pyrimidinyl]amino]-4-methyl-5-thiazolecarboxylic acid, ethyl ester; 2-[[4-[[(3,4-Dimethoxyphenyl)methyl]amino]-6-[4-(dimethylamino)-1-piperidinyl]-2-pyrimidinyl]amino]-4-methyl-thiazolecarboxylic acid, ethyl ester; 2-[[4-[4-(Hydroxyethyl)piperidin-1-yl]-6-[4-(dimethylamino)-1-piperidinyl]-2-pyrimidinyl]amino]-4-methyl-5-thiazolecarboxylic acid, ethyl ester; 2-[[4-[4-(Dimethylamino)-1-piperidinyl]-6-[methyl(3-pyridinylmethyl)amino]-2-pyrimidinyl]amino]-4-methyl-5-thiazolecarboxylic acid, ethyl ester; 2-[[4-[4-(Hydroxy)piperidin-1-yl]-6-[4-(methoxycarbonyl)-1-piperidinyl]-2-pyrimidinyl]amino]-4-methyl-5-thiazolecarboxylic acid, ethyl ester; 2-[[4-[4-(Hydroxy)piperidin-1-yl]-6-[4-(methyl)-4-(hydroxy)-1-piperidinyl]-2-pyrimidinyl]amino]-4-methyl-5-thiazolecarboxylic acid, ethyl ester; 2-[4-(3-oxopiperazin-1-yl)-6-(4-methylpiperazin-1-yl)-pyrimidin-2-ylamino]-4-methyl-thiazole-5-carboxylic acid ethyl ester; 2-[[4-[[(4-Cyanophenyl)methyl]amino]-6-[4-dimethylamino)-1-piperidinyl]-2-pyrimidinyl]amino]-4-methyl-5-thiazolecarboxylic acid, ethyl ester; 4-Methyl-2-[[4-[[(3-nitrophenyl)methyl]amino]-6-(1-piperazinyl)-2-pyrimidinyl]amino]-5-thiazolecarboxylic acid, ethyl ester, trifluoroacetate (1:1); 2-[[4-(4-Hydroxy-1-piperidinyl)-6-[[(3,4,5-trimethoxyphenyl)methyl]amino]-2-pyrimidinyl]amino]-4-methyl-5-thiazolecarboxylic acid, ethyl ester; 2-[4-(Dimethylamino)-piperazin-1-yl)-6-(4-methylpiperazin-1-yl)-pyrimidin-2-2-ylamino]-4-methyl-thiazole-5-carboxylic acid ethyl ester; 2-[4-(Dimethylamino)-piperidin-1-yl)-6-(3-(aminocarbonyl)-1-piperazinyl)-pyrimidin-2-ylamino]-4-methyl-thiazole-5-carboxylic acid ethyl ester; 2-[4-(2-Hydroxyethyl)-piperazin-1-yl)-6-(4-methyl-1-piperazinyl)-pyrimidin-2-ylamino]-4-methyl-thiazole-5-carboxylic acid ethyl ester; 2-[[4-[4-(Aminocarbonyl)-1-piperidinyl]-6-[[[4-(methylsulfonyl)phenyl]methyl]amino]-2-pyrimidinyl]amino]-4-methyl-5-thiazolecarboxylic acid, ethyl ester; 2-[[4-[4-(Hydroxymethyl)-1-piperidinyl]-6-[N-methyl-N-(3-pyridinylmethyl)amino]-2-pyrimidinyl]amino]-4-methyl-5-thiazolecarboxylic acid, ethyl ester; 2-[[4-[4-Methylpiperazin-1-yl]-6-[[(3,4-dimethoxyphenyl)methyl]amino]-2-pyrimidinyl]amino]-4-methyl-5-thiazolecarboxylic acid, ethyl ester; 2-[[4-[piperazin-1-yl]-6-[[(4-carboxyphenyl)methyl]amino]-2-pyrimidinyl]amino]-4-methyl-5-thiazolecarboxylic acid, ethyl ester; 2-[[4-[3-Hydroxymethylpiperidin-1-yl]-6-[[N-[(3,4,5-trimethoxyphenyl)methyl]]-N-(methyl)amino]-2-pyrimidinyl]amino]-4-methyl-5-thiazolecarboxylic acid, ethyl ester; 2-[4-(4-Hydroxypiperidin-1-yl)-6-(4-carboxypiperidin-1-yl)-pyrimidin-2-ylamino]-4-methyl-thiazole-5-carboxylic acid ethyl ester; 2-[[4-[piperazin-1-yl]-6-[[(3,4-dimethoxyphenyl)methyl]amino]-2-pyrimidinyl]amino]-4-methyl-5-thiazolecarboxylic acid, ethyl ester; 2-[[4-(4-Formyl-1-piperazinyl)-6-[[[4-(methylsulfonyl)phenyl]methyl]amino]-2-pyrimidinyl]amino]-4-methyl-5-thiazolecarboxylic acid, ethyl ester; 2-[4-(4-Hydroxypiperidin-1-yl)-6-(4-(hydroxy)-4-(4-chlorophenyl)piperidin-1-yl)-pyrimidin-2-ylamino]-4-methyl-thiazole-5-carboxylic acid ethyl ester; 4-Methyl-2-[[4-[4-dimethylamino-1-piperidinyl]-6-[[(tetrahydro-2-furanyl)methyl]amino]-2-pyrimidinyl]amino]-5-thiazolecarboxylic acid ethyl ester; 2-[[4-[Piperazin-1-yl]-6-[[N-methyl-N-(5- tetrazolylmethyl]amino]-2-pyrimidinyl]amino]-4-methyl-5-thiazolecarboxylic acid, ethyl ester; 2-[[4-[4-Morpholinyl]-6-[4-[tetrazol-5-yl]-4-hydroxypiperidin-1-yl]-2-pyrimidinyl]amino]-4-methyl-5-thiazolecarboxylic acid, ethyl ester; 2-[[4-[4-Hydroxy-1-piperidinyl]-6-[[(1,1-dioxido-3-oxo-1,2-benzisothiazol-2-(3H)-yl)methyl]amino]-2-pyrimidinyl]amino]-4-methyl-5-thiazolecarboxylic acid, ethyl ester; 2-[4-(4-Hydroxypiperidin-1-yl)-6-(4-(1-methyl-1-hydroxyethyl)piperidin-1-yl)-pyrimidin-2-ylamino]-4-methyl-thiazole-5-carboxylic acid ethyl ester; 2-[[4-[3-(Aminocarbonyl)-1-piperidinyl]-6-[[N-methyl-N-(3-pyridinylmethyl)]amino]-2-pyrimidinyl]amino]-4-methyl-5-thiazolecarboxylic acid, ethyl ester; 2-[[4-[4-Hydroxymethyl-1-piperidinyl]-6-[[(4-(ethylsulfonylamino)phenyl)methyl]amino]-2-pyrimidinyl]amino]-4-methyl-5-thiazolecarboxylic acid, ethyl ester; 2-[[4-[4-Hydroxy-1-piperidinyl]-6-[4-[tetrazol-5-yl]-4-hydroxypiperidin-1-yl]2-pyrimidinyl]amino]-4-methyl-5-thiazolecarboxylic acid, ethyl ester; 2-[[4-[4-tertButyloxycarbonylamino-1-piperidinyl]-6-[[N-[(3,4,5-trimethoxyphenyl)methyl]]-N-(methyl)amino]-2-pyrimidinyl]amino]-4-methyl-5-thiazolecarboxylic acid, ethyl ester; 2-[[4-[[(4-Cyanophenyl)methyl]amino]-6-(4-methyl-1-piperazinyl)-2-pyrimidinyl]amino]-4-methyl-5-thiazolecarboxylic acid, ethyl ester, trifluoroacetate (1:1); 2-[[4-[4-[[(2-Ethoxy-2-oxoethyl)amino]carbonyl]-1-piperazinyl]-6-[methyl(3-pyridinylmethy)amino]-2-pyrimidinyl]amino]-4-methyl-5-thiazolecarboxylic acid, ethyl ester, trifluoroacetate (1:1); 2-[4-(4-Hydroxypiperidin-1-yl)-6-(3-hydroxypiperidin-1-yl)-pyrimidin-2-ylamino]-4-methyl-thiazole-5-carboxylic acid ethyl ester; 2-[4-(4-Hydroxypiperidin-1-yl)-6-(4-hydroxy-4-phenyl-1-piperidinyl)-pyrimidin-2-ylamino]-4-methyl-thiazole-5-carboxylic acid ethyl ester; 4-Methyl-2-[[4-[4-morpholinyl]-6-[[(tetrahydro-2-furanyl)methyl]amino]-2-pyrimidinyl]amino]-5-thiazolecarboxylic acid ethyl ester; 2-[[4-[(Tetrahydro-2-furanyl)methyl]amino]-6-[[N-[(3,4,5-trimethoxyphenyl)methyl]]-N-(methyl)amino]-2-pyrimidinyl]amino]-4-methyl-5-thiazolecarboxylic acid, ethyl ester; 2-[[4-[4-Morpholinyl]-6-[[(4-(hydroxysulfonyl)phenyl)methyl]amino]-2-pyrimidinyl]amino]-4-methyl-5-thiazolecarboxylic acid, ethyl ester; 2-[Bis-4,6-(4-Cyano-1-piperidinyl)-pyrimidin-2-ylamino]-4-methyl-thiazole-5-carboxylic acid ethyl ester; 2-[[4-[4-(Cyclopentylaminocarbonyl)-1-piperazinyl]-6-[N-methyl-N-(3-pyridinylmethyl)amino]-2-pyrimidinyl]amino]-4-methyl-5-thiazolecarboxylic acid, ethyl ester; 2-[4-(2-Methoxyethyl)-piperazin-1-yl]-6-(4-methyl-1-piperzinyl)-pyrimidin-2-ylamino]-4-methyl-thiazole-5-carboxylic acid ethyl ester; 2-[4-(4-Hydroxypiperidin-1-yl)-6-(3-carboxypiperidin-1-yl)-pyrimidin-2-ylamino]-4-methyl-thiazole-5-carboxylic acid ethyl ester; 2-[[4-[4-Methylpiperazin-1-yl]-6-[3-(acetylamino)-1-pyrrolidinyl]-2-pyrimidinyl]amino]-4-methyl-5-thiazolecarboxylic acid, ethyl ester; 2-[[4-[3-(Aminocarbonyl)-1-piperazinyl]-6-[[N-methyl-N-(3-pyridinylmethyl)]amino]-2-pyrimidinyl]amino]-4-methyl-5-thiazolecarboxylic acid, ethyl ester; 2-[[4-[2-Methyl-3-oxol-piperizinyl]-6-[4-methyl-1-piperazinyl]-2-pyrimidinyl]amino]-4-methyl-5-thiazolecarboxylic acid, ethyl ester; 2-[[4-[3-(Aminocarbonyl)-1-piperazinyl]-6-(4-methyl-1-piperazinyl)-2-pyrimidinyl]amino]-4-methyl-5-thiazolecarboxylic acid, ethyl ester; 2-[[4-[3-(Aminocarbonyl)-1-piperidinyl]-6-(4-dimethylamino-1-piperidinyl)-2-pyrimidinyl]amino]-4-methyl-5-thiazolecarboxylic acid, ethyl ester; 2-[[4-[1-piperazinyl]-6-[[N-methyl-N-(2-furylmethyl)]amino]-2-pyrimidinyl]amino]-4-methyl-5-thiazolecarboxylic acid, ethyl ester; 2-[[4-[[(4-Methoxycarbonylphenyl)methyl]amino]-6-(4-dimethyl-1-piperidinyl)-2-pyrimidinyl]amino]-4-methyl-5-thiazolecarboxylic acid, ethyl ester, trifluoroacetate (1:1); 2-[[4-[3-Oxo-1-piperazinyl]-6-[[(4-(methylsulfonylamino)phenyl)methyl]amino]-2-pyrimidinyl]amino]-4-methyl-5-thiazolecarboxylic acid, ethyl ester; 2-[[4-[3-Oxo-1-piperazinyl]-6-[[(4-(propylsulfonylamino)phenyl)methyl]amino]-2-pyrimidinyl]amino]-4-methyl-5-thiazolecarboxylic acid, ethyl ester; 2-[[4-[3-(Aminocarbonyl)-1-piperidinyl]-6-[[(3,4,5-trimethoxyphenyl)methyl]amino]-2-pyrimidinyl]amino]-4-methyl-5-thiazolecarboxylic acid, ethyl ester; 2-[Bis-4,6-(4-Hydroxy-4-methyl-1-piperidinyl)-pyrimidin-2-ylamino]-4-methyl-thiazole-5-carboxylic acid ethyl ester; 4-Methyl-2-[[4-[4-dimethylamino-1-piperidinyl]-6-[[(2-oxo-1-pyrrolidinyl)propyl]amino]-2-pyrimidinyl]amino]-5-thiazolecarboxylic acid ethyl ester; 2-[[4-[3-Oxo-1-piperazinyl]-6-[[(4-(iso-propylsulfonylamino)phenyl)methyl]amino]-2-pyrimidinyl]amino]-4-methyl-5-thiazolecarboxylic acid, ethyl ester; 2-[4-(4-Hydroxypiperidin-1-yl)-6-(3-hydroxymethyl-1-piperidinyl)-pyrimidin-2-ylamino]-4-methyl-thiazole-5-carboxylic acid ethyl ester; 4-Methyl-2-[[4-[4-hydroxy-1-piperidinyl]-6-[[(2-(4-morpholinyl)ethyl]amino]-2-pyrimidinyl]amino]-5-thiazolecarboxylic acid ethyl ester; 2-[[4-[[[4-(Ethylaminosulfonyl)phenyl]methyl]amino]-6-methoxy-2-pyrimidinyl]amino]-4-methyl-5-thiazolecarboxylic acid, methyl ester, trifluoroacetate (1:1); 2-[[4-[4-Morpholinyl]-6-[(1-oxa-3,8-diazaspiro[4.5]decan-2,4, dion-8-yl]-2-pyrimidinyl]amino]-4-methyl-5-thiazolecarboxylic acid, ethyl ester; 2-[[4-[4-Hydroxy-1-piperidinyl]-6-[[(4-(ethylsulfonylamino)phenyl)methyl]amino]-2-pyrimidinyl]amino]-4-methyl-5-thiazolecarboxylic acid, ethyl ester; 2-[[4-[tertButyloxycarbonyl-1-piperazinyl]-6-[[(3,4,5-trimethoxyphenyl)methyl]amino]-2-pyrimidinyl]amino]-4-methyl-5-thiazolecarboxylic acid, ethyl ester; 2-[[4-[3-(Aminocarbonyl)-1-piperidinyl]-6-[[(3,4-dimethoxyphenyl)methyl]amino]-2-pyrimidinyl]amino]-4-methyl-5-thiazolecarboxylic acid, ethyl ester; 2-[[4-[4-ethoxycarbonyl-1-piperazinyl]-6-[[N-methyl-N-(5-tetrazolylmethyl]amino]-2-pyrimidinyl]amino]-4-methyl-5-thiazolecarboxylic acid, ethyl ester; 2-[[4-[3-Oxo-1-piperizinyl]-6-[[(4-(cyclopropylsulfonylamino)phenyl)methyl]amino]-2-pyrimidinyl]amino]-4-methyl-5-thiazolecarboxylic acid, ethyl ester; 2-[[4-[4-Hydroxymethyl-1-piperidinyl]-6-[[(4-(methylsulfonylamino)phenyl)methyl]amino]-2-pyrimidinyl]amino]-4-methyl-5-thiazolecarboxylic acid, ethyl ester; 2-[4-(4-Dimethylamino-1-piperazinyl)-6-(4-tert-butyloxycarbonylamino-1-piperidinyl)-pyrimidin-2-ylamino]-4-methyl-thiazole-5-carboxylic acid ethyl ester; 2-[4-(4-Hydroxypiperidin-1-yl)-6-(4-methoxymethyl-1-piperidinyl)-pyrimidin-2-ylamino]-4-methyl-thiazole-5-carboxylic acid ethyl ester; 2-[4-(4-Hydroxypiperidin-1-yl)-6-(4-hydroxyethyl-1-piperidinyl)-pyrimidin-2-ylamino]-4-methyl-thiazole-5-carboxylic acid ethyl ester; 2-[4-(4-Hydroxypiperidin-1-yl)-6-(4-(hydroxy)-4-(3-trifluoromethylphenyl)piperidin-1-yl)-pyrimidin-2-ylamino]-4-methyl-thiazole-5-carboxylic acid ethyl ester; 2-[[4-[4-morpholinyl]-6-[4-[1-methyl-1-hydroxyethyl]-1-piperidinyl]-2-pyrimidinyl]amino]-4-methyl-5-thiazolecarboxylic acid, ethyl ester; 2-[[4-(3-Oxo-1-piperizinyl]-6-[[3-pyridyl]oxy]-2-pyrimidinyl]amino]-4-methyl-5-thiazolecarboxylic acid, ethyl ester; 2-[[4-[4-Methyl-1-piperazinyl]-6-[(1,4-dioxaspiro[4.5]decan-8-yl]-2-pyrimidinyl]amino]-4-methyl-5-thiazolecarboxylic acid, ethyl ester; 2-[[4-[4-Morpholinyl]-6-[[(4-(methylsulfonylamino)phenyl)methyl]amino]-2-pyrimidinyl]amino]-4-methyl-5-thiazolecarboxylic acid, ethyl ester; 2-[[4-[3-oxo-1-piperazinyl]-6-[(1-oxa-3,8-diazospiro[4.5]decan-2,4, dion- 8-yl]-2-pyrimidinyl]amino]-4-methyl-5-thiazolecarboxylic acid, ethyl ester; 2-[[4-[4-Hydroxy-1-piperidinyl]-6-[[(4-(carboxy)phenyl)methyl]amino]-2-pyrimidinyl]amino]-4-methyl-5-thiazolecarboxylic acid, ethyl ester; 2-[4-(4-Hydroxypiperidin-1-yl)-6-(4-(hydroxy)-4-(4-bromophenyl) piperidin-1-yl)-pyrimidin-2-ylamino]-4-methyl-thiazole-5-carboxylic acid ethyl ester; 2-[[4-[4-Morholinyl]-6-[[(4-ethylsulfonylamino)phenyl)methyl]amino]-2-pyrimidinyl] amino]-4-methyl]-5-thiazolecarboxylic acid, ethyl ester; 2-[[4-[3-(Aminocarbonyl)-1-piperazinyl]-6-[[(3,4-dimethoxyphenyl)methyl]amino]-2-pyrimidinyl]amino]-4-methyl-5-thiazolecarboxylic acid, ethyl ester; 2-[[4-[4-Formyl-1-piperazinyl]-6-[[(3-(5-(1H)tetrazolyl)phenyl) methyl]amino]-2-pyrimidinyl]amino]-4-methyl-5-thiazolecarboxylic acid, ethyl ester; 2-[[4-[4-(Hydroxymethyl)-1-Piperidinyl]-6-[[N-methyl-N-(5-tetrazolylmethyl]amino]-2-pyrimidinyl]amino]-4-methyl-5-thiazolecarboxylic acid, ethyl ester; 2-[[4-[4-Methyl-1-piperazinyl]-6-[[(2,5-dimethyl)phenyl)methyl]amino]-2-pyrimidinyl]amino]-4-methyl-5-thiazolecarboxylic acid, ethyl ester; 2-[[4-[3-(2-oxo-1-pyrrolidinyl)propyl]amino]-6-[N-methyl-N-(3-pyridinylmethyl)amino]-2-pyrimidinyl] amino]-4-methyl-5-thiazolecarboxylic acid, ethyl ester; 2-[[4-[(1-Morpholinyl)]-6-[[N-methyl-N-(5-tetrazolylmethyl]amino]-2-pyrimidinyl]amino]-4-methyl-5-thiazolecarboxylic acid, ethyl ester; 2-[[4-[4-methyl-1-piperazinyl]-6-[4-[methylsulfonylamino]-1-piperidinyl]-2-pyrimidinyl] amino]-4-methyl-5-thiazolecarboxylic acid, ethyl ester; 2-[[4-[4-hydroxy-1-piperidinyl]-6-[[(2,5-dimethyl)phenyl) methyl]amino]-2-pyrimidinyl]amino]-4-methyl-5-thiazolecarboxylic acid, ethyl ester; 4-Methyl-2-[[4-(4-morpholinyl)-6-[[(3,4,5-trimethoxyphenyl)methyl]amino-2-pyrimidinyl]amino]-5-thiazolecarboxylic acid, ethyl ester; 2-[4-(4-Hydroxypiperidin-1-yl)-6-(3-hydroxy-1-piperidinyl)-pyrimidin-2-ylamino]-4-methyl-thiazole-5-carboxylic acid ethyl ester; 4-Methyl-2-[[4-(4-methyl-1-piperazinyl)-6-[methyl(3-pyridinylmethyl)amino]-2-pyrimidinyl]amino]-5-thiazolecarboxylic acid, ethyl ester; 2-[[4-[3-Oxo-1-piperazinyl]-6-[[(2-(5-(1H)tetrazolyl)phenyl)methyl]amino]-2-pyrimidinyl]amino]-4-methyl-4-thiazolecarboxylic acid, ethyl ester; 2-[[4-[(2-Furanylmethyl)amino]-6-(1-piperazinyl)-2-pyrimidinyl]amino]-4-methyl-5-thiazolecarboxylic acid, ethyl ester, trifluoroacetate (1:1); 2-[[4-[[(3,4-Dimethoxyphenyl)methyl]amino]-6-(4-morpholinyl)-2-pyrimidinyl]amino]-4-methyl-5-thiazolecarboxylic acid, ethyl ester; 4-Methyl-2-[[4-[methyl(3-pyridinylmethyl)amino]-6-[[[(tetrahydro-2-furanyl)methyl]amino]-2-pyrimidinyl] amino]-5-thiazolecarboxylic acid, ethyl ester; 2-[[4-[(4-hydroxy-1-piperidinyl)]-6-[[N-methyl-N-(5-tetrazolylmethyl] amino]-2-pyrimidinyl]amino]-4-methyl-5-thiazolecarboxylic acid, ethyl ester; 2-[4-(4-Hydroxypiperidin-1-yl)-6-[(4-(hydroxy)-4-(phenylmethyl) piperidin-1-yl)]-pyrimidin-2-ylamino]-4-methyl-thiazole-5-carboxylic acid ethyl ester; 2-[4-(4-Dimethylamino-1-piperazinyl)-6-[[2-(1-morpholinyl)ethyl]amino]pyrimidin-2-ylamino]-4-methyl-thiazole-5-carboxylic acid ethyl ester; 2-[[4-[4-hydroxy-1-piperidinyl]-6-[[(3-pyridinylmethyl)] oxy]-2-pyrimidinyl]amino]-4-methyl-5-thiazolecarboxylic acid, ethyl ester; 2-[[4-[3-(Aminocarbonyl)-1-piperidinyl]-6-[[[(2,6-dimethylphenyl)methyl]amino]-2-pyrimidinyl] amino]-4-methyl-5-thiazolecarboxylic acid, ethyl ester; 2-[[4-[4-hydroxy-1-piperidinyl]-6-[[(4-(methylsulfonylamino)phenyl)methyl]amino]-2-pyrimidinyl]amino]-4-methyl-5-thiazolecarboxylic acid, ethyl ester; 2-[[4-[4-hydroxy-1-piperidinyl]-6-[[(4-(propylsulfonylamino)phenyl)methyl] amino]-2-pyrimidinyl]amino]-4-methyl-5-thiazolecarboxylic acid, ethyl ester; 2-[[4-[3-(Aminocarbonyl)-1-piperidinyl]-6-(4-methyl-1-piperazinyl)-2-pyrimidinyl]amino]-4-methyl-5-thiazolecarboxylic acid, ethyl ester; 2-[[4-(3,4-Dihydro-6,7-dimethoxy-2(1H)-isoquinolinyl)-6-(4-methyl-1-piperazinyl)-2-pyrimidinyl]amino]-4-methyl-5-thiazolecarboxylic acid, ethyl ester; 2-[[4-[4-Formyl-1-piperazinyl]-6-[[N-methyl-N-(5-tetrazolylmethyl]amino]-2-pyrimidinyl]amino]-4-methyl-5-thiazolecarboxylic acid, ethyl ester; 2-[[4-[[(4-Carboxyphenyl)methyl]amino]-6-[4-(hydroxymethyl)-1-piperidinyl]-2-pyrimidinyl]amino]-4-methyl-5-thiazolecarboxylic acid, ethyl ester; 2-[[4-[[(4-Carboxyphenyl)methyl]amino]-6-(4-methyl-1-piperazinyl)-2-pyrimidinyl]amino]-4-methyl-5-thiazolecarboxylic acid, ethyl ester, monohydrochloride; 4-Methyl-2-[[4-(4-methyl-1-piperazinyl)-6-[[(tetrahydro-2-furanyl)methyl]amino]-2-pyrimidinyl]amino]-5-thiazolecarboxylic acid, ethyl ester; 2-[[4-[[(4-Carboxyphenyl)methyl]amino]-6-[3-(hydroxymethyl)-1-piperidinyl]-2-pyrimidinyl]amino]-4-methyl-5-thiazolecarboxylic acid, ethyl ester; 2-[[4-[[[4-[[(2-Methoxyethyl)amino]carbonyl]phenyl]methyl]amino]-6-(4-methyl-1-piperazinyl)-2-pyrimidinyl]amino]-4-methyl-5-thiazolecarboxylic acid, ethyl ester, trifluoroacetate (1:1); 2-[4,6-Bis-(1-morpholinyl)-pyrimidin-2-ylamino]-4-methyl-thiazole-5-carboxylic acid ethyl ester; 2-[[4-[3-(Aminocarbonyl)-1-piperazinyl]-6-[[N-methyl-N-(5-tetrazolylmethyl]amino]-2-pyrimidinyl]amino]-4-methyl-5-thiazolecarboxylic acid ethyl ester; 4-Methyl-2-[[4-[-methyl(3-pyridinylmethyl)amino]-6-[4-morpholinyl]-2-pyridinylmethyl]amino]-5-thiazolecarboxylic acid, ethyl ester; 2-[[4-[3-(Aminocarbonyl)-1-piperazinyl]-6-[[[4-(methoxycarbonyl)phenyl]methyl]amino]-2-pyrimidinyl] amino]-4-methyl-5-thiazolecarboxylic acid, ethyl ester; 2-[[4-Chloro-6-[(1-oxa-3,8-diazaspiro[4.5]decan-2,4,dion-8-yl]-2-pyrimidinyl]amino]-4-methyl-5-thiazolecarboxylic acid, ethyl ester; 2-[[4-[4-(Hydroxymethyl)-1-piperidinyl]-6-[[(3,4,5-trimethoxyphenyl)methyl]amino]-2-pyrimidinyl] amino]-4-methyl-5-thiazolecarboxylic acid, ethyl ester; 2-[[4-[3-(Hydroxymethyl)-1-Piperidinyl]-6-[[N-methyl-N-(5-tetrazolylmethyl]amino]-2-pyrimidinyl]amino]-4-methyl-5-thiazolecarboxylic acid, ethyl ester; 2-[[4-[3-(Hydroxymethyl)-1-pyrrolidinyl]-6-[[N-methyl-N-(5-tetrazolylmethyl]amino]-2-pyrimidinyl]amino]-4-methyl-5-thiazolecarboxylic acid, ethyl ester; 4-Methyl-2-[[4-[methyl (phenylmethyl)amino]-6-(4-methyl-1-piperazinyl)-2-pyrimidinyl]amino]-5-thiazolecarboxylic acid, ethyl ester; 2-[[4-(Dimethylamino)-6-[[[4-(methylsulfonyl)phenyl]methyl]amino]-2-pyrimidinyl]amino]-4-methyl-5-thiazolecarboxylic acid, ethyl ester; 2-[[4-[4-Hydroxy-1-piperidinyl]-6-[[(3-(5-(1H)tetrazolyl)phenyl)methyl]amino]-2-pyrimidinyl]amino]-4-methyl-5-thiazolecarboxylic acid, ethyl ester; 2-[[4-[4-hydroxymethyl-1-piperidinyl]-6-[[(4-(propylsulfonylamino)phenyl)methyl]amino]-2-pyrimidinyl]amino]-4-methyl-5-thiazolecarboxylic acid, ethyl ester; 2-[[4-[4-hydroxymethyl-1-piperidinyl]-6-[[(4-(cyclopropylsulfonylamino)phenyl)methyl]amino]-2-pyrimidinyl] amino]-4-methyl-5-thiazolecarboxylic acid, ethyl ester; 2-[[4-[3-(Hydroxymethyl)-1-piperidinyl]-6-[[(3,4,5-trimethoxyphenyl)methyl]amino]-2-pyrimidinyl]amino]-4-methyl-5-thiazolecarboxylic acid, ethyl ester; 2-[[4-[4-tetrahydropyranyl)oxy-6-[[N-[(3,4,5-trimethoxyphenyl) methyl]]-N-(methyl)amino]-2-pyrimidinyl]amino]-4-methyl-5-thiazolecarboxylic acid, ethyl ester; 2-[[4-[4-Methyl-1-piperazinyl]-6-[(4-methoxyphenyl)oxy]-2-pyrimidinyl]amino]-4-methyl-5-thiazolecarboxylic acid, ethyl ester; 4-Methyl-2-[4-(4-methyl-piperazin-1-yl)-6-[[[4-(aminosulfonyl)phenyl]methyl]amino]pyrimidin-2-ylamino]-thiazole-5-carboxylic acid ethyl ester; 2-[4-Isopropyl-6-(4-sulfamoyl-benzylamino)-pyrimidin-2-ylamino]-4-methyl-thiazole-5-carboxylic acid ethyl ester; 4-Methyl-2-[4-(4-sulfamoyl-benzylamino)-6-methyl-pyrimidin-2-ylamino]-thiazole-5-carboxylic acid ethyl ester; 4-Methyl-2-[4-(4-sulfamoyl-benzylamino)-6-hydroxymethyl-pyrimidin-2-ylamino]-thiazole-5-carboxylic acid ethyl ester; 4-Methyl-2-[4-(4-methyl-piperazin-1-yl)-6-[4-(1H-tetrazol-5-yl)-benzylamino]-pyrimidin-2-ylamino]thiazole-5-carboxylic acid ethyl ester; 2-[4-(4-Hydroxy-piperidin-1-yl)-6-[4-(1H-tetrazol-5-yl)-benzylamino]-pyrimidin-2-ylamino]-4-methyl-thiazole-5-carboxylic acid ethyl ester; 4-Methyl-2-[4-[(tetrahydro-furan-2-ylmethyl)-amino]-6-[4-(1H-tetrazol-5-yl)-benzylamino]-pyrimidin-2-ylamino]-thiazole-5-carboxylic acid ethyl ester; 4-Methyl-2-[4-morpholin-4-yl-6-[4-(1H-tetrazol-5-yl)-benzylamino]-pyrimidin-2-ylamino]-thiazole-5-carboxylic acid ethyl ester; 2-[4-(3-Carbamoyl-piperidin-1-yl)-6-[4-(1H-tetrazol-5-yl)-benzylamino]-pyrimidin-2-ylamino])-4-methyl-thiazole-5-carboxylic acid ethyl ester; 2-[4-(4-Hydroxymethylpiperidin-1-yl)-6-[4-(1H-tetrazol-5-yl)-benzylamino]-pyrimidin-2-ylamino]-4-methyl-thiazole-5-carboxylic acid ethyl ester; 2-[4-(2-Hydroxymethyl-1-pyrrolidinyl)-6-[4-(1H-tetrazol-5-yl)-benzylamino]-pyrimidin-2-ylamino]-4-methyl-thiazole-5-carboxylic acid ethyl ester; 2-[4-(3-N,N-Diethylcarbamoyl-1-piperidinyl)-6-[4-(1H-tetrazol-5-yl)-benzylamino]-pyrimidin-2-ylamino]-4-methyl-thiazole-5-carboxylic acid ethyl ester; 2-[4-(3-Hydroxy-1-pyrrolidinyl)-6-[4-(1H-tetrazol-5-yl)-benzylamino]-pyrimidin-2-ylamino]-4-methyl-thiazole-5-carboxylic acid ethyl ester; 4-Methyl-2-[[[2-[4-morpholin-4-yl]ethyl]amino-6-[4-(1H-tetrazol-5-yl)-benzylamino]pyrimidin-2-ylamino]-thiazole-5-carboxylic acid ethyl ester; 4-Methyl-2-[[[4-hydroxyl]butyl]amino-6-[4-(1H-tetrazol-5-yl)-benzylamino]-pyrimidin-2-ylamino]thiazole-5-carboxylic acid ethyl ester; 2-[4-(4-Formyl-1-piperazinyl)-6-[4-(1H-tetrazol-5-yl)-benzylamino]-pyrimidin-2-ylamino]-4-methyl-thiazole-5-carboxylic acid ethyl ester; 2-[[4-[[(4-Chlorophenyl)methyl]amino]-6-(5-oxazolyl)-2-pyrimidinyl]amino]-4-methyl-5-thiazolecarboxylic acid ethyl ester; 2-[[4-[[(4-Aminosylfonylphenyl)methyl]amino]-6-(5-oxazolyl)-2-pyrimidinyl]amino]-4-methyl-5-thiazolecarboxylic acid ethyl ester; 2-[[4-Morpholino-6-(5-oxazolyl)-2-pyrimidinyl]amino]-4-methyl-5-thiazolecarboxylic acid ethyl ester; 2-[[4-[[(3,4-Dimethoxyphenyl)methyl]amino]-6-(5-oxazolyl)-2-pyrimidinyl]amino]-4-methyl-5-thiazolecarboxylic acid ethyl ester; 2-[[4-(1,4-Dioxa-8-aza-spiro[4.5]dec-8-yl)-6-(5-oxazoly)-2-pyrimidinyl]amino]-4-methyl-5-thiazolecarboxylic acid ethyl ester; 2-[[4-[4-Hydroxy-4-phenyl-piperidinyl]-6-(5-oxazolyl)-2-pyrimidinyl]amino]-4-methyl-5-thiazolecarboxylic acid ethyl ester; 2-[[4-[[(4-Methylsulfonylphenyl)methyl]amino]-6-(5-oxazolyl)-2-pyrimidinyl]amino]-4-methyl-5-thiazolecarboxylic acid ethyl ester; 2-[[4-[4-Hydroxy-piperidinyl]-6-(5-oxazolyl)-2-pyrimidinyl]amino]-4-methyl-5-thiazolecarboxylic acid ethyl ester; 2-[[4-[4-Ethoxycarbonyl-piperidinyl]-6-(5-oxazolyl)-2-pyrimidinyl]amino]-4-methyl-5-thiazolecarboxylic acid ethyl ester; 2-[[4-Piperidinyl-6-(5-oxazolyl)-2-pyrimidinyl]amino]-4-methyl-5-thiazolecarboxylic acid ethyl ester; 2-[[4-[N-Methylpiperazinyl-6-(5-oxazolyl)-2-pyrimidinyl]amino]-4-methyl-5-thiazolecarboxylic acid ethyl ester; 2-[[4-[N-(2-Furylcarbonyl)piperazinyl-6-(5-oxazolyl)-2-pyrimidinyl]amino]-4-methyl-5-thiazolecarboxylic acid ethyl ester; 2-[[4-[N-Acetyl-[1,4-diazepyl]-6-(5-oxazolyl)-2-pyrimidinyl]amino]-4-methyl-5-thiazolecarboxylic acid ethyl ester; 2-[[4-[N-Methyl-N—(N-methyl-4-piperidinyl)-amino]-6-(5-oxazolyl)-2-pyrimidinyl]amino]-4-methyl-5-thiazolecarboxylic acid ethyl ester; 2-[[4-[N-Methyl-[1,4]-diazepyl]-6-(5-oxazolyl)-2-pyrimidinyl]amino]-4-methyl-5-thiazolecarboxylic acid ethyl ester; 2-[[4-N,N-Dimethoxyethylamino-6-(5-oxazolyl)-2-pyrimidinyl]amino]-4-methyl-5-thiazolecarboxylic acid ethyl ester; 2-[[4-[(1',4)-Bipiperidinyl]-6-(5-oxazolyl)-2-pyrimidinyl]amino]-4-methyl-5-thiazolecarboxylic acid ethyl ester; 2-[4-(4-Hydroxy-piperidin-1-yl)-6-(3,4,5-trimethoxy-phenyl)-pyrimidin-2-ylamino]-4-methylthiazole-5-carboxylic acid ethyl ester; 2-[(4-(4-Hydroxy-piperidin-1-yl)-6-[4-(1H-tetrazol-5-yl)-phenyl]-pyrimidin-2-ylamino]-4-methylthiazole-5-carboxylic acid ethyl ester; 2-[4-(4-Hydroxy-piperidin-1-yl)-6-pyridin-3-yl-pyrimidin-2-ylamino]-4-methylthiazole-5-carboxylic acid ethyl ester; 2-[4-(4-Methanesulfonyl-benzylamino)-6-pyridin-3-yl-pyrimidin-2-ylamino]-4-methylthiazole-5-carboxylic acid ethyl ester; 2-[4-(4-Hydroxy-piperidin-1-yl)-6-pyrimidin-4-yl-pyrimidin-2-ylamino]-4-methylthiazole-5-carboxylic acid ethyl ester; 2-[4-(4-Cyano-phenyl)-6-(4-hydroxy-piperidin-1-yl)-pyrimidin-2-ylamino]-4-methylthiazole-5-carboxylic acid ethyl ester; 2-[4-(4-Acetyl-phenyl)-6-(4-hydroxy-piperidin-1-yl)-pyrimidin-2-ylamino]-4-methylthiazole-5-carboxylic acid ethyl ester; 2-[4-(4-Hydroxymethyl-phenyl)-6-(4-hydroxy-piperidin-1-yl)-pyrimidin-2-ylamino]-4-methylthiazole-5-carboxylic acid ethyl ester; 2-[4-(4-Hydroxy-phenyl)-6-(4-hydroxy-piperidin-1-yl)-pyrimidin-2-ylamino]-4-methylthiazole-5-carboxylic acid ethyl ester; 2-[4-(4-Methanesulfonyl-benzylamino)-6-(3,4,5-trimethoxy-phenyl)-pyrimidin-2-ylamino]-4-methylthiazole-5-carboxylic acid ethyl ester; 2-[4-(4-Methanesulfinylphenyl)-6-(4-hydroxypiperidin-1-yl)-pyrimidin-2-ylamino]-4-methylthiazole-5-carboxylic acid ethyl ester; 2-[4-(4-(Amino)phenyl)-6-(4-hydroxy-piperidin-1-yl)-pyrimidin-2-ylamino]-4-methylthiazole-5-carboxylic acid ethyl ester; 2-[4-(4-Carboxymethyl-phenyl)-6-(4-hydroxy-piperidin-1-yl)-pyrimidin-2-ylamino]-4-methylthiazole-5-carboxylic acid ethyl ester; 2-[4-(4-(Trifluoromethylcarbonylamino)phenyl)-6-(4-hydroxy-piperidin-1-yl)-pyrimidin-2-ylamino]-4-methylthiazole-5-carboxylic acid ethyl ester; 2-[4-(4-(Ethoxycarbonylmethyl)phenyl)-6-(4-hydroxy-piperidin-1-yl)-pyrimidin-2-ylamino]-4-methylthiazole-5-carboxylic acid ethyl ester; 2-[4-(1,2,3,6-Tetrahydropyridin-4-yl)-6-(4-hydroxy-piperidin-1-yl)-pyrimidin-2-ylamino]-4-methylthiazole-5-carboxylic acid ethyl ester; 2-[4-(3-(cyano)phenyl)-6-(4-hydroxy-piperidin-1-yl)-pyrimidin-2-ylamino]-4-methylthiazole-5-carboxylic acid ethyl ester; 2-[4-(4-(Methoxycarbonyl)phenyl)-6-(4-hydroxy-piperidin-1-yl)-pyrimidin-2-ylamino]-4-methylthiazole-5-carboxylic acid ethyl ester; 2-[4-(2-(Methoxy)-5-pyridinyl)-6-(4-hydroxy-piperidin-1-yl)-pyrimidin-2-ylamino]-4-methylthiazole-5-carboxylic acid ethyl ester; 2-[4-(4-tertButyloxycarbonyl-1,2,3,6-Tetrahydropyridin-4-yl)-6-(4-hydroxy-piperidin-1-yl)-pyrimidin-2-ylamino]-4-methylthiazole-5-carboxylic acid ethyl ester; 2-[4-(1,4-Dioxaspiro[4.5]dec-7-en-8-yl)-6-(4-hydroxy-piperidin-1-yl)-pyrimidin-2-ylamino]-4-methylthiazole-5-carboxylic acid ethyl ester; 2-[4-(4-Methyl-1-piperazin-yl)-6-(3,4,5-trimethoxy-phenyl)-pyrimidin-2-ylamino]-4-methylthiazole-5-carboxylic acid ethyl ester; 2-[4-(4-Morpholinyl)-6-(3,4,5-trimethoxy-phenyl)-pyrimidin-2-ylamino]-4-methylthiazole-5-carboxylic acid ethyl ester; 2-[4-(4-Morpholinyl)-6-(3-pyridinyl)-pyrimidin-2-ylamino]-4-methylthiazole-5-carboxylic acid ethyl ester; 2-[4-(Piperadin-4-yl)-6-(4-hydroxy-piperidin-1-yl)-pyrimidin-2-ylamino]-4-methylthiazole-5-carboxylic acid ethyl ester; 2-[[4-[4-Hydroxy-piperidinyl]-6-(3,5-dimethyl-4-isoxazolyl)-2-pyrimidinyl]amino]-4-methyl-5-thiazolecarboxylic acid ethyl ester; 2-[4-(4-tert-Butoxycarbonylamino-phenyl)-6-(4-hydroxy-piperidin-1-yl)-pyrimidin-2-ylamino]-4-methyl-5-thiazolecarboxylic acid ethyl ester; 2-[4-(4-Cyano-phenyl)-6-(4-methanesulfonyl-benzylamino)-pyrimidin-2-ylamino]-4-methyl-5-thiazolecarboxylic acid ethyl ester; 2-[4-(4-Methanesulfonylphenyl)-6-(4-hydroxypiperidin-1-yl)-pyrimidin-2-ylamino]-4-methylthiazole-5-carboxylic acid ethyl ester; 2-[4-(4-Methanesulfanylphenyl)-6-(4-hydroxypiperidin-1-yl)-pyrimidin-2-ylamino]-4-methylthiazole-5-carboxylic acid ethyl ester; 2-[4-(4-Carboxy-phenyl)-6-(4-hydroxy-piperidin-1-yl)-pyrimidin-2-ylamino]-4-methyl-thiazole-5-carboxylic acid ethyl ester; 2-[4-(4-Carboxy-phenyl)-6-(3-oxo-piperazin-1-yl)-pyrimidin-2-ylamino]-4-methylthiazole-5-carboxylic acid ethyl ester; 2-[4-(4-Carboxy-phenyl)-6-(4-methyl-piperazin-1-yl)-pyrimidin-2-ylamino]-4-methylthiazole-5-carboxylic acid ethyl ester; 2-[4-(4-Carboxy-phenyl)-6-morpholin-4-yl-pyrimidin-2-ylamino]-4-methylthiazole-5-carboxylic acid ethyl ester; 2-[4-(4-Carboxy-phenyl)-6-(4-methyl-[1,4]diazepan-1-yl)-pyrimidin-2-ylamino]-4-methylthiazole-5-carboxylic acid ethyl ester; 2-[4-(4-Carboxy-phenyl)-6-(3-R-hydroxy-piperidin-1-yl)-pyrimidin-2-ylamino]-4-methylthiazole-5-carboxylic acid ethyl ester; 2-[4-(4-Carboxy-phenyl)-6-(3-hydroxymethyl-piperidin-1-yl)-pyrimidin-2-ylamino]-4-methylthiazole-5-carboxylic acid ethyl ester; 2-[4-(4-Acetyl-[1,4]diazepan-1-yl)-6-(4-carboxy-phenyl)-pyrimidin-2-ylamino]-4-methylthiazole-5-carboxylic acid ethyl ester; 2-[4-(4-Carboxy-phenyl)-6-[N-methyl-N-(1-N-methyl-piperidin-4-yl)-amino]-pyrimidin-2-ylamino]-4-methylthiazole-5-carboxylic acid ethyl ester; 2-[4-(4-Carboxy-phenyl)-6-piperazin-1-yl-pyrimidin-2-ylamino]-4-methylthiazole-5-carboxylic acid ethyl ester; 2-[4-(4-Carboxy-phenyl)-6-(4-sulfamoyl-benzylamino)-pyrimidin-2-ylamino]-4-methylthiazole-5-carboxylic acid ethyl ester; 2-[[4-[[5-Allyl[4-(aminosulfonyl)phenyl]methyl]amino]-6-chloro-2-pyrimidinyl]amino]-4-methyl-5-thiazolecarboxylic acid, ethyl ester; 2-[[4-[[[4-(Aminosulfonyl)phenyl]methyl]amino]-5-methyl-6-(1-piperazinyl)-2-pyrimidinyl]amino]-4-methyl-5-thiazolecarboxylic acid, ethyl ester, trifluoroacetate (1:3); 2-[[4-[[[4-(Aminosulfonyl)phenyl]methyl]amino]-5-methyl-6-(4-morpholinyl)-2-pyrimidinyl]amino]-4-methyl-5-thiazolecarboxylic acid, ethyl ester; 2-[[4-[[5-Allyl[4-(aminosulfonyl)phenyl]methyl]amino]-6-(4-methylpiperazinyl)-2-pyrimidinyl]amino]-4-methyl-5-thiazolecarboxylic acid, ethyl ester; 2-[[4-[[5-[2-[2-Methylprop-3-en]]-4-[4-(aminosulfonyl)phenyl]methyl]amino]-6-(4-methylpiperazinyl)-2-pyrimidinyl]amino]-4-methyl-5-thiazolecarboxylic acid, ethyl ester; 2-[[4-[[[(3,4,5-(Trimethoxy)phenyl]methyl]amino]-5-methyl-6-(1-piperazinyl)-2-pyrimidinyl]amino]-4-methyl-5-thiazolecarboxylic acid, ethyl ester, trifluoroacetate; 2-[[4-[[5-[2,3-propandiol][4-(aminosulfonyl)phenyl]methyl]amino]-6-(4-methylpiperazinyl)-2-pyrimidinyl]amino]-4-methyl-5-thiazolecarboxylic acid, ethyl ester; 2-[[4-[[[3,4,5-(Trimethoxy)phenyl]methyl]amino]-5-methyl-6-(4-methyl-1-piperazinyl)-2-pyrimidinyl]amino]-4-methyl-5-thiazolecarboxylic acid, ethyl ester, trifluoroacetate; 2-[[4-[[5-[2-[2-Methylprop-3-en]]-4-[4-(aminosulfonyl)phenyl]methyl]amino]-6-chloro-2-pyrimidinyl]amino]-4-methyl-5-thiazolecarboxylic acid, ethyl ester; 2-[[4-[[[4-(Aminosulfonyl)phenyl]methyl]amino]-5-methyl-6-(4-tertbutyloxycarbonyl-1-piperazinyl)-2-pyrimidinyl]amino]-4-methyl-5-thiazolecarboxylic acid, ethyl ester; 2-[[4-[N-[[3,4,5-(Trimethoxy)phenyl]methyl]-N-methylamino]-5-methyl-6-(4-methyl-1-piperazinyl)-2-pyrimidinyl]amino]-4-methyl-5-thiazolecarboxylic acid, ethyl ester; 2-[4,6-Bis-(4-hydroxy-piperidin-1-yl)-5-methylpyrimidin-2-ylamino]-4-methyl-thiazole-5-carboxylic acid ethyl ester; 2-[4,6-Bis-(3-oxo-piperazin-1-yl)-5-[ethoxycarbonylmethyl]pyrimidin-2-ylamino]-4-methyl-thiazole-5-carboxylic acid ethyl ester; 2-[4,6-Bis-(4-hydroxy-piperidin-1-yl)-5-methoxypyrimidin-2-ylamino]-4-methyl-thiazole-5-carboxylic acid ethyl ester; 2-[[4-[N-[[3,4,5-(Trimethoxy)phenyl]methyl]-N-methylamino]-5-methoxy-6-(4-methyl-1-piperazinyl)-2-pyrimidinyl]amino]-4-methyl-5-thiazolecarboxylic acid, ethyl ester; 2-[[4-[[3-pyridyl]methyloxy]-5-(2-propenyl-6-(4-morpholinyl)-2-pyrimidinyl]amino]-4-methyl-5-thiazolecarboxylic acid, ethyl ester; 2-[(4-Ethoxycarbonylmethyl-6-morpholin-4-yl-pyrimidin-2-yl)-amino]-4-methyl-5-thiazolecarboxylic acid ethyl ester; 2-[(4-Ethoxycarbonylmethyl-6-[3-oxo-1-piperazinyl]-pyrimidin-2-yl)-amino]-4-methyl-5-thiazolecarboxylic acid ethyl ester; 2-[(4-Carboxymethyl-6-morpholin-4-yl-pyrimidin-2-yl)-amino]-4-methyl-5-thiazolecarboxylic acid; 2-[4-Morpholin-4-yl-6-[(3,4,5-trimethoxy-phenylcarbamoyl)-methyl]-pyrimidin-2-ylamino]-4-methyl-5-thiazolecarboxylic acid ethyl ester; 2-[[4-[2-oxo-2-(3-oxo-piperazin-1-yl)-ethyl]-6-(4-sulfamoyl-benzylamino)-2-pyrimidinyl]amino]-4-methyl-5-thiazolecarboxylic acid ethyl ester; 2-[[4-(4-sulfamoyl-benzylamino)-6-[(4-sulfamoyl-benzylcarbamoyl)-methyl]-2-pyrimidinyl]amino]-4-methyl-5-thiazolecarboxylic acid ethyl ester; 2-[4-[2-(1,4-Dioxa-8-aza-spiro[4.5]dec-8-yl)-2-oxo-ethyl]-6-(4-sulfamoyl-benzylamino)-2-pyrimidinyl]amino]-4-methyl-5-thiazolecarboxylic acid ethyl ester; 2-[[4-[[(4-Chlorophenyl)-methyl-carbamoyl]-methyl]-6-(4-sulfamoyl-benzylamino)$_2$-pyrimidinyl]amino]-4-methyl-5-thiazolecarboxylic acid ethyl ester; 2-[[4-[2-(4-Hydroxy-piperidin-1-yl)-2-oxo-ethyl]-6-(4-sulfamoyl-benzylamino)-2-pyrimidinyl]amino]-4-methyl-5-thiazolecarboxylic acid ethyl ester; 2-[[4-[2-(4-Ethoxycarbonyl-piperidin-1-yl)-2-oxo-ethyl]-6-(4-sulfamoyl-benzylamino)-2-pyrimidinyl]amino]-4-methyl-5-thiazolecarboxylic acid ethyl ester; 2-[[4-(2-oxo-2-piperidin-1-yl-ethyl)-6-(4-sulfamoyl-benzylamino)2-pyrimidinyl]amino]-4-methyl-5-thiazolecarboxylic acid ethyl ester; 2-[[4-[2-[4-(Furan-2-carbonyl)-piperazin-1-yl]-2-oxo-ethyl]-6-(4-sulfamoyl-benzylamino)2-pyrimidinyl]amino]-4-methyl-5-thiazolecarboxylic acid ethyl ester; 2-[[4-[(Cyclohexyl-methyl-carbamoyl)-methyl]-6-(4-sulfamoyl-benzylamino)2-pyrimidinyl]amino]-4-methyl-5-thiazolecarboxylic acid ethyl ester; 2-[[4-[2-(4-Acetyl-[1,4]diazepan-1-yl)-2-oxo-ethyl]-6-(4-sulfamoyl-benzylamino)-2-pyrimidinyl]amino]-4-methyl-5-thiazolecarboxylic acid ethyl ester; 2-[[4-[[Methyl-(1-methyl-piperidin-4-yl)-carbamoyl]-methyl]-6-(4-sulfamoyl-benzylamino)-2-pyrimidinyl]amino]-4-methyl-5-thiazolecarboxylic acid ethyl ester; 2-[[4-[2-(4-methyl-[1,4]diazepan-1-yl)-2-oxo-ethyl]-6-(4-sulfamoyl-benzylamino)-2-pyrimidinyl]amino]-4-methyl-5-thiazolecarboxylic acid ethyl ester; 2-[[4-[[Bis-(2-methoxy-ethyl)-carbamoyl]-methyl]-6-(4-sulfamoyl-benzylamino)-2-pyrimidinyl]amino]-4-methyl-5-thiazolecarboxylic acid ethyl ester; 2-[[4-(2-[1,4']Bipiperidinyl-1'-yl-2-oxo-ethyl)-6-(4-sulfamoyl-benzylamino)-2-pyrimidinyl]amino]-4-methyl-5-thiazolecarboxylic acid ethyl ester; 2-[[4-[2-(4-Hydroxy-4-phenyl-piperidin-1-yl)-2-oxo-ethyl]-6-(4-sulfamoyl-benzylamino)-2-pyrimidinyl]amino]-4-methyl-5-thiazolecarboxylic acid ethyl ester; 2-[[4-Ethoxycarbonyl-6-(4-sulfamoyl-benzylamino)-2-pyrimidinyl]amino]-4-methyl-5-thiazolecarboxylic acid ethyl ester; 2-[[4-Carboxyl-6-(4-sulfamoyl-benzylamino)-2-pyrimidinyl]amino]-4-methyl-5-thiazolecarboxylic acid ethyl ester; 2-[[4-(Carboxymethyl-carbamoyl)-6-(4-sulfamoyl-benzylamino)-2-pyrimidinyl]amino]-4-methyl-5-thiazolecarboxylic acid ethyl ester; 2-[4-(4-Hydroxy-piperidin-1-yl)-6-(4-methylsulfanyl-benzyl)-pyrimidin-2-ylamino]-4-methyl-5-thiazolecarboxylic acid ethyl ester; 2-[4-(4-Hydroxy-piperidin-1-yl)-6-(4-methanesulfinyl-benzyl)-pyrimidin-2-ylamino]-4-methyl-5-thiazolecarboxylic acid ethyl ester; 2-[[4-(4-Hydroxy-piperidin-1-yl)-6-(4-methanesulfonyl-benzyl)-2-pyrimidinyl]amino]-4-methyl-5-thiazolecarboxylic acid ethyl ester; 2-[[4-[4-methyl-1-piperazinyl]-6-[N-methyl-N-[(3,4,5-trimethoxyphenyl)methyl]amino]-2-pyrimidinyl]amino]-4-trifluoromethyl-5-thiazolecarboxylic acid, ethyl ester; 2-[[4-[4-Methylpiperazin-1-yl]-6-(N-methyl-N-[[(3,4,5-trimethoxyphenyl)methyl]amino]-2-pyrimidinyl]amino]-4-methyl-5-cyanothiazole; 2-[[4-[4-Methylpiperazin-1-yl]-6-methyl-6-[[(3,4,5-trimethoxyphenyl)methyl]amino]-2-pyrimidinyl]amino]-4-methyl-5-thiazolecarboxylic acid, 2-methoxyethyl ester; 2-[[4-[4-Hydroxy-piperidin-1-yl]-6-[N-methyl[[N-[(3,4,5-trimethoxyphenyl)methyl]1-N-methyl]amino]-2-pyrimidinyl]amino]-4-methyl-5-thiazolecarboxylic acid, butyl ester; 2-[[4-[1-morpholinyl]-6-[[2-[1-morpholinyl]ethyl]amino]-2-pyrimidinyl]amino]-4-methyl-5-thiazolecarboxylic acid, butyl ester; 2-[[4-[4-methyl-1-piperazinyl]-6-[[N-[(3,4,5-trimethoxyphenyl)methyl]]-N-(methyl)amino]-2-pyrimidinyl]amino]-4-isopropyl-5-thiazolecarboxylic acid, ethyl ester; 2-[[4-[4-methyl-1-piperazinyl]-6-[[N-[(3,4,5-trimethoxyphenyl)methyl]]-N-(methyl)amino]-2-pyrimidinyl]amino]-4-methyl-5-thiazolecarboxylic acid, methyl amide; 2-[4-[4-(2-Diisopropylamino-ethylcarbamoyl)-phenyl]-6-(4-hydroxy-piperidin-1-yl)-pyrimidin-2-ylamino]-4-methyl-5-thiazolecarboxylic acid ethyl ester; 2-[4-[4-(3-Dimethylamino-propylcarbamoyl)-phenyl]-6-(4-hydroxy-piperidin-1-yl)-pyrimidin-2-ylamino]-4-methyl-5-thiazolecarboxylic acid ethyl ester; 2-[4-[4-(Cyclohexylmethylcarbamoyl)-phenyl]-6-(4-hydroxy-piperidin-1-yl)-pyrimidin-2-ylamino]-4-methyl-5-thiazolecarboxylic acid ethyl ester; 2-[4-[4-(Pyridin-4-ylmethylcarbamoyl)-phenyl]-6-(4-hydroxy-piperidin-1-yl)-pyrimidin-2-ylamino]-4-methyl-5-thiazolecarboxylic acid ethyl ester; 2-[4-[4-(Isobutylcarbomoyl)-phenyl]-6-(4-hydroxy-piperidin-1-yl)-pyrimidin-2-ylamino]-4-methyl-5-thiazolecarboxylic acid ethyl ester; 2-[4-[4-(N-Cyclohexyl-N-methylcarbamoyl)-phenyl]-6-(4-hydroxy-piperidin-1-yl)-pyrimidin-2-ylamino]-4-methyl-5-thiazolecarboxylic acid ethyl ester; 2-[4-[4-(N-Cyclopropylmethyl-N-propylcarbamoyl)-phenyl]-6-(4-hydroxy-piperidin-1-yl)-pyrimidin-2-ylamino]-4-methyl-5-thiazolecarboxylic acid ethyl ester; 2-[4-[4-(4-Ethoxycarbonylpyperidine-1-carbamoyl)-phenyl]-6-(4-hydroxy-piperidin-1-yl)-pyrimidin-2-ylamino]-4-methyl-5-thiazolecarboxylic acid ethyl ester; 2-[4-[4-(3-Hydroxymethyl-piperidine-1-carbonyl)-phenyl]-6-(4-hydroxy-piperidin-1-yl)-pyrimidin-2-ylamino]-4-methyl-5-thiazolecarboxylic acid ethyl ester; 2-[4-[4-(N-2-Hydroxyethyl-N-ethylcarbamoyl)-phenyl]-6-(4-hydroxy-piperidin-1-yl)-pyrimidin-2-ylamino]-4-methyl-5-thiazolecarboxylic acid ethyl ester; 2-[4-[4-(Thiomorpholine-1-carbonyl)-phenyl]-6-(4-hydroxy-piperidin-1-yl)-pyrimidin-2-ylamino]-4-methyl-5-thiazolecarboxylic acid ethyl ester; 2-[4-[4-(Morpholine-1-carbonyl)-phenyl]-6-(4-hydroxy-piperidin-1-yl)-pyrimidin-2-ylamino]-4-methyl-5-thiazolecarboxylic acid ethyl ester; and 2-[4-[4-(4-Chloro-phenylcarbamoyl)-phenyl]-6-(4-hydroxy-piperidin-1-yl)-pyrimidin-2-ylamino]-4-methyl-5-thiazolecarboxylic acid ethyl ester; or a stereoisomer, a pharmaceutically acceptable salt, or a hydrate thereof.

In another related embodiment, PDE7 inhibitors useful in the methods of the present invention include the following compounds:

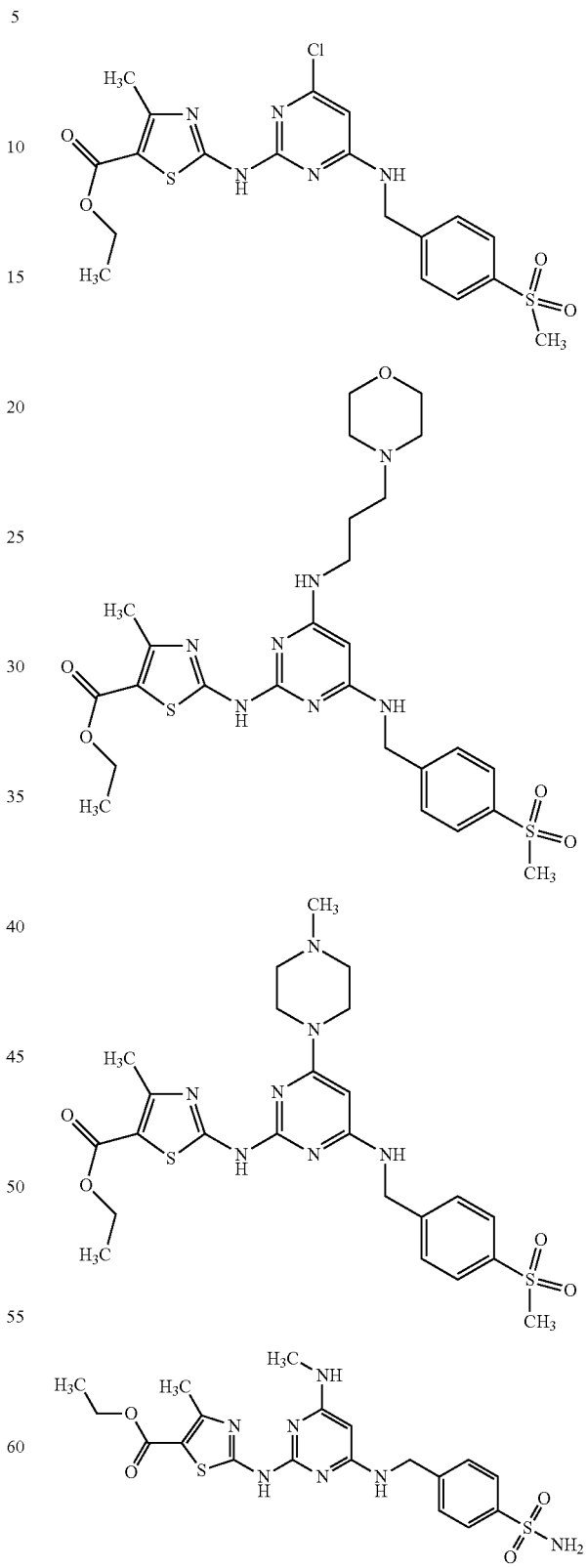

141
-continued
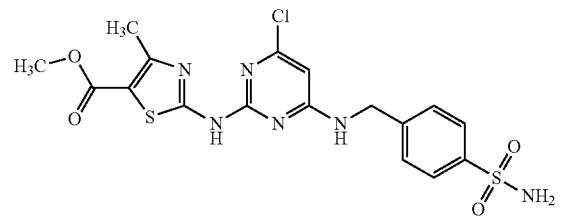
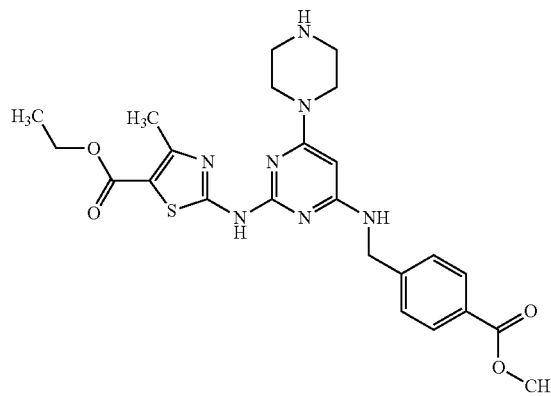
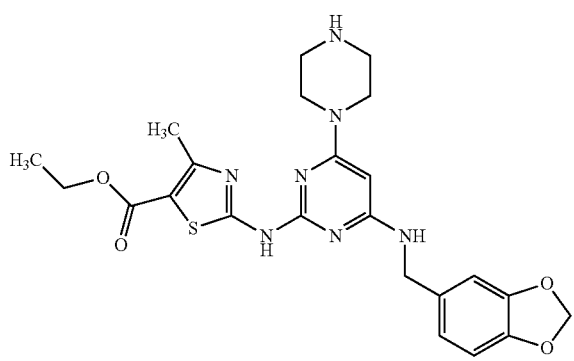
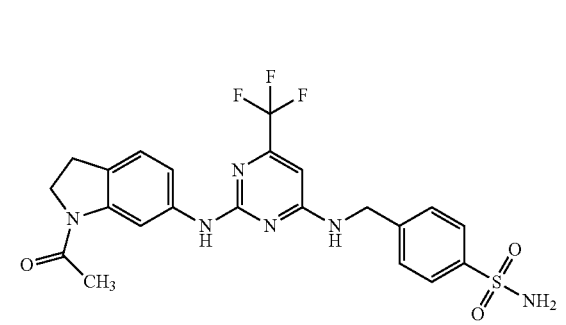
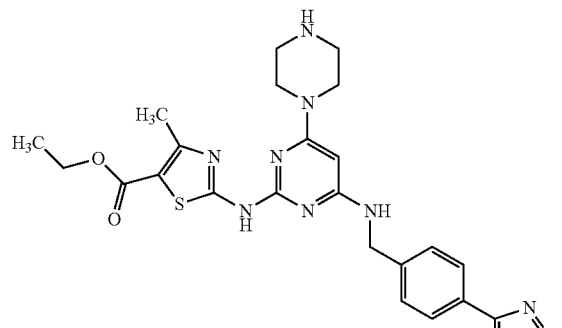
142
-continued
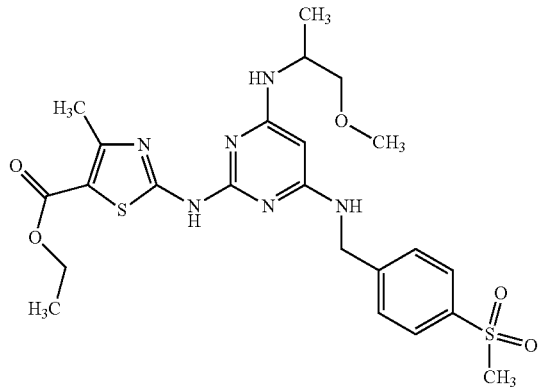
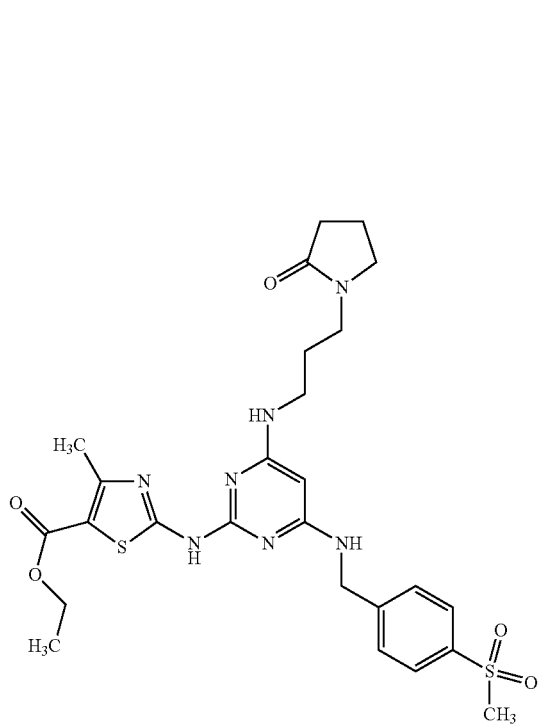
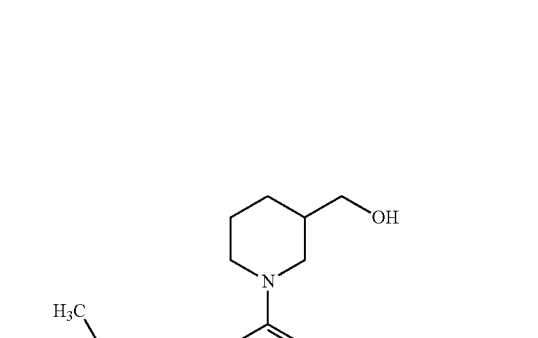

143
-continued
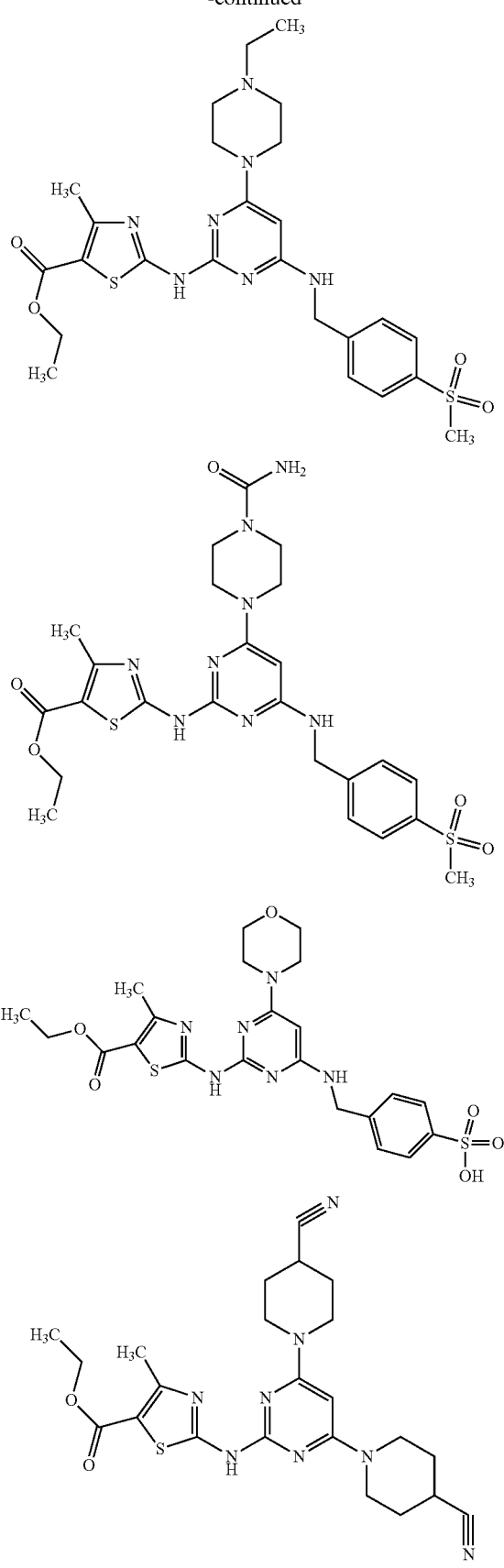
144
-continued
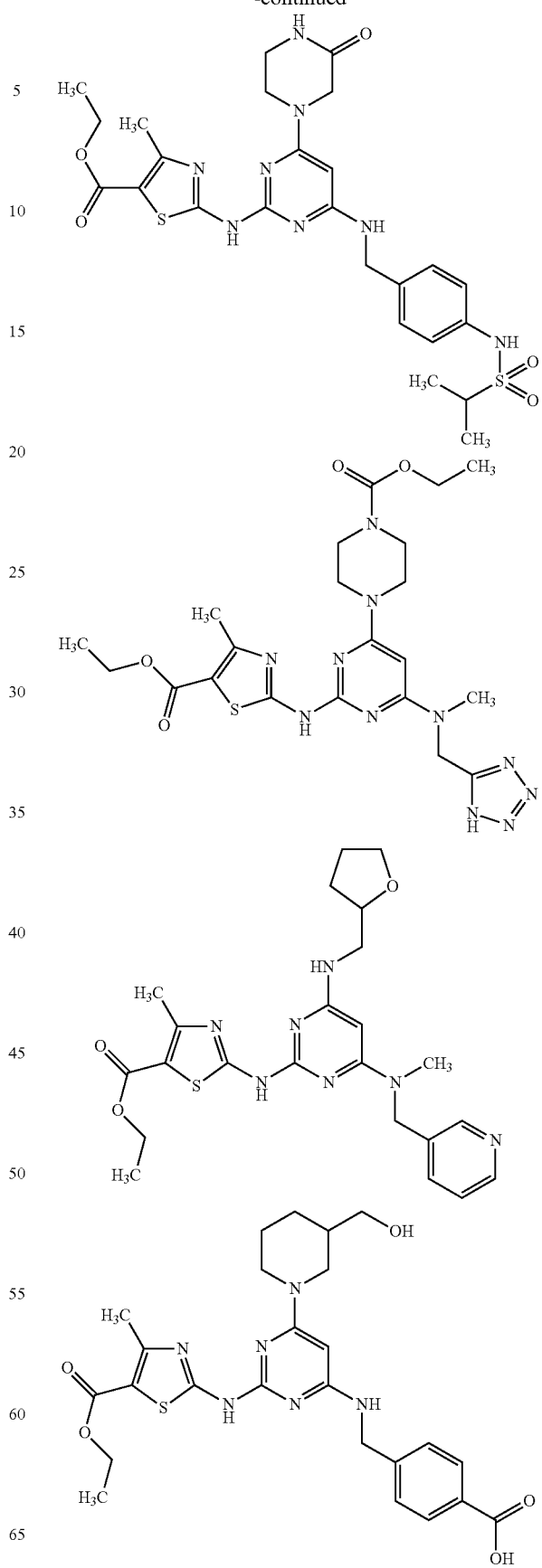

145
-continued
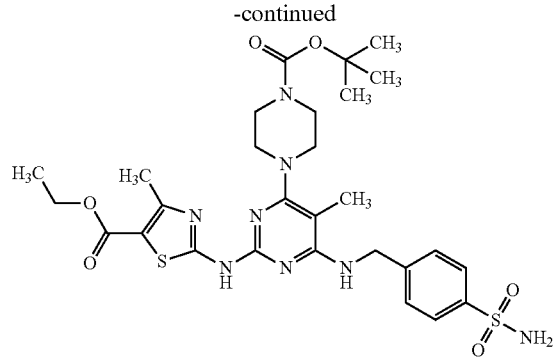
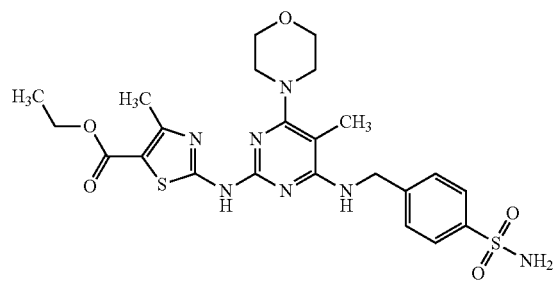
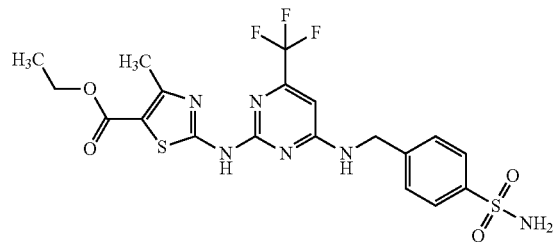
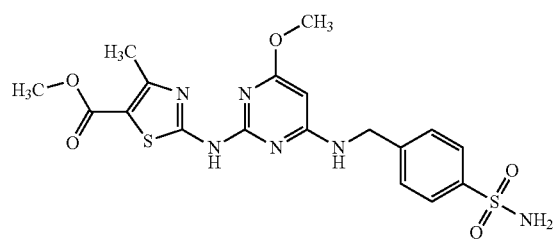
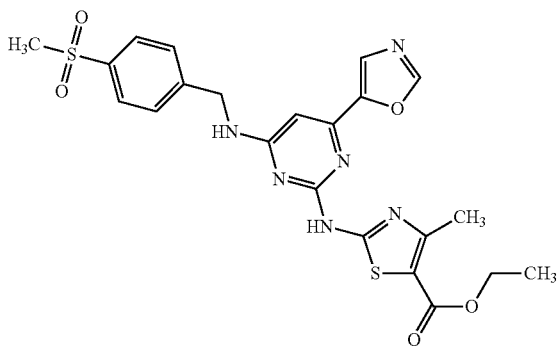
146
-continued
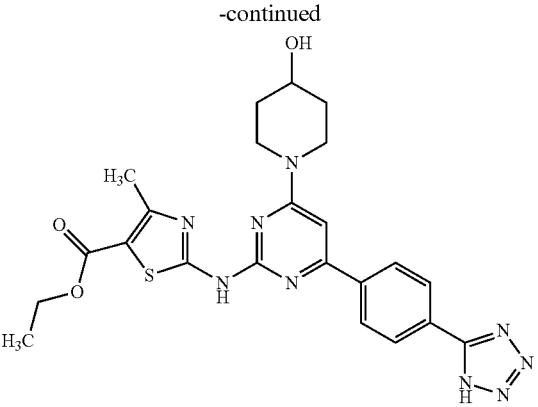
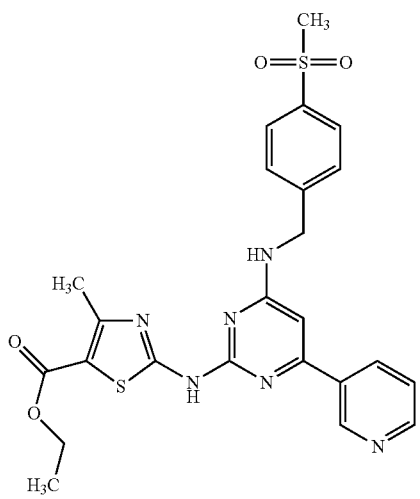
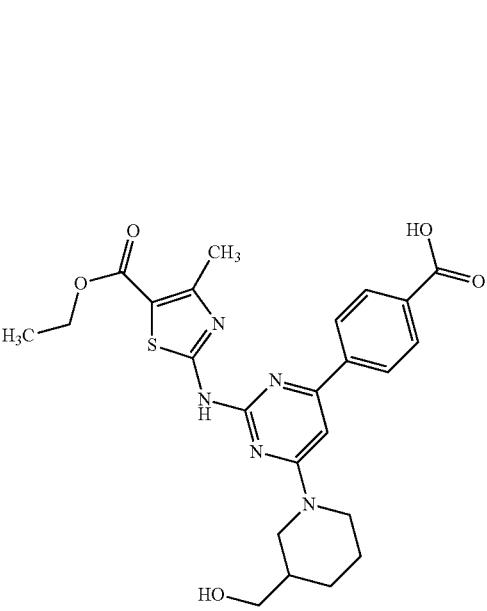

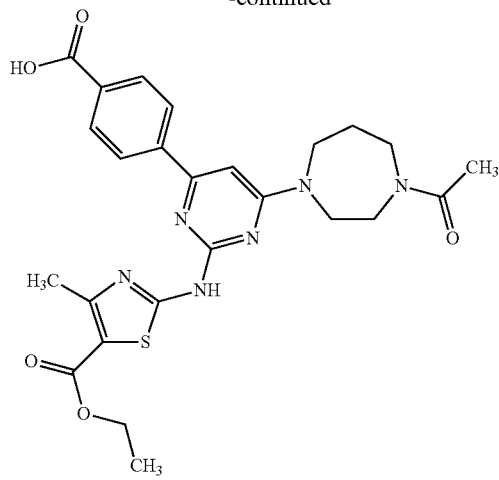

and

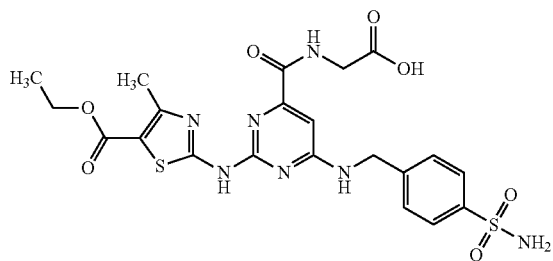 [SMILES: CCOC(=O)c1sc(Nc2nc(NCc3ccc(S(N)(=O)=O)cc3)cc(C(=O)NCC(=O)O)n2)nc1C]

or a stereoisomer, a pharmaceutically acceptable salt, or a hydrate thereof.

The preparation of these compounds is described in U.S. Pat. No. 7,087,614, U.S. 20030162802, and WO 2002/102313.

In another embodiment, PDE7 inhibitors useful in the methods of the invention are selected from those compounds generally or specifically disclosed in US 2007/0129388 and WO 2007/063391, each expressly incorporated by reference herein in its entirety. In one embodiment, PDE7 inhibitors useful in the methods of the invention have the formula:

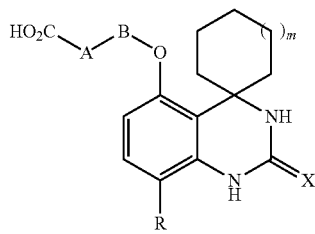

(44)

The substituents for the above compounds are defined as follows:

m is 0, 1 or 2; X is O, S or N—CN; R is F, Cl or CN; A is a $C_{3-6}$ cycloalkylene group optionally substituted with a $C_{1-4}$ alkyl group; and B is a single bond or a $C_{1-2}$ alkylene group; or a pharmaceutically acceptable salt, solvate, polymorph or prodrug thereof.

In regard to the above compounds, the term "alkylene" denotes a divalent saturated hydrocarbon chain having 1 or 2 carbon atoms. Examples of alkylene groups include methylene, ethylene and methylmethylene, of which methylene is preferred.

The term "cycloalkylene" denotes a divalent saturated carbocyclic ring having 3 to 6 carbon atoms. Examples of cycloalkylene groups include cyclopropylene (e.g., 1,1-cyclopropylene and cis- and trans-1,2-cyclopropylene), cyclobutylene (e.g., 1,1-cyclobutylene, cis and trans-1,2-cyclobutylene, and cis and trans-1,3-cyclobutylene), cyclopentylene (e.g., 1,1-cyclopentylene, cis and trans-1,2-cyclopentylene, and cis- and trans-1,3-cyclopentylene) and cyclohexylene (e.g., 1,1-cyclohexylene, cis- and trans-1,2-cyclohexylene, cis- and trans-1,3-cyclohexylene) and cis- and trans-1,4-cyclohexylene).

Preferred examples include cyclobutylene and cyclohexylene, more preferably cyclobutylene, even more preferably 1,3-cyclobutylene, and most preferably trans-1,3-cyclobutylene.

The term "alkyl" denotes a monovalent, straight or branched, saturated hydrocarbon chain containing 1 to 4 carbon atoms. Examples of alkyl groups include methyl, ethyl, n-propyl, isopropyl, n-butyl, isobutyl, sec-butyl and tert-butyl. Preferred examples include methyl and ethyl, especially methyl.

The cycloalkylene group is optionally substituted with a $C_{1-4}$ alkyl group. Preferably, the alkyl substituent, if present, is a methyl or ethyl group, more preferably a methyl group. The alkyl substituent, if present, may be present at any position on the ring, but is preferably present at the 1-position (i.e., the same position as the carboxylic acid group).

Preferably, m is 1 or 2, more preferably 1.

Preferably, X is O or N—CN, more preferably O.

Preferably, R is F or Cl, more preferably Cl.

Preferably, A is a cyclobutylene or cyclohexylene group optionally substituted with a methyl group. More preferably, A is a cyclobutylene group. Even more preferably, A is a 1,3-cyclobutylene group, especially a trans-1,3-cyclobutylene group.

Preferably, B is a single bond or a methylene group. More preferably, B is a single bond.

In another embodiment, a PDE7 inhibitor useful in the methods of the invention is selected from the following compounds:

cis-3-[(8'-Chloro-2'-oxo-2',3'-dihydro-1'H-spiro[cyclohexane-1,4'-quinazo-lin]-5yl)oxy]cyclobutanecarboxylic acid; trans-3-[(8'-Chloro-2'-oxo-2',3'-dihydro-1'H-spiro[cyclohexane-1,4'-quina-zolin]-5'-yl)oxy]cyclobutanecarboxylic acid; 3-[(8'-fluoro-2'-oxo-2',3'-dihydro-1'H-spiro[cyclohexane-1,4'-quinazolin]-5-yl)oxymethyl]cyclobutanecarboxylic acid; trans-3-[(8'-cyano-2'-oxo-2',3'-dihydro-1'H-spiro[cyclohexane-1,4'-quinaz-olin]-5'-yl)oxy]cyclobutanecarboxylic acid; 1-[(8'-fluoro-2'-oxo-2',3'-dihydro-1'H-spiro[cyclohexane-1,4'-quinazolin]-5'-yl) oxymethyl]cyclobutanecarboxylic acid; trans-3-[(8'-chloro-2'-oxo-2',3'-dihydro-1'H-spiro[cycloheptyl-1,4'-quinazolin]-5'-yl)oxy]cyclobutanecarboxylic acid; and trans-3-[(8'-chloro-2'-oxo-2',3'-dihydro-1'H-spiro[cyclopentyl-1,4'-quinazolin]-5'-yl)oxy]cyclobutanecarboxylic acid; or a pharmaceutically acceptable salt, solvate, polymorph or prodrug thereof.

The preparation of the above compounds is described in US 2007/0129388 and WO 2007/063391.

In another embodiment, PDE7 inhibitors useful in the methods of the invention include the compound ASB16165 (1-Cyclohexyl-N-[6-(4-hydroxy-1-piperidinyl)-3-pyridinyl]-3-methyl-1H-thieno[2,3-c]pyrazole-5-carboxamide monohydrate) described in Kadoshima-Yamaoka, K. et al., "ASB16165, a novel inhibitor for phosphodiesterase 7A (PDE7A), suppresses IL-12-induced IFN-g production by mouse activated T lymphocytes," Immunology Letters 122:

193-197, 2009, expressly incorporated by reference herein. In one embodiment, a PDE7 inhibitor useful in the methods of the invention has the formula:

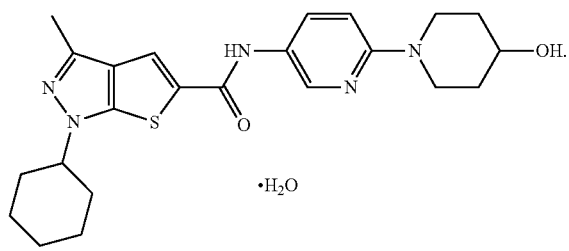

(45)

·H₂O

Methods for preparing the above compound are described in WO 2006/004040.

In another embodiment, PDE7 inhibitors useful in the methods of the invention include the compound YM-393059 ((±)-N-(4,6-dimethylpyrimidin-2-yl)-4-[2-(4-methoxy-3-methylphenyl)-5-(4-methylpiperazin-1-yl)-4,5,6,7-tetrahydro-1H-indol-1-yl]benzenesulfonamide difumarate) described in Yamamoto, S. et al., "The effects of a novel phosphodiesterase 7A and -4 dual inhibitor, YM-393059, on T-cell-related cytokine production in vitro and in vivo." *European Journal of Pharmacology* 541:106-114, 2006, expressly incorporated by reference herein in its entirety. In one embodiment, PDE7 inhibitors useful in the methods of the invention have the formula:

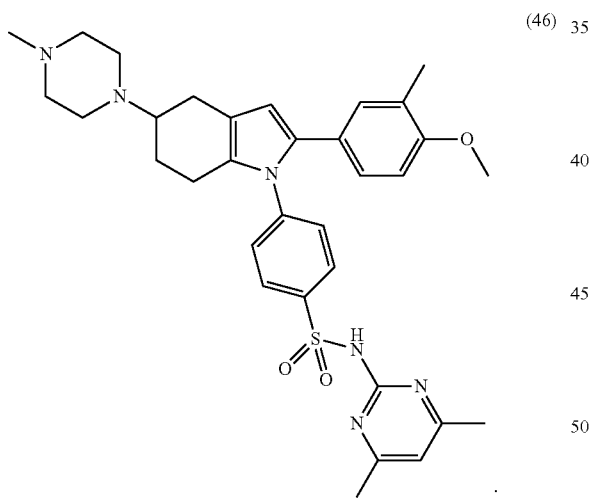

(46)

In another embodiment, PDE7 inhibitors useful in the methods of the invention are selected from those compounds generally or specifically disclosed in Martinez et al., "Benzyl derivatives of 2,1,3-benzo- and benzothieno 3,2-aathiadiazine 2,2-dioxides: first phosphodiesterase 7 inhibitors," *J. Med. Chem.* 43:683-689, 2000, which is expressly incorporated herein by reference in its entirety. In one embodiment, PDE7 inhibitors useful in the methods of the invention include the following compounds:
1-[(4-Methoxyphenyl)carbonylmethyl]benzothieno-[3,2-a]-1,2,6-thiadiazin-493H)-one 2,2-dioxide; and 1-[(3,4-dichlorophenyl)-methyl]-2,1,3-benzothiadiazin-4(3H)-one 2,2dioxide.

The preparation of the above compounds is described in *J. Med. Chem.* 43:683-689, 2000.

In another embodiment, PDE7 inhibitors useful in the methods of the invention are selected from those compounds generally or specifically disclosed in Castro, A. et al., "CODES, a novel procedure for ligand-based virtual screening: PDE7 inhibitors as an application example," *J. Med. Chem.* 43:1349-1359, 2008, which is expressly incorporated herein by reference in its entirety. In one embodiment, PDE7 inhibitors useful in the methods of the invention include the following compounds:

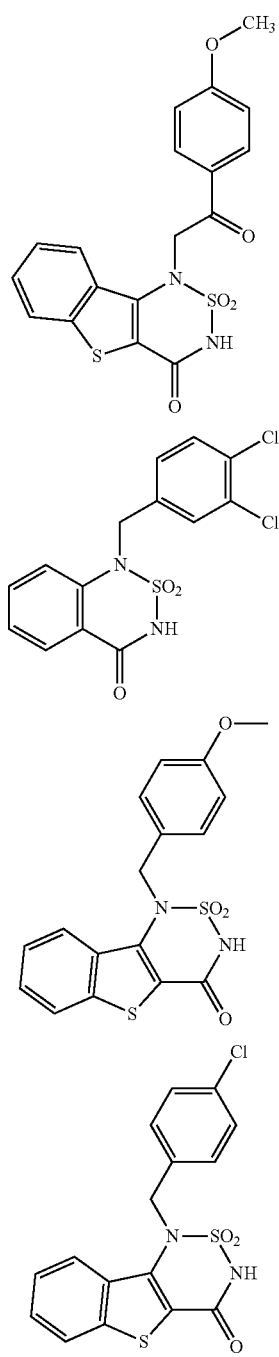

-continued

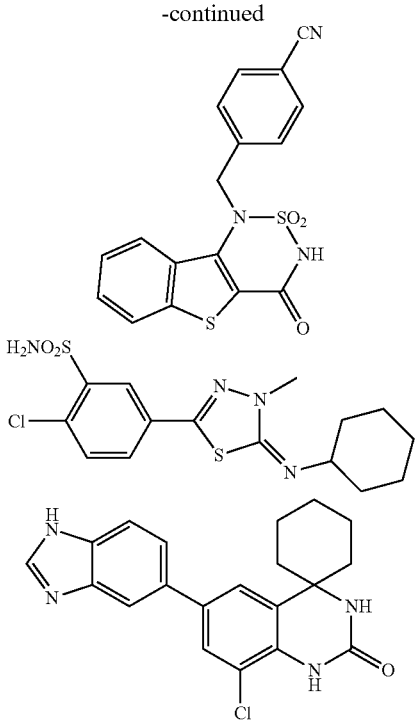

In another embodiment, PDE7 inhibitors useful in the methods of the invention have the formulas:

(47)

(48)

(49)

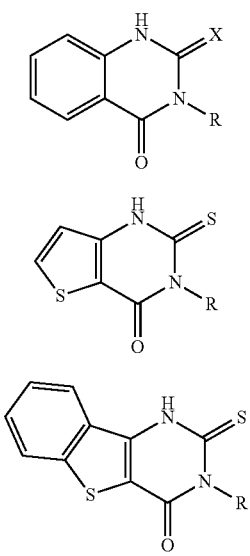

The substituents for the above compounds are defined as follows:
X=O or S,
R=H, Ph, 4-OMePh, 2,6-diFPh, 2,3,4-triFPh, 2-BrPh, Bn, Naphthyl, or Me.

In another embodiment, PDE7 inhibitors useful in the methods of the invention include the following compounds:
5.2.4.3-(2,3,4-Trifluorophenyl)-2-thioxo-(1H)-quinazolin-4-one;
5.3.2.3-Phenyl-2-thioxo-(1H)-thieno[3,2-d]pyrimidin-4-one;
5.3.3.3-(2,6-Difluorophenyl)-2-thioxo-(1H)-thieno[3,2-d]pyrimidin-4-one; and
5.4.2.3-(2,6-Difluorophenyl-2-thioxo-(1H)-benzo[4,5]-thieno[3,2-d]-pyrimidin-4-one.

The preparation of the above compounds is described in *J. Med. Chem.* 43:1349-1359, 2008.

In another embodiment, PDE7 inhibitors useful in the methods of the invention include BMS-586353, as described in Yang, G. et al., "Phosphodiesterase 7A-deficient mice have functional T cells," *J. Immunol.* 171:6414-6420, 2003, which is expressly incorporated herein by reference in its entirety.

In another embodiment, PDE7 inhibitors useful in the methods of the invention are selected from those compounds generally or specifically disclosed in Pitts, W. J. et al., "Identification of purine inhibitors of phosphodiesterase 7 (PDE7)," *Bioorg. Med. Chem. Lett.* 14:2955-2958, 2004, and Kempson, J. et al., "Fused pyrimidine based inhibitors of phosphodiesterase 7 (PDE7): synthesis and initial structure-activity relationships," *Bioorg. Med. Chem. Lett.* 15:1829-1833, 2005, each expressly incorporated herein by reference in its entirety. In one embodiment, PDE7 inhibitors useful in the methods of the invention have the formula:

(50)

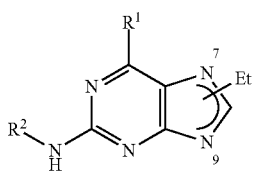

The substituents for the above compounds are defined as follows:
R1 is

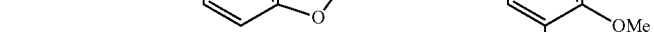

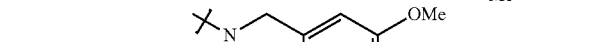

-continued

R2 is

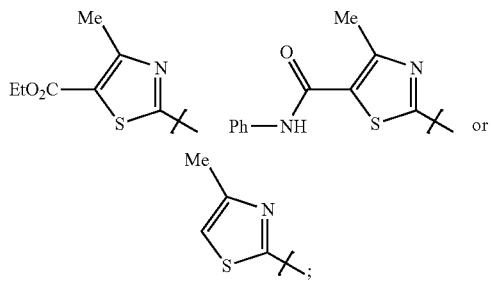

wherein the ethyl group may be attached to the 7 or 9 position.

In a related embodiment, PDE7 inhibitors useful in the methods of the invention have the formulas:

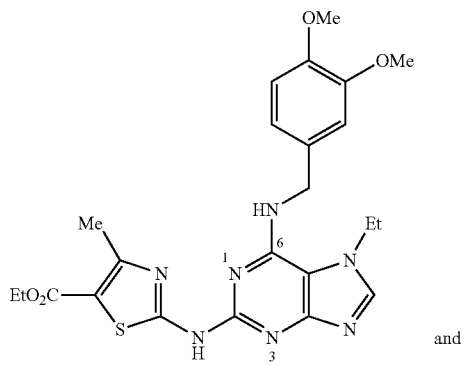

In another related embodiment, PDE7 inhibitors useful in the methods of the invention have the formula:

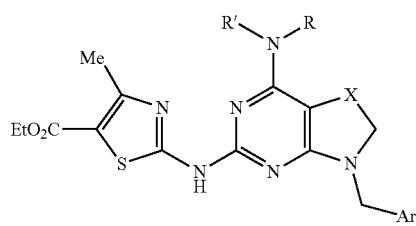

where X=CH2, CH2CH2 or OCH2;

Ar is

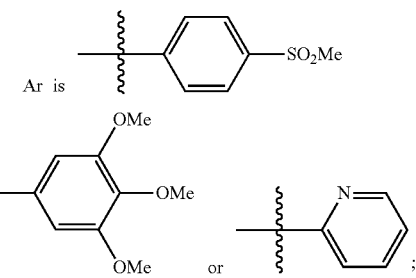

and NRR' is

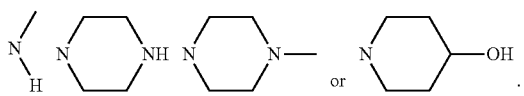

In another embodiment, PDE7 inhibitors useful in the methods of the invention are selected from those compounds generally or specifically disclosed in Kang, N. S. et al., "Docking and 3-D QSAR studies of dual PDE4-PDE7 inhibitors," *Molecular Simulation* 33:1109-1117, 2007, expressly incorporated by reference herein in its entirety. In one embodiment, PDE7 inhibitors useful in the methods of the invention include the following compounds:

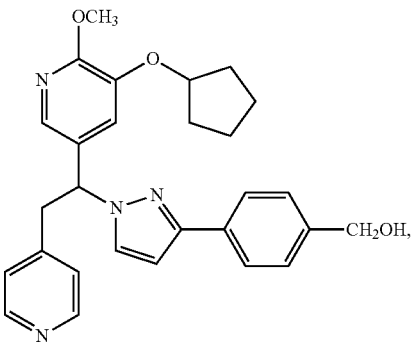

(51)

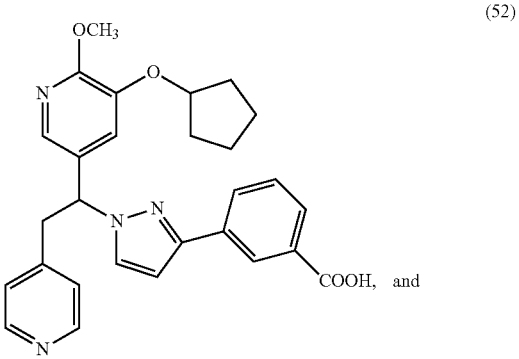

(52)

(53)

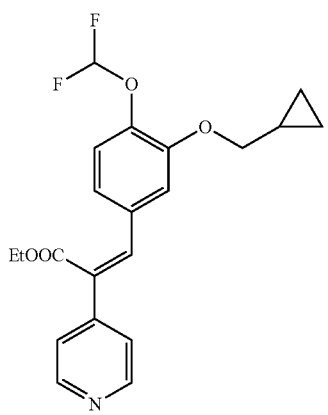

Methods for preparing the above compounds are described in *Molecular Simulation* 33:1109-1117, 2007.

Polypeptide or Peptide Inhibitors

In some embodiments, the PDE7 inhibitory agent comprises isolated PDE7 polypeptide or peptide inhibitors, including isolated natural peptide inhibitors and synthetic peptide inhibitors that inhibit PDE7 activity. As used herein, the term "isolated PDE7 polypeptide or peptide inhibitors" refers to polypeptides or peptides that inhibit PDE7 dependent cleavage of cAMP by binding to PDE7, competing with PDE7 for binding to a substrate, and/or directly interacting with PDE7 to inhibit PDE7-dependent cleavage of cAMP, that are substantially pure and are essentially free of other substances with which they may be found in nature to an extent practical and appropriate for their intended use.

Peptide inhibitors have been used successfully in vivo to interfere with protein-protein interactions and catalytic sites. For example, peptide inhibitors to adhesion molecules structurally related to LFA-1 have recently been approved for clinical use in coagulopathies (Ohman, E. M., et al., *European Heart J.* 16:50-55, 1995). Short linear peptides (<30 amino acids) have been described that prevent or interfere with integrin-dependent adhesion (Murayama, O., et al., *J. Biochem.* 120:445-51, 1996). Longer peptides, ranging in length from 25 to 200 amino acid residues, have also been used successfully to block integrin-dependent adhesion (Zhang, L., et al., *J. Biol. Chem.* 271 (47):29953-57, 1996). In general, longer peptide inhibitors have higher affinities and/or slower off-rates than short peptides and may therefore be more potent inhibitors. Cyclic peptide inhibitors have also been shown to be effective inhibitors of integrins in vivo for the treatment of human inflammatory disease (Jackson, D. Y., et al., *J. Med. Chem.* 40:3359-68, 1997). One method of producing cyclic peptides involves the synthesis of peptides in which the terminal amino acids of the peptide are cysteines, thereby allowing the peptide to exist in a cyclic form by disulfide bonding between the terminal amino acids, which has been shown to improve affinity and half-life in vivo for the treatment of hematopoietic neoplasms (e.g., U.S. Pat. No. 6,649,592 to Larson).

Synthetic PDE7 Peptide Inhibitors

PDE7 inhibitory peptides useful in the methods of the invention are exemplified by amino acid sequences that mimic the target regions important for PDE7 enzyme activity, such as the catalytic domain of PDE7. PDE7A and PDE7B have an identity of 70% in the catalytic domain. (Hetman, J. M., et al., *PNAS* 97(1):472-476, 2000.) The catalytic domain of PDE7A1 is from amino acid residue 185 to 456 of SEQ ID NO:2. The catalytic domain of PDE7A2 is from amino acid residue 211 to 424 of SEQ ID NO:4. The catalytic domain of PDEB is from amino acid residue 172 to 420 of SEQ ID NO:6. The inhibitory peptides useful in the practice of the methods of the invention range in size from about 5 amino acids to about 250 amino acids. One may also use molecular modeling and rational molecular design to generate and screen for peptides that mimic the molecular structure of the PDE7 catalytic regions and inhibit the enzyme activity of PDE7. The molecular structures used for modeling include the CDR regions of anti-PDE7 monoclonal antibodies. Methods for identifying peptides that bind to a particular target are well known in the art. For example, molecular imprinting may be used for the de novo construction of macromolecular structures such as peptides that bind to a particular molecule. See, for example, Shea, K. J., "Molecular Imprinting of Synthetic Network Polymers: The De Novo Synthesis of Macromolecular Binding and Catalytic Sties," *TRIP* 2(5), 1994.

As an illustrative example, one method of preparing mimics of PDE7 binding peptides is as follows. Functional monomers of a binding region of an anti-PDE7 antibody that exhibits PDE7 inhibition (the template) are polymerized. The template is then removed, followed by polymerization of a second class of monomers in the void left by the template, to provide a new molecule that exhibits one or more desired properties that are similar to the template. In addition to preparing peptides in this manner, other PDE7 binding molecules that are PDE7 inhibitory agents, such as polysaccharides, nucleosides, drugs, nucleoproteins, lipoproteins, carbohydrates, glycoproteins, steroids, lipids, and other biologically active materials, can also be prepared. This method is useful for designing a wide variety of biological mimics that are more stable than their natural counterparts because they are typically prepared by free radical polymerization of functional monomers, resulting in a compound with a nonbiodegradable backbone.

The PDE7 inhibitory peptides can be prepared using techniques well known in the art, such as the solid-phase synthetic technique initially described by Merrifield in *J. Amer. Chem. Soc.* 85:2149-2154, 1963. Automated synthesis may be achieved, for example, using Applied Biosystems 431A Peptide Synthesizer (Foster City, Calif.) in accordance with the instructions provided by the manufacturer. Other techniques may be found, for example, in Bodanszky, M., et al., *Peptide Synthesis*, second edition, John Wiley & Sons, 1976, as well as in other reference works known to those skilled in the art. The peptides can also be prepared using standard genetic engineering techniques known to those skilled in the art.

A candidate PDE7 inhibitory peptide may be tested for the ability to function as a PDE7 inhibitory agent in one of several assays, including, for example, a PDE7 phosphodiesterase assay.

Expression Inhibitors of PDE7

In some embodiments of the methods of the invention, the PDE7 inhibitory agent is a PDE7 expression inhibitor capable of inhibiting PDE7-dependent cAMP cleavage (PDE7A, PDE7B, or both). In the practice of this embodiment of the invention, representative PDE7 expression inhibitors include PDE7 antisense nucleic acid molecules (such as antisense mRNA, antisense DNA, or antisense oligonucleotides), PDE7 ribozymes, and PDE7 RNAi molecules.

Anti-sense RNA and DNA molecules act to directly block the translation of PDE7 mRNA by hybridizing to PDE7 mRNA and preventing translation of PDE7 protein. An antisense nucleic acid molecule may be constructed in a number of different ways provided that it is capable of interfering with the expression of PDE7. For example, an antisense nucleic acid molecule can be constructed by inverting the coding region (or a portion thereof) of PDE7A1 cDNA (SEQ ID NO:1), PDE7A2 cDNA (SEQ ID NO:3) or PDE7B cDNA (SEQ ID NO:5) relative to its normal orientation for transcription to allow for the transcription of its complement. Methods for designing and administering antisense oligonucleotides are well known in the art and are described, e.g., in Mautino et al., *Hum Gene Ther* 13:1027-37, 2002; and Pachori et al., *Hypertension* 39:969-75, 2002, each of which is hereby incorporated by reference.

The antisense nucleic acid molecule is usually substantially identical to at least a portion of the target gene or genes. The nucleic acid, however, need not be perfectly identical to inhibit expression. Generally, higher homology can be used to compensate for the use of a shorter antisense nucleic acid molecule. The minimal percent identity is typically greater than about 65%, but a higher percent identity may exert a more effective repression of expression of the endogenous sequence. Substantially greater percent identity of more than about 80% typically is preferred, though about 95% to absolute identity is typically most preferred.

The antisense nucleic acid molecule need not have the same intron or exon pattern as the target gene, and non-coding segments of the target gene may be equally effective in achieving antisense suppression of target gene expression as coding segments. A DNA sequence of at least about 8 or so nucleotides may be used as the antisense nucleic acid molecule, although a longer sequence is preferable. In the present invention, a representative example of a useful inhibitory agent of PDE7 is an antisense PDE7 nucleic acid molecule that is at least ninety percent identical to the complement of a portion of the PDE7A1 cDNA consisting of the nucleic acid sequence set forth in SEQ ID NO:1. Another representative example of a useful inhibitory agent of PDE7 is an antisense PDE7 nucleic acid molecule which is at least ninety percent identical to the complement of a portion of the PDE7A2 cDNA consisting of the nucleic acid sequence set forth in SEQ ID NO:3. Another representative example of a useful inhibitory agent of PDE7 is an antisense PDE7 nucleic acid molecule which is at least ninety percent identical to the complement of a portion of the PDE7B cDNA consisting of the nucleic acid sequence set forth in SEQ ID NO:5.

The targeting of antisense oligonucleotides to bind PDE7 mRNA is another mechanism that may be used to reduce the level of PDE7 protein synthesis. For example, the synthesis of polygalacturonase and the muscarine type 2 acetylcholine receptor is inhibited by antisense oligonucleotides directed to their respective mRNA sequences (U.S. Pat. No. 5,739,119 to Cheng, and U.S. Pat. No. 5,759,829 to Shewmaker). Furthermore, examples of antisense inhibition have been demonstrated with the nuclear protein cyclin, the multiple drug resistance gene (MDG1), ICAM-1, E-selectin, STK-1, striatal $GABA_A$ receptor and human EGF (see, e.g., U.S. Pat. No. 5,801,154 to Baracchini; U.S. Pat. No. 5,789,573 to Baker; U.S. Pat. No. 5,718,709 to Considine; and U.S. Pat. No. 5,610,288 to Reubenstein).

A system has been described that allows one of ordinary skill to determine which oligonucleotides are useful in the invention, which involves probing for suitable sites in the target mRNA using Rnase H cleavage as an indicator for accessibility of sequences within the transcripts. Scherr, M., et al., *Nucleic Acids Res.* 26:5079-5085, 1998; Lloyd, et al., *Nucleic Acids Res.* 29:3665-3673, 2001. A mixture of antisense oligonucleotides that are complementary to certain regions of the PDE7 transcript is added to cell extracts expressing PDE7 and hybridized in order to create an RNAseH vulnerable site. This method can be combined with computer-assisted sequence selection that can predict optimal sequence selection for antisense compositions based upon their relative ability to form dimers, hairpins, or other secondary structures that would reduce or prohibit specific binding to the target mRNA in a host cell. These secondary structure analysis and target site selection considerations may be performed using the OLIGO primer analysis software (Rychlik, I., 1997) and the BLASTN 2.0.5 algorithm software (Altschul, S. F., et al., *Nucl. Acids Res.* 25:3389-3402, 1997). The antisense compounds directed towards the target sequence preferably comprise from about 8 to about 50 nucleotides in length. Antisense oligonucleotides comprising from about 9 to about 35 or so nucleotides are particularly preferred. The inventors contemplate all oligonucleotide compositions in the range of 9 to 35 nucleotides (i.e., those of 9, 10, 11, 12, 13, 14, 15, 16, 17, 18, 19, 20, 21, 22, 23, 24, 25, 26, 27, 28, 29, 30, 31, 32, 33, 34, or 35 or so bases in length) are highly preferred for the practice of antisense oligonucleotide-based methods of the invention. Highly preferred target regions of the PDE7 mRNA are those that are at or near the AUG translation initiation codon, and those sequences that are substantially complementary to 5' regions of the mRNA, e.g., between the 0 and +10 regions of the PDE7 gene nucleotide sequence (SEQ ID NO:1, SEQ ID NO:3, SEQ ID NO:5).

The term "oligonucleotide" as used herein refers to an oligomer or polymer of ribonucleic acid (RNA) or deoxyribonucleic acid (DNA) or mimetics thereof. This term also covers those oligonucleobases composed of naturally occurring nucleotides, sugars and covalent internucleoside (backbone) linkages as well as oligonucleotides having non-naturally occurring modifications. These modifications allow one to introduce certain desirable properties that are not offered through naturally occurring oligonucleotides, such as reduced toxic properties, increased stability against nuclease degradation and enhanced cellular uptake. In illustrative embodiments, the antisense compounds of the invention differ from native DNA by the modification of the phosphodiester backbone to extend the life of the antisense oligonucleotide in which the phosphate substituents are replaced by phosphorothioates. Likewise, one or both ends of the oligonucleotide may be substituted by one or more acridine derivatives that intercalate between adjacent basepairs within a strand of nucleic acid.

Another alternative to antisense is the use of "RNA interference" (RNAi). Double-stranded RNAs (dsRNAs) can provoke gene silencing in mammals in vivo. The natural function of RNAi and co-suppression appears to be protection of the genome against invasion by mobile genetic elements such as retrotransposons and viruses that produce aberrant RNA or dsRNA in the host cell when they become active (see, e.g., Jensen, J., et al., *Nat. Genet.* 21:209-12, 1999). The double-stranded RNA molecule may be prepared by synthesizing two RNA strands capable of forming a double-stranded RNA molecule, each having a length from about 19 to 25 (e.g., 19-23 nucleotides). For example, a dsRNA molecule useful in the methods of the invention may comprise the RNA corresponding to a portion of at least one of SEQ ID NO:1, SEQ ID NO:3, SEQ ID NO:5 and its complement. Preferably, at least one strand of RNA has a 3' overhang from 1-5 nucleotides. The synthesized RNA strands are combined under conditions that form a double-stranded molecule. The RNA sequence may comprise at least an 8 nucleotide portion of SEQ ID NO:1, SEQ ID NO:3 or SEQ ID NO:5 with a total length of 25 nucleotides or less. The design of siRNA sequences for a given target is within the ordinary skill of one in the art. Commercial services are available that design siRNA sequence and guarantee at least 70% knockdown of expression (Qiagen, Valencia, Calif.). Exemplary PDE7 shRNAs and siRNAs are commercially available from Sigma-Aldrich Company (product # SHDNA_-NM_002603; SASI_Hs01_00183420 to SASI_Hs01_00010490).

The dsRNA may be administered as a pharmaceutical composition and carried out by known methods, wherein a nucleic acid is introduced into a desired target cell. Commonly used gene transfer methods include calcium phosphate, DEAE-dextran, electroporation, microinjection and viral methods. Such methods are taught in Ausubel et al., *Current Protocols in Molecular Biology*, John Wiley & Sons, Inc., 1993. Therapeutic nucleic acid molecules may be modified to cross the blood-brain barrier. For example, it has been demonstrated that a phosphorothiolate antisense oligonucleotide directed towards the Abeta midregion of amyloid precursor protein (APP) given by i.c.v. administration can reverse the learning and memory deficits in an Alzheimer mouse model. Banks W. A. et al., *Journal of Pharm. and Exp. Therapeutics*, 297(3): 1113-1121, 2001.

Ribozymes:

In some embodiments, a PDE7 inhibitory agent is a ribozyme that specifically cleaves the mRNA of a target PDE7, such as PDE7A, PDE7B or both. Ribozymes that target PDE7 may be utilized as PDE7 inhibitory agents to decrease the amount and/or biological activity of PDE7. Ribozymes are catalytic RNA molecules that can cleave nucleic acid molecules having a sequence that is completely or partially homologous to the sequence of the ribozyme. It is possible to design ribozyme transgenes that encode RNA ribozymes that specifically pair with a target RNA and cleave the phosphodiester backbone at a specific location, thereby functionally inactivating the target RNA. In carrying out this cleavage, the ribozyme is not itself altered, and is thus capable of recycling and cleaving other molecules. The inclusion of ribozyme sequences within antisense RNAs confers RNA-cleaving activity upon them, thereby increasing the activity of the antisense constructs.

Ribozymes useful in the practice of the invention typically comprise a hybridizing region of at least about nine nucleotides, which is complementary in nucleotide sequence to at least part of the target PDE7 mRNA, and a catalytic region that is adapted to cleave the target PDE7 mRNA (see generally, European patent No. 0 321 201; WO 88/04300; Haseloff, J., et al., *Nature* 334:585-591, 1988; Fedor, M. J., et al., *Proc. Natl. Acad. Sci. USA* 87:1668-1672, 1990; Cech, T. R., et al., *Ann. Rev. Biochem.* 55:599-629, 1986).

Ribozymes can either be targeted directly to cells in the form of RNA oligonucleotides incorporating ribozyme sequences, or introduced into the cell as an expression vector encoding the desired ribozymal RNA. Ribozymes may be used and applied in much the same way as described for antisense polynucleotides.

Anti-sense RNA and DNA, ribozymes and RNAi molecules useful in the methods of the invention may be prepared by any method known in the art for the synthesis of DNA and RNA molecules. These include techniques for chemically synthesizing oligodeoxyribonucleotides and oligoribonucleotides well known in the art, such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well known modifications of the DNA molecules may be introduced as a means of increasing stability and half-life. Useful modifications include, but are not limited to, the addition of flanking sequences of ribonucleotides or deoxyribonucleotides to the 5' and/or 3' ends of the molecule or the use of phosphorothioate or 2'O-methyl rather than phosphodiesterase linkages within the oligodeoxyribonucleotide backbone.

SCREENING METHODS FOR PDE7 INHIBITORS USEFUL TO TREAT ADDICTION

In another aspect, methods are provided for identifying an agent that inhibits PDE7 activity useful for treating an addiction in a mammalian subject in need thereof. The methods of this aspect of the invention comprise: (a) determining the $IC_{50}$ for inhibiting PDE7 activity for each of a plurality of agents; (b) selecting agents from the plurality of agents having an $IC_{50}$ for inhibition of PDE7 activity of less than about 1 μM; (c) determining the $IC_{50}$ for inhibiting PDE4 activity of the agents having an $IC_{50}$ for inhibiting PDE7 activity of less than about 1 μM; (d) identifying agents useful for treating an addiction by selecting compounds having an $IC_{50}$ for inhibiting PDE4 activity greater than 10 times the $IC_{50}$ for inhibiting PDE7; and (e) evaluating the activity of the identified compounds in model system of addiction, wherein an agent that has an $IC_{50}$ for PDE7 inhibition of less than about 1 μM, and an $IC_{50}$ for inhibiting PDE4 activity greater than 10 times the $IC_{50}$ for inhibiting PDE7, and is determined to be effective to treat an addiction in an animal model is indicative of a PDE7 inhibitory agent useful for treating an addiction in a mammalian subject.

Representative agents that may be used in the practice of the methods of this aspect of the invention include molecules that bind to PDE7 and inhibit the enzyme activity of PDE7 (such as small molecule inhibitors or blocking peptides that bind to PDE7 and reduce enzymatic activity), and molecules that decrease the expression of PDE7 at the transcriptional and/or translational level (such as PDE7 antisense nucleic acid molecules, PDE7 specific RNAi molecules and PDE7 ribozymes), thereby preventing PDE7 from cleaving cAMP.

GENERAL COMPOSITION DESCRIPTION AND DEFINITIONS

In one aspect, the invention provides a method of treating an addiction comprising administering to a patient in need thereof an amount of a PDE7 inhibitory agent effective to inhibit the enzymatic activity of PDE7, wherein such inhibition of PDE7 enzymatic activity is the principal therapeutic mode of action of the PDE7 inhibitor in the treatment of the addiction. Addictions include addictions to addictive agents or to addictive behaviors. Addictive agents include without limitation psychostimulants, alcohol, opioids, and nicotine. A preferred psychostimulant for treatment of addiction using PDE7 inhibitors is cocaine or methamphetamine. A preferred addictive behavior for treatment using PDE7 inhibitors is binge eating.

For each of the PDE7 inhibitory chemical compounds useful in the method of the present invention, all possible stereoisomers and geometric isomers are included. The compounds include not only racemic compounds, but also the optically active isomers. When a PDE7 inhibitory agent is desired as a single enantiomer, it can be obtained either by resolution of the final product or by stereospecific synthesis from either isomerically pure starting material or use of a chiral auxiliary reagent, for example, see Ma, Z., et al., *Tetrahedron: Asymmetry* 8(6):883-888, 1997. Resolution of the final product, an intermediate, or a starting material can be achieved by any suitable method known in the art. Additionally, in situations where tautomers of the compounds are possible, the present invention is intended to include all tautomeric forms of the compounds.

The PDE7 inhibitory agents that contain acidic moieties can form pharmaceutically acceptable salts with suitable cations. Suitable pharmaceutically acceptable cations include alkali metal (e.g., sodium or potassium) and alkaline earth metal (e.g., calcium or magnesium) cations. The pharmaceutically acceptable salts of the PDE7 inhibitory agents, which contain a basic center, are acid addition salts formed with pharmaceutically acceptable acids. Examples include the hydrochloride, hydro bromide, sulfate or bisulfate, phosphate or hydrogen phosphate, acetate, benzoate, succinate, fumarate, maleate, lactate, citrate, tartarate, gluconate, methanefulgonate, benzenesulphonate, and p-toluenesulphonate salts. In light of the foregoing, any reference to compounds useful in the method of the invention appearing herein is intended to include PDE7 inhibitory agents, as well as pharmaceutically acceptable salts and solvates thereof.

The compounds of the present invention can be therapeutically administered as the neat chemical, but it is preferable to administer the PDE7 inhibitory agents as a pharmaceutical composition or formulation. Accordingly, the present invention further provides for pharmaceutical compositions or formulations comprising a PDE7 inhibitory agent, or pharmaceutically acceptable salts thereof, together with one or more pharmaceutically acceptable carriers and, optionally, other therapeutic and/or prophylactic ingredients. Suitable carriers are compatible with the other ingredients of the formulation and not deleterious to the recipient thereof. Compounds of the present invention may also be carried in a delivery system to provide for sustained release or enhanced uptake or activity of the compound, such as a liposomal or hydrogel system for injection, a microparticle, nanopartical, or micelle system for oral or parenteral delivery, or a staged capsule system for oral delivery.

Blood-Brain Barrier:

In some embodiments, the PDE7 inhibitory agent is administered so as to either pass through or bypass the blood-brain barrier. Preferably the inhibitory agent, compound or composition administered in the method of treatment can cross through the blood-brain barrier in sufficient quantities and at a sufficient rate so as to allow the treatment of the movement disorder. Methods for allowing agents to pass through the blood-brain barrier are known in the art, and include minimizing the size of the agent, providing hydrophobic factors which facilitate passage, and conjugation to a carrier molecule that has substantial permeability across the blood-brain barrier.

In some embodiments, an effective amount of a PDE7 inhibitory agent is an amount that achieves a concentration within brain tissue at or above the $IC_{50}$ for activity of a given PDE7 inhibitory agent. In some embodiments, the PDE7 inhibitory agent is administered in a manner and dosage that gives a peak concentration of about 1, 1.5, 2, 2.5, 5, 10, 20 or more times the $IC_{50}$ concentration for inhibiting the greater of PDE7A or PDE7B.

EXAMPLES

Example 1

PDE7 Inhibition Alleviates Cocaine Addiction a. Reduction of Self-Administration of Cocaine The ability of PDE7 inhibition to reduce cocaine use by reducing relapse to cocaine addiction and reducing chronic cocaine self-administration was demonstrated in a rat model of cocaine addiction. Cocaine hydrochloride (obtained from the National Institute on Drug Abuse, Bethesda, Md.) was dissolved in sterile physiological saline at a concentration of 0.25 mg/0.1 mL. Drug or vehicle solution was infused at a volume of 0.1 mL over 4 seconds. Two PDE7 inhibitors in accordance with Formulas 1A (OMS182056) and 1B (OMS181869) herein above and one PDE7 inhibitor in accordance with Formula 6 herein above (OMS182401) were tested for effects on cocaine self-administration. OMS182056 and OMS181869 were given intraperitoneally (i.p.) procedure 12 hours and 1 hour before the beginning of cocaine self-administration. OMS182401 was given intraperitoneally.

Male Wistar rats weighing between 180 and 200 g at the time of arrival in the lab were used. The rats were housed in groups of three in a humidity—(45-55%) and temperature-controlled (22 degrees C.) vivarium on a 12 h: 12 h reverse light/dark cycle (on, 17:00; off, 05:00) with ad libitum access to food and water. Experiments were conducted during the dark phase of the light/dark cycle. One week after arrival, rats were subjected to surgery, and a silastic catheter was implanted into the right jugular vein. The experimental stations consisted of operant conditioning chambers (Med Associate Inc.) enclosed in sound-attenuating, ventilated environmental cubicles. Cocaine was delivered by a plastic tube connected to the catheter before the beginning of the session. An infusion pump was activated by responses on the active lever, while responses on the inactive lever were recorded but did not result in any programmed consequences. Activation of the pump resulted in a delivery of 0.1 mL of fluid. An IBM-compatible computer controlled the delivery of fluids and recording of the behavioral data.

For the studies evaluating the PDE7 inhibitors OMS182056 and OMS181869, rats were trained to self-administer cocaine in 2-h daily sessions on a fixed-ratio 5 schedule of reinforcement, in which each response resulted in delivery of 0.25 mg/0.1 ml of fluid cocaine solution. Cocaine self-administration training continued until a stable baseline of responding was reached (less than 10% variation for 3 consecutive days calculated for each single rat). At this point, drug testing began.

Rats were treated with PDE7 inhibitors (0.0, 0.3, 1.0 and 3.0 mg/kg) given i.p. 12 hours and 1 hour before the beginning of the self-administration session. The number of responses to the active and inactive levers was recorded. A 3-day interval was allowed between drug testing. During these intervals, cocaine self-administration was continued to re-establish baseline lever responses.

Figure 2:
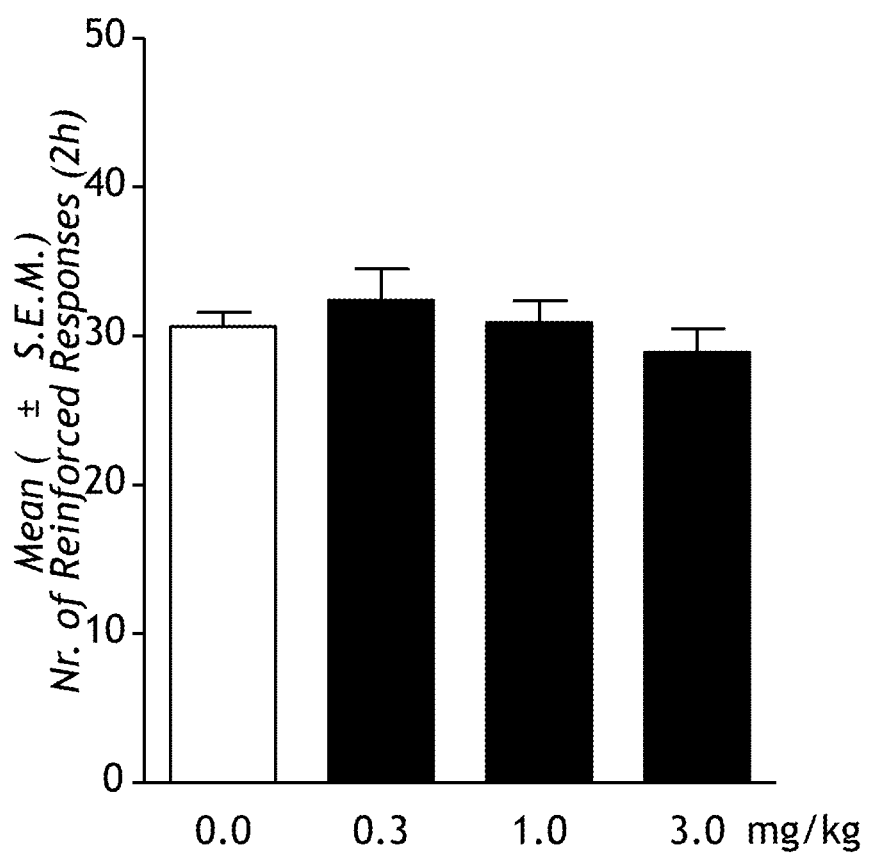
FIG. 2 demonstrates the effect of OMS181869, a PDE7 inhibitor, on cocaine self-administration by rats.

Results are shown in FIGS. 1 and 2. Treatment with either OMS182056 or OMS181869 did not significantly reduce cocaine self-administration, although there was a trend towards reduction at higher dosages.

For the studies evaluating OMS182401, rats were trained to self-administer cocaine in daily 2-hour (short access) or 6-hour (long access) training sessions in which each press of the active lever triggered delivery of 0.25 mg cocaine while pressing of the inactive lever did not deliver cocaine; after 1 week, the ratio was increased so that 5 lever presses were required to receive an equal amount of cocaine. Cocaine self-administration training continued until a stable baseline of responding was reached (less than 10% variation for 3 consecutive days calculated for each single rat). At this point, drug testing began. The animals were injected with vehicle or drug 15 minutes before the test session. The number of responses on the active and inactive levers was recorded.

Figure 3:
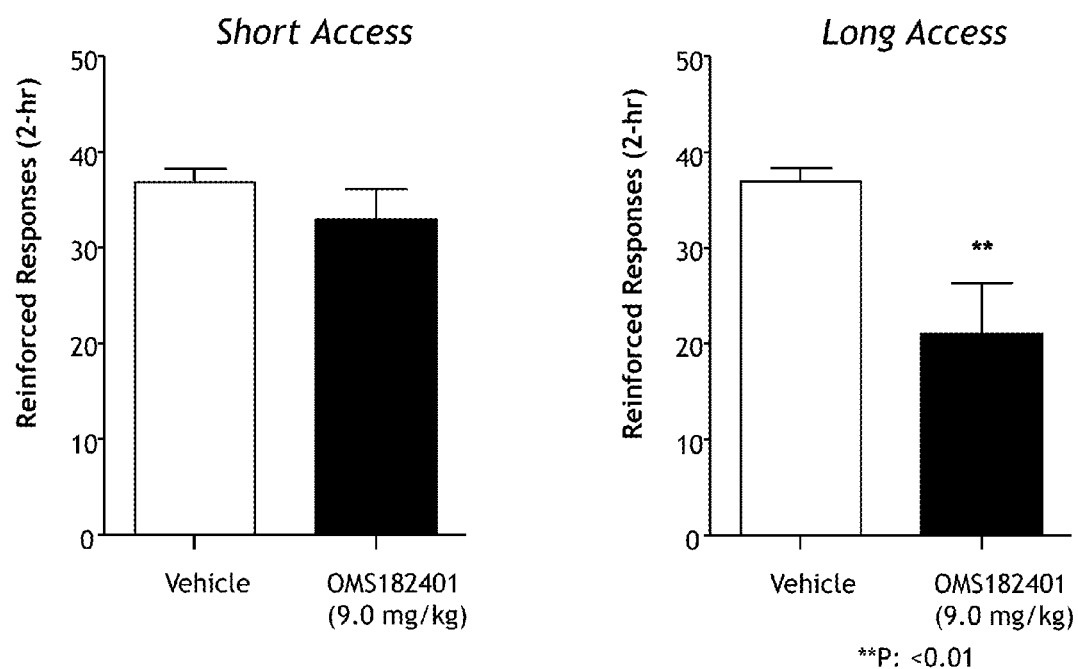
FIG. 3 demonstrates the effect of OMS182401, a PDE7 inhibitor, on cocaine self-administration by rats.

Results are shown in FIG. 3. Treatment with OMS182401 significantly reduced cocaine self-administration in the long-access but not in the short-access model.

Figure 4:
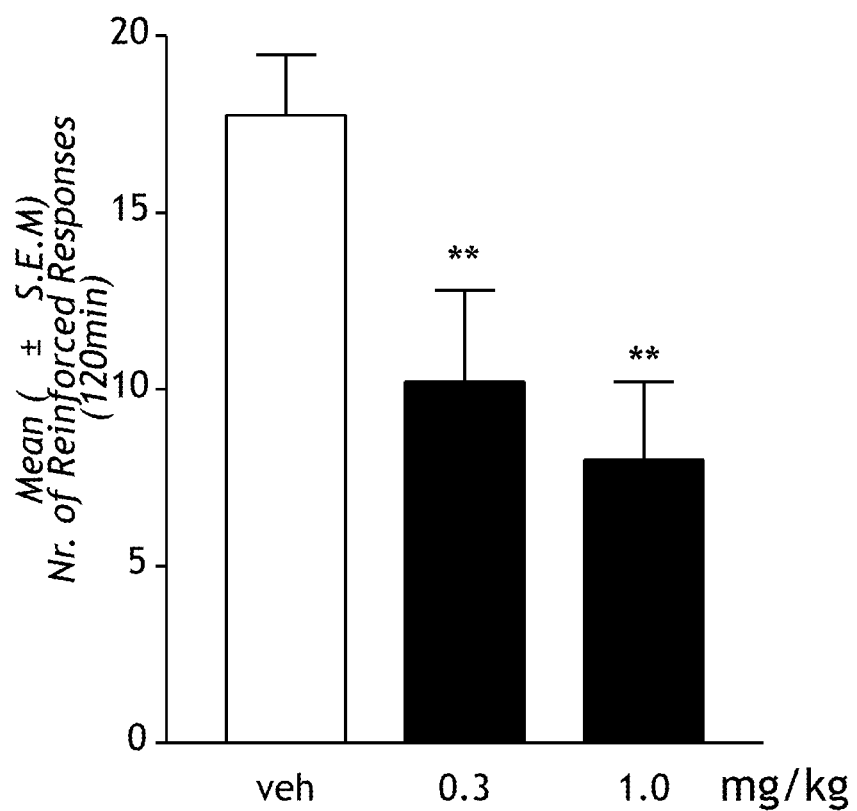
FIG. 4 demonstrates the effect of SKF82958, a dopamine D1 agonist, on cocaine self-administration by rats.

PDE7 inhibitors raise cellular levels of cAMP by reducing degradation of cAMP through phosphodiesterase-7 activity. Cellular cAMP levels also increase through activation of Gs-selective G protein-coupled receptors, e.g., the dopamine D1 receptor (DRD1). In order to test the effect of raising cAMP levels through activation of DRD1 on cocaine self-administration, the DRD1 agonist SKF82958 was administered i.p. to rats trained to self-administer cocaine. (±)-SKF-82958 hydrobromide [(±)-6-Chloro-7,8-dihydroxy-3-allyl-1-phenyl-2,3,4,5-tetrahydro-1H-3-benzazepine hydrobromide 6-Chloro-N-allyl-SKF-38393 hydrobromide], or "SKF82958", is available from Sigma Aldrich. SKF82958 was administered at 1.0 mg/kg. Results are shown in FIG. 4. Treatment with SKF82958 significantly reduced cocaine self-administration in the short-access model. The long-access model was not evaluated in this case. In the first hour after treatment, a significant reduction in self-administration was observed at both doses. Two hours after treatment, the trend of self-administration reduction was non-significant (data not shown). However, the animals also exhibited significantly abnormal behavior and were extremely aggressive, suggesting that their ability to press the lever was compromised by administration of SK82958 with cocaine. The exhibited behavior was similar to that exhibited after cocaine overdose (data not shown).

Figure 5:
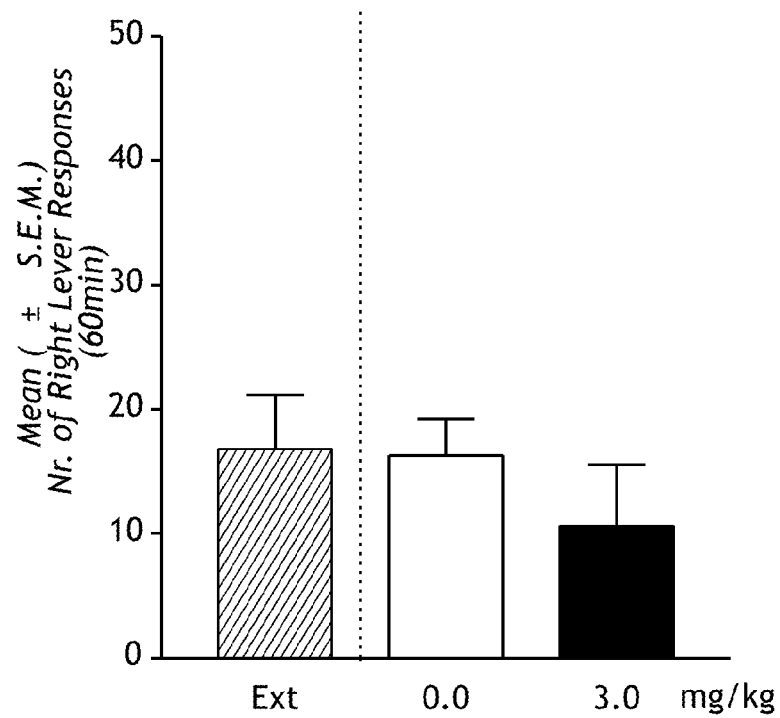
FIG. 5 demonstrates the effect of OMS182056, a PDE7 inhibitor, on non-reinforced lever-press response by rats.
Figure 6:
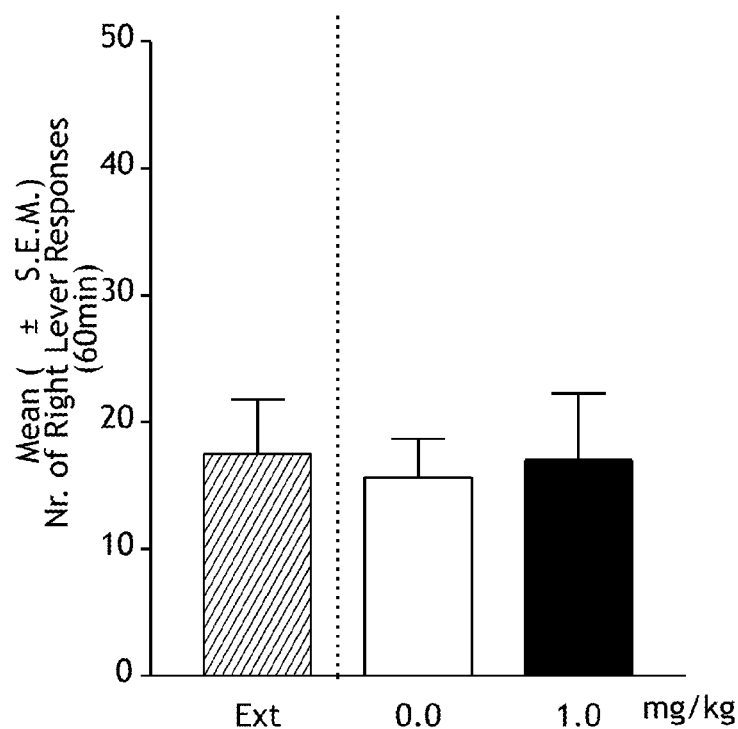
FIG. 6 demonstrates the effect of SKF82958, a dopamine D1 agonist, on non-reinforced lever-press response by rats.

The PDE7 inhibitor OMS182056 and the dopamine D1 agonist SKF82958 were administered without cocaine during an extinction period to determine whether these agents have addictive properties. Results are shown in FIGS. 5 and 6. Neither agent caused increased lever pressing by rats when administered on its own. OMS182056 did exhibit a slight, but statistically non-significant, trend toward decreased lever pressing. Thus, neither agent exhibited addictive properties.

Although both PDE7 inhibitors and dopamine D1 agonists can increase cellular levels of cAMP, these two classes of agents produce very different effects when administered with cocaine.

OMS182401 was also tested for its effect on cocaine-self administration over a longer period of time. Rats were surgically implanted with jugular catheters and allowed to recover for one week. Animals then underwent daily six-hour (long-access) training sessions in which each press of the active lever triggered delivery of 0.25 mg cocaine. After one week, the ratio was increased so that five lever presses were required to receive the same amount of cocaine. The animal training continued for about six weeks. After achieving a stable rate of active lever pressing for six consecutive days, the animals were injected i.p. with vehicle or drug (4.5 mg/kg) twice per day. Reinforced responses were assessed over two hour periods.

Figure 7:
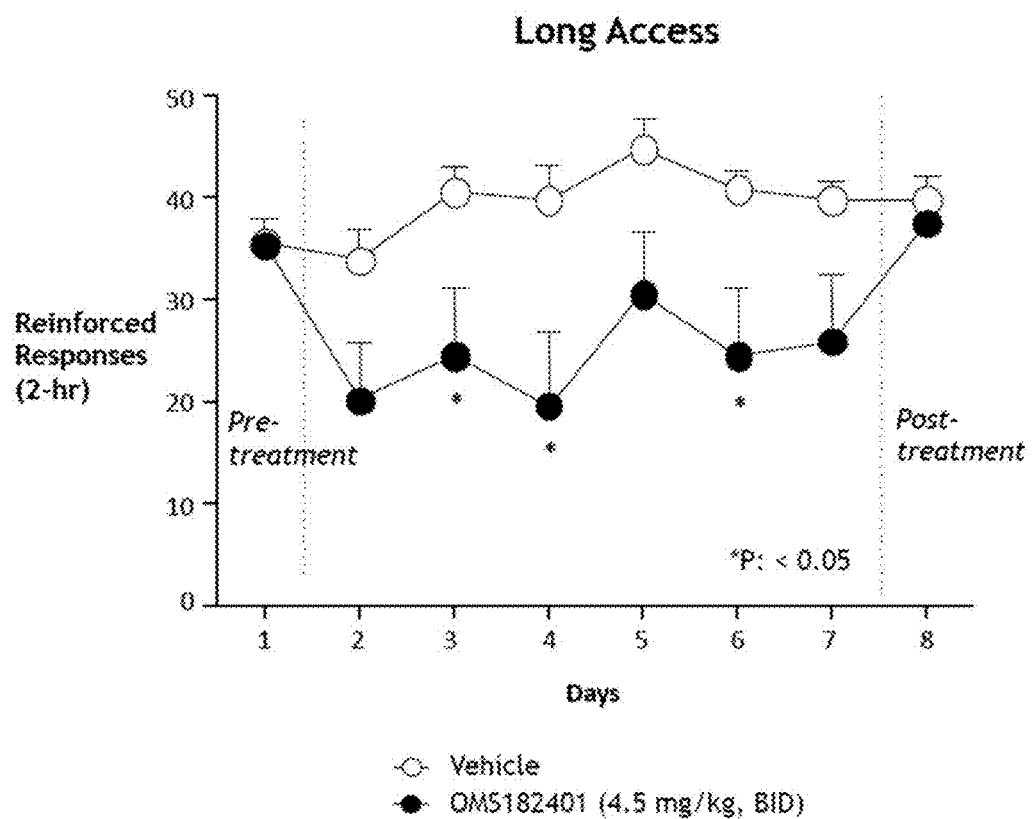
FIG. 7 demonstrates the chronic effect of OMS182401, a PDE7 inhibitor, on cocaine self-administration in rats.

Results are shown in FIG. 7. Chronic OMS182401 treatment reduced cocaine self-administration in the long-access rat model. The effect of OMS182401 remained stable over at least six treatment days. Cocaine self-administration returned to baseline level when treatment with OMS182401 was stopped. OMS182401 did not alter pressing of the inactive lever (data not shown). This experiment confirms the efficacy of PDE7 inhibitors observed in acute models of treatment of cocaine addiction and indicates that OMS182401 may be suitable for chronic dosing.

b. Reduction of Cocaine Seeking Following Extinction

Figure 8:
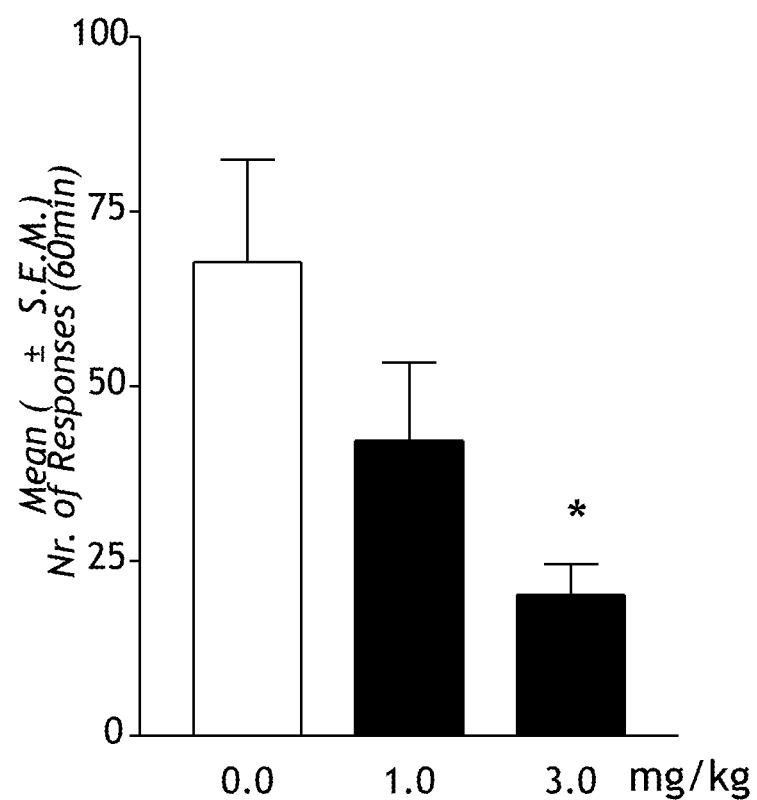
FIG. 8 demonstrates the effect of OMS182056, a PDE7 inhibitor, on lever-press response by rats on the first day of extinction following cocaine addiction.

OMS182056 was tested for its effect on cocaine-seeking behavior immediately after extinction. Rats were trained to self-administer cocaine, as above, and were then exposed to extinction conditions. On the first day, cocaine was replaced with saline solution, OMS182056 (1.0 and 3.0 mg/kg) was administered to the rats i.p. and lever presses were counted. Results are shown in FIG. 8. OMS182056 at 3 mg/kg significantly reduced the amount of cocaine seeking behavior at the beginning of the extinction process, indicating that OMS182056 facilitates cocaine extinction.

c. Reduction of Cocaine Seeking Following Relapse

Figure 9:
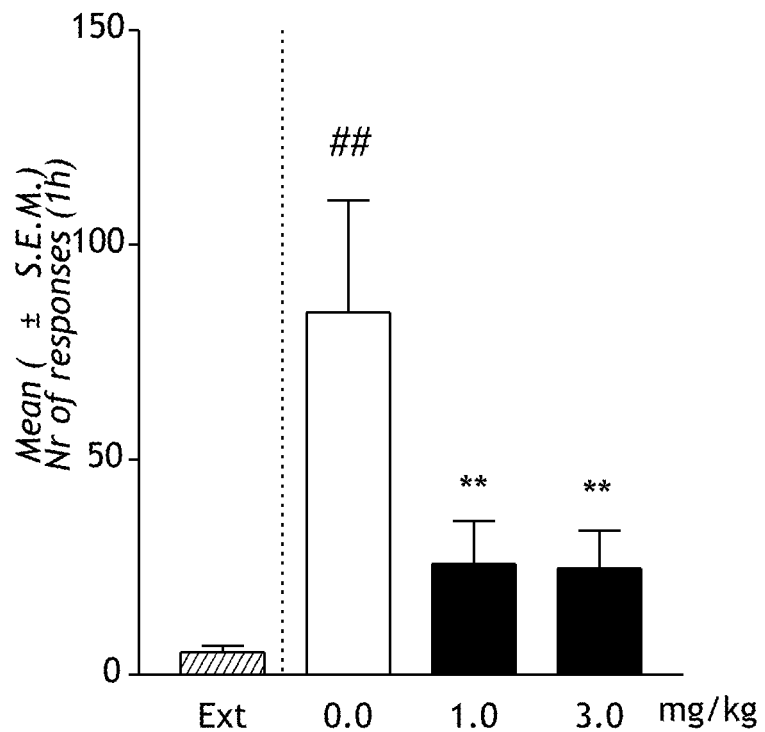
FIG. 9 demonstrates the effect of OMS182056, a PDE7 inhibitor, on yohimbine-induced relapse to cocaine seeking by rats.
Figure 10:
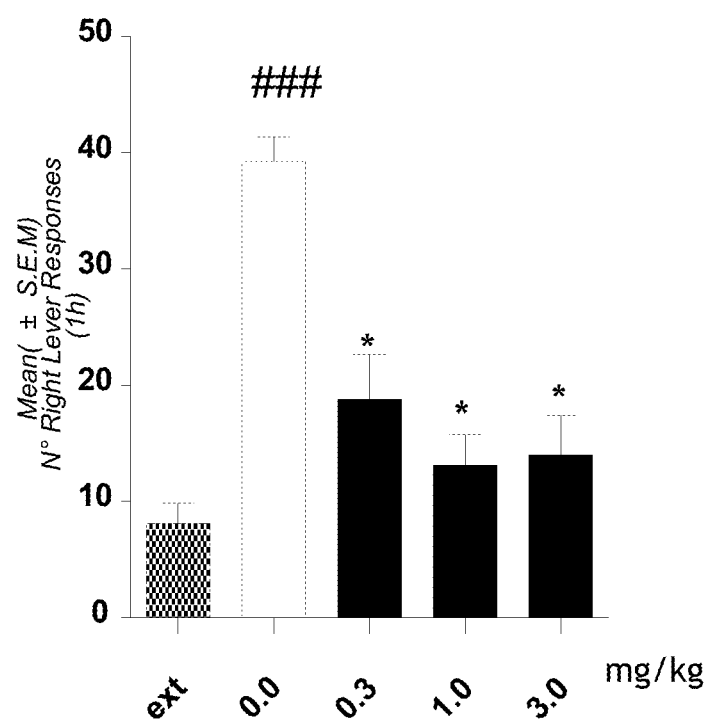
FIG. 10 demonstrates the effect of OMS182401, a PDE7 inhibitor, on yohimbine-induced relapse to cocaine seeking by rats.

OMS182056 and OMS182401 were also tested for their effects on cocaine seeking behavior after a stress-induced relapse of addiction. Rats were trained to self-administer cocaine, as above, and were then exposed to extinction conditions. For the reinstatement phase, the day after the last extinction session, rats were injected with yohimbine (1.25 mg/kg) and after thirty minutes were placed in the operant chamber and lever presses were monitored for thirty minutes. It is known that administration of the α-2 adrenoreceptor antagonist yohimbine, increasing brain noradrenaline cell firing and release, acts as a pharmacological stressor and facilitates relapse to alcohol seeking. (Lê et al., *Psychopharmacology* 179:366-73 (2005)). Results are shown in FIGS. 9 and 10. At doses of 1.0 and 3.0 mg/kg (FIG. 9), OMS182056 exhibited significant effects in preventing stress induced relapse to cocaine addiction. Similarly, at doses of 0.3, 1.0 and 3.0 mg/kg (FIG. 10), OMS182401 exhibited significant effects in preventing stress induced relapse to cocaine addiction.

Figure 11:
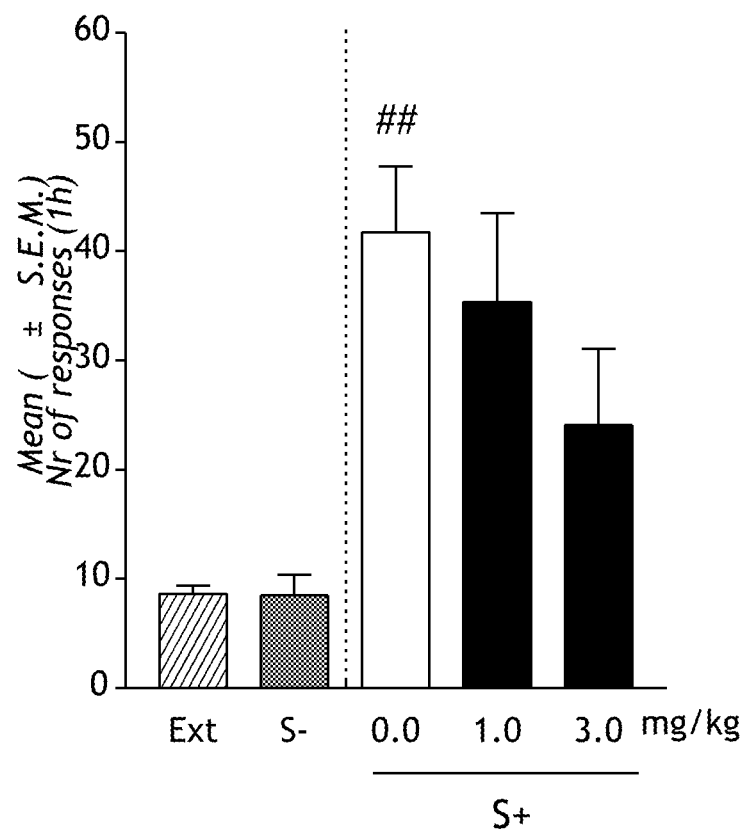
FIG. 11 demonstrates the effect of OMS182056, a PDE7 inhibitor, on cue-induced relapse to cocaine seeking by rats.
Figure 12:
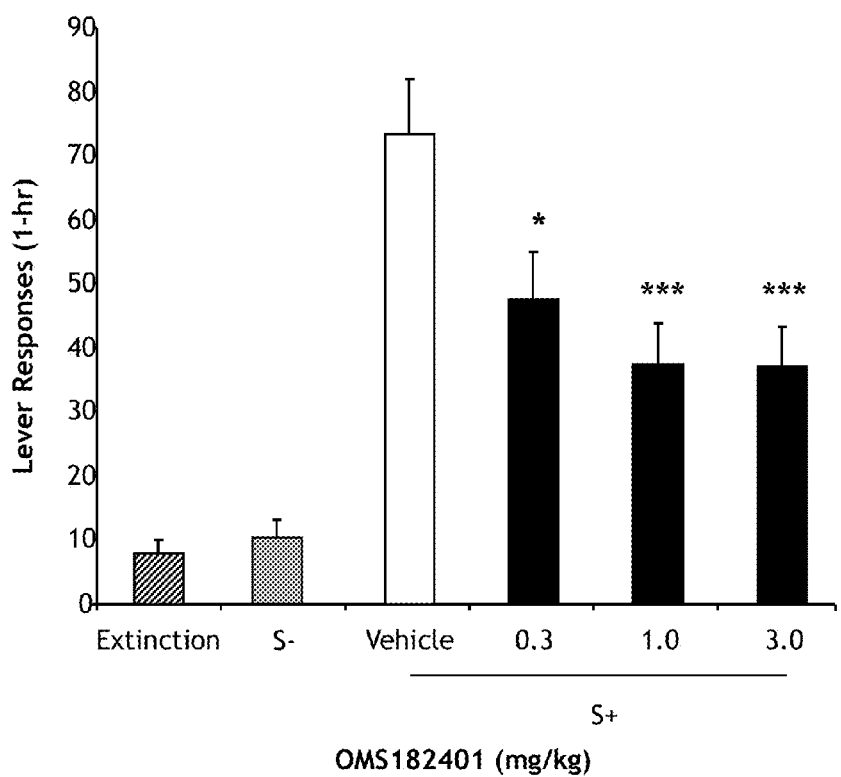
FIG. 12 demonstrates the effect of OMS182401, a PDE7 inhibitor, on cue-induced relapse to cocaine seeking by rats.

OMS182056 was tested for its effect on cocaine-seeking behavior after a cue-induced relapse of addiction. Rats were trained to self-administer cocaine, with the addition of a visual or olfactory cue, and were then exposed to extinction conditions without cocaine. For the reinstatement phase, the day after the last extinction session, rats were reexposed to previously learned cues. Lever presses were monitored and results are shown in FIG. 11. Although the results were not statistically significant, administration of increasing amounts of OMS182056 (1.0 or 3.0 mg/kg) resulted in a trend toward dose-related reduction of cue-induced relapse in the animals. OMS182401 was also tested for its effect on cocaine-seeking behavior after a cue-induced relapse of addiction. Results are shown in FIG. 12. Three concentrations of OMS182401 were tested: 0.3 mg/kg, 1.0 mg/kg, and 3.0 mg/kg, and results were statistically significant at all three concentrations. Administration of increasing amounts of OMS182401 resulted in statistically significant reduction of cue-induced relapse in the animals, in a dose-related fashion.

Figure 13:
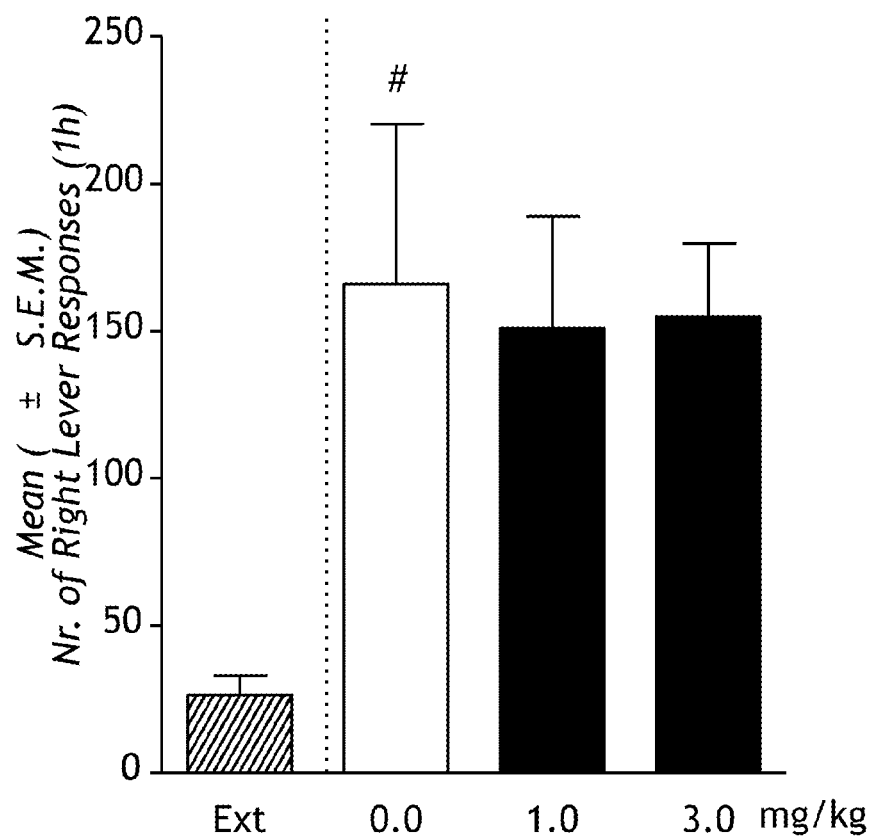
FIG. 13 demonstrates the effect of OMS182056, a PDE7 inhibitor, on cocaine priming-induced relapse by rats.
Figure 14:
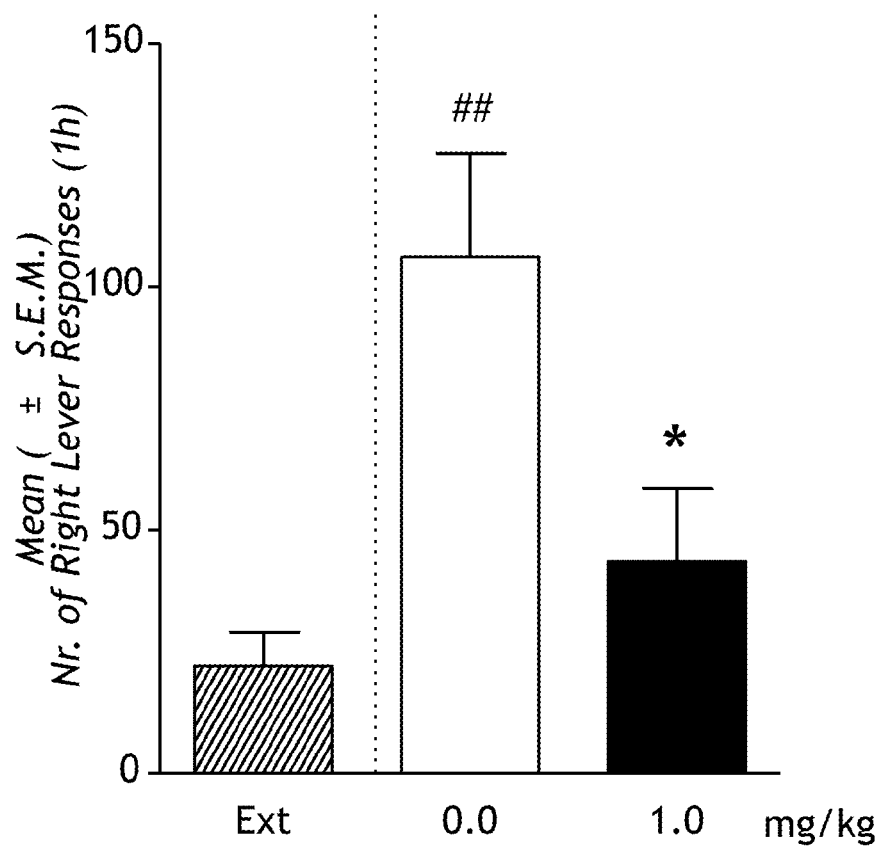
FIG. 14 demonstrates the effect of SKF82958, a dopamine D1 agonist, on cocaine priming-induced relapse by rats.

PDE7 inhibitors and DRD1 agonists were next tested for their effect on cocaine priming-induced relapse. Rats were trained to self-administer cocaine, as above, and were then exposed to extinction conditions. Cocaine was replaced with saline solution. After lever pressing was significantly reduced, reinstatement procedures were begun. Rats were treated with vehicle or agent and ten minutes later were administered cocaine. Lever pressing was counted for one hour following cocaine administration. Results for the PDE7 inhibitor OMS182056 are shown in FIG. 13. Administration of OMS182056 did not have a significant effect on cocaine-induced priming response. Results for the DRD1 agonist SKF82958 are shown in FIG. 14. Treatment with SKF82958 significantly reduced lever pressing induced by cocaine priming. However, as above the animals treated with SKF82958 exhibited significantly abnormal behavior. Once again, administration of PDE7 inhibitors and dopamine D1 agonist had very different results in cocaine addicted animals.

Example 2

PDE7 Inhibition Alleviates Nicotine Addiction a. Reduction of Self Administration of Nicotine The ability of PDE7 inhibition to reduce nicotine use was demonstrated in a rat model of nicotine addiction. Male Wistar rats weighing between 180 and 200 g at the time of arrival in the lab were used. The rats were housed in groups of three in a humidity- and temperature-controlled (22° C.) vivarium on a 12 hour: 12 hour reverse light/dark cycle (on, 17:00; off, 05:00) with ad libitum access to food and water.

Figure 15:
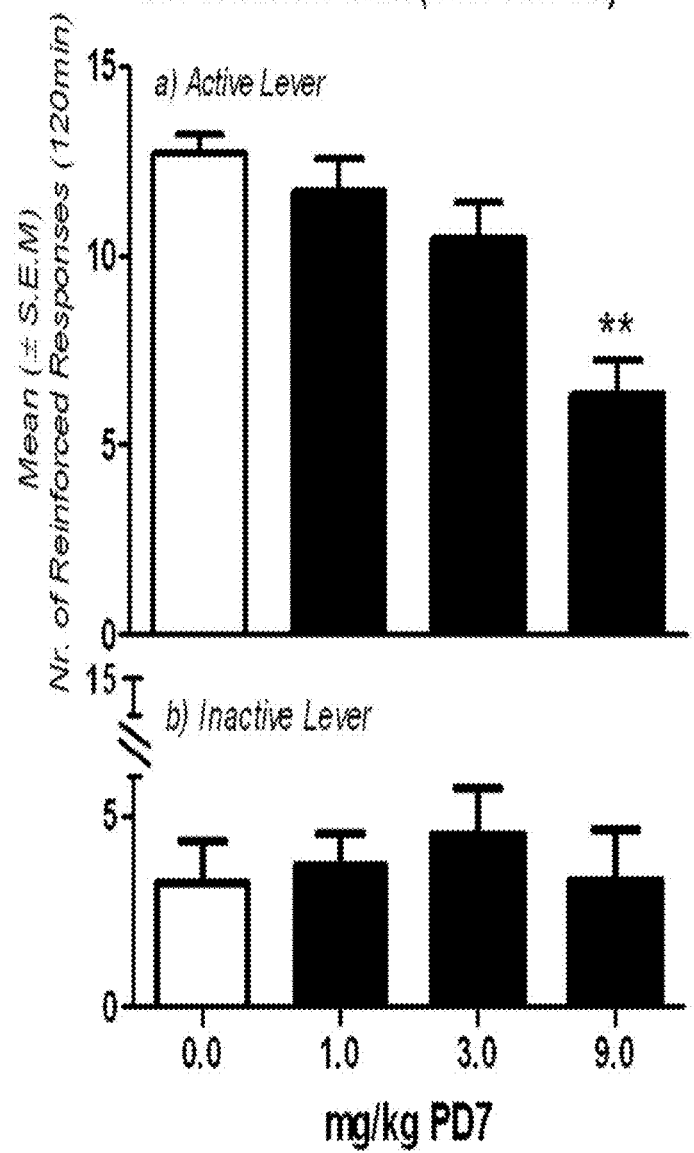
FIG. 15 demonstrates the effect of OMS182401, a PDE7 inhibitor, on nicotine self-administration in rats using a short access model.
Figure 16:
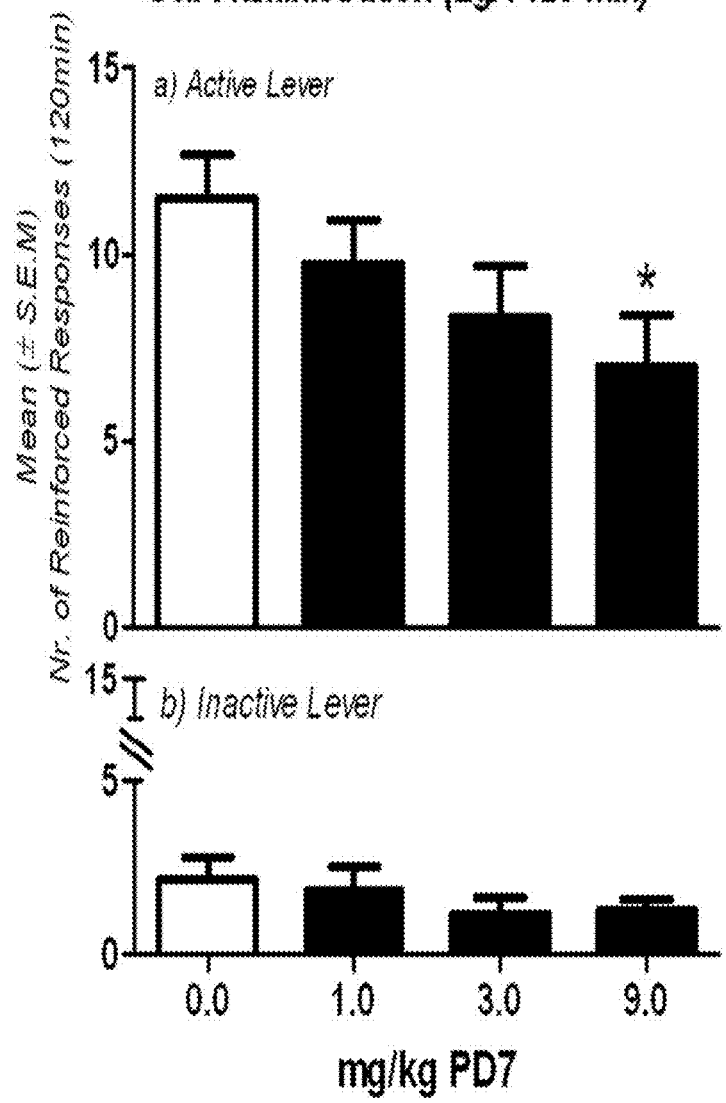
FIG. 16 demonstrates the effect of OMS182401, a PDE7 inhibitor, on nicotine self-administration in rats using a long access model.
Figure 17:
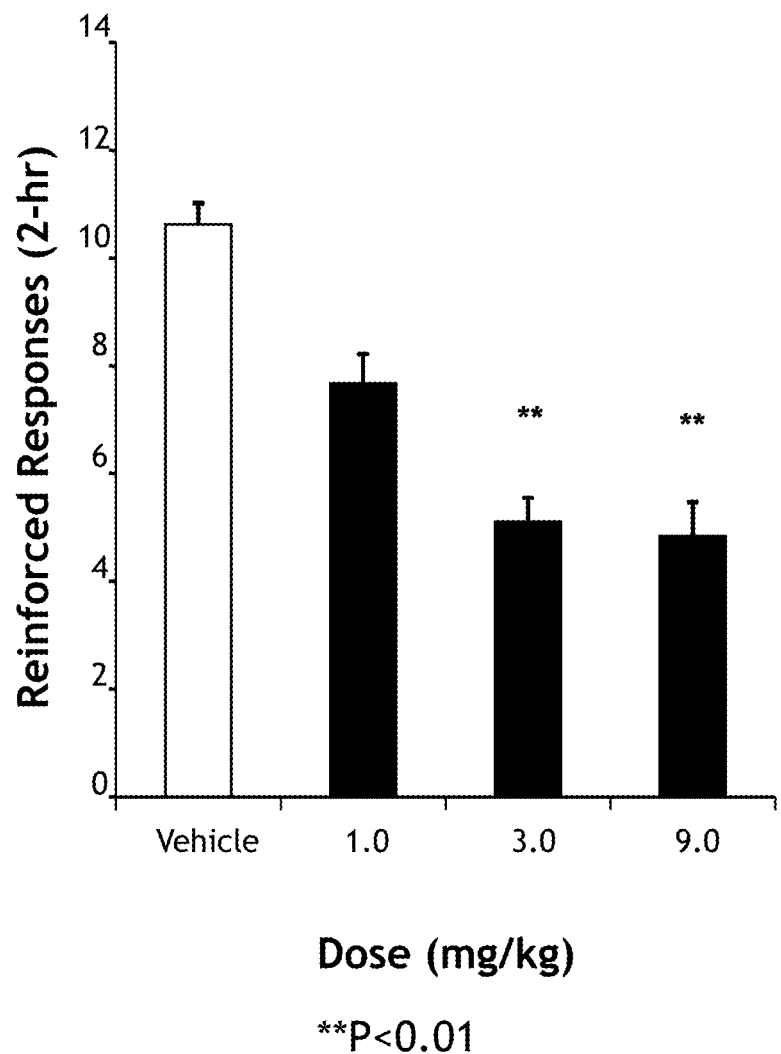
FIG. 17 demonstrates the effect of OMS182399, a PDE7 inhibitor, on nicotine self-administration in rats using a short access model.

Rats were surgically implanted with jugular catheters and allowed to recover for one week. The animals underwent daily two-hour (short access) or six-hour (long access) training sessions in which every three active lever presses triggered the delivery of 0.03 mg of nicotine. After achieving a stable rate of active lever pressing, the animals were injected IP with vehicle or drug (either OMS182401 or OMS182399, another PDE7 inhibitor in accordance with Formula 6 above) 15 minutes before the test session. The measured read-out was the number of reinforced responses over two hours. The half-life of OMS182401 in rats is between 1.7-4.9 hours. Results are shown in FIG. 15 (OMS182401, short access), 16 (OMS182401, long access) and 17 (OMS182399, short access). PDE7 inhibition by OMS182401 reduced nicotine self-administration in a dose-dependent manner in both the short- and long-access rat models. PDE7 inhibition by OMS182399 reduced nicotine self-administration at 3.0 mg/kg and 9.0 mg/kg in the short-access rat model. The compounds did not alter pressing of the inactive lever in either case.

b. Effect of PDE7 Inhibition on Food Self-Administration

The effect of PDE7 inhibitors OMS182399 and OMS1823401 on food self-administration was evaluated to evaluate whether the effect of PDE7 inhibition is specific for drugs of abuse. Eight male Wistar rats were tested for each compound. Each drug was tested at concentrations of 0.0, 3.0 and 9.0 mg/kg formulated in 0.03 M tartaric acid. Solutions were administered intraperitoneally (i.p.).

The self-administration stations consisted of operant conditioning chambers (Med Associate Inc.) enclosed in light, sound-attenuating, ventilated environmental cubicles. The front door and the back wall of the chamber were made of transparent plastic, and the other walls were opaque metal. Each chamber was equipped with two retractable levers located in the front panel of the chamber. Minimal downward pressure (about 25 g) on a lever was sufficient to result in a programmed response. A recessed food receptacle into which food pellets (45 mg each; Bio-ServInc., Frenchtown, N.J.) could be dispensed from a pellet dispenser was located between the two levers. An IBM compatible computer controlled the delivery of fluids and recording of the behavioral data.

For data evaluation, the analysis of variance (ANOVA) was used followed by post-hoc (Newman-Keuls) tests when appropriate. Data were analyzed for the effect of treatment. Statistical significance was set at $p<0.05$.

Figure 18A:
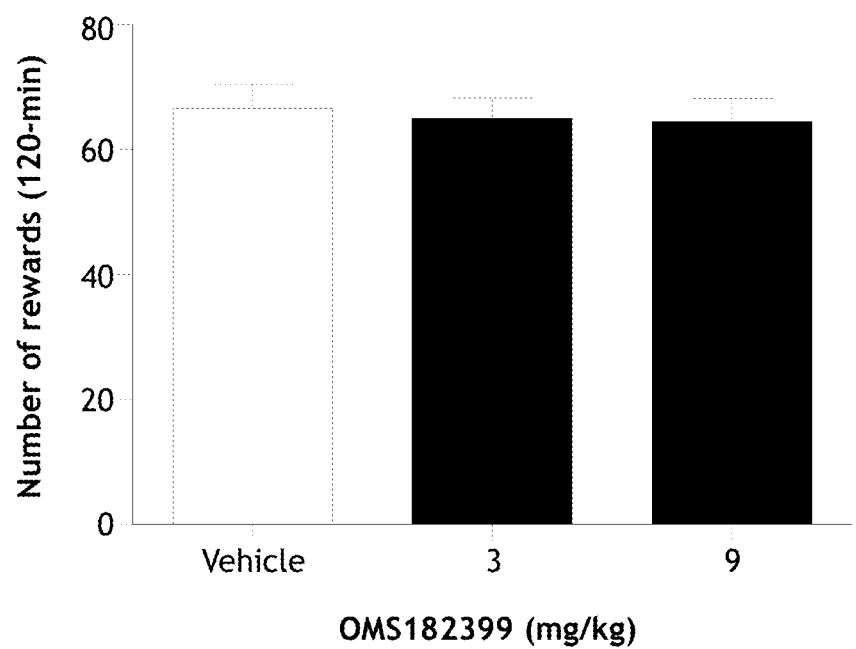
FIGS. 18A and 18B demonstrate that the PDE7 inhibitors OMS182399 and OMS182401, respectively, do not have an effect on food self-administration.
Figure 18B:
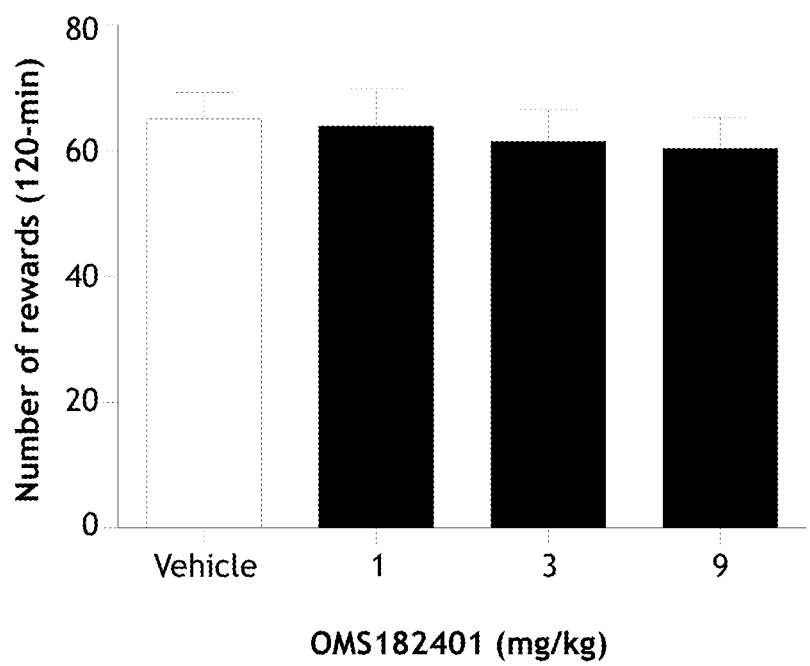

FIGS. 18A and 18B show the results obtained for OMS182399 and OMS182401, respectively. Neither compound exhibited a statistically significant effect on food self-administration as compared to vehicle, demonstrating that the effect of PDE7 inhibition is specific for drugs of abuse. The study provides evidence that the previously observed inhibition of nicotine and cocaine-related operant responding by these PDE7 inhibitors is selective and does not depend upon a general inhibition of locomotor activity or motivation.

c. Reduction of Nicotine Self-Administration in a Progressive Ratio Study

Male Wistar rats were first trained to self-administer nicotine as described above in this Example 2 under a feature release 1 (FR1) schedule of reinforcement. Following the establishment of a stable baseline of responding with nicotine, animals were tested under progressive ratio conditions, in which the response requirement (i.e., the number of lever responses required to receive one dose of 0.03 mg nicotine) was progressively increased.

Each nicotine-reinforced response resulted in a 20 second illumination of the house light. Sessions were terminated when more than 60 minutes had elapsed since the last reinforced response. The data collected were the break point (the number of lever presses in the last session), the total number of lever presses (active lever) throughout the study and the total number of rewards. Fifteen animals were tested using a Latin square design, i.e., each animal received each dose. The effect of the PDE7 inhibitor OMS182401 at different doses was compared to vehicle alone.

Figure 19A:
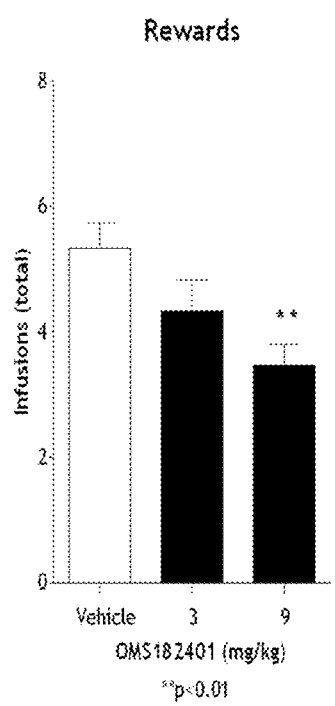
FIGS. 19A-19C demonstrate the effect of OMS182401, a PDE7 inhibitor, on motivation of nicotine-addicted mice to acquire nicotine in a self-administration progressive ratio study.
Figure 19B:
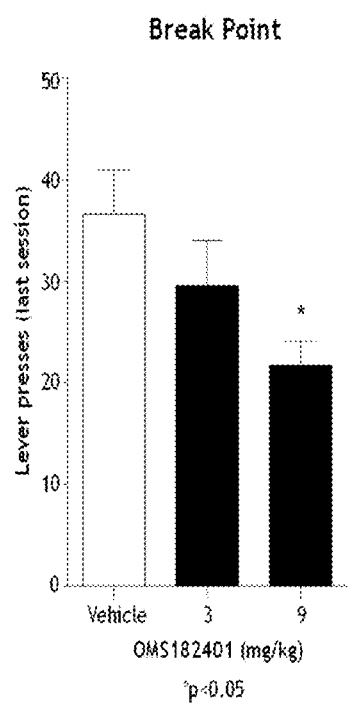
Figure 19C:
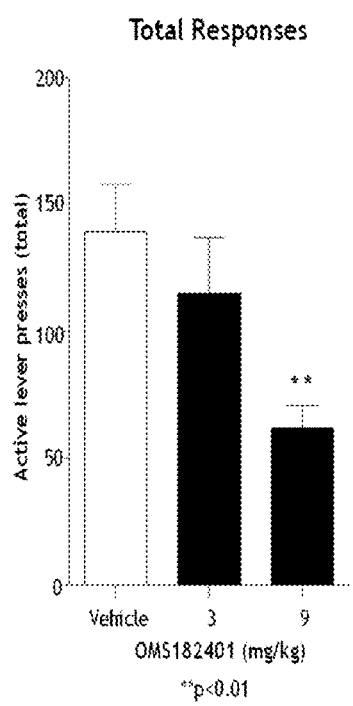

The results for the total number of rewards, break point and total active lever presses are shown in FIGS. 19A-19C, respectively. These data illustrate that the PDE7 inhibitor reduces in dose-dependent fashion the motivation of the addicted animal to acquire nicotine, i.e., motivation for nicotine.

Example 3

Reduction of Self Administration of Nicotine Extinction

Figure 20:
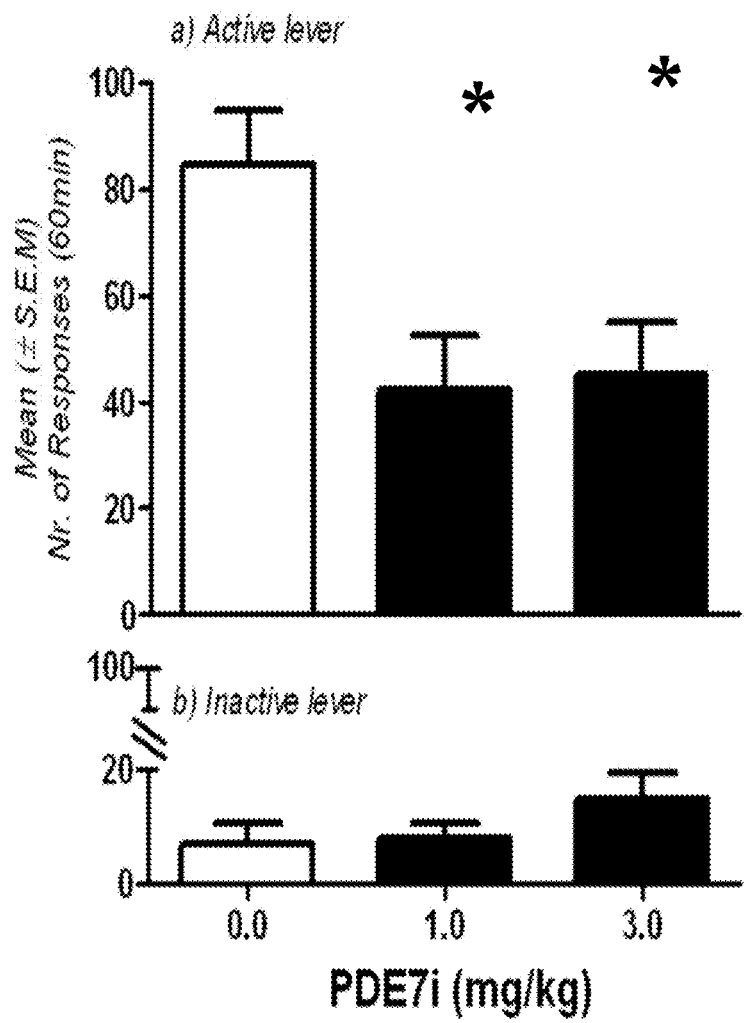
FIG. 20 demonstrates the effect of OMS182401, a PDE7 inhibitor, on the first day of extinction of nicotine self-administration.

The ability of PDE7 inhibition to accelerate nicotine extinction was demonstrated in a rat model of nicotine addiction. Rats were trained to a stable level of nicotine self-administration. The active lever was not associated with any reinforced reward. Prior to the first extinction session, animals were injected with vehicle or OMS182401. The total responses at the active lever during the first hour of the first extinction session were counted. Results are shown in FIG. 20. OMS182401 facilitated nicotine extinction in a statistically significant manner.

Another study evaluated the effect of OMS182401 on non-reinforced responding on the first day of extinction in rats that had been trained to food pellets to confirm the specificity of the effect of OMS182401 on drugs of abuse. Sixteen male Wistar rats were trained to self administer food pellets for eight days and then were divided into two groups and injected with either OMS182401 (9.0 mg/kg in 0.03 M tartaric acid) or vehicle 15 minutes before the first extinction session. The results demonstrated that OMS182401 did not lower the non-reinforced responding in food pellets-trained rats (data not shown), providing further support for the specificity of the effect of OMS182401 on drugs of abuse.

Example 4

Reduction of Nicotine Use Following Reinstatement

Figure 21:
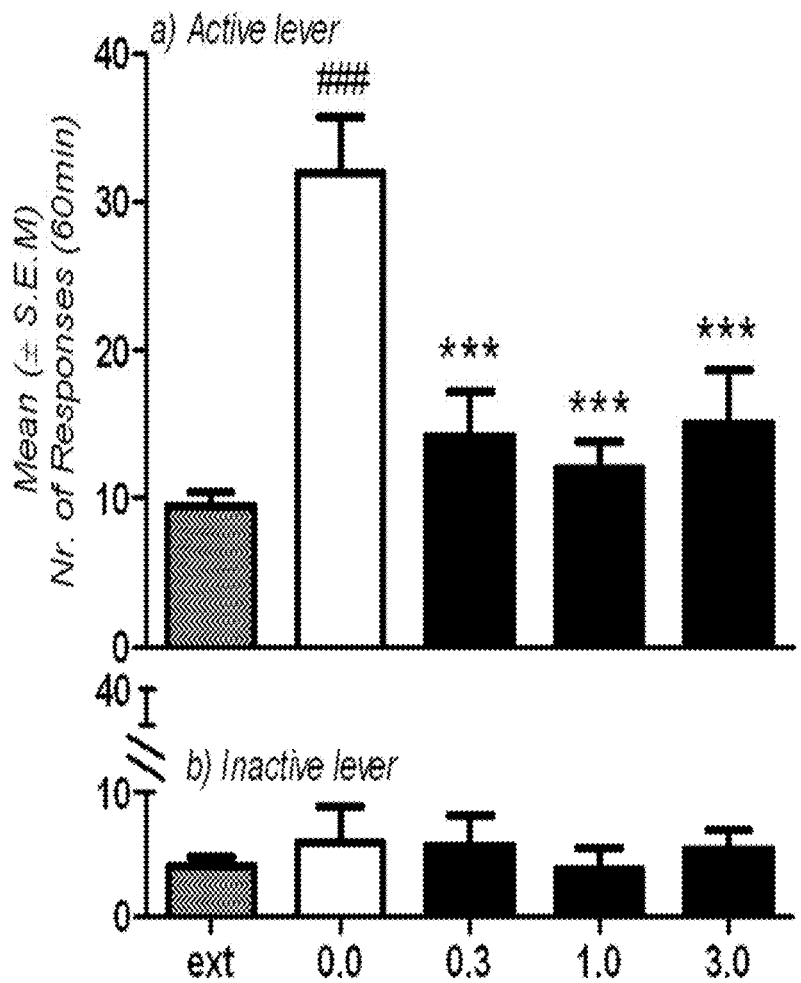
FIG. 21 demonstrates the effect of OMS182401, a PDE7 inhibitor, on cue-induced reinstatement of nicotine seeking behavior.

The ability of PDE7 inhibition to reduce nicotine use after cue-induced reinstatement was demonstrated in a rat model of nicotine addiction. Rats were trained to a stable rate of nicotine self-administration and to discriminate between nicotine and saline availability. During the nicotine sessions, a tone (7 kHz, 70 dB) was present throughout and the cue light (above the active lever) was on after the responses. During the saline sessions, the testing chamber was always illuminated by the house light and the white noise was on after each response. The discrimination phase was followed by an extinction period that was continued until lever pressing was less than 20% of the stable rate. To test the compound, vehicle or OMS182401 was injected and the animals were exposed to the nicotine stimulus conditions. Total responses at the active lever were counted during the first hour of the nicotine stimulus condition. Results are shown in FIG. 21. PDE7 inhibition by OMS182401 statistically significantly reduced cue-induced nicotine relapse in the subject animals. The response at the inactive lever was not affected by OMS182401 administration.

Figure 22:
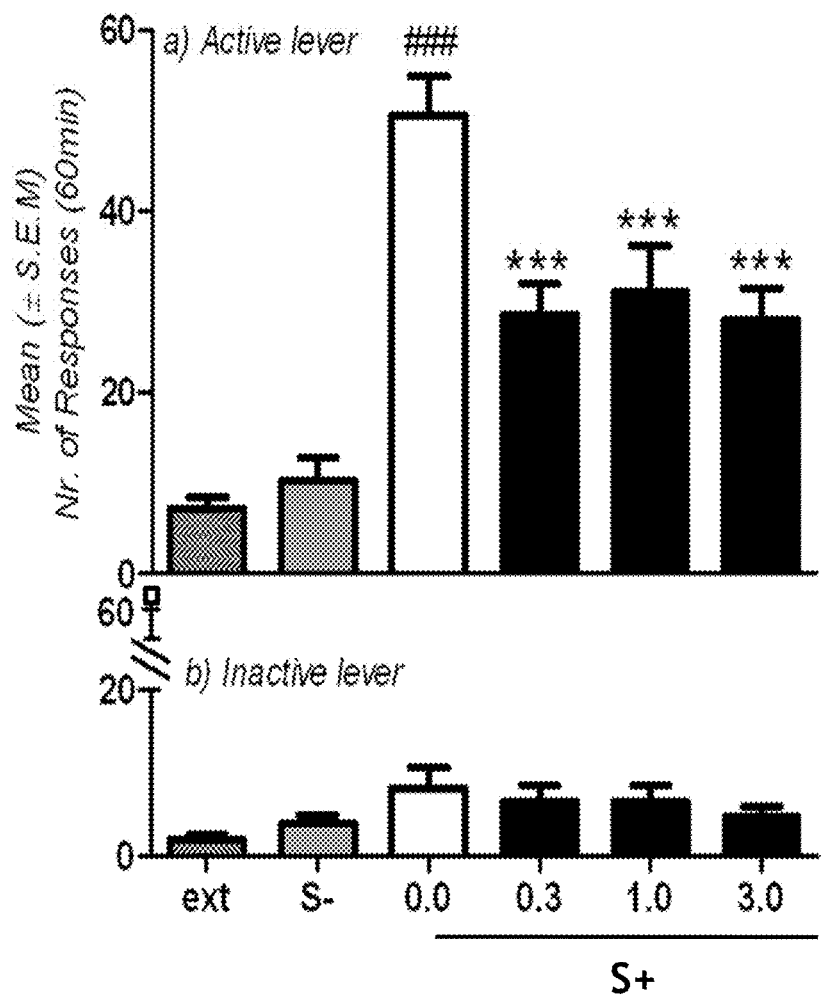
FIG. 22 demonstrates the effect of OMS182401, a PDE7 inhibitor, on yohimbine-induced reinstatement of nicotine seeking behavior.
Figure 23A:
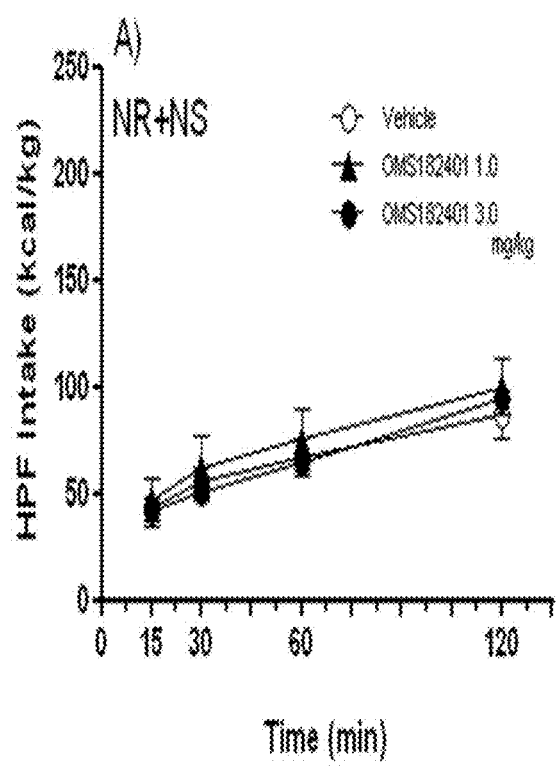
FIGS. 23A-23D demonstrates the effect of OMS182401, a PDE7 inhibitor, on stress induce binge eating by rats.
Figure 23B:
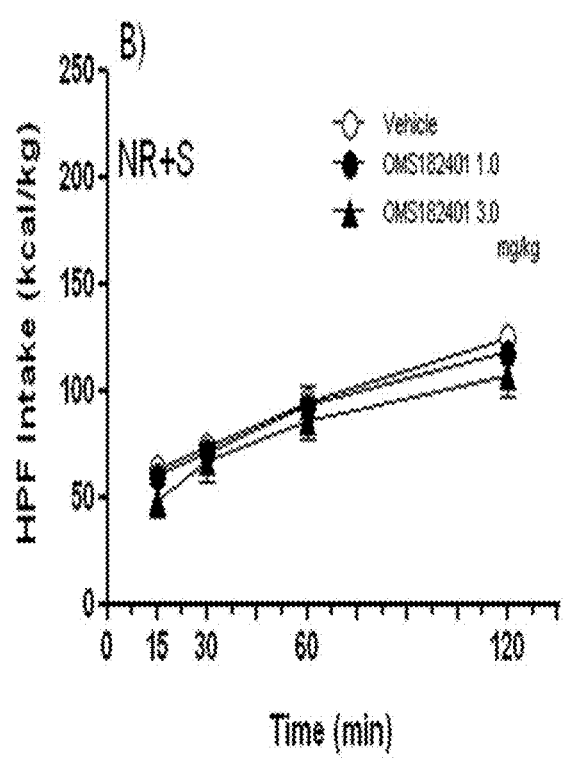
Figure 23C:
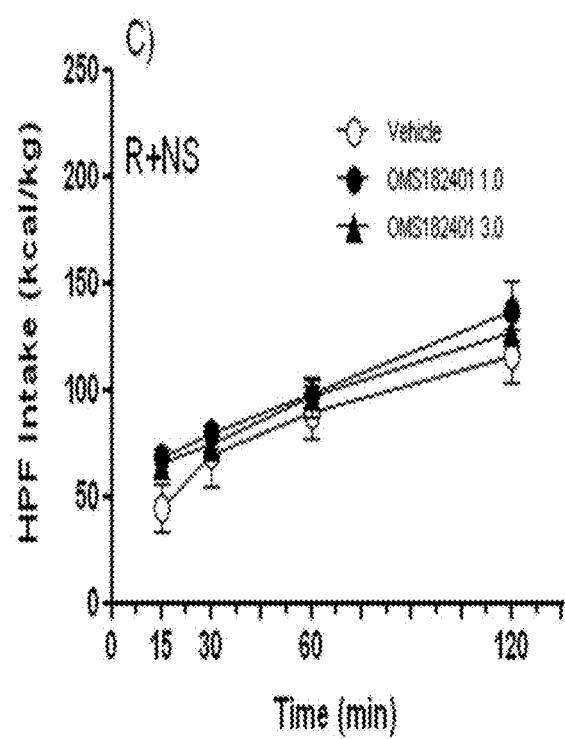
Figure 23D:
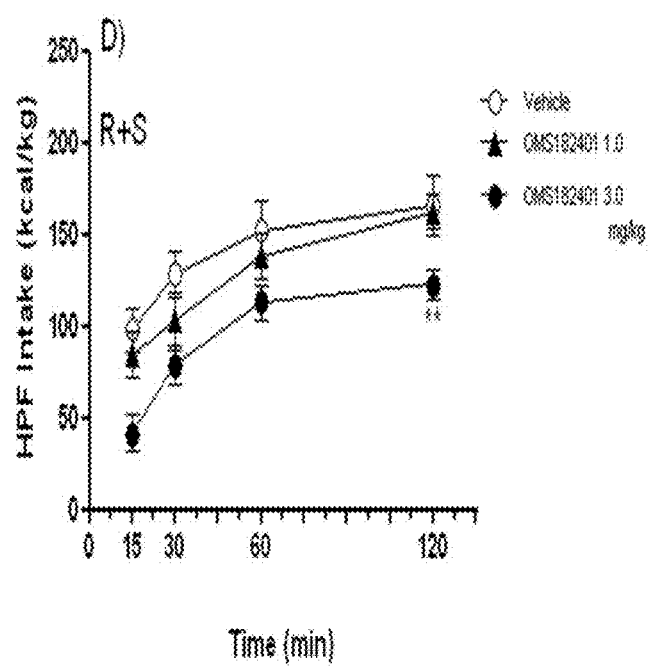
Figure 24A:
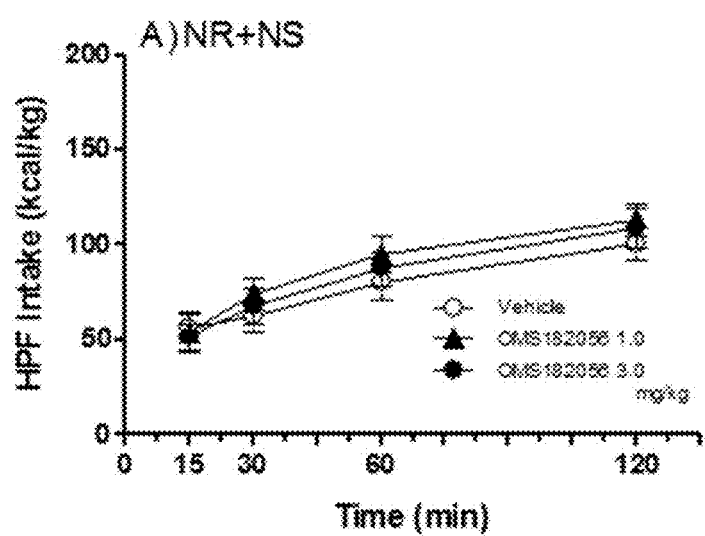
FIGS. 24A-24D demonstrates the effect of OMS182056, a PDE7 inhibitor, on stress induce binge eating by rats.
Figure 24B:
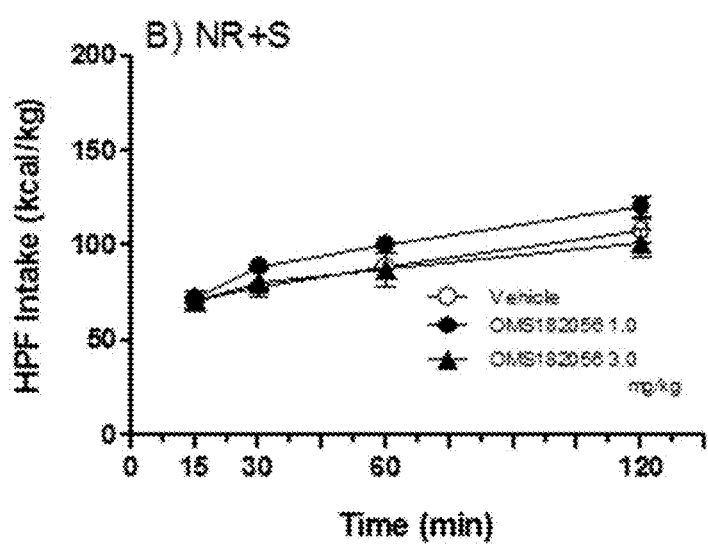
Figure 24C:
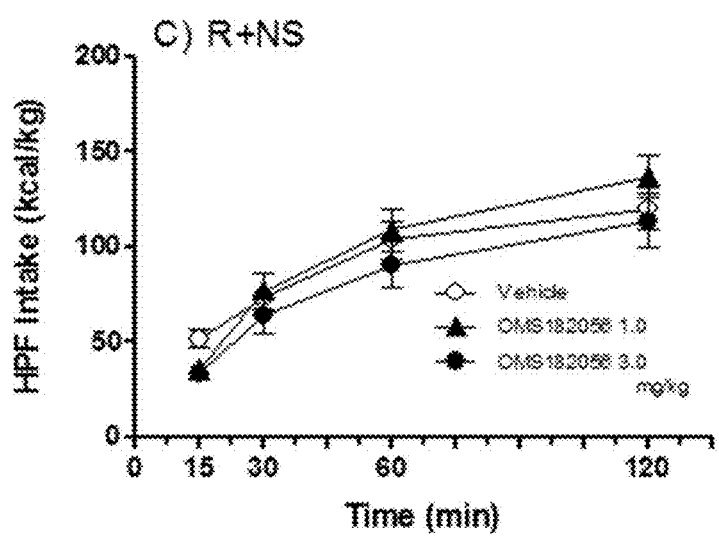
Figure 24D:
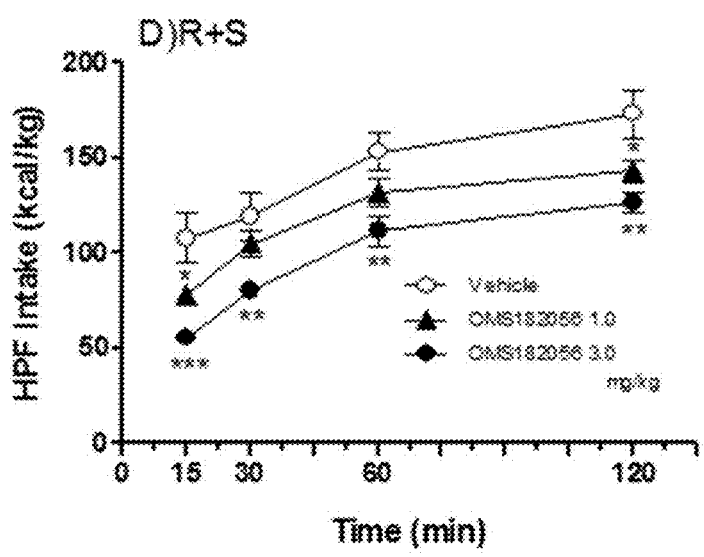
Figure 25A:
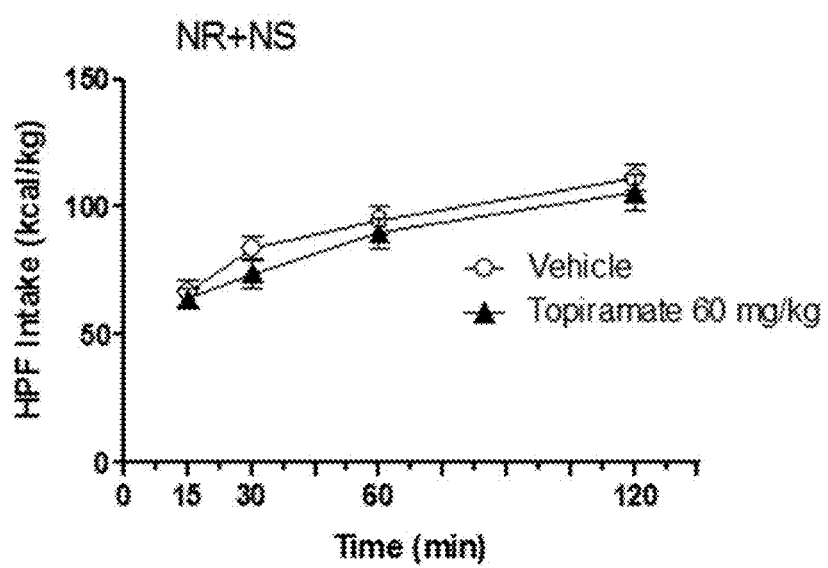
Figure 25B:
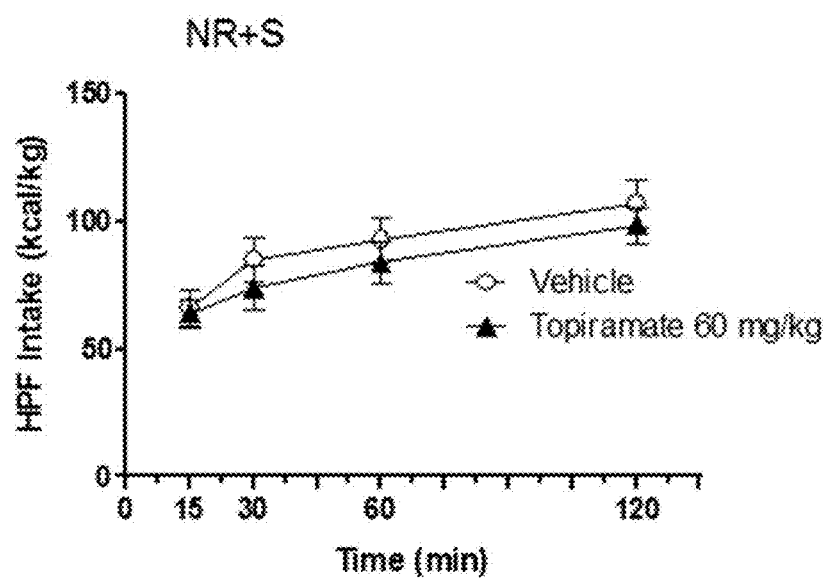
FIG. 25B shows the results for experimental animals that were not stressed and were subjected to dietary restriction.
Figure 25C:
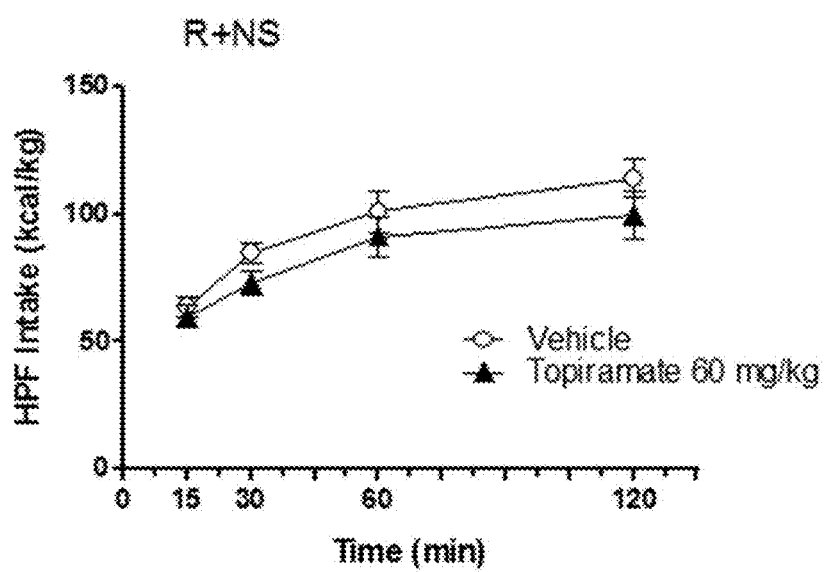
FIG. 25C shows the results for experimental animals that were stressed and were not subjected to dietary restriction.
Figure 25D:
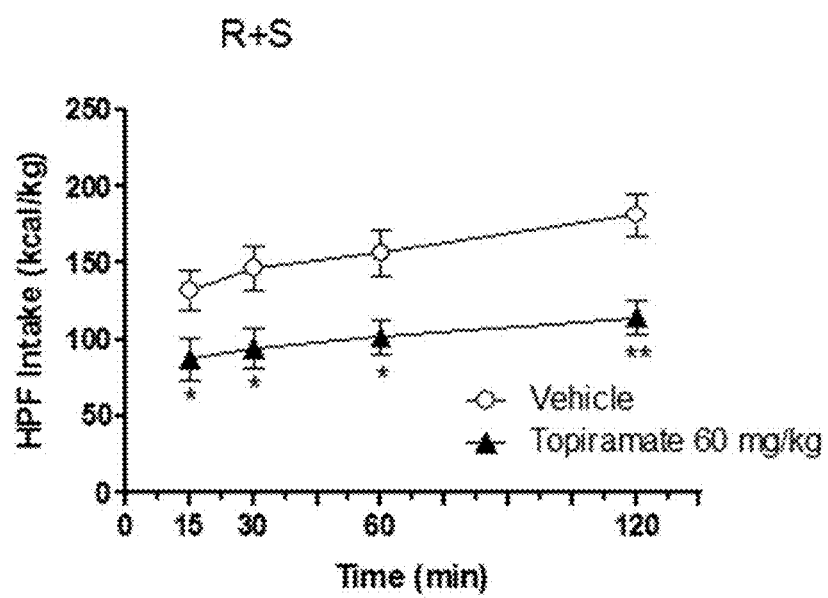

The ability of PDE7 inhibition to reduce nicotine use after stress-induced reinstatement was demonstrated in a rat model using yohimbine, an α2-adrenergic antagonist, as a stressor. Yohimbine acts as a pharmacological stressor and facilitates relapse to nicotine seeking OMS182401 was tested for its effect on nicotine-seeking behavior. Rats were trained to a stable rate of nicotine self-administration. The active lever was not associated with any reinforced reward (extinction), and the rate of "active" lever pressing declined over several sessions. When the lever-press rate declined to less than 20% of the stable rate, the animals were injected with 1.25 mg/kg yohimbine intraperitoneal (i.p.) with either vehicle or test compound. Total responses at the active lever were counted during the first hour after yohimbine administration. Results are shown in FIG. 22. PDE7 inhibition by OMS182401 statistically significantly reduced stress-induced relapse to nicotine seeking by the subject animals. Inactive lever response was not affected by administration of either yohimbine or OMS182401.

Example 5

PDE7 Inhibition Reduces Binge Eating in Response to Stress

To mimic binge eating disorder in laboratory animals, a binge eating model was developed where binge eating is elicited by yo-yo dieting and stressful exposure to Highly Palatable Food (HPF). In this model, female rats are exposed to repeated cycles of restriction and a stressful procedure characterized by exposure of animals to HPF without the possibility of accessing it. This procedure elicits a selective increase of highly palatable food intake that is overconsumed during a very short period of time. As described below, using this model, endowed with significant predictive and face validity, the effect of PDE7 inhibitors on binge eating (one of the most significant forms of food addiction) was investigated.

Reinstatement of binge eating behavior has been obtained in experimental animals through a combination of repeated food restriction and stress. [Cifani et al, *Psychopharmacology* 204:113-125 (2009)]. For the present invention, stress-induced binge eating was tested as in Cifani. The effects of two different PDE7 inhibitors, OMS182401 and OMS182056, were evaluated and compared to vehicle and to topiramate, an antiepileptic drug that has been shown in clinical trials to inhibit binge-eating episodes.

Rats were housed in individual cages and were given chow and water ad libitum for two weeks prior to the experiment. During the experiment, rats were given one of two food sources: standard rat food pellets (chow) or highly palatable food (HPF) consisting of a mixture of 52% Nutella™ chocolate cream, 33% rat food pellets, and 15% water (5.33 kcal/g; 56%, 31%, and 7% from carbohydrate, fat, and protein, respectively).

Rats were divided into four groups. Individual groups were subjected to the following 8-day cycles, three consecutive times. Rats were administered a PDE7 inhibitor or vehicle on day 25.

(1) Control group—Non-restricted, non-stressed (NR+NS). Rats had chow ad libitum for four days. On days 5 and 6, they received chow ad libitum and HPF for two hours. On days 7 and 8, rats had chow ad libitum. On day 25 the animals were not exposed to stress.

(2) Restricted, non-stressed (R+NS). Rats had chow restricted to 66% of normal intake for four days. On days 5 and 6, they received chow ad libitum and HPF for two hours. On days 7 and 8, rats had 66% of normal chow intake. On day 25 the animals were not exposed to stress.

(3) Non-restricted, stressed (NR+S). Rats had chow ad libitum for four days. On days 5 and 6, they received chow ad libitum and HPF for two hours. On days 7 and 8, rats had chow ad libitum. On day 25 the animals were exposed to stress.

(4) Restricted and stressed (R+S). Rats had chow restricted to 66% of normal intake for four days. On days 5 and 6, they received chow ad libitum and HPF for two hours. On days 7 and 8, rats had 66% of normal chow intake. On day 25 the animals were exposed to stress.

Stress was induced by placing HPF in an unreachable container within sight and smell of the animal for fifteen minutes before allowing the animal to eat the HPF.

On day 25, after appropriate animals were stressed, animals were administered either the PDE7 inhibitor OMS182401 (1.0 or 3.0 mg/kg i.p.), the PDE7 inhibitor OMS182056 (1.0 or 3.0 mg/kg i.p.), topirimate (60 mg/kg i.p.) or a control vehicle. After one hour, animals were given HPF and ad libitum chow. Intake of HPF was measured after two hours.

Results are shown in FIGS. 23A-23D for OMS182401, in FIGS. 24A-24D for OMS182056 and in FIGS. 25A-25D for topirimate.

In all groups, animals ate increasing amounts of HPF over the two-hour period. In NR+NS, NR+S and R+NS groups administration of OMS182401 did not significantly affect the amount of HPF consumed by the animals. In the R+S group, both the initial rate of HPF consumption and the total amount eaten in two hours were greater than in the other three groups. Thus the R+S condition models human binge eating. In addition, in the R+S group, animals administered 3.0 mg/kg OMS182401 consumed less HPF than other animals. By the end of the two-hour period, the difference in HPF consumption between the control animals and the animals given 3.0 mg/kg OMS182401 was significant. Thus, administration of the PDE7 inhibitor OMS182401 reduced stress-induced binge eating in a rat model of the condition.

A statistically significant OMS182056 effect was observed in only one (R+S) of the four groups of rats: R+S group [$F(2,22)=10.79$, $p<0.001$], NR+NS group [$F(2,24)=0.31$, $p>0.05$]; R+NS group [$F(2,24)=0.84$, $p>0.05$]; NR+S group [$F(2,24)=1.41$, $p>0.05$]. Post-hoc comparisons showed statistical significant differences in HPF intake in response to both doses of OMS182056 in the R+S group. The effect of the higher dose (3 mg/kg i.p.) was observed at all the times of observation, while the dose of 1 mg/kg i.p. was effective only at 15 and 120 min (*$p<0.05$).

Topiramate (60 mg/kg i.p.) also reduced HPF intake only in the R+S group: [F(1,15)=9.03, p<0.01] but not in the others: NR+NS group [F(1,16)=0.84, p>0.05]; R+NS group [F(1,16) =1.59, p>0.05]; NR+S group [F(1,16)=0.49, p>0.05]. Post-hoc comparisons showed that the effect was evident at all the times of observation (*p<0.05).

Statistical analysis showed that stress exposure in animals with a history of food restriction elicits a marked binge-eating behavior. These animals (R+S group) eat a significantly higher amount of HPF compared to control rats (NR+NS) that were not subjected to food restriction experiences and stress. The efficacy of OMS182401 and of OMS182056 in reducing HPF in the R+S group but not in the other groups (in which animals do not demonstrate binge-eating behavior) further demonstrates the validity of the model. These drugs appear to reduce binge eating behavior without affecting general food consumption. Interestingly, at the highest dose, OMS182056 appeared to decrease compulsive eating more potently than the reference drug topiramate.

Example 6

PDE7 Inhibition Reduces Stress Induced Relapse to Food Seeking

In order to assess the ability of PDE7 inhibitors to prevent relapse to excess food intake in food addicts, the PDE7 inhibitor OMS182399 was evaluated in a model of yohimbine-induced relapse to food seeking Sixteen male Long Evans rats were first habituated and then fed a diet of 60% of normal food intake daily during a two-month training phase. During the training phase, the rats were trained to a stable rate of highly palatable food self-administration. Rats were trained to press an active lever in a test chamber for the delivery of 45 mg pellets of highly palatable food (HPF) containing high levels of fat (35% w/w) and moderate levels of carbohydrates (45% w/w), available from Bioserve, Frenchtown N.J. Rats were trained for three hours/day, every other day, on a fixed-ratio-1 schedule of reinforcement, with each lever press being reinforced with a pellet of HPF and a 20-second timeout between presses. Depression of an inactive lever did not lead to food reinforcement.

This self-administration phase was then followed by an extinction phase, during which depression of the active lever did not lead to any HPF or other reward. The extinction phase continued daily for fourteen sessions. During the last four sessions, the rats were habituated to injections.

Figure 26:
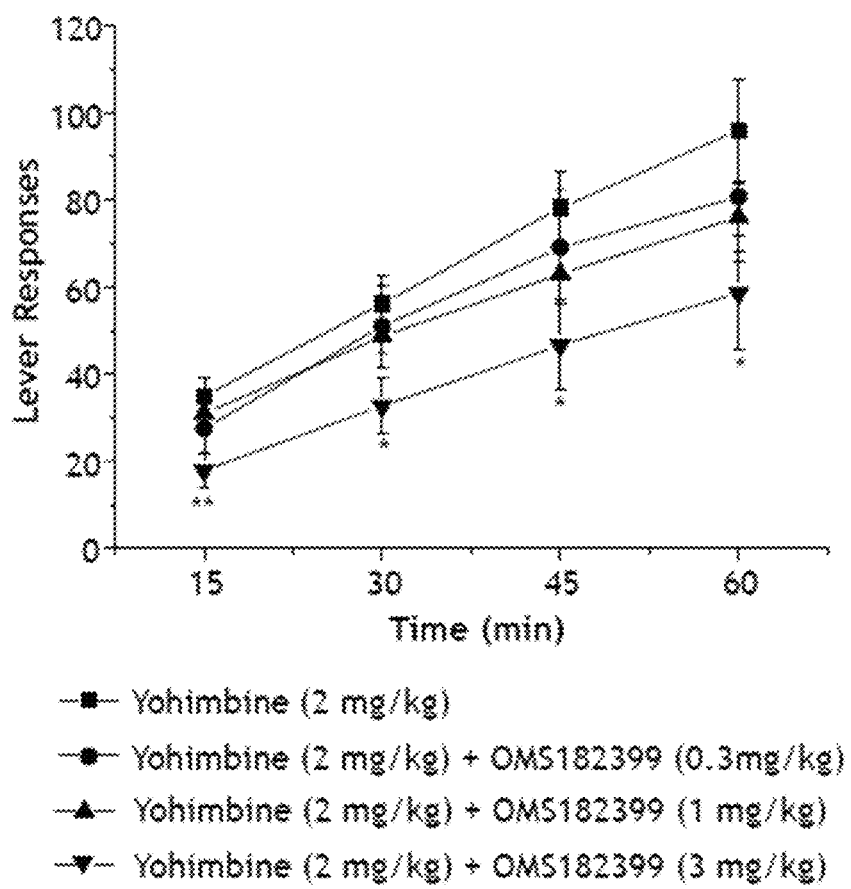

Following the extinction phase, the test phase was commenced, in which rats were injected with yohimbine, which acts as a pharmacologic stressor and facilitates relapse to excess food seeking Rats were injected i.p. with either OMS182399 (0.3, 1.0 or 3.0 mg/kg) or saline, followed 10 minutes later by injections of yohimbine or distilled water. A testing session started 30 minutes after the yohimbine or distilled water injection, in which rats were again placed in a test chamber with an active lever delivering HPF and an inactive lever. Reinstatement behavior (depression of the active lever) was measured at 14-, 30-, 45-, 60- and 180-minute time points. When total active lever responses over the first hour were compared in yohimbine treated rats, OMS182399 was shown to have reduced stress-induced relapse to food seeking in a statistically significant and dose-dependent fashion, as shown in FIG. 26. Inactive lever response was not affected by either yohimbine or OMS182399 (data not shown). In contrast to the effect of OMS182399 in yohombine-treated rats, in a further experiment, OMS182399 injection did not reduce lever presses in vehicle-treated rats (data not shown).

Example 7

Effect on Basal and Nicotine-Induced Dopamine Release in the Nucleus Accumbens

To elucidate the mechanism of action of the PDE7 inhibitors on addictive behaviors, we examined their impact on the dopamine (DA) levels in the nucleus accumbens (NAc). Drugs of abuse are known to increase DA levels in the NAc shell, an effect directly implicated on their addictive properties (Laviolette, S. R., Van der Kooy, D., 2004. The neurobiology of nicotine addiction: bridging the gap from molecules to behavior. Nat. Rev. Neurosci. 5, 55-65). A study was performed to evaluate the effect of OMS182399 on basal and nicotine-induced DA release in the NAc of Wistar rats by an in vivo microdialysis study. Male Wistar rats (Harlan, Italy) weighing 275-300 g were housed in groups of six per cage with standard food (Morini, Italy) and water ad libitum, for at least five days in the central animal room under constant temperature (23° C.), humidity (60%) and a 12 hour light/dark cycle (light from 8 a.m. to 8 p.m.).

Concentric dialysis probes with a dialysing portion of 1.5 mm were prepared with AN69 (acrylonitrile sodium methallyl sulfonate copolymer) dialysis fiber (310 µm o.d. 220 µm i.d. Hospal, Dasco, Italy), according to the method of De Luca et al. (2007). Rats were anaesthetized with chloral hydrate (400 mg/kg i.p.) and placed in a stereotaxic apparatus. The scalp was incised and the skull leveled between lambda and bregma. Two small holes were drilled to expose the dura and two probes were inserted vertically at the level of the NAc shell and core according to the atlas by Paxinos and Watson (1998) (coordinates shell: A: 2.2, L: 1.0 from bregma, V: −7.8 from dura; coordinates core: A, 1.4; L, 1.6 from bregma; V −7.6 from dura). Probes were fixed to the skull with glasionomeric cement (CX-Plus, Shofu Inc., Japan). Experiments were performed on freely moving rats 24 hours after probe implant. A Ringer's solution (147 mM NaCl, 4 mM KCl, 2.2 mM $CaCl_2$) was pumped through the dialysis probe at a constant rate of 1 µl/min. Samples from each of the NAc shell and core were taken every 10 or 20 minutes (depending on the experiments) and analyzed.

Dialysate samples (10 or 20 µl) were injected into an HPLC equipped with a reverse phase column (C8 3.5 um, Waters, Mildford, Mass., USA) and a coulometric detector (ESA, Coulochem II, Bedford, Mass.) to quantify DA. The first electrode was set at +125 mV and the second electrode at −175 mV. The following solution was utilized as the mobile phase: 50 mM $NaH_2PO4$, 0.1 mM $Na_2$-EDTA, 0.5 mM n-octyl sodium sulfate, 15% (v/v) methanol, pH 5.5. The mobile phase was pumped with a Jasco pump with a flow rate of 0.6 ml/min. The sensitivity of the assay for DA was 5 fmol per sample. At the end of the experiment, animals were sacrificed by transcardial perfusion with 100 ml of saline (0.9% NaCl) and 100 ml of formaldehyde (10%). The probes were removed and the brains cut on a vibratome in serial coronal slices to locate the position of the microdialysis probes. Analysis of variance (ANOVA) for repeated measures was applied to the raw data obtained from the serial assays of DA after each treatment. Results from treatments showing significant over-all changes were subjected to post hoc Tukey test, with p<0.05 being considered as statistically significant. The means of three consecutive samples differing by no more than 10% were considered as basal values.

To determine the effect of OMS182399 on basal and nicotine-induced DA release in the NAc shell and core, rats were implanted with dual microdialysis probes and, 24 hours later, administered either vehicle or OMS182399 (9 mg/kg, i.p.). NAc shell and core dialysate DA was monitored for at least three hours. If no effect on extracellular DA levels was observed, or, in case of any effect, at least two hours after the return to basal DA levels, the same animals were injected with vehicle or OMS182399 10 minutes prior to an injection of nicotine (0.4 mg/kg subcutaneopusly (sc)). Dialysate DA was monitored for at least three hours after nicotine treatment.

Figure 27:
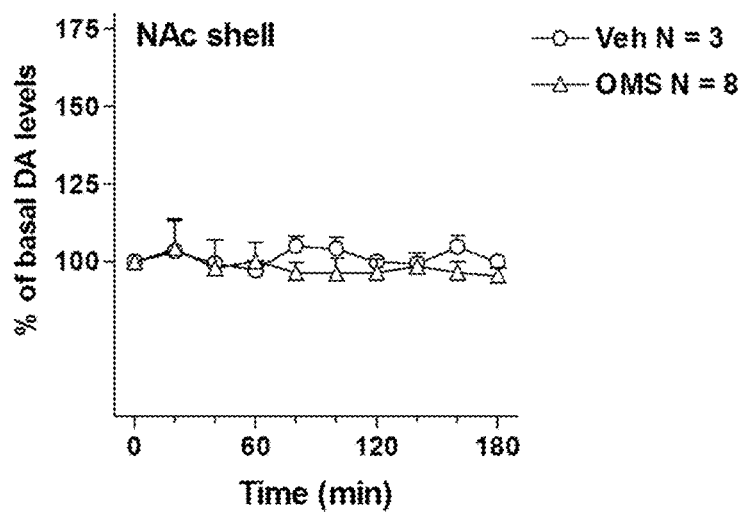
Figure 27:
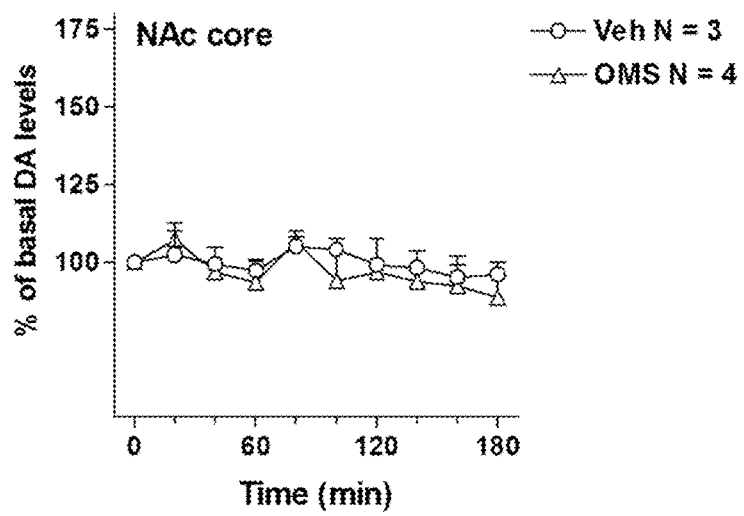

FIG. 27 shows the resulting effect of OMS182399 (9 mg/kg i.p.) on NAc shell/core extracellular DA levels. Results are indicated as mean±SEM of change in DA extracellular levels expressed as the percentage of basal values. OMS182399 has no effect on the basal DA levels of either region of the NAc.

Figure 28:
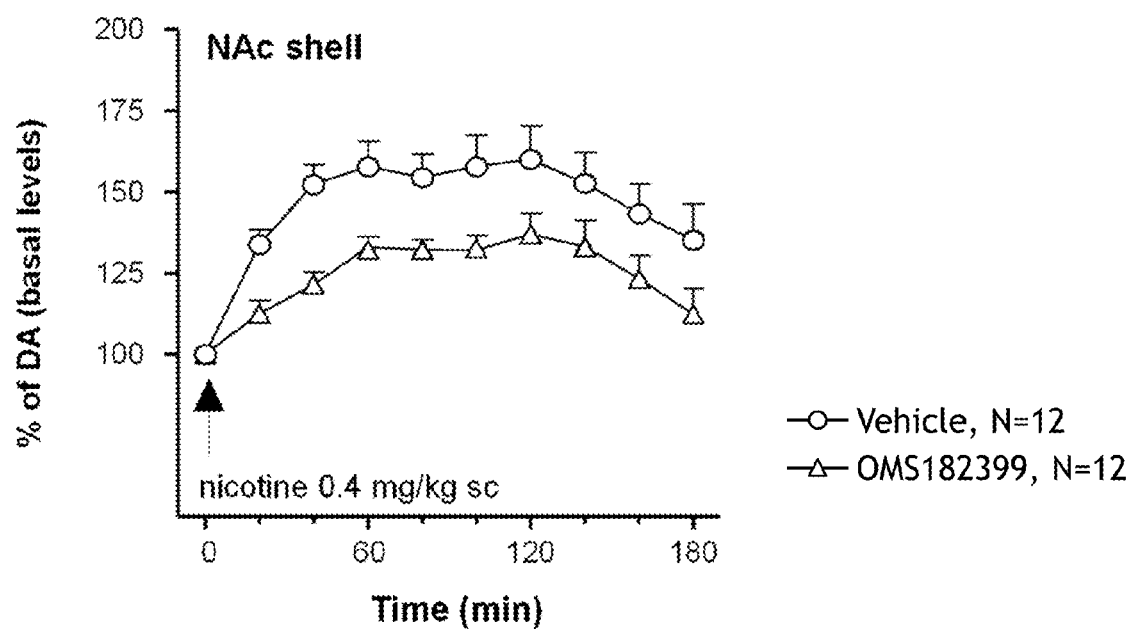

FIG. 28 shows the resulting effect of nicotine (0.4 mg/kg sc) on NAc shell extracellular DA levels in rats pre-treated with OMS182399 (9 mg/kg i.p.; 10 minutes before nicotine). Results are indicated as mean±SEM of change in DA extracellular levels expressed as the percentage of basal values. Administration of nicotine increases DA release in the NAc shell and this effect is substantially reduced by OMS182399.

Example 8

Effect of PDE7 Inhibition on Spontaneous Activity of Dopaminergic Ventral Tegmental Area Neurons and Against Nicotine The following electrophysiology studies demonstrate that selective PDE7 inhibitors are effective in a model of nicotine addiction and act by enhancing dopamine signaling through DRD1. The reinforcing effects of nicotine are believed to result from its activation of dopaminergic neurons in the ventral tegmental area (VTA) (Pidoplichko V I et al., *Nature* 390:401-404 (1997); Liu L, et al., Nicotine persistently activates ventral tegmental area dopaminergic neurons via nicotinic acetylcholine receptors containing α4 and α6 subunits. *Mol Pharmacol*, 81(4):541-8 (2012)). The inventors sought to evaluate the anti-addictive potential of PDE7 inhibitors by studying their ability to modify basal and drug of abuse-induced changes in VTA dopamine activity by performing whole-cell current clamp recordings from rat VTA horizontal slices ex vivo. For this purpose nicotine was used as an example of drugs of abuse. Moreover, considering that the PDE7 isoform is widely expressed in all major brain areas and is frequently co-expressed in the same neurons with the DRD1 [Reyes-Irisarri, et al., "Neuronal expression of cAMP-specific phosphodiesterase 7B mRNA in the rat brain," *Neuroscience* 132:1173-85 (2005); Miró, X., et al., "Differential distribution of cAMP-specific phosphodiesterase 7A mRNA in rat brain and peripheral organs," *Synapse* 40:201-214 (2001)], and that in the open-field activity assay DRD1 agonism activity is potentiated by PDE7 inhibition (Example 10 below), the effects of these agents were also compared in an electrophysiological study.

Figure 29A:
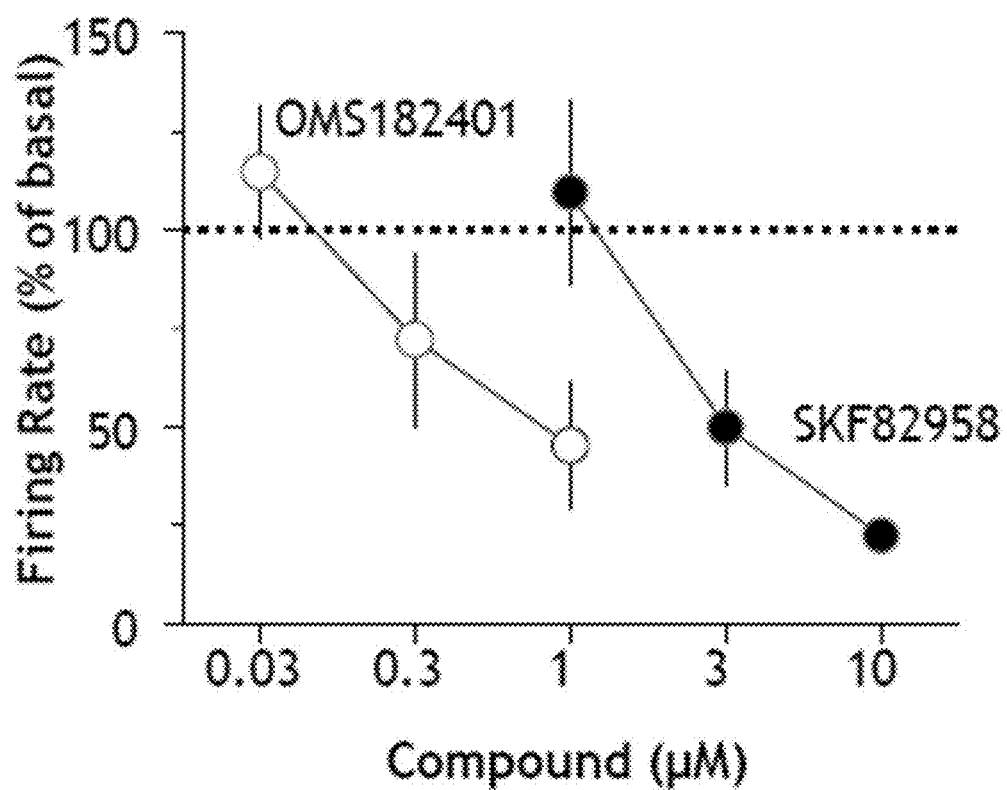
FIGS. 29A-29B demonstrate that OMS182401, a PDE7 inhibitor, inhibits spontaneous activity of dopaminergic ventral tegmental area (VTA) neurons, and potentiates the inhibitory effect of SKF82958, a dopamine D1 agonist.

Dopaminergic neurons were identified by the presence of a large hyperpolarizing current. Johnson, S. W., et al., "Opioids excite dopamine neurons by hyperpolarization of local interneurons," *J Neurosci* 12:483-488 (1992). Application of the PDE7 inhibitor OMS182401 significantly decreased the spontaneous firing rate of the dopaminergic VTA neurons (FIG. 29A) at 0.3 and 1.0 µM. Notably, a similar effect was observed by application of the DR D1 agonist SKF82958 at concentrations of 3.0 and 10.0 uM as also shown in FIG. 29A.

Figure 29B:
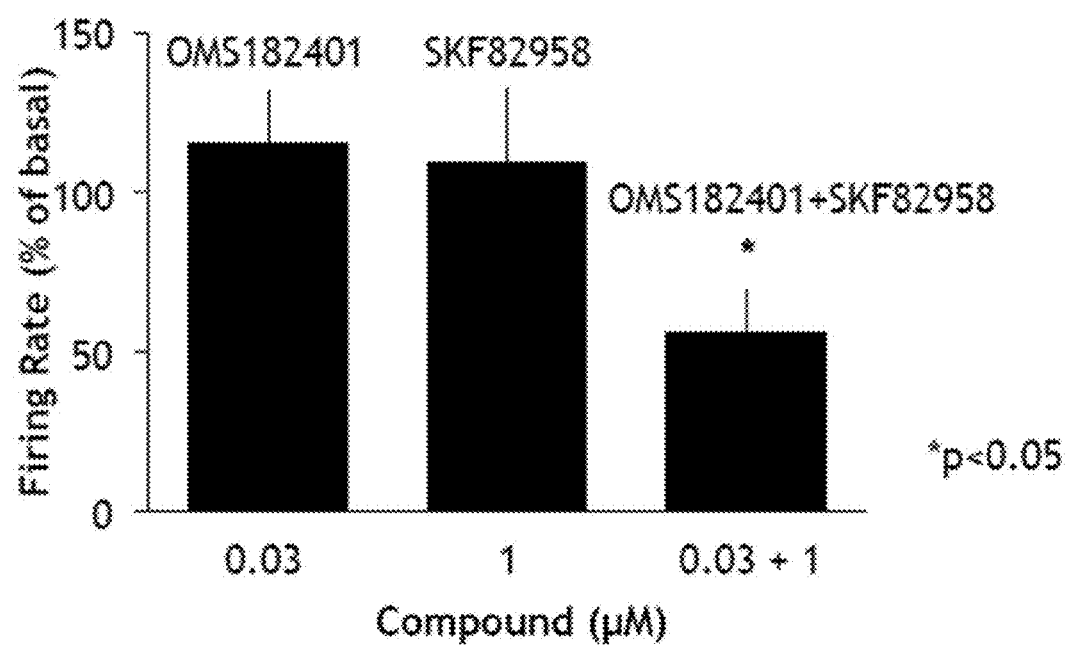

Moreover, when ineffective concentrations (i.e., too low of a concentration) of both SKF82958 and OMS182399 were applied together, the combination also produced a substantial decrease in activity (FIG. 29B), indicating that PDE7 inhibition potentiates the action of DRD1 activation and that the PDE7 inhibitor and the DRD1 agonist acted synergistically in this regard.

Figure 30:
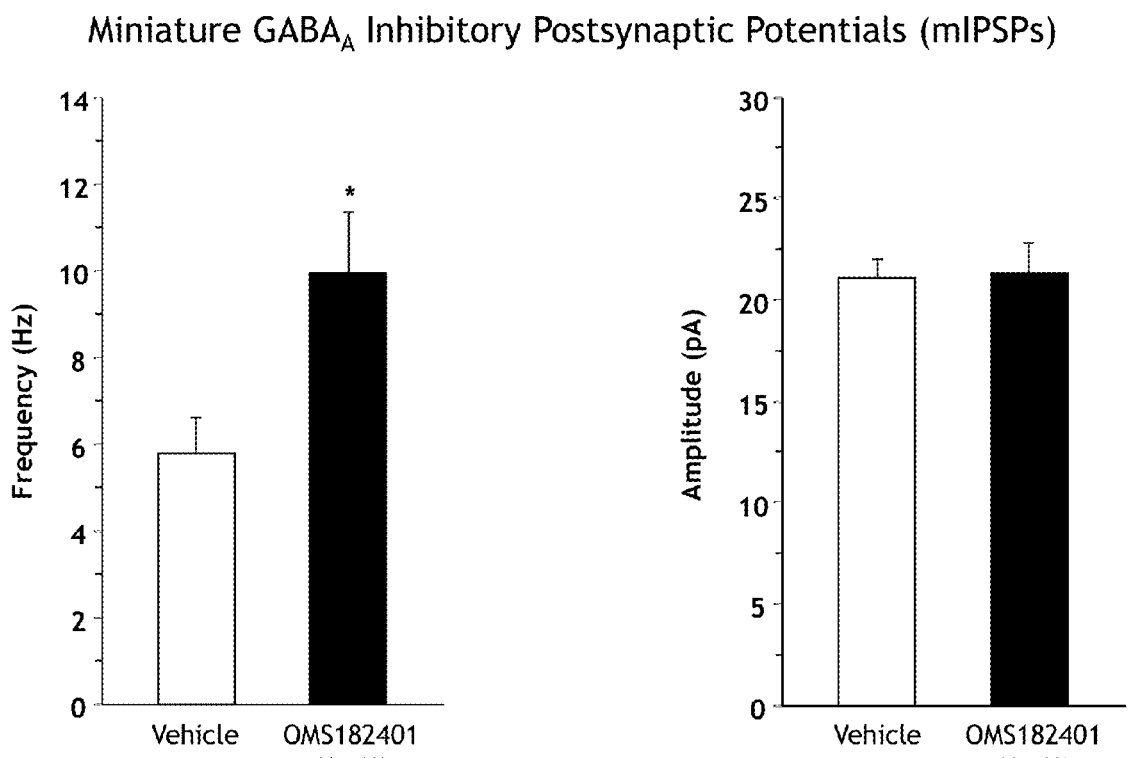

Because DRD1 stimulation increases the amplitude of GABAB-mediated inhibitory postsynaptic potentials (IPSPs), and cAMP-PKA enhanced GABAA-mediated inhibitory postsynaptic currents (IPSCs) [Bonci, A., et al., "Increased probability of GABA release during withdrawal from morphine," *J Neurosci* 17:796-803 (1997)], the inventors hypothesized that this observation (i.e., reduction of spontaneous activity of VTA DA neurons following either PDE7 inhibition or DRD1 activation) could be ascribed to an increased probability of GABA release from presynaptic terminals. This hypothesis was in part confirmed by analysis of miniature inhibitory postsynaptic potentials (mIPSPs) (FIG. 30), which demonstrated an increase in frequency but not in amplitude of mIPSPs following PDE7 inhibition. In addition, when the PDE7 inhibitor was applied in the presence of the GABA-A receptor antagonist picrotoxin (100 microM, data not shown), the inhibition was still present, suggesting the involvement of GABA-B receptors in PDE7 inhibitor effects. Indeed, in the presence of the GABA-B antagonist CGP35348 (100 uM), the inhibitory effect of OMS182401 on the spontaneous firing of the VTA DA neurons was no longer observed (data not shown).

Figure 31:
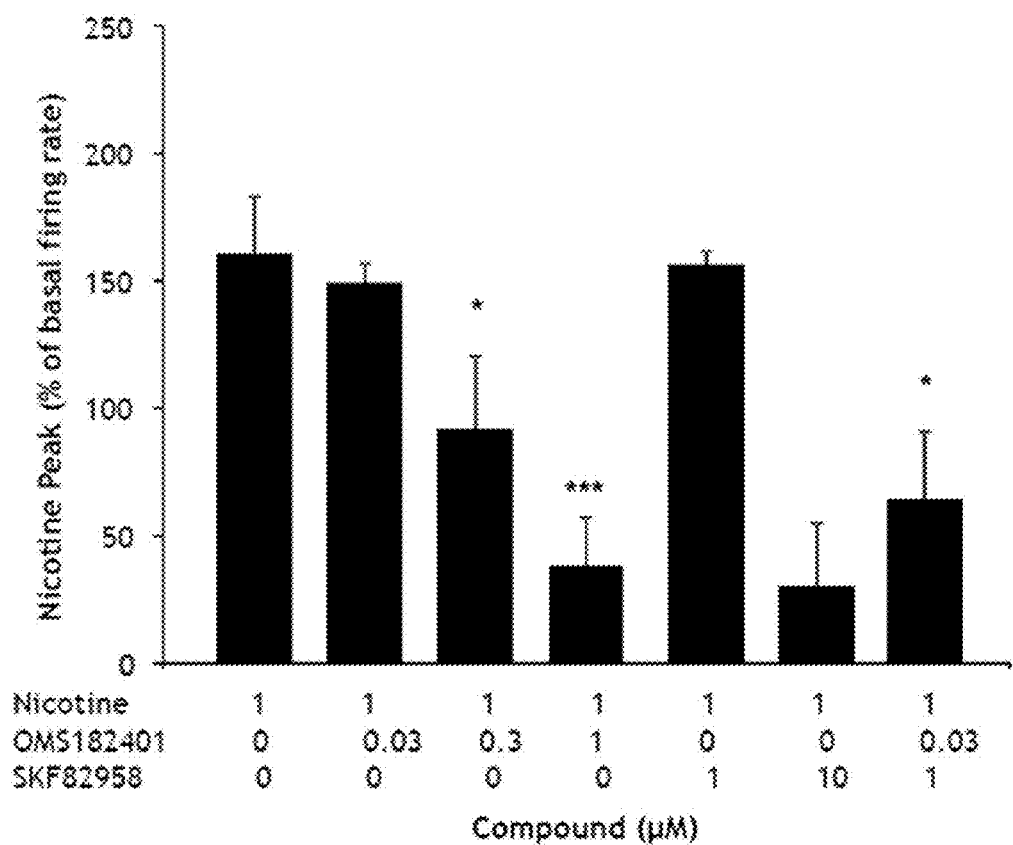
FIG. 31 demonstrates that the PDE7 inhibitor OMS182401 inhibits the activation of dopaminergic VTA neurons by nicotine and acts synergistically with the dopamine D1 agonist SKF82958.

In an additional study, OMS182401 was observed to reverse the activation of the VTA dompaminergic neurons by nicotine (FIG. 31). Additionally, while 30 nM OMS182401 or 1 uM SKF82958 alone were ineffective, the combination of 30 nM OMS182401 with 1 uM SKF82958 reversed the nicotine-induced activation (p<0.05). This demonstrates that PDE7 inhibition potentiates DRD1 signaling and that the combination of the PDE7 inhibitor and the DRD1 agonist acted greater than additively in this regard.

Figure 32:
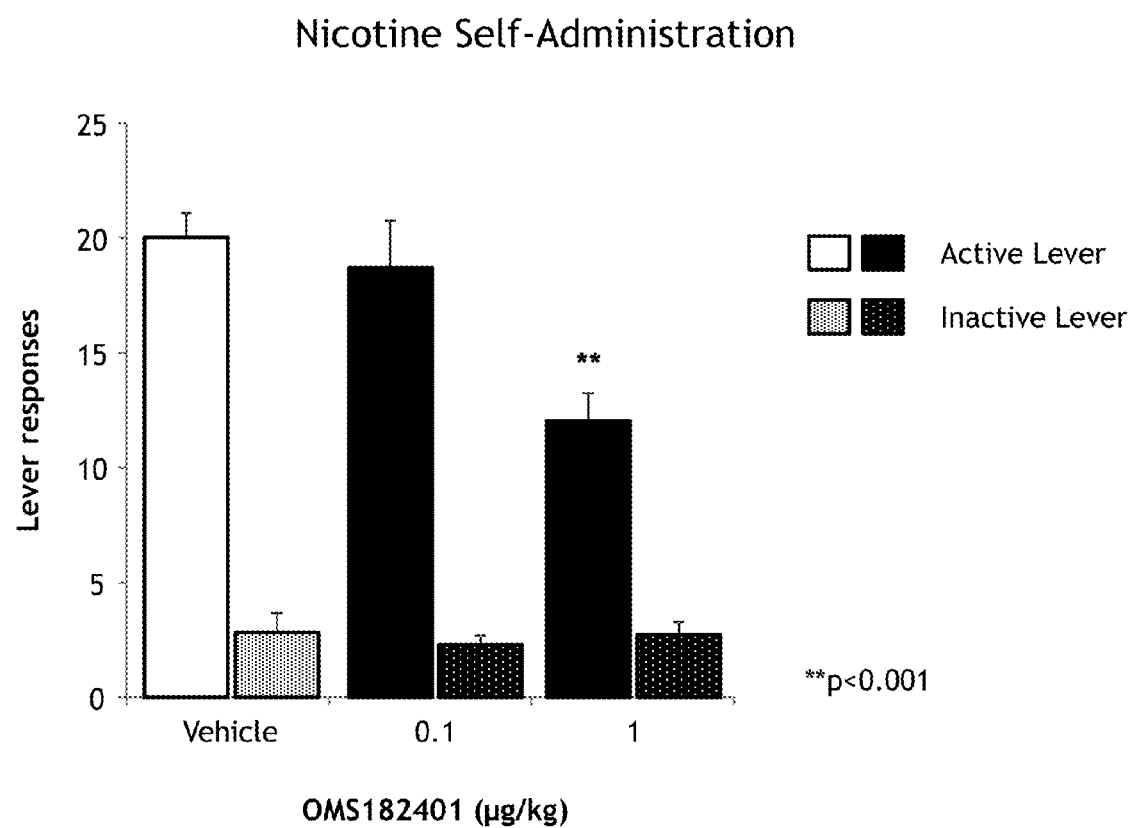
FIG. 32 demonstrates the effect of direct administration of the PDE7 inhibitor OMS182401 into rat VTA.

To demonstrate in vivo that VTA is the site of action of the effects of PDE7 inhibition, OMS182401 was directly delivered into the rat VTA and its effects on nicotine self-administration were assessed. Rats were surgically implanted with jugular catheters and allowed to recover for one week. They were then subjected to intracranial surgery for bilateral implantation of guide cannulae in the VTA. Following recovery, they underwent daily two-hour (short-access) training sessions, in which every active-lever press triggered the delivery of 0.03 mg of nicotine. After achieving a stable rate of active-lever pressing, vehicle or drug was injected into the VTA immediately before the test session. Reinforced responses were recorded in a Latin-square design (i.e., each animal receives each dose) experiment. The location of the jugular catheters was confirmed histologically at the conclusion of the experiments. As shown in FIG. 32, direct administration of the PDE7 inhibitor into the rat VTA reduced nicotine self-administration, confirming that the VTA is the site of action of the effects of PDE7 inhibition in animals.

Example 9

Effect of PDE7 Inhibition on Ventral Tegmental Area Dopamine Neuronal Activity and Against Cocaine, Morphine and Alcohol An additional electrophysiology study was completed to evaluate the effect of the PDE7 inhibitor OMS182399 on VTA DA neuronal activity in the setting of cocaine, morphine or alcohol. The preparation of VTA slices was as described above in Example 8.

Drug-induced changes in firing rate were calculated by averaging the effects after drug administration (five minutes) and normalizing to the pre-drug baseline. All the numerical data are given as mean±s.e.m. Data were compared and analyzed by utilizing two-way ANOVA for repeated measures (treatment×time), or Student's t-test for repeated measures, when appropriate. Statistical analysis was performed by means of the GraphPad Prism program. The significance level was established at $P<0.05$.

Figure 33:
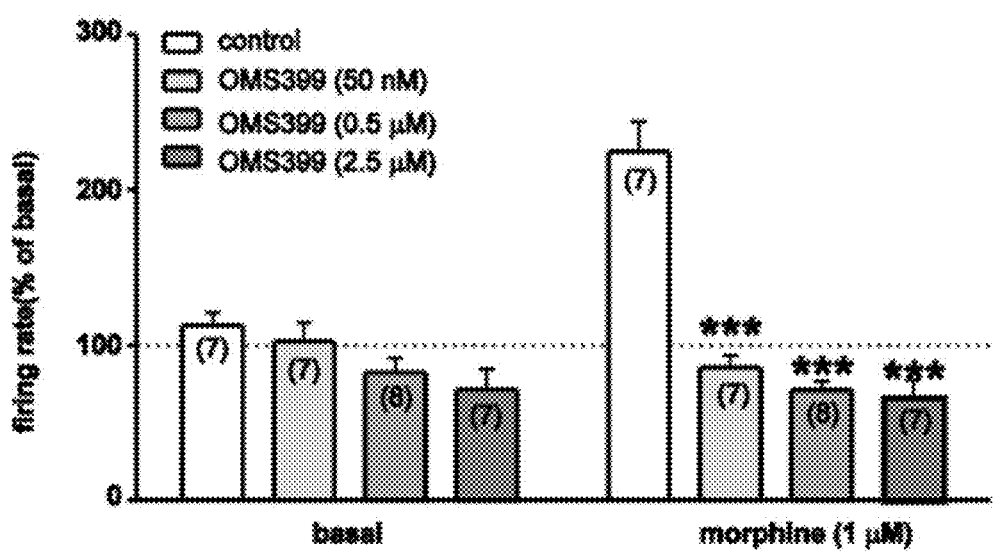
FIG. 33 demonstrates that the PDE7 inhibitor OMS182399 dose-dependently blocks morphine-induced excitation of VTA dopamine cells.

The acute effect of OMS182399 was investigated on dopamine neurons of the VTA in a rat horizontal brain slice preparation containing the midbrain. Whole-cell current-clamp recordings were performed from VTA dopamine neurons. Acute bath application of OMS182399 (0.05, 0.5 and 2.5 µM, 5 min) significantly decreased the spontaneous activity of VTA dopamine neurons in a dose-dependent fashion, as shown in FIG. 33. One way ANOVA for repeated measures revealed that the means were significantly different: $F_{3,42}=5.67$, $P=0.002$ (n=15). Data are expressed as mean±SEM. **$P<0.005$.

As also shown in FIG. 33, acute application of the PDE7 inhibitor OMS182399 (five minutes before morphine application) was able to block morphine-induced excitation of VTA DA cells (morphine 1 µM, 3 min: 224.4±19.5% of basal firing rate, n=7) in a dose-dependent manner, with statistical significance (unpaired t-test) at the dose of 50 nM ($P<0.0001$, n=7); 0.5 µM ($P=0.0001$, n=8); 2.5 µM ($P=0.0002$, n=7); which per se did not affect basal spontaneous activity of DA neurons. The dashed line in FIG. 33 represents the normalized basal spontaneous activity of VTA DA cells. Data are expressed as mean±SEM, ***$P<0.0001$. Notably, statistical analysis (paired t-test) did not reveal any difference on firing activity of VTA DA cells between the effects of OMS182399 in the presence or absence of morphine, i.e., the addition of morphine could not overcome the effect of OMS182399 ($P>0.05$ at all concentrations tested).

Figure 34:
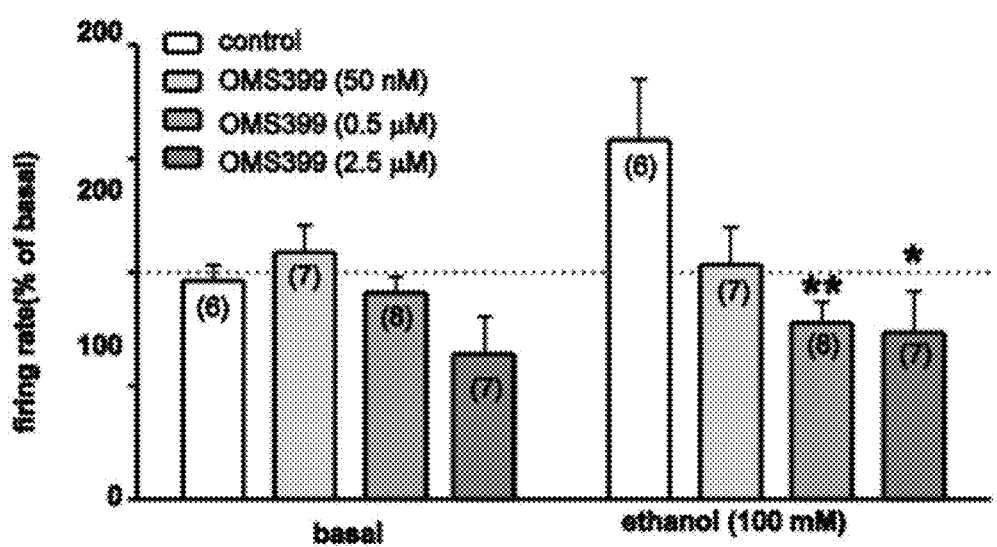
FIG. 34 demonstrates that acute application of the PDE7 inhibitor OMS182399 dose-dependently blocks ethanol-induced excitation of VTA dopamine cells.

As shown in FIG. 34, acute application of the PDE7 inhibitor OMS182399 (five minutes before bath application of ethanol) blocked ethanol-induced excitation of VTA DA cells (Ethanol 100 mM, 5 min: 158.3±26.7% of basal firing rate, n=6) in a dose-dependent manner, with statistical significance (unpaired t-test) at the dose of 500 nM ($P=0.007$, n=8); 0.05 µM ($P>0.05$, n=7); 2.5 µM ($P=0.02$, n=7); which per se decreased basal spontaneous activity of DA neurons. The dashed line in FIG. 34 represents the normalized basal spontaneous activity of VTA DA cells. Data are expressed as mean±SEM, **$P<0.001$, *$P<0.05$. Notably, statistical analysis (paired t-test) revealed a difference on firing activity of VTA DA cells between the effects of OMS182399 in th presence and absence of ethanol at an OMS182399 dose of 500 nM ($P=0.01$, n=8), whereas no statistical difference was revealed for the other two doses tested ($P=0.6$ at both concentrations tested).

Figure 35:
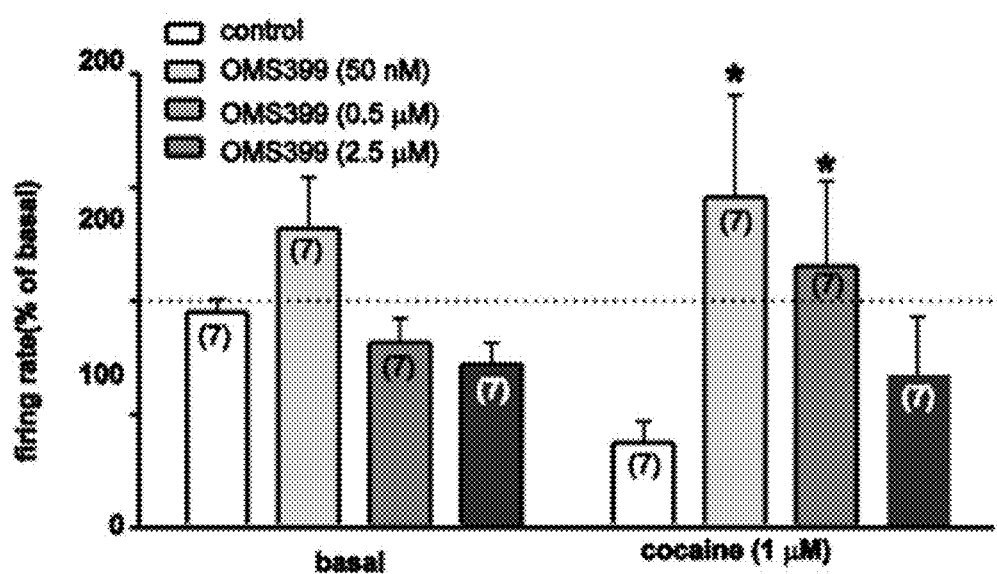
FIG. 35 demonstrates that acute application of the PDE7 inhibitor OMS182399 dose-dependently reverts cocaine-induced excitation of VTA dopamine cells.

As shown in FIG. 35, acute application of the PDE7 inhibitor OMS182399 (five minutes before bath application of cocaine) was able to block cocaine-induced inhibition of VTA DA cells (cocaine 1 µM, 5 min: 36.4±9.1% of basal firing rate, n=7) at the doses of 50 nM ($P=0.036$, n=7) and 0.5 µM ($P=0.049$, n=7). The dashed line in FIG. 35 represents the normalized basal spontaneous activity of VTA DA cells. Data are expressed as mean±SEM, *$P<0.05$. Notably, at the highest dose tested (2.5 µM), which per se produces a qualitatively similar effect to cocaine (i.e., decrease of firing rate of dopamine neurons), OMS182399 failed to prevent cocaine-induced inhibition of spontaneous activity of dopamine neurons (unpaired t-test vs cocaine $P=0.5$; paired t-test vs OMS182399 $P=0.8$). Remarkably, in the presence of the lowest dose tested (i.e., 50 nM) cocaine's effects on dopamine neuronal activity are opposite to control (i.e., excitation as opposed to inhibition).

As shown in the electrophysiology studies described above, PDE7 inhibition blocks the effects of commonly used drugs of abuse irrespective of the chemical structure and mechanism of action of the drugs of abuse. Notably, as shown above, OMS182401 can block nicotine-induced excitation of dopamine cell firing rate, which may be ascribed to activation of α4β2 nAChRs located on dopamine somata [Picciotto M R; et al., Nature, 391:173-177 (1998)]. Similarly, the structurally related compound OMS182399 can block both morphine- and ethanol-induced excitation of dopamine neurons, both of which are due to disinhibitory mechanisms on dopamine cells [Theile J W, et al. Neuroscience, 172:94-103; Jalabert M, et al., Proc Natl Acad Sci USA, 108:16446-16450 (2011)]. Interestingly, OMS182399 can also revert cocaine effects. The effects on cocaine are more complex because cocaine induces both fast dopamine increases in striatal regions and a reduction of midbrain dopamine cell firing (through activation of D2 receptors located in the soma).

Example 10

Figure 36:
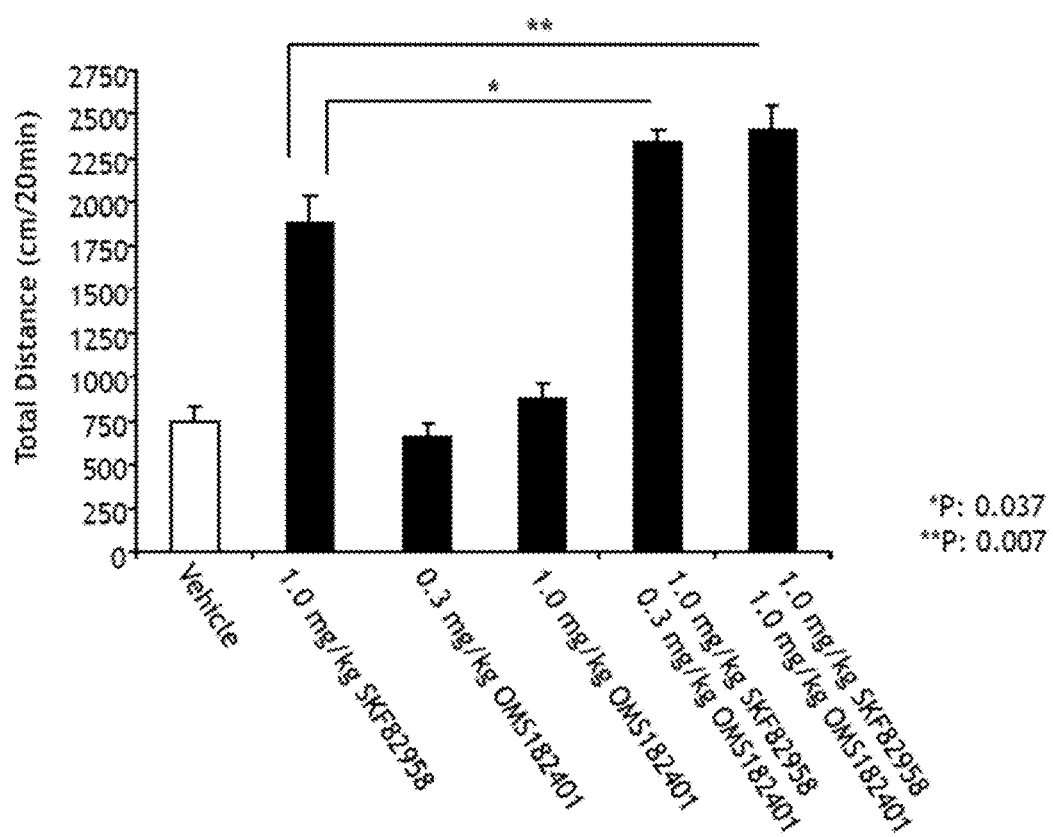
FIG. 36 demonstrates that the PDE7 inhibitor OMS182401 potentiates the activity of the dopamine D1 agonist SKF82958 in an open field activity model.

Effect of PDE7 Inhibition on Dopamine D1 Subtype Receptor-Mediated Stimulation of Open Field Activity In order to assess the ability of PDE7 inhibitors to enhance DRD1 signaling in vivo, the effects of the PDE7 inhibitor OMS182401 and the DRD1 agonist SKF82958, alone and in combination, were evaluated in an open field activity model using wild type C57BL/6 mice. As shown in FIG. 36, the DRD1 agonist stimulated open-field activity at 1 mg/kg. OMS182401 had no effect as a single agent (even at doses higher than 1 mg/kg, data not shown), but significantly enhanced the stimulatory effect of the DRD1 agonist SKF82958.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method of treating an addiction that is an addiction to an addictive substance or that is the practice of an addictive or compulsive behavior associated with a primary impulse-control disorder or an obsessive-compulsive disorder, comprising:
   determining that a subject has or is at risk of developing an addiction; and
   administering to the subject an amount of an inhibitor of a phosphodiesterase 7 (PDE7) effective for the treatment of the addiction or reducing the likelihood that a subject will become addicted.

2. The method of claim 1, wherein the subject is addicted to an addictive agent.

3. The method of claim 2, wherein the subject is addicted to an addictive agent selected from the group consisting of: alcohol, nicotine, marijuana, a marijuana derivative, an opioid agonist, a benzodiazepine, a barbiturate, and a psychostimulant.

4. The method of claim 3, wherein the addictive agent is alcohol.

5. The method of claim 3, wherein the addictive agent is nicotine.

6. The method of claim 3, wherein the opioid agonist is selected from the group consisting of: morphine, methadone, fentanyl, sufentanil and heroin.

7. The method of claim 3, wherein the psychostimulant is cocaine, amphetamine or an amphetamine derivative.

8. The method of claim 7, wherein the psychostimulant is cocaine.

9. The method of claim 1, wherein the addiction is an addictive or compulsive behavior associated with a primary impulse-control disorder or an obsessive-compulsive disorder.

10. The method of claim 9, wherein the primary impulse-control disorder is selected from the group consisting of: binge eating, pathological gambling, pathological use of electronic devices, pathological use of electronic video games, pathological use of electronic communication devices, pathological use of cellular telephones, addiction to pornography, sex addiction, compulsive spending, anorexia, bulimia, intermittent explosive disorder, kleptomania, pyromania, trichotillomania, compulsive over-exercising, and compulsive overworking.

11. The method of claim 10, wherein the primary impulse-control disorder is binge eating.

12. The method of claim 1, wherein the PDE7 inhibitory agent has an $IC_{50}$ for inhibiting PDE7A and/or PDE7B activity of less than about 1 μM.

13. The method of claim 1, wherein the PDE7 inhibitory agent has an $IC_{50}$ for inhibiting PDE7A and/or PDE7B activity of less than about 100 nM.

14. The method of claim 1, wherein the PDE7 inhibitory agent is a selective PDE7 inhibitor for which the lesser of the $IC_{50}$ for inhibiting PDE7A activity and the $IC_{50}$ for inhibiting PDE7B activity is less than one-tenth the $IC_{50}$ that the agent has for inhibiting the activity of any other PDE enzyme from the PDE1-6 and PDE8-11 enzyme families.

15. The method of claim 1, wherein the PDE7 inhibitory agent is a highly selective PDE7 inhibitor for which the lesser of the $IC_{50}$ for inhibiting PDE7A activity and the $IC_{50}$ for inhibiting PDE7B activity is less than one-fiftieth the $IC_{50}$ that the agent has for inhibiting the activity of any other PDE enzyme from the PDE1-6 and PDE8-11 enzyme families.

16. The method of claim 1, wherein the PDE7 inhibitory agent has a molecular weight of less than about 450 g/mole.

17. The method of claim 1, wherein the PDE7 inhibitory agent is a member selected from the group consisting of formula 1A, formula 1B, formula 29, formula 30, formula 31, formula 32, formula 33, formula 34, formula 35, formula 36, formula 37, formula 38, formula 39, formula 40, formula 41, formula 42, formula 43A, formula 43B, formula 44, formula 45, formula 46, formula 47, formula 48, formula 49, formula 50, formula 51, formula 52, formula 53, formula 54, formula 6A, formula 6B, formula 6C, formula 6D, formula 6E, formula 6F, formula 6G, formula 6H, formula 16A, compound 1, compound 2, compound 3, and compound 4.

18. The method of claim 1, wherein the PDE7 inhibitory agent is able to cross the blood/brain barrier.

19. The method of claim 1, further comprising administering an additional therapeutic agent with the PDE7 inhibitor, wherein each of the PDE7 inhibitor and the additional therapeutic agent contribute to the effective treatment of the addiction or reducing the likelihood that a subject will become addicted.

20. The method of claim 19, wherein said additional therapeutic agent is selected from the group consisting of: an opioid antagonist, a mixed opioid partial agonist/antagonist, an antidepressant, an antiepileptic, an antiemetic, a corticotrophin-releasing factor-1 (CRF-1) receptor antagonist, a selective serotonin-3 (5-HT3) antagonist, a 5-HT2A/2C antagonist, and a cannabinoid-1 (CB1) receptor antagonist.

21. The method of claim 20, wherein the opioid antagonist is naltrexone or nalmefene.

22. The method of claim 20, wherein the antidepressant is fluoxetine, mirtazapine, or bupropion.

23. The method of claim 20, wherein the antiepileptic is selected from the group consisting of: topiramate, levetiracetam, and gabapentin.

24. The method of claim 20, wherein the CRF-1 receptor antagonist is antalarmin.

25. The method of claim 20, wherein the selective serotonin-3 (5-HT3) antagonist is ondansetron.

26. The method of claim 20, wherein the cannabinoid-1 (CB1) receptor antagonist is rimonabant or tanarabant.

27. The method of claim 20, wherein the mixed opioid agonist/antagonist is buprenorphine.

28. The method of claim 19, wherein the additional therapeutic agent is topiramate.

29. The method of claim 9, wherein the primary impulse-control disorder is binge eating or food addiction.

30. The method of claim 1, further comprising administering to the subject an amount of a dopaminergic agent, wherein the PDE7 inhibitory agent and the dopaminergic agent are effective for the treatment or reduction of use of the addictive agent or practice of the compulsive behavior.

31. The method of claim 30, wherein the dopaminergic agent is selected from dopamine precursors, dopamine cothctors, inhibitors of enzymes that metabolize dopamine, dopamine receptor agonists, precursor compounds that are metabolically converted to a dopamine receptor agonist, dopamine reuptake inhibitors and facilitators of dopamine release.

32. The method of claim 31, wherein the dopaminergic agent is selected from levodopa, carbidopa, bromocriptine, pergolide, pramipexole, ropinirole, cabergoline, apomorphine, lisuride, rotigotine and quinagolide and fenoldopam.

33. The method of claim 30, wherein the dopaminergic agent is selective for dopamine receptor D1.

34. The method of claim 33, wherein the doparninergic agent is a dopamine agonist.

* * * * *

UNITED STATES PATENT AND TRADEMARK OFFICE
CERTIFICATE OF CORRECTION

PATENT NO. : 9,220,715 B2  
APPLICATION NO. : 13/835607  
DATED : December 29, 2015  
INVENTOR(S) : Gregory A. Demopulos et al.

Page 1 of 1

It is certified that error appears in the above-identified patent and that said Letters Patent is hereby corrected as shown below:

| COLUMN | LINE | ERROR |
|---|---|---|
| In the Specification | | |
| 13 | 11 | "25A-30D" should read --25A-25D-- |
| 13 | 18 | "26D" should read --25D-- |

Signed and Sealed this  
Twenty-sixth Day of April, 2016

Michelle K. Lee  
*Director of the United States Patent and Trademark Office*

SEQUENCE LISTING

<160> NUMBER OF SEQ ID NOS: 6

<210> SEQ ID NO 1
<211> LENGTH: 1739
<212> TYPE: DNA
<213> ORGANISM: Homo sapiens
<220> FEATURE:

```
<221> NAME/KEY: CDS
<222> LOCATION: (157)..(1527)

<400> SEQUENCE: 1
ggggatcact gttggaaggc agctgcttga ggtccaaggc agtcagtgtc ccctctcttt     60
tgcctcggga cagctggtat ttatcagact cctaagaagt tttccttgct ccctagtaga    120
agagagagat tatgcagcgg gcttttgatt gatcca atg gga att aca ttg atc      174
                                          Met Gly Ile Thr Leu Ile
                                            1               5 tgg tgt ctg gcc ttg gtt ctt atc aag tgg atc acc tct aag agg cgt      222
Trp Cys Leu Ala Leu Val Leu Ile Lys Trp Ile Thr Ser Lys Arg Arg
         10                  15                  20 gga gct att tcc tat gac agt tct gat cag act gca tta tac att cgt      270
Gly Ala Ile Ser Tyr Asp Ser Ser Asp Gln Thr Ala Leu Tyr Ile Arg
             25                  30                  35 atg cta gga gat gta cgt gta agg agc cga gca gga ttt gaa tca gaa      318
Met Leu Gly Asp Val Arg Val Arg Ser Arg Ala Gly Phe Glu Ser Glu
 40                  45                  50 aga aga ggt tct cac cca tat att gat ttt cgt att ttc cac tct caa      366
Arg Arg Gly Ser His Pro Tyr Ile Asp Phe Arg Ile Phe His Ser Gln
 55                  60                  65                  70 tct gaa att gaa gtg tct gtc tct gca agg aat atc aga agg cta cta      414
Ser Glu Ile Glu Val Ser Val Ser Ala Arg Asn Ile Arg Arg Leu Leu
                 75                  80                  85 agt ttc cag cga tat ctt aga tct tca cgc ttt ttt cgt ggt act gcg      462
Ser Phe Gln Arg Tyr Leu Arg Ser Ser Arg Phe Phe Arg Gly Thr Ala
             90                  95                 100 gtt tca aat tcc cta aac att tta gat gat gat tat aat gga caa gcc      510
Val Ser Asn Ser Leu Asn Ile Leu Asp Asp Asp Tyr Asn Gly Gln Ala
        105                 110                 115 aag tgt atg ctg gaa aaa gtt gga aat tgg aat ttt gat atc ttt cta      558
Lys Cys Met Leu Glu Lys Val Gly Asn Trp Asn Phe Asp Ile Phe Leu
120                 125                 130 ttt gat aga cta aca aat gga aat agt cta gta agc tta acc ttt cat      606
Phe Asp Arg Leu Thr Asn Gly Asn Ser Leu Val Ser Leu Thr Phe His
135                 140                 145                 150 tta ttt agt ctt cat gga tta att gag tac ttc cat tta gat atg atg      654
Leu Phe Ser Leu His Gly Leu Ile Glu Tyr Phe His Leu Asp Met Met
                155                 160                 165 aaa ctt cgt aga ttt tta gtt atg att caa gaa gat tac cac agt caa      702
Lys Leu Arg Arg Phe Leu Val Met Ile Gln Glu Asp Tyr His Ser Gln
            170                 175                 180 aat cct tac cat aac gca gtc cac gct gcg gat gtt act cag gcc atg      750
Asn Pro Tyr His Asn Ala Val His Ala Ala Asp Val Thr Gln Ala Met
        185                 190                 195 cac tgt tac tta aag gaa cct aag ctt gcc aat tct gta act cct tgg      798
His Cys Tyr Leu Lys Glu Pro Lys Leu Ala Asn Ser Val Thr Pro Trp
    200                 205                 210 gat atc ttg ctg agc tta att gca gct gcc act cat gat ctg gat cat      846
Asp Ile Leu Leu Ser Leu Ile Ala Ala Ala Thr His Asp Leu Asp His
215                 220                 225                 230 cca ggt gtt aat caa cct ttc ctt att aaa act aac cat tac ttg gca      894
Pro Gly Val Asn Gln Pro Phe Leu Ile Lys Thr Asn His Tyr Leu Ala
                235                 240                 245 act tta tac aag aat acc tca gta ctg gaa aat cac cac tgg aga tct      942
Thr Leu Tyr Lys Asn Thr Ser Val Leu Glu Asn His His Trp Arg Ser
            250                 255                 260 gca gtg ggc tta ttg aga gaa tca ggc tta ttc tca cat ctg cca tta      990
Ala Val Gly Leu Leu Arg Glu Ser Gly Leu Phe Ser His Leu Pro Leu
```

```
                 265                 270                 275
gaa agc agg caa caa atg gag aca cag ata ggt gct ctg ata cta gcc    1038
Glu Ser Arg Gln Gln Met Glu Thr Gln Ile Gly Ala Leu Ile Leu Ala
    280                 285                 290 aca gac atc agt cgc cag aat gag tat ctg tct ttg ttt agg tcc cat    1086
Thr Asp Ile Ser Arg Gln Asn Glu Tyr Leu Ser Leu Phe Arg Ser His
295                 300                 305                 310 ttg gat aga ggt gat tta tgc cta gaa gac acc aga cac aga cat ttg    1134
Leu Asp Arg Gly Asp Leu Cys Leu Glu Asp Thr Arg His Arg His Leu
                315                 320                 325 gtt tta cag atg gct ttg aaa tgt gct gat att tgt aac cca tgt cgg    1182
Val Leu Gln Met Ala Leu Lys Cys Ala Asp Ile Cys Asn Pro Cys Arg
            330                 335                 340 acg tgg gaa tta agc aag cag tgg agt gaa aaa gta acg gag gaa ttc    1230
Thr Trp Glu Leu Ser Lys Gln Trp Ser Glu Lys Val Thr Glu Glu Phe
        345                 350                 355 ttc cat caa gga gat ata gaa aaa aaa tat cat ttg ggt gtg agt cca    1278
Phe His Gln Gly Asp Ile Glu Lys Lys Tyr His Leu Gly Val Ser Pro
    360                 365                 370 ctt tgc gat cgt cac act gaa tct att gcc aac atc cag att ggt ttt    1326
Leu Cys Asp Arg His Thr Glu Ser Ile Ala Asn Ile Gln Ile Gly Phe
375                 380                 385                 390 atg act tac cta gtg gag cct tta ttt aca gaa tgg gcc agg ttt tcc    1374
Met Thr Tyr Leu Val Glu Pro Leu Phe Thr Glu Trp Ala Arg Phe Ser
                395                 400                 405 aat aca agg cta tcc cag aca atg ctt gga cac gtg ggg ctg aat aaa    1422
Asn Thr Arg Leu Ser Gln Thr Met Leu Gly His Val Gly Leu Asn Lys
            410                 415                 420 gcc agc tgg aag gga ctg cag aga gaa cag tcg agc agt gag gac act    1470
Ala Ser Trp Lys Gly Leu Gln Arg Glu Gln Ser Ser Ser Glu Asp Thr
        425                 430                 435 gat gct gca ttt gag ttg aac tca cag tta tta cct cag gaa aat cgg    1518
Asp Ala Ala Phe Glu Leu Asn Ser Gln Leu Leu Pro Gln Glu Asn Arg
    440                 445                 450 tta tca taa cccccagaac cagtgggaca aactgcctcc tggaggtttt           1567
Leu Ser
455 tagaaatgtg aaatggggtc ttgaggtgag agaacttaac tcttgactgc caaggtttcc    1627 aagtgagtga tgccagccag cattatttat ttccaagatt tcctctgttg gatcatttga    1687 acccacttgt taattgcaag acccgaacat acagcaatat gaatttggct tt            1739

<210> SEQ ID NO 2
<211> LENGTH: 456
<212> TYPE: PRT
<213> ORGANISM: Homo sapiens

<400> SEQUENCE: 2

Met Gly Ile Thr Leu Ile Trp Cys Leu Ala Leu Val Leu Ile Lys Trp
1               5                   10                  15

Ile Thr Ser Lys Arg Arg Gly Ala Ile Ser Tyr Asp Ser Ser Asp Gln
            20                  25                  30

Thr Ala Leu Tyr Ile Arg Met Leu Gly Asp Val Arg Val Arg Ser Arg
        35                  40                  45

Ala Gly Phe Glu Ser Glu Arg Arg Gly Ser His Pro Tyr Ile Asp Phe
    50                  55                  60

Arg Ile Phe His Ser Gln Ser Glu Ile Glu Val Ser Val Ser Ala Arg
65                  70                  75                  80
```

```
Asn Ile Arg Arg Leu Leu Ser Phe Gln Arg Tyr Leu Arg Ser Ser Arg
                85                  90                  95

Phe Phe Arg Gly Thr Ala Val Ser Asn Ser Leu Asn Ile Leu Asp Asp
            100                 105                 110

Asp Tyr Asn Gly Gln Ala Lys Cys Met Leu Glu Lys Val Gly Asn Trp
        115                 120                 125

Asn Phe Asp Ile Phe Leu Phe Asp Arg Leu Thr Asn Gly Asn Ser Leu
    130                 135                 140

Val Ser Leu Thr Phe His Leu Phe Ser Leu His Gly Leu Ile Glu Tyr
145                 150                 155                 160

Phe His Leu Asp Met Met Lys Leu Arg Arg Phe Leu Val Met Ile Gln
                165                 170                 175

Glu Asp Tyr His Ser Gln Asn Pro Tyr His Asn Ala Val His Ala Ala
            180                 185                 190

Asp Val Thr Gln Ala Met His Cys Tyr Leu Lys Glu Pro Lys Leu Ala
        195                 200                 205

Asn Ser Val Thr Pro Trp Asp Ile Leu Leu Ser Leu Ile Ala Ala Ala
    210                 215                 220

Thr His Asp Leu Asp His Pro Gly Val Asn Gln Pro Phe Leu Ile Lys
225                 230                 235                 240

Thr Asn His Tyr Leu Ala Thr Leu Tyr Lys Asn Thr Ser Val Leu Glu
                245                 250                 255

Asn His His Trp Arg Ser Ala Val Gly Leu Leu Arg Glu Ser Gly Leu
            260                 265                 270

Phe Ser His Leu Pro Leu Glu Ser Arg Gln Gln Met Glu Thr Gln Ile
        275                 280                 285

Gly Ala Leu Ile Leu Ala Thr Asp Ile Ser Arg Gln Asn Glu Tyr Leu
    290                 295                 300

Ser Leu Phe Arg Ser His Leu Asp Arg Gly Asp Leu Cys Leu Glu Asp
305                 310                 315                 320

Thr Arg His Arg His Leu Val Leu Gln Met Ala Leu Lys Cys Ala Asp
                325                 330                 335

Ile Cys Asn Pro Cys Arg Thr Trp Glu Leu Ser Lys Gln Trp Ser Glu
            340                 345                 350

Lys Val Thr Glu Glu Phe Phe His Gln Gly Asp Ile Glu Lys Lys Tyr
        355                 360                 365

His Leu Gly Val Ser Pro Leu Cys Asp Arg His Thr Glu Ser Ile Ala
    370                 375                 380

Asn Ile Gln Ile Gly Phe Met Thr Tyr Leu Val Glu Pro Leu Phe Thr
385                 390                 395                 400

Glu Trp Ala Arg Phe Ser Asn Thr Arg Leu Ser Gln Thr Met Leu Gly
                405                 410                 415

His Val Gly Leu Asn Lys Ala Ser Trp Lys Gly Leu Gln Arg Glu Gln
            420                 425                 430

Ser Ser Ser Glu Asp Thr Asp Ala Ala Phe Glu Leu Asn Ser Gln Leu
        435                 440                 445

Leu Pro Gln Glu Asn Arg Leu Ser
    450                 455

<210> SEQ ID NO 3
<211> LENGTH: 2990
<212> TYPE: DNA
<213> ORGANISM: Homo sapiens
<220> FEATURE:
<221> NAME/KEY: CDS
```

<222> LOCATION: (1)..(1275)

<400> SEQUENCE: 3

| | | | | | | | | | | | | | | | | |
|---|---|---|---|---|---|---|---|---|---|---|---|---|---|---|---|---|
| atg | gaa | gtg | tgt | tac | cag | ctg | ccg | gta | ctg | ccc | ctg | gac | agg | ccg | gtc | 48 |
| Met | Glu | Val | Cys | Tyr | Gln | Leu | Pro | Val | Leu | Pro | Leu | Asp | Arg | Pro | Val | |
| 1 | | | | 5 | | | | | 10 | | | | | 15 | | |
| ccc | cag | cac | gtc | ctc | agc | cgc | cga | gga | gcc | atc | agc | ttc | agc | tcc | agc | 96 |
| Pro | Gln | His | Val | Leu | Ser | Arg | Arg | Gly | Ala | Ile | Ser | Phe | Ser | Ser | Ser | |
| | | | 20 | | | | | 25 | | | | | 30 | | | |
| tcc | gct | ctc | ttc | ggc | tgc | ccc | aat | ccc | cgg | cag | ctc | tct | cag | agg | cgt | 144 |
| Ser | Ala | Leu | Phe | Gly | Cys | Pro | Asn | Pro | Arg | Gln | Leu | Ser | Gln | Arg | Arg | |
| | | 35 | | | | | 40 | | | | | 45 | | | | |
| gga | gct | att | tcc | tat | gac | agt | tct | gat | cag | act | gca | tta | tac | att | cgt | 192 |
| Gly | Ala | Ile | Ser | Tyr | Asp | Ser | Ser | Asp | Gln | Thr | Ala | Leu | Tyr | Ile | Arg | |
| | 50 | | | | | 55 | | | | | 60 | | | | | |
| atg | cta | gga | gat | gta | cgt | gta | agg | agc | cga | gca | gga | ttt | gaa | tca | gaa | 240 |
| Met | Leu | Gly | Asp | Val | Arg | Val | Arg | Ser | Arg | Ala | Gly | Phe | Glu | Ser | Glu | |
| 65 | | | | | 70 | | | | | 75 | | | | | 80 | |
| aga | aga | ggt | tct | cac | cca | tat | att | gat | ttt | cgt | att | ttc | cac | tct | caa | 288 |
| Arg | Arg | Gly | Ser | His | Pro | Tyr | Ile | Asp | Phe | Arg | Ile | Phe | His | Ser | Gln | |
| | | | | 85 | | | | | 90 | | | | | 95 | | |
| tct | gaa | att | gaa | gtg | tct | gtc | tct | gca | agg | aat | atc | aga | agg | cta | cta | 336 |
| Ser | Glu | Ile | Glu | Val | Ser | Val | Ser | Ala | Arg | Asn | Ile | Arg | Arg | Leu | Leu | |
| | | | 100 | | | | | 105 | | | | | 110 | | | |
| agt | ttc | cag | cga | tat | ctt | aga | tct | tca | cgc | ttt | ttt | cgt | ggt | act | gcg | 384 |
| Ser | Phe | Gln | Arg | Tyr | Leu | Arg | Ser | Ser | Arg | Phe | Phe | Arg | Gly | Thr | Ala | |
| | | 115 | | | | | 120 | | | | | 125 | | | | |
| gtt | tca | aat | tcc | cta | aac | att | tta | gat | gat | gat | tat | aat | gga | caa | gcc | 432 |
| Val | Ser | Asn | Ser | Leu | Asn | Ile | Leu | Asp | Asp | Asp | Tyr | Asn | Gly | Gln | Ala | |
| | 130 | | | | | 135 | | | | | 140 | | | | | |
| aag | tgt | atg | ctg | gaa | aaa | gtt | gga | aat | tgg | aat | ttt | gat | atc | ttt | cta | 480 |
| Lys | Cys | Met | Leu | Glu | Lys | Val | Gly | Asn | Trp | Asn | Phe | Asp | Ile | Phe | Leu | |
| 145 | | | | | 150 | | | | | 155 | | | | | 160 | |
| ttt | gat | aga | cta | aca | aat | gga | aat | agt | cta | gta | agc | tta | acc | ttt | cat | 528 |
| Phe | Asp | Arg | Leu | Thr | Asn | Gly | Asn | Ser | Leu | Val | Ser | Leu | Thr | Phe | His | |
| | | | | 165 | | | | | 170 | | | | | 175 | | |
| tta | ttt | agt | ctt | cat | gga | tta | att | gag | tac | ttc | cat | tta | gat | atg | atg | 576 |
| Leu | Phe | Ser | Leu | His | Gly | Leu | Ile | Glu | Tyr | Phe | His | Leu | Asp | Met | Met | |
| | | | 180 | | | | | 185 | | | | | 190 | | | |
| aaa | ctt | cgt | aga | ttt | tta | gtt | atg | att | caa | gaa | gat | tac | cac | agt | caa | 624 |
| Lys | Leu | Arg | Arg | Phe | Leu | Val | Met | Ile | Gln | Glu | Asp | Tyr | His | Ser | Gln | |
| | | 195 | | | | | 200 | | | | | 205 | | | | |
| aat | cct | tac | cat | aac | gca | gtc | cac | gct | gcg | gat | gtt | act | cag | gcc | atg | 672 |
| Asn | Pro | Tyr | His | Asn | Ala | Val | His | Ala | Ala | Asp | Val | Thr | Gln | Ala | Met | |
| | 210 | | | | | 215 | | | | | 220 | | | | | |
| cac | tgt | tac | tta | aag | gaa | cct | aag | ctt | gcc | aat | tct | gta | act | cct | tgg | 720 |
| His | Cys | Tyr | Leu | Lys | Glu | Pro | Lys | Leu | Ala | Asn | Ser | Val | Thr | Pro | Trp | |
| 225 | | | | | 230 | | | | | 235 | | | | | 240 | |
| gat | atc | ttg | ctg | agc | tta | att | gca | gct | gcc | act | cat | gat | ctg | gat | cat | 768 |
| Asp | Ile | Leu | Leu | Ser | Leu | Ile | Ala | Ala | Ala | Thr | His | Asp | Leu | Asp | His | |
| | | | | 245 | | | | | 250 | | | | | 255 | | |
| cca | ggt | gtt | aat | caa | cct | ttc | ctt | att | aaa | act | aac | cat | tac | ttg | gca | 816 |
| Pro | Gly | Val | Asn | Gln | Pro | Phe | Leu | Ile | Lys | Thr | Asn | His | Tyr | Leu | Ala | |
| | | | 260 | | | | | 265 | | | | | 270 | | | |
| act | tta | tac | aag | aat | acc | tca | gta | ctg | gaa | aat | cac | cac | tgg | aga | tct | 864 |
| Thr | Leu | Tyr | Lys | Asn | Thr | Ser | Val | Leu | Glu | Asn | His | His | Trp | Arg | Ser | |
| | | 275 | | | | | 280 | | | | | 285 | | | | |
| gca | gtg | ggc | tta | ttg | aga | gaa | tca | ggc | tta | ttc | tca | cat | ctg | cca | tta | 912 |
| Ala | Val | Gly | Leu | Leu | Arg | Glu | Ser | Gly | Leu | Phe | Ser | His | Leu | Pro | Leu | |
| | 290 | | | | | 295 | | | | | 300 | | | | | |

```
gaa agc agg caa caa atg gag aca cag ata ggt gct ctg ata cta gcc    960
Glu Ser Arg Gln Gln Met Glu Thr Gln Ile Gly Ala Leu Ile Leu Ala
305                 310                 315                 320 aca gac atc agt cgc cag aat gag tat ctg tct ttg ttt agg tcc cat   1008
Thr Asp Ile Ser Arg Gln Asn Glu Tyr Leu Ser Leu Phe Arg Ser His
                325                 330                 335 ttg gat aga ggt gat tta tgc cta gaa gac acc aga cac aga cat ttg   1056
Leu Asp Arg Gly Asp Leu Cys Leu Glu Asp Thr Arg His Arg His Leu
            340                 345                 350 gtt tta cag atg gct ttg aaa tgt gct gat att tgt aac cca tgt cgg   1104
Val Leu Gln Met Ala Leu Lys Cys Ala Asp Ile Cys Asn Pro Cys Arg
        355                 360                 365 acg tgg gaa tta agc aag cag tgg agt gaa aaa gta acg gag gaa ttc   1152
Thr Trp Glu Leu Ser Lys Gln Trp Ser Glu Lys Val Thr Glu Glu Phe
    370                 375                 380 ttc cat caa gga gat ata gaa aaa aaa tat cat ttg ggt gtg agt cca   1200
Phe His Gln Gly Asp Ile Glu Lys Lys Tyr His Leu Gly Val Ser Pro
385                 390                 395                 400 ctt tgc gat cgt cac act gaa tct att gcc aac atc cag att ggt aac   1248
Leu Cys Asp Arg His Thr Glu Ser Ile Ala Asn Ile Gln Ile Gly Asn
                405                 410                 415 tat aca tat tta gat ata gct ggt tag aaaaatgcca ctgtttttat         1295
Tyr Thr Tyr Leu Asp Ile Ala Gly
                420 caagaaggga aatatatttg aaatataaaa tattaaaatt atgctcattt ctattttaa   1355 aaataattta agaaatttta cccttgtttt cccttgttat ggctcttcta attctcattt  1415 aattttagga tgtaaaaagt atattttgc agaacaggca gcagcaataa cttgtttctg   1475 ttcttatgta aataagaatc cattattcgc tcatgtggaa gcttcttttg catcatttgg  1535 gactgccatt taaaaaagga taggtaaaca aagaaatgac aaaaataaaa taaataaaat  1595 aaaaatggat aggtggtgac ccactgagcc tgatcataat acgaagacca gcttctgcca  1655 ctgcctttcc agactcttac cactgcctgt tgattaaatc taactcttca acatcctaga  1715 caggccctta taatcttgct tcaaatgctg tgcagccatc ttgcctcaac ttccctctca  1775 tttgcctaca gcatctcggg acgcttctgt gtttcccaag tatacgctgt tctttcgctc  1835 tttgtgcttc gccagtgctt tccatgtgcc tcgtagagtt attttctctt aagaggcagc  1895 tcaaatgtca ccttctccag aagctgctct ccacttgctt taggcagagt cagtcacttt  1955 tcttctagat tccaaagtgc ctgatccact tggttgtgga ttcctggagc ctagcaccac  2015 accagaagca cgaggcccctt gagaactgtg tgttgagtga actaataact gtattataga  2075 aagcataatg aaaatgtcct gtgactgaag tatgtgtagc ttgttgcagg agtcacagga  2135 aagttgacta ggattgagtg tgttgggctt tgggtataaa ggaggggat tctacggggg   2195 cagtagctca acaaggaata gagggaggag tgtaattttg gtagctggtg ttgaataggg  2255 cctttgagaa tcagactgaa cacagtgaaa tatgtgccca agttcagaa agatgaagtt   2315 tccagaaact aagaaggtag cacaatatgt ggcatcatac tcagaaagga agaccatgcc  2375 atggggccag aaattcagaa acgtaattct tacattgtga ttgcaatgga tactcatgaa  2435 agaaagtggg tagtggccga tttgccttca gagtgacagg tagagaaggg aagagcgtgt  2495 agaactgtgg ccatacttta ggagtgtgag ggatgctgaa tctcccagag agctcacact  2555 ggccaggaat gctgagagta gcagatgctt ttcttttggg aggatagtaa aacaatttag  2615 aaccagatat gctttgtctt gattctcaag tagaataatc ttcaaatgca aaagaataca  2675
```

-continued

```
ttagaaatgg acaaaagtgg ccaggagcgg tagctcatac ttgtaaccca gcactttggg    2735
aagccgaggc gggctgatcg cttgaggtca ggagttcgag accagcctgg ccaaaatagt    2795
gaaactcacg tttctactaa aaatacaaaa attagctggg tgtgatggcc acttgggagg    2855
ctgagatagg agaatcgctt gaacctggga ggcagaggtt gcagtgagcc aatatcgtgc    2915
cactgcattc cagcctgggt gacagaatga aactccatca ctccatctca aaaaaaaaaa    2975
aaaaaaaaaa aaaaa                                                     2990
```

<210> SEQ ID NO 4
<211> LENGTH: 424
<212> TYPE: PRT
<213> ORGANISM: Homo sapiens

<400> SEQUENCE: 4

```
Met Glu Val Cys Tyr Gln Leu Pro Val Leu Pro Leu Asp Arg Pro Val
1               5                   10                  15

Pro Gln His Val Leu Ser Arg Arg Gly Ala Ile Ser Phe Ser Ser Ser
            20                  25                  30

Ser Ala Leu Phe Gly Cys Pro Asn Pro Arg Gln Leu Ser Gln Arg Arg
        35                  40                  45

Gly Ala Ile Ser Tyr Asp Ser Ser Asp Gln Thr Ala Leu Tyr Ile Arg
    50                  55                  60

Met Leu Gly Asp Val Arg Val Arg Ser Arg Ala Gly Phe Glu Ser Glu
65                  70                  75                  80

Arg Arg Gly Ser His Pro Tyr Ile Asp Phe Arg Ile Phe His Ser Gln
                85                  90                  95

Ser Glu Ile Glu Val Ser Val Ser Ala Arg Asn Ile Arg Arg Leu Leu
            100                 105                 110

Ser Phe Gln Arg Tyr Leu Arg Ser Ser Arg Phe Phe Arg Gly Thr Ala
        115                 120                 125

Val Ser Asn Ser Leu Asn Ile Leu Asp Asp Tyr Asn Gly Gln Ala
    130                 135                 140

Lys Cys Met Leu Glu Lys Val Gly Asn Trp Asn Phe Asp Ile Phe Leu
145                 150                 155                 160

Phe Asp Arg Leu Thr Asn Gly Asn Ser Leu Val Ser Leu Thr Phe His
                165                 170                 175

Leu Phe Ser Leu His Gly Leu Ile Glu Tyr Phe His Leu Asp Met Met
            180                 185                 190

Lys Leu Arg Arg Phe Leu Val Met Ile Gln Glu Asp Tyr His Ser Gln
        195                 200                 205

Asn Pro Tyr His Asn Ala Val His Ala Ala Asp Val Thr Gln Ala Met
    210                 215                 220

His Cys Tyr Leu Lys Glu Pro Lys Leu Ala Asn Ser Val Thr Pro Trp
225                 230                 235                 240

Asp Ile Leu Leu Ser Leu Ile Ala Ala Thr His Asp Leu Asp His
                245                 250                 255

Pro Gly Val Asn Gln Pro Phe Leu Ile Lys Thr Asn His Tyr Leu Ala
            260                 265                 270

Thr Leu Tyr Lys Asn Thr Ser Val Leu Glu Asn His His Trp Arg Ser
        275                 280                 285

Ala Val Gly Leu Leu Arg Glu Ser Gly Leu Phe Ser His Leu Pro Leu
    290                 295                 300

Glu Ser Arg Gln Gln Met Glu Thr Gln Ile Gly Ala Leu Ile Leu Ala
305                 310                 315                 320
```

```
Thr Asp Ile Ser Arg Gln Asn Glu Tyr Leu Ser Leu Phe Arg Ser His
            325                 330                 335

Leu Asp Arg Gly Asp Leu Cys Leu Glu Asp Thr Arg His Arg His Leu
        340                 345                 350

Val Leu Gln Met Ala Leu Lys Cys Ala Asp Ile Cys Asn Pro Cys Arg
            355                 360                 365

Thr Trp Glu Leu Ser Lys Gln Trp Ser Glu Lys Val Thr Glu Glu Phe
    370                 375                 380

Phe His Gln Gly Asp Ile Glu Lys Lys Tyr His Leu Gly Val Ser Pro
385                 390                 395                 400

Leu Cys Asp Arg His Thr Glu Ser Ile Ala Asn Ile Gln Ile Gly Asn
                405                 410                 415

Tyr Thr Tyr Leu Asp Ile Ala Gly
            420

<210> SEQ ID NO 5
<211> LENGTH: 2100
<212> TYPE: DNA
<213> ORGANISM: Homo sapiens
<220> FEATURE:
<221> NAME/KEY: CDS
<222> LOCATION: (304)..(1656)

<400> SEQUENCE: 5
cagtcagttg gtctgggcac tgcagcaggc tcggctctgt cccagcactt gtctgggaga        60
aaagtggtgt tactcaccca gggagagtct ctctttctac cttccttctt tctcgatctc       120
cttgtgtgct tttgtgtttc tttatttctt ttccttttt ttcttttttt tttttgtta         180 cttaattata ttcctaatcc tggatgaagt tgctggattc tgcagcacaa gtcttcatga       240
acaagcagca ccgctcagag atttcacggc attcaaaggt cacagaactg ccactatggt       300 taa atg tct tgt tta atg gtt gag agg tgt ggc gaa atc ttg ttt gag        348
    Met Ser Cys Leu Met Val Glu Arg Cys Gly Glu Ile Leu Phe Glu
    1               5                   10                  15 aac ccc gat cag aat gcc aaa tgt gtt tgc atg ctg gga gat ata cga        396
Asn Pro Asp Gln Asn Ala Lys Cys Val Cys Met Leu Gly Asp Ile Arg
                20                  25                  30 cta agg ggt cag acg ggg gtt cgt gct gaa cgc cgt ggc tcc tac cca        444
Leu Arg Gly Gln Thr Gly Val Arg Ala Glu Arg Arg Gly Ser Tyr Pro
            35                  40                  45 ttc att gac ttc cgc cta ctt aac agt aca aca tac tca ggg gag att        492
Phe Ile Asp Phe Arg Leu Leu Asn Ser Thr Thr Tyr Ser Gly Glu Ile
        50                  55                  60 ggc acc aag aaa aag gtg aaa aga cta tta agc ttt caa aga tac ttc        540
Gly Thr Lys Lys Lys Val Lys Arg Leu Leu Ser Phe Gln Arg Tyr Phe
65                  70                  75 cat gca tca agg ctg ctt cgt gga att ata cca caa gcc cct ctg cac        588
His Ala Ser Arg Leu Leu Arg Gly Ile Ile Pro Gln Ala Pro Leu His
80                  85                  90                  95 ctg ctg gat gaa gac tac ctt gga caa gca agg cat atg ctc tcc aaa        636
Leu Leu Asp Glu Asp Tyr Leu Gly Gln Ala Arg His Met Leu Ser Lys
                100                 105                 110 gtg gga atg tgg gat ttt gac att ttc ttg ttt gat cgc ttg aca aat        684
Val Gly Met Trp Asp Phe Asp Ile Phe Leu Phe Asp Arg Leu Thr Asn
            115                 120                 125 gga aac agc ctg gta aca ctg ttg tgc cac ctc ttc aat acc cat gga        732
Gly Asn Ser Leu Val Thr Leu Leu Cys His Leu Phe Asn Thr His Gly
        130                 135                 140
```

```
ctc att cac cat ttc aag tta gat atg gtg acc tta cac cga ttt tta     780
Leu Ile His His Phe Lys Leu Asp Met Val Thr Leu His Arg Phe Leu
    145                 150                 155 gtc atg gtt caa gaa gat tac cac agc caa aac ccg tat cac aat gct     828
Val Met Val Gln Glu Asp Tyr His Ser Gln Asn Pro Tyr His Asn Ala
160                 165                 170                 175 gtt cac gca gcc gac gtc acc cag gcc atg cac tgc tac ctg aaa gag     876
Val His Ala Ala Asp Val Thr Gln Ala Met His Cys Tyr Leu Lys Glu
                180                 185                 190 cca aag ctt gcc agc ttc ctc acg cct ctg gac atc atg ctt gga ctg     924
Pro Lys Leu Ala Ser Phe Leu Thr Pro Leu Asp Ile Met Leu Gly Leu
            195                 200                 205 ctg gct gca gca gca cac gat gtg gac cac cca ggg gtg aac cag cca     972
Leu Ala Ala Ala Ala His Asp Val Asp His Pro Gly Val Asn Gln Pro
        210                 215                 220 ttt ttg ata aaa act aac cac cat ctt gca aac cta tat cag aat atg    1020
Phe Leu Ile Lys Thr Asn His His Leu Ala Asn Leu Tyr Gln Asn Met
225                 230                 235 tct gtg ctg gag aat cat cac tgg cga tct aca att ggc atg ctt cga    1068
Ser Val Leu Glu Asn His His Trp Arg Ser Thr Ile Gly Met Leu Arg
240                 245                 250                 255 gaa tca agg ctt ctt gct cat ttg cca aag gaa atg aca cag gat att    1116
Glu Ser Arg Leu Leu Ala His Leu Pro Lys Glu Met Thr Gln Asp Ile
                260                 265                 270 gaa cag cag ctg ggc tcc ttg atc ttg gca aca gac atc aac agg cag    1164
Glu Gln Gln Leu Gly Ser Leu Ile Leu Ala Thr Asp Ile Asn Arg Gln
            275                 280                 285 aat gaa ttt ttg acc aga ttg aaa gct cac ctc cac aat aaa gac tta    1212
Asn Glu Phe Leu Thr Arg Leu Lys Ala His Leu His Asn Lys Asp Leu
        290                 295                 300 aga ctg gag gat gca cag gac agg cac ttt atg ctt cag atc gcc ttg    1260
Arg Leu Glu Asp Ala Gln Asp Arg His Phe Met Leu Gln Ile Ala Leu
    305                 310                 315 aag tgt gct gac att tgc aat cct tgt aga atc tgg gag atg agc aag    1308
Lys Cys Ala Asp Ile Cys Asn Pro Cys Arg Ile Trp Glu Met Ser Lys
320                 325                 330                 335 cag tgg agt gaa agg gtc tgt gaa gaa ttc tac agg caa ggt gaa ctt    1356
Gln Trp Ser Glu Arg Val Cys Glu Glu Phe Tyr Arg Gln Gly Glu Leu
                340                 345                 350 gaa cag aaa ttt gaa ctg gaa atc agt cct ctt tgt aat caa cag aaa    1404
Glu Gln Lys Phe Glu Leu Glu Ile Ser Pro Leu Cys Asn Gln Gln Lys
            355                 360                 365 gat tcc atc cct agt ata caa att ggt ttc atg agc tac atc gtg gag    1452
Asp Ser Ile Pro Ser Ile Gln Ile Gly Phe Met Ser Tyr Ile Val Glu
        370                 375                 380 ccg ctc ttc cgg gaa tgg gcc cat ttc acg ggt aac agc acc ctg tcg    1500
Pro Leu Phe Arg Glu Trp Ala His Phe Thr Gly Asn Ser Thr Leu Ser
    385                 390                 395 gag aac atg ctg ggc cac ctc gca cac aac aag gcc cag tgg aag agc    1548
Glu Asn Met Leu Gly His Leu Ala His Asn Lys Ala Gln Trp Lys Ser
400                 405                 410                 415 ctg ttg ccc agg cag cac aga agc agg ggc agt ggc agc ggg cct        1596
Leu Leu Pro Arg Gln His Arg Ser Arg Gly Ser Ser Gly Ser Gly Pro
                420                 425                 430 gac cac gac cac gca ggc caa ggg act gag agc gag gag cag gaa ggc    1644
Asp His Asp His Ala Gly Gln Gly Thr Glu Ser Glu Glu Gln Glu Gly
            435                 440                 445 gac agc ccc tag gggccggccc aacttagacg cggctctcct ccggcagggc        1696
Asp Ser Pro
        450
```

```
cccagaggg cagaagcagc gtggaggggc cctcacgcag cagcccagcc actttctgag    1756
tgttgtcctg gggctctttg gaacgccatc ttcctcccac ttacctgcct cccctccttt    1816
tcgcaaatgt acagaagcca tttgtcacct cagcattcgc tgccgaaatg agcaactcca    1876
ttcagtaacg tgggagctga tcccacgggc aggctctccc tgctccagga gaagactagg    1936
aggaagaatg aggtgctcct gccgtgtccg ccttgttccg ggtcgcactg gaacaggcag    1996
caattcctaa gtccggagcg tttgagcgtt tgctatctga ctgctgatct gcgtgacaga    2056
aacaccagca tatttgcaac gccaaggata ttggtcttaa gtgc                    2100
```

<210> SEQ ID NO 6
<211> LENGTH: 450
<212> TYPE: PRT
<213> ORGANISM: Homo sapiens

<400> SEQUENCE: 6

```
Met Ser Cys Leu Met Val Glu Arg Cys Gly Glu Ile Leu Phe Glu Asn
1               5                   10                  15

Pro Asp Gln Asn Ala Lys Cys Val Cys Met Leu Gly Asp Ile Arg Leu
            20                  25                  30

Arg Gly Gln Thr Gly Val Arg Ala Glu Arg Arg Gly Ser Tyr Pro Phe
        35                  40                  45

Ile Asp Phe Arg Leu Leu Asn Ser Thr Thr Tyr Ser Gly Glu Ile Gly
    50                  55                  60

Thr Lys Lys Lys Val Lys Arg Leu Leu Ser Phe Gln Arg Tyr Phe His
65                  70                  75                  80

Ala Ser Arg Leu Leu Arg Gly Ile Ile Pro Gln Ala Pro Leu His Leu
                85                  90                  95

Leu Asp Glu Asp Tyr Leu Gly Gln Ala Arg His Met Leu Ser Lys Val
            100                 105                 110

Gly Met Trp Asp Phe Asp Ile Phe Leu Phe Asp Arg Leu Thr Asn Gly
        115                 120                 125

Asn Ser Leu Val Thr Leu Leu Cys His Leu Phe Asn Thr His Gly Leu
    130                 135                 140

Ile His His Phe Lys Leu Asp Met Val Thr Leu His Arg Phe Leu Val
145                 150                 155                 160

Met Val Gln Glu Asp Tyr His Ser Gln Asn Pro Tyr His Asn Ala Val
                165                 170                 175

His Ala Ala Asp Val Thr Gln Ala Met His Cys Tyr Leu Lys Glu Pro
            180                 185                 190

Lys Leu Ala Ser Phe Leu Thr Pro Leu Asp Ile Met Leu Gly Leu Leu
        195                 200                 205

Ala Ala Ala Ala His Asp Val Asp His Pro Gly Val Asn Gln Pro Phe
    210                 215                 220

Leu Ile Lys Thr Asn His His Leu Ala Asn Leu Tyr Gln Asn Met Ser
225                 230                 235                 240

Val Leu Glu Asn His His Trp Arg Ser Thr Ile Gly Met Leu Arg Glu
                245                 250                 255

Ser Arg Leu Leu Ala His Leu Pro Lys Glu Met Thr Gln Asp Ile Glu
            260                 265                 270

Gln Gln Leu Gly Ser Leu Ile Leu Ala Thr Asp Ile Asn Arg Gln Asn
        275                 280                 285

Glu Phe Leu Thr Arg Leu Lys Ala His Leu His Asn Lys Asp Leu Arg
    290                 295                 300
```

```
Leu Glu Asp Ala Gln Asp Arg His Phe Met Leu Gln Ile Ala Leu Lys
305                 310                 315                 320
Cys Ala Asp Ile Cys Asn Pro Cys Arg Ile Trp Glu Met Ser Lys Gln
                325                 330                 335
Trp Ser Glu Arg Val Cys Glu Glu Phe Tyr Arg Gln Gly Glu Leu Glu
            340                 345                 350
Gln Lys Phe Glu Leu Glu Ile Ser Pro Leu Cys Asn Gln Gln Lys Asp
        355                 360                 365
Ser Ile Pro Ser Ile Gln Ile Gly Phe Met Ser Tyr Ile Val Glu Pro
    370                 375                 380
Leu Phe Arg Glu Trp Ala His Phe Thr Gly Asn Ser Thr Leu Ser Glu
385                 390                 395                 400
Asn Met Leu Gly His Leu Ala His Asn Lys Ala Gln Trp Lys Ser Leu
                405                 410                 415
Leu Pro Arg Gln His Arg Ser Arg Gly Ser Ser Gly Ser Gly Pro Asp
            420                 425                 430
His Asp His Ala Gly Gln Gly Thr Glu Ser Glu Glu Gln Glu Gly Asp
        435                 440                 445
Ser Pro
    450
```